(12) United States Patent
Aburatani et al.

(10) Patent No.: US 9,017,684 B2
(45) Date of Patent: Apr. 28, 2015

(54) DIAGNOSIS AND TREATMENT OF CANCER USING ANTI-EREG ANTIBODY

(75) Inventors: Hiroyuki Aburatani, Tokyo (JP); Hirotaka Ito, Tokyo (JP); Kenji Yoshida, Tokyo (JP)

(73) Assignees: Chugai Seiyaku Kabushiki Kaisha, Tokyo (JP); The University of Tokyo, Tokyo (JP)

(*) Notice: Subject to any disclaimer, the term of this patent is extended or adjusted under 35 U.S.C. 154(b) by 234 days.

(21) Appl. No.: 12/444,916

(22) PCT Filed: Oct. 12, 2007

(86) PCT No.: PCT/JP2007/069988
§ 371 (c)(1),
(2), (4) Date: Jun. 23, 2009

(87) PCT Pub. No.: WO2008/047723
PCT Pub. Date: Apr. 24, 2008

(65) Prior Publication Data
US 2009/0324491 A1 Dec. 31, 2009

(30) Foreign Application Priority Data
Oct. 12, 2006 (JP) ................................. 2006-278819

(51) Int. Cl.
C07K 16/22 (2006.01)
A61K 39/395 (2006.01)
A61K 51/10 (2006.01)
G01N 33/574 (2006.01)
C07K 16/30 (2006.01)

(52) U.S. Cl.
CPC ...... *G01N 33/57407* (2013.01); *A61K 51/1045* (2013.01); *C07K 16/30* (2013.01); *C07K 2316/96* (2013.01); *C07K 2317/24* (2013.01); *C07K 2317/56* (2013.01); *C07K 2317/565* (2013.01); *C07K 2317/73* (2013.01); *C07K 2317/732* (2013.01); *C07K 2317/734* (2013.01); *G01N 2333/485* (2013.01)

(58) Field of Classification Search
USPC .......................... 424/158.1; 530/387.1, 387.9
See application file for complete search history.

(56) References Cited

U.S. PATENT DOCUMENTS

| | | |
|---|---|---|
| 5,190,858 A | 3/1993 | Sorvillo et al. |
| 5,783,417 A | 7/1998 | Komurasaki et al. |
| 6,949,245 B1 | 9/2005 | Sliwkowski |
| 2002/0160014 A1 | 10/2002 | Rodriguez et al. |
| 2006/0154333 A1 | 7/2006 | Pienkos et al. |
| 2006/0188497 A1 | 8/2006 | Rodriguez et al. |
| 2006/0252105 A1 | 11/2006 | Komurasaki |
| 2008/0166756 A1 | 7/2008 | Tsuchiya et al. |
| 2009/0324491 A1 | 12/2009 | Aburatani et al. |
| 2010/0092490 A1 | 4/2010 | Uenaka et al. |
| 2012/0141501 A1 | 6/2012 | Yoshida et al. |

FOREIGN PATENT DOCUMENTS

| | | |
|---|---|---|
| CN | 1761682 A | 4/2006 |
| EP | 1 350 521 A1 | 10/2003 |
| EP | 1 607 404 A1 | 12/2005 |
| EP | 1 829 962 A1 | 9/2007 |
| EP | 2 070 548 A1 | 6/2009 |
| JP | 2003-503366 | 1/2003 |
| JP | 2005-519023 | 6/2005 |
| JP | 2006-516893 A | 7/2006 |
| JP | 2008-527978 A | 7/2008 |
| KR | 10-2005-0108389 A | 11/2005 |
| RU | U2270029 C2 | 9/2003 |
| WO | WO 94/29340 | 12/1994 |
| WO | WO 01/00245 A2 | 1/2001 |
| WO | WO 02/45747 A1 | 6/2002 |
| WO | WO 2004/003019 * | 6/2004 |
| WO | WO 2004/065540 A2 | 8/2004 |
| WO | WO 2004/081047 A1 | 9/2004 |
| WO | WO 2005/068503 A2 | 7/2005 |
| WO | WO 2005/076979 A2 | 8/2005 |
| WO | WO 2006/029497 A1 | 3/2006 |
| WO | WO 2006/067913 A1 | 6/2006 |
| WO | WO 2007/015578 A1 | 2/2007 |
| WO | WO 2008/047723 A1 | 4/2008 |
| WO | WO 2010/142952 A2 | 12/2010 |
| WO | WO 2010/142990 A1 | 12/2010 |
| WO | WO 2013/100120 A1 | 7/2013 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*

(Continued)

Primary Examiner — Lynn Bristol
(74) Attorney, Agent, or Firm — Sterne, Kessler, Goldstein & Fox P.L.L.C.

(57) ABSTRACT

Methods that entail detection of an epiregulin (EREG) protein for cancer diagnosis are disclosed. In colon cancer, lung adenocarcinoma, pancreatic cancer, stomach cancer, and kidney cancer, the gene and protein expressions of EREG were frequently found to be elevated. Antibodies that recognize an EREG protein are used for diagnosing or treating cancer in the present invention. Pharmaceutical compositions, cell proliferation inhibitors, and anticancer agents containing an EREG-binding antibody as an active ingredient are also disclosed. Methods of inducing cell damage in EREG-expressing cells and methods of suppressing the proliferation of EREG-expressing cells by contacting the EREG-expressing cells with EREG-binding antibodies are also disclosed.

4 Claims, 24 Drawing Sheets

(56) References Cited

OTHER PUBLICATIONS

Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007));.*
Thurber et al. (Adv. Drug Deliv. Rev. 60:1421-1434 (2008)).*
Rudnick et al. (Can. Biotherp. & Radiopharm. 24: 155-162 (2009)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Kuntz et al. (Growth Factors 23(4):285-293 (Dec. 2005); Abstract only).*
Spinelli et al. (JOP, Sep. 10, 2006;7(5):486-91.*
Flessner et al., Clin Cancer Res. Apr. 15, 2005:11 (8):3117-25.*
Jain, R., Cancer Research, Feb. 1990;50:814s-819.*
Koo, B.-H and Kim, D.-S., "Factor Xa Induces Mitogenesis of Vascular Smooth Muscle Cells via Autocrine Production of Epiregulin," *J. Biol. Chem.* 278(52):52578-52586, The American Society for Biochemistry and Molecular Biology, Inc., United States (2003).
Asano, R., et al., "The advance on the antibody therapy—The expectation to the clinical application," *Igaku no Ayumi* 211:723-727, Maruzen Co Ltd., Tokyo, Japan (2004).
Baba, I., et al., "Involvement of Deregulated Epiregulin Expression in Tumorigenesis in Vivo through Activated Ki-Ras Signaling Pathway in Human Colon Cancer Cells," *Cancer Res.* 60:6886-6889, American Association for Cancer Research, Philadelphia, PA (2000).
Hanai, Nobuo, "Antibody Modification and Transgenic Mice," *Biotherapy* 17:415-421, Kluwer Academic Publishers, Dordrecht, Netherlands (2003).
Minn, A.J., et al., "Genes that mediate breast cancer metastasis to lung," *Nature* 436:518-524, Nature Publishing Group, London, England (Jul. 2005).
R&D Systems, Inc., "Monoclonal Anti-human Epiregulin Antibody," *R&D Systems Catalog, Catalog Number*: MAB1425, 1 page, Minneapolis, MN (2003).
R&D Systems, Inc., "Anti-human Epiregulin Antibody," *R&D Systems Catalog*, Catalog No. AF1195, 2 pages, Minneapolis, MN (2003).
Shirakata, Y., et al., "Epiregulin, a Novel Member of the Epidermal Growth Factor Family, Is an Autocrine Growth Factor in Normal Human Keratinocytes," *J. Biol. Chem.* 275:5748-5753, American Society for Biochemistry and Molecular Biology, Bethesda, MD (2000).
Shirasawa, S., et al., "Dermatitis due to epiregulin deficiency and a critical role of epiregulin in immune-related responses of keratinocyte and macrophage," *Proc. Natl. Acad. Sci. U.S.A.* 101:13921-13926, National Academy of Sciences, Washington, DC (2004).
Sunanaga, N., et al., "Haigan ni okeru Epiregulin Idenshi no Hatsugen ni tsuite no Kento," *The Journal of the Japanese Respiratory Society* 45:167, The Japanese Respiratory Society (2007).
Takahashi, M., et al., "Epiregulin as a Major Autocrine/Paracrine Factor Released From ERK- and p38MAPK-Activated Vascular Smooth Muscle Cells," *Circulation* 108:2524-2529, American Heart Association, Inc. (2003).
Toyoda, H., et al., "Distribution of mRNA for human epiregulin, a differentially expressed member of the epidermal growth factor family," *Biochem. J.* 326:69-75, Portland Press, London, England (1997).
Toyoda, H., et al., "Epiregulin. A Novel Epidermal Growth Factor With Mitogenic Activity for Rat Primary Hepatocytes," *J. Biol. Chem.* 270:7495-7500, American Society for Biochemistry and Molecular Biology, Bethesda, MD (1995).
Zhu, Z., et al., "Epiregulin Is Up-Regulated in Pancreatic Cancer and Stimulates Pancreatic Cancer Cell Growth," *Biochem. Biophys. Res. Commun.* 273:1019-1024, Academic Press, Burlington, MA (2000).
International Search Report for International Patent Application No. PCT/JP2007/069988, filed Oct. 12, 2007, mailed on Nov. 20, 2007, Japanese Patent Office, Tokyo, Japan.
Friedberg, J.W., "Unique Toxicities and Resistance Mechanisms Associated with Monoclonal Antibody Therapy," *Hematology* 2005:329-334, American Society of Hematology (2005).
Dean. C., et al., "Immunotherapy With Antibodies to the EGF Receptor," *Int. J. Cancer Supplement* 8:103-107, Wiley-Liss, Inc., United States (1994).
Force, T., et al., "Molecular mechanisms of cardiotoxicity of tyrosine kinase inhibition," *Nature Reviews Cancer* 7:332-334, Nature Publishing Group, England (2007).
Higashiyama, S., et al., "Membrane-anchored growth factors, the epidermal growth factor family: Beyond receptor ligands," *Cancer Sci.* 99(2):215-220, Japanese Cancer Association, Japan (2008).
Ito, M., et al., "Expression of several growth factors and their receptors genes in human colon carcinomas," *Virchows Archiv B Cell Pathol.* 59:173-178, Springer-Velag, Germany (1990).
Johnson, G.R., et al., "Autocrine Action of Amphiregulin in a Colon Carcinoma Cell Line and Immunocytochemical Localization of Amphiregulin in Human Colon," *J. Cell Biol.* 118(3):741-751, The Rockefeller University Press, United States (1992).
Lacouture, M.E., "Mechanisms of cutaneous toxicities to EGFR inhibitors," *Nature Reviews Cancer* 6:803-812, Nature Publishing Group, England (2006).
Lu, Y., et al., "Immunogene Therapy of Tumors with Vaccine Based on Xenogenic Epidermal Growth Factor Receptor," *J. Immunol.* 170:3162-3170, The American Association of Immunologists, Inc., United States (2003).
Modjtahedi, H., et al., "Anti-EGFR Monoclonal Antibodies Which Act as EGF, TGFα, HB-EGF and BTC Antagonists Block the Binding of Epiregulin to EGFR-Expressing Tumors," *Int. J. Cancer* 75:310-316, Wiley-Liss, Inc., United States (1998).
Qian, J.F., et al., "Human transforming growth factor alpha: sequence analysis of the 4.5k-b mRNA species," *Gene* 132:291-296, Elsevier Science Publishers B.V., Netherlands (1993).
Schneider, M.R. and Wolf, E., "The Epidermal Growth Factor Receptor Ligands at a Glance," *J. Cell Physiol.* 218:460-466, Wiley-Liss, Inc., United States (2008).
Seth, D., et al., "Complex post-transciptional regulation of EGF-receptor expression by EGF and TGF-α in human prostate cancer cells, " *Br. J. Cancer* 80(5/6):657-669, Cancer Research Campaign, England (1999).
Tejpar, S., et al., "Magnesium wasting associated with epidermal-growth-factor receptor-targeting antibodies in colorectal cancer: a prospective study," *Lancet Oncol.* 8:387-394, Lancet Publishing Group, England (2007).
Tiel Groenestege, W.M., et al., "Impaired basolateral sorting of pro-EGF causes isolated recessive renal hypomagnesemia," *J. Clin. Invest.* 117(8):2260-2267, American Society for Clinical Investigation, United States (2007).
Willmarth, N. E., and Ethier S.P., "Autocrine and Juxtacrine Effects of Amphiregulin on the Proliferative, Invasive, and Migratory Properties of Normal and Neoplastic Human Mammary Epithelial Cells," *J. Biol. Chem.* 281(49):37728-37737, The American Society for Biochemistry and Molecular Biology, (2006).
Wilson, K.J., et al., "Functional selectivity of EGF family peptide growth factors: Implications for cancer," *Pharmacol. Ther.122*(1):1-8, Elsevier B.V., Netherlands (2009).
Unverified English language translation of WO 2008/047723 A1, published Jun. 24, 2008.
Nicholson, B.E. et al., "Profiling the Evolution of Human Metastic Bladder Cancer," *Cancer Res.* 64:7813-7821, American Association for Cancer Research, United States (2004).
Kurachi, H. et al., "Improtance of Transforming Growth Factor α/Epidermal Growth Factor Receptor Autocrine Growth Mechanism

(56) References Cited

OTHER PUBLICATIONS in an Ovarian Cancer Cell Line in Vivo," *Cancer Res. 51*:5956-5959, American Association American Association.

Zhang, J. et al., "Intratumoral Epiregulin is a Marker of Advanced Disease in Non-Small Cell Lung Cancer Patients and Confers Invasive Properties on EGFR-Mutant Cells," *Cancer Prev. Res. 1*(3,) American Association for Cancer Research, United States (2008)

Office Action mailed Jul. 11, 2013, in co-pending U.S. Appl. No. 13/375,050, § 371(c) Date: Feb. 13, 2012, U.S. and Trademark Office, Alexandria, VA.

Normanno, N. et al., "Target-based agents against ErbB receptors and their ligands: a novel approach to cancer treatment," *Endocrine-Related Cancer 10*:1-21, Society for Endorcrinology, United Kingdom (2003).

Sato, K., et al., "Solution structure of epiregulin and the effect of its C-terminal domain for receptor binding affinity," *FEBS Letters 553*:232-238, Elsevier Science B.V., Netherlands (2003).

Tamura, M. et al., "Structural Correlates of an Anticarcinoma Antibody: Identification of Specificity-Determining Residues (SDRs) and Development of a Minimally Immunogenic Antibody Variant by Retention of SDRs Only," *J. Immunol. 164*:1432-1441, The American Association of Immunologists (2000).

Kairemo, K.J.A., "Positron Emission Tomography of Monoclonal Antibodies," *Acta Oncol. 32*:825-830, Informa Healthcare, London (1993).

NCBI GenBank Accession No. AAX36706, Hines, L., et al., 2005 Entry Date Mar. 16, 2005.

NCBI GenBank Accession No. AAE61510, Cassady-Cain, R.L. Entry Date May 2, 2006 and Kaushik, A.K., Entry Date May 2, 2006.

NCBI GenBank Accession No. AAR90995, Liang, Z., et al., Entry Date Mar. 15, 2004.

Bugelski, P.J., et al., "Preclinical development of keliximab, a Primatized anti-CD4 monocolonal antibody, in human CD4 transgenic mice: characterization of the model and safety studies," *Human & Experiemental Toxicology*, 19:230-243, Nature America, Inc., United States (2000).

Database NCBI on STN, Accession No. NP_001423, "epiregulin [*Homo sapiens*]," Entry Date Apr. 22, 2005.

Nautiyal, J. et al., "Targeting EGFRs and SRC signaling with a modified ectodomain of human EGFR (EBIP) and dasatinib in breast cancer," *Cancer Research* 69(2) Suppl 1:3069, American Association for Cancer Research, United States (2009) (Abstract #3069).

Sandusky, G.E., et al., "Use of Monoclonal Antibodies to Human Lymphocytes to Identify Lymphocyte Subsets in Lymph Nodes of the Rhesus Monkey and the Dog," *J. Med. Primatol* 15:441-451, Alan R. Liss, Inc., United States (1986).

Schlereth, B., et al., "T-cell activation and B-cell depletion in chimpanzees treated with a bispecific anti-CD19/anti CD3 single-chain antibody construct," *Cancer Immunol Immunother* 55:503-514, Springer-Verlag, Germany (2005).

Uda, A., et al., "CD3 polymorphism in cynomolgus monkeys (*Macaca fascicularis*)," *J. Med. Primatol*, 30:141-147, Munksgaard, Copenhagen, Denmark (2001).

International Search Report for International Patent Application No. PCT/JP2007/069988, mailed on Nov. 20, 2007 Japanese Patent Office, Japan.

International Preliminary Report on Patentability of the International Searching Authority for International Application No. PCT/JP2007/069988, issued on Apr. 22, 2009, The International Bureau of WIPO, Switzerland.

International Preliminary Report on Patentability of the International Searching Authority for International Application No. PCT/JP2010/059008, issued on Dec. 12, 2011, The International Bureau of WIPO, Switzerland (Not a Corresponding Application).

International Search Report for International Application No. PCT/JP2010/059008, Japanese Patent Office, mailed Jul. 6, 2010 (Not a Corresponding Application).

International Search Report for International Patent No. PCT/JP2012/084042, mailed on Feb. 5, 2013, Japanese Patent Office, Japan (Not a Corresponding Application).

Supplementary European Search Report in European Patent Application No. 07 82 9724, completed on Jul. 14, 2010, European Patent Office, Germany.

\* cited by examiner

COLON CANCER (PRIMARY)    NON-CANCEROUS PART

ANTI-EREG CHIMERIC ANTIBODY DETECTED

| | | EP03 | | | | EP08 | | | |
|---|---|---|---|---|---|---|---|---|---|
| Antigenic protein captured by mouse anti-EREG antibody — EREG(63-108) | EP26 | -0.001 | 0.001 | -0.001 | -0.002 | 0.002 | 0.001 | 0.001 | -0.004 |
| | EP30 | 0.002 | 0.004 | 0.001 | -0.002 | -0.007 | 0.001 | -0.006 | -0.006 |
| | EP29 | 0.010 | 0.007 | -0.001 | -0.002 | 0.001 | 0.006 | 0.005 | 0.000 |
| | EP33 | 0.012 | 0.011 | 0.005 | 0.005 | 0.009 | 0.010 | 0.010 | 0.004 |
| | EP18 | 0.007 | 0.010 | 0.007 | 0.008 | 0.007 | 0.004 | 0.002 | 0.000 |
| | EP31 | -0.007 | 0.005 | 0.003 | -0.001 | 0.005 | 0.010 | 0.007 | 0.001 |
| | EP04 | 0.022 | 0.018 | 0.008 | 0.006 | 0.019 | 0.012 | 0.007 | 0.001 |
| | EP09 | 0.009 | 0.012 | 0.005 | 0.003 | 0.013 | 0.012 | 0.008 | 0.001 |
| | EP22 | 0.001 | 0.002 | 0.000 | 0.000 | 0.000 | 0.000 | 0.001 | -0.003 |
| | EP32 | 0.004 | 0.006 | 0.002 | 0.001 | 0.003 | 0.005 | 0.003 | 0.001 |
| | EP19 | -0.006 | -0.001 | -0.009 | -0.008 | 0.014 | 0.014 | 0.007 | -0.001 |
| | EP24 | -0.006 | 0.004 | 0.000 | 0.002 | 0.002 | 0.003 | 0.005 | 0.003 |
| | EP06 | 0.012 | 0.015 | 0.007 | 0.006 | 0.012 | 0.014 | 0.010 | 0.005 |
| | EP10 | 0.019 | 0.018 | 0.004 | 0.002 | 0.017 | 0.008 | 0.008 | 0.001 |
| | EP14 | 0.007 | 0.009 | 0.009 | 0.007 | 0.008 | 0.009 | 0.011 | 0.007 |
| | EP25 | -0.001 | 0.003 | -0.001 | 0.000 | 0.004 | 0.004 | 0.004 | 0.003 |
| | EP15 | 0.164 | 0.085 | 0.035 | 0.020 | 0.016 | 0.008 | 0.007 | 0.003 |
| | EP08 | 0.014 | 0.019 | 0.010 | 0.007 | 0.012 | 0.015 | 0.013 | 0.003 |
| | EP13 | 0.017 | 0.015 | 0.007 | 0.008 | 0.010 | 0.011 | 0.008 | 0.003 |
| | EP27 | 0.011 | 0.009 | 0.002 | 0.001 | 0.007 | 0.006 | 0.008 | 0.002 |
| | EP28 | -0.003 | 0.026 | -0.004 | -0.007 | 0.031 | -0.001 | -0.001 | -0.003 |
| | EP23 | 0.005 | 0.011 | 0.008 | 0.009 | 0.008 | 0.010 | 0.006 | 0.003 |
| | EP05 | 0.009 | 0.007 | -0.001 | -0.005 | 0.006 | 0.002 | -0.002 | -0.006 |
| | EP11 | 0.010 | 0.009 | 0.000 | 0.003 | 0.001 | 0.004 | 0.006 | 0.001 |
| | EP16 | 0.007 | 0.008 | 0.005 | 0.003 | 0.002 | 0.008 | 0.011 | 0.005 |
| | EP02 | 0.070 | 0.068 | 0.056 | 0.051 | 0.089 | 0.066 | 0.050 | 0.029 |
| | EP03 | -0.005 | -0.004 | -0.014 | -0.017 | -0.001 | -0.011 | 0.070 | 0.034 |
| | EP20 | 1.585 | 1.502 | 1.088 | 0.722 | 1.375 | 1.110 | 0.900 | 0.536 |
| | EP12 | 0.568 | 0.388 | 0.189 | 0.088 | -0.012 | -0.015 | -0.019 | -0.023 |
| | EP07 | 0.493 | 0.294 | 0.132 | 0.054 | 0.015 | 0.013 | 0.011 | 0.002 |
| | EP17 | 0.574 | 0.395 | 0.207 | 0.101 | 0.002 | 0.001 | -0.004 | -0.007 |
| EREG extracellular domain-Fc | EP26 | 0.007 | 0.007 | 0.007 | 0.008 | 0.005 | 0.005 | 0.004 | 0.005 |
| | EP30 | 0.012 | 0.005 | 0.001 | -0.003 | 0.005 | -0.005 | -0.002 | -0.006 |
| | EP29 | 0.002 | 0.004 | 0.004 | 0.010 | 0.038 | 0.035 | 0.029 | 0.011 |
| | EP33 | 0.004 | 0.007 | 0.006 | 0.007 | 0.053 | 0.048 | 0.045 | 0.025 |
| | EP18 | 0.005 | 0.009 | 0.008 | 0.006 | 0.001 | 0.002 | 0.002 | 0.001 |
| | EP31 | -0.002 | -0.003 | 0.000 | -0.002 | 0.005 | 0.009 | 0.011 | 0.005 |
| | EP04 | 0.006 | 0.008 | 0.007 | 0.009 | 0.001 | -0.003 | -0.001 | -0.001 |
| | EP09 | 0.006 | 0.007 | 0.007 | 0.004 | 0.005 | 0.003 | 0.003 | 0.001 |
| | EP22 | 0.003 | 0.000 | 0.004 | 0.004 | 0.000 | -0.003 | 0.000 | 0.000 |
| | EP32 | 0.000 | 0.000 | 0.004 | 0.002 | 0.000 | 0.001 | 0.003 | -0.001 |
| | EP19 | 0.010 | 0.016 | 0.017 | 0.018 | 0.015 | 0.017 | 0.017 | 0.013 |
| | EP24 | 0.014 | 0.007 | 0.009 | 0.003 | 0.001 | -0.001 | 0.002 | -0.003 |
| | EP06 | 0.014 | 0.013 | 0.012 | 0.007 | 0.012 | 0.011 | 0.008 | 0.004 |
| | EP10 | 0.031 | 0.033 | 0.014 | 0.014 | 0.004 | -0.001 | -0.003 | 0.001 |
| | EP14 | 0.025 | 0.024 | 0.020 | 0.008 | 0.010 | 0.007 | 0.009 | 0.004 |
| | EP25 | 0.061 | 0.021 | 0.022 | 0.008 | 0.016 | 0.010 | 0.007 | 0.000 |
| | EP15 | 0.613 | 0.596 | 0.498 | 0.329 | 0.006 | 0.007 | 0.009 | 0.010 |
| | EP08 | 0.460 | 0.415 | 0.300 | 0.142 | 0.010 | 0.013 | 0.013 | 0.007 |
| | EP13 | 0.377 | 0.364 | 0.288 | 0.167 | 0.006 | 0.002 | 0.003 | 0.002 |
| | EP27 | 0.004 | 0.004 | 0.007 | 0.002 | 0.006 | 0.001 | 0.000 | -0.002 |
| | EP28 | -0.003 | -0.010 | 0.002 | -0.002 | 0.002 | 0.004 | 0.005 | -0.005 |
| | EP23 | 0.003 | 0.005 | 0.006 | 0.005 | 0.003 | 0.003 | 0.006 | 0.004 |
| | EP05 | 0.088 | 0.069 | 0.046 | 0.022 | -0.001 | 0.002 | -0.001 | -0.004 |
| | EP11 | 0.080 | 0.075 | 0.057 | 0.033 | 0.001 | -0.001 | -0.001 | 0.000 |
| | EP16 | 0.086 | 0.064 | 0.039 | 0.023 | 0.008 | 0.005 | -0.002 | 0.001 |
| | EP02 | 0.017 | 0.020 | 0.015 | 0.016 | 0.015 | 0.006 | 0.001 | -0.005 |
| | EP03 | -0.011 | -0.014 | -0.012 | -0.012 | 0.196 | 0.134 | 0.097 | 0.001 |
| | EP20 | 0.919 | 0.849 | 0.647 | 0.391 | 0.268 | 0.223 | 0.163 | 0.087 |
| | EP12 | 0.839 | 0.833 | 0.681 | 0.418 | -0.011 | -0.013 | -0.013 | -0.015 |
| | EP07 | 0.992 | 0.949 | 0.718 | 0.422 | 0.012 | 0.016 | 0.011 | 0.009 |
| | EP17 | 1.012 | 1.009 | 0.873 | 0.556 | 0.005 | 0.008 | 0.014 | 0.027 |

FIG. 21-1

ANTI-EREG CHIMERIC ANTIBODY DETECTED

ANTIGENIC PROTEIN CAPTURED BY MOUSE ANTI-EREG ANTIBODY

EREG(63-108)

| | EP20 | | | | EP24 | | | |
|---|---|---|---|---|---|---|---|---|
| EP26 | 0.743 | 0.841 | 0.719 | 0.563 | 0.736 | 0.623 | 0.419 | 0.290 |
| EP30 | 0.564 | 0.610 | 0.642 | 0.496 | 0.764 | 0.660 | 0.588 | 0.424 |
| EP29 | -0.008 | -0.003 | 0.002 | -0.004 | 0.209 | 0.067 | 0.018 | -0.001 |
| EP33 | 0.000 | 0.003 | 0.001 | 0.002 | 0.210 | 0.073 | 0.022 | 0.003 |
| EP18 | 0.001 | -0.001 | -0.002 | -0.005 | 0.196 | 0.061 | 0.021 | 0.001 |
| EP31 | 0.001 | 0.004 | 0.001 | -0.003 | 0.197 | 0.063 | 0.022 | 0.009 |
| EP04 | 0.023 | 0.009 | 0.004 | 0.000 | 0.374 | 0.124 | 0.031 | 0.001 |
| EP09 | 0.004 | 0.006 | 0.001 | -0.002 | 0.295 | 0.106 | 0.030 | 0.009 |
| EP22 | 0.000 | 0.000 | 0.001 | -0.002 | 0.270 | 0.105 | 0.054 | 0.032 |
| EP32 | -0.002 | 0.005 | 0.000 | -0.002 | 0.242 | 0.088 | 0.029 | 0.007 |
| EP19 | -0.008 | -0.004 | -0.006 | -0.009 | 0.240 | 0.066 | 0.007 | 0.000 |
| EP24 | -0.003 | 0.002 | 0.003 | 0.000 | 0.231 | 0.077 | 0.025 | 0.006 |
| EP06 | 0.044 | 0.068 | 0.073 | 0.087 | 0.351 | 0.160 | 0.063 | 0.021 |
| EP10 | 0.029 | 0.020 | 0.017 | 0.013 | 0.326 | 0.134 | 0.056 | 0.020 |
| EP14 | 0.010 | 0.012 | 0.014 | 0.009 | 0.239 | 0.086 | 0.037 | 0.012 |
| EP25 | 0.000 | 0.006 | 0.002 | 0.000 | 0.266 | 0.092 | 0.035 | 0.011 |
| EP15 | 0.005 | 0.000 | 0.001 | -0.004 | 0.259 | 0.085 | 0.022 | 0.000 |
| EP08 | 0.096 | 0.115 | 0.105 | 0.079 | 0.269 | 0.101 | 0.032 | 0.004 |
| EP13 | 0.087 | 0.111 | 0.173 | 0.166 | 0.232 | 0.084 | 0.091 | 0.036 |
| EP27 | 0.385 | 0.474 | 0.391 | 0.311 | 0.506 | 0.332 | 0.197 | 0.075 |
| EP28 | 0.351 | 0.433 | 0.470 | 0.371 | 0.482 | 0.325 | 0.220 | 0.114 |
| EP23 | 0.047 | 0.072 | 0.056 | 0.040 | 0.782 | 0.575 | 0.463 | 0.300 |
| EP05 | 0.156 | 0.169 | 0.163 | 0.147 | 0.443 | 0.193 | 0.090 | 0.035 |
| EP11 | 0.109 | 0.118 | 0.087 | 0.067 | 0.302 | 0.125 | 0.047 | 0.014 |
| EP16 | 0.024 | 0.033 | 0.039 | 0.037 | 0.267 | 0.117 | 0.056 | 0.024 |
| EP02 | 0.338 | 0.357 | 0.329 | 0.238 | 0.378 | 0.164 | 0.066 | 0.018 |
| EP03 | 0.082 | 0.128 | 0.138 | 0.116 | 0.291 | 0.081 | 0.019 | -0.014 |
| EP20 | -0.033 | -0.026 | 0.036 | -0.030 | 0.206 | 0.039 | 0.004 | 0.010 |
| EP12 | -0.021 | -0.022 | 0.036 | -0.024 | 0.219 | 0.050 | 0.018 | 0.004 |
| EP07 | 0.006 | 0.003 | 0.008 | 0.029 | 0.274 | 0.080 | 0.017 | 0.024 |
| EP17 | -0.008 | -0.006 | -0.011 | -0.013 | 0.220 | 0.062 | 0.016 | -0.013 |

EREG EXTRACELLULAR DOMAIN-Fc

| | EP20 | | | | EP24 | | | |
|---|---|---|---|---|---|---|---|---|
| EP26 | 0.575 | 0.567 | 0.440 | 0.312 | 0.602 | 0.510 | 0.386 | 0.248 |
| EP30 | 0.605 | 0.559 | 0.513 | 0.329 | 0.680 | 0.605 | 0.546 | 0.363 |
| EP29 | -0.002 | -0.005 | -0.001 | -0.001 | 0.190 | 0.074 | 0.028 | 0.013 |
| EP33 | 0.000 | -0.003 | -0.003 | 0.000 | 0.174 | 0.070 | 0.016 | 0.011 |
| EP18 | -0.005 | -0.005 | -0.004 | -0.002 | 0.179 | 0.057 | 0.013 | 0.003 |
| EP31 | 0.003 | -0.003 | -0.003 | 0.000 | 0.173 | 0.058 | 0.023 | 0.018 |
| EP04 | 0.003 | -0.004 | -0.003 | -0.005 | 0.269 | 0.094 | 0.033 | 0.005 |
| EP09 | 0.009 | 0.005 | 0.004 | 0.000 | 0.253 | 0.093 | 0.035 | 0.007 |
| EP22 | -0.002 | -0.002 | -0.001 | -0.001 | 0.201 | 0.072 | 0.025 | 0.010 |
| EP32 | -0.002 | -0.002 | -0.002 | 0.000 | 0.222 | 0.079 | 0.026 | 0.012 |
| EP19 | 0.016 | 0.015 | 0.016 | 0.012 | 0.318 | 0.139 | 0.060 | 0.028 |
| EP24 | -0.002 | -0.003 | -0.001 | -0.002 | 0.214 | 0.073 | 0.026 | 0.011 |
| EP06 | 0.072 | 0.047 | 0.019 | 0.006 | 0.344 | 0.147 | 0.053 | 0.015 |
| EP10 | 0.126 | 0.085 | 0.034 | 0.015 | 0.363 | 0.172 | 0.076 | 0.028 |
| EP14 | 0.056 | 0.035 | 0.021 | 0.007 | 0.232 | 0.093 | 0.043 | 0.013 |
| EP25 | 0.086 | 0.048 | 0.031 | 0.009 | 0.289 | 0.143 | 0.092 | 0.044 |
| EP15 | 0.000 | 0.001 | 0.005 | 0.010 | 0.259 | 0.098 | 0.038 | 0.019 |
| EP08 | 0.335 | 0.253 | 0.144 | 0.058 | 0.276 | 0.112 | 0.044 | 0.012 |
| EP13 | 0.274 | 0.214 | 0.141 | 0.064 | 0.287 | 0.098 | 0.036 | 0.015 |
| EP27 | 0.336 | 0.255 | 0.207 | 0.145 | 0.403 | 0.247 | 0.131 | 0.055 |
| EP28 | 0.345 | 0.355 | 0.251 | 0.156 | 0.406 | 0.290 | 0.156 | 0.075 |
| EP23 | 0.002 | 0.003 | 0.005 | 0.004 | 0.330 | 0.224 | 0.184 | 0.122 |
| EP05 | 0.259 | 0.182 | 0.103 | 0.034 | 0.418 | 0.231 | 0.120 | 0.036 |
| EP11 | 0.161 | 0.150 | 0.079 | 0.036 | 0.277 | 0.138 | 0.048 | -0.003 |
| EP16 | 0.199 | 0.138 | 0.082 | 0.040 | 0.335 | 0.172 | 0.085 | 0.037 |
| EP02 | 0.095 | 0.035 | 0.009 | 0.005 | 0.253 | 0.088 | 0.028 | 0.002 |
| EP03 | 0.239 | 0.175 | 0.127 | 0.022 | 0.242 | 0.111 | 0.064 | -0.005 |
| EP20 | 0.053 | 0.034 | 0.000 | 0.006 | 0.315 | 0.172 | 0.056 | 0.030 |
| EP12 | -0.016 | 0.049 | -0.015 | -0.016 | 0.255 | 0.079 | 0.016 | -0.002 |
| EP07 | 0.029 | 0.090 | 0.003 | 0.004 | 0.309 | 0.151 | 0.037 | 0.015 |
| EP17 | -0.002 | 0.001 | 0.004 | 0.012 | 0.262 | 0.107 | 0.040 | 0.023 |

FIG. 21-2

ANTI-EREG CHIMERIC ANTIBODY DETECTED

ANTIGENIC PROTEIN CAPTURED BY MOUSE ANTI-EREG ANTIBODY

EREG(63-108)

| | EP27 | | | | EP29 | | | |
|---|---|---|---|---|---|---|---|---|
| EP26 | -0.002 | -0.001 | -0.005 | -0.007 | 0.001 | 0.006 | -0.001 | -0.008 |
| EP30 | -0.002 | -0.004 | -0.010 | -0.013 | 0.013 | 0.010 | -0.005 | -0.012 |
| EP29 | -0.005 | 0.001 | -0.003 | -0.011 | -0.010 | -0.001 | -0.005 | -0.013 |
| EP33 | 0.000 | 0.001 | 0.001 | -0.003 | -0.003 | 0.003 | -0.001 | -0.008 |
| EP18 | -0.002 | -0.005 | -0.003 | -0.008 | -0.001 | -0.008 | -0.003 | -0.010 |
| EP31 | 0.000 | 0.011 | 0.013 | 0.001 | -0.004 | 0.000 | 0.008 | 0.003 |
| EP04 | 0.005 | -0.006 | -0.015 | -0.016 | 0.005 | -0.001 | -0.012 | -0.016 |
| EP09 | -0.005 | 0.001 | -0.001 | -0.002 | -0.010 | 0.001 | -0.005 | -0.005 |
| EP22 | 0.006 | 0.005 | 0.004 | 0.001 | -0.001 | -0.002 | 0.000 | -0.005 |
| EP32 | -0.006 | -0.002 | 0.002 | -0.003 | -0.002 | -0.003 | -0.001 | -0.004 |
| EP19 | 0.104 | 0.117 | 0.090 | 0.034 | -0.007 | 0.001 | 0.001 | -0.004 |
| EP24 | 0.105 | 0.193 | 0.187 | 0.086 | -0.007 | -0.004 | 0.002 | -0.005 |
| EP06 | -0.004 | 0.005 | -0.002 | -0.005 | -0.004 | 0.005 | -0.002 | -0.009 |
| EP10 | 0.007 | 0.004 | -0.002 | -0.007 | 0.004 | -0.001 | 0.004 | -0.008 |
| EP14 | -0.006 | -0.006 | -0.006 | -0.004 | -0.008 | -0.005 | -0.007 | 0.127 |
| EP25 | -0.003 | 0.016 | 0.009 | 0.006 | -0.004 | 0.003 | 0.007 | 0.008 |
| EP15 | -0.004 | -0.002 | -0.012 | -0.011 | 0.012 | 0.006 | -0.010 | -0.014 |
| EP08 | -0.006 | -0.005 | -0.010 | -0.010 | -0.006 | -0.004 | -0.007 | -0.011 |
| EP13 | -0.008 | -0.009 | 0.018 | 0.014 | -0.010 | -0.009 | 0.031 | 0.036 |
| EP27 | -0.004 | -0.005 | 0.000 | 0.000 | -0.004 | 0.003 | 0.002 | -0.002 |
| EP28 | -0.004 | -0.005 | 0.018 | -0.007 | -0.004 | 0.001 | 0.002 | -0.009 |
| EP23 | -0.003 | -0.001 | -0.003 | -0.005 | 0.015 | 0.015 | 0.009 | -0.006 |
| EP05 | 0.002 | 0.001 | -0.005 | -0.006 | 0.003 | 0.002 | -0.007 | -0.009 |
| EP11 | -0.011 | -0.009 | -0.008 | -0.010 | -0.005 | -0.009 | -0.011 | -0.004 |
| EP16 | -0.004 | -0.001 | -0.002 | 0.000 | -0.007 | -0.002 | -0.002 | 0.001 |
| EP02 | 0.056 | 0.011 | 0.004 | -0.012 | 0.064 | 0.014 | -0.002 | -0.021 |
| EP03 | -0.016 | 0.036 | -0.020 | -0.033 | -0.020 | 0.036 | -0.022 | -0.037 |
| EP20 | 1.770 | 1.400 | 1.078 | 0.630 | -0.020 | -0.029 | -0.037 | 0.004 |
| EP12 | -0.019 | -0.025 | -0.004 | -0.010 | 0.095 | 0.049 | 0.064 | 0.003 |
| EP07 | -0.004 | -0.012 | -0.013 | 0.007 | 0.078 | 0.034 | 0.014 | 0.073 |
| EP17 | -0.013 | -0.016 | -0.016 | -0.025 | 0.061 | 0.026 | 0.002 | -0.022 |

EREG EXTRACELLULAR DOMAIN-Fc

| | EP27 | | | | EP29 | | | |
|---|---|---|---|---|---|---|---|---|
| EP26 | 0.005 | 0.003 | 0.002 | 0.003 | 0.537 | 0.501 | 0.404 | 0.287 |
| EP30 | 0.038 | 0.023 | 0.016 | 0.009 | 0.486 | 0.513 | 0.462 | 0.261 |
| EP29 | 0.021 | 0.028 | 0.032 | 0.014 | -0.006 | -0.005 | -0.002 | -0.006 |
| EP33 | 0.042 | 0.043 | 0.033 | 0.022 | -0.007 | -0.006 | -0.006 | -0.003 |
| EP18 | -0.009 | -0.010 | -0.010 | -0.006 | -0.012 | -0.008 | -0.009 | -0.006 |
| EP31 | 0.033 | 0.020 | 0.027 | 0.009 | 0.006 | -0.004 | -0.003 | 0.003 |
| EP04 | -0.015 | -0.014 | -0.010 | -0.012 | -0.020 | -0.012 | -0.008 | -0.008 |
| EP09 | -0.005 | -0.005 | 0.000 | -0.007 | -0.007 | -0.006 | -0.001 | -0.008 |
| EP22 | -0.006 | -0.004 | -0.004 | -0.001 | -0.002 | -0.002 | -0.003 | 0.001 |
| EP32 | -0.002 | -0.005 | -0.003 | -0.002 | -0.006 | -0.005 | -0.002 | -0.002 |
| EP19 | 0.049 | 0.034 | 0.031 | 0.018 | 0.008 | 0.011 | 0.013 | 0.012 |
| EP24 | 0.031 | 0.072 | 0.033 | 0.018 | -0.008 | -0.007 | -0.008 | -0.012 |
| EP06 | -0.002 | -0.002 | -0.002 | -0.004 | 0.042 | 0.027 | 0.014 | 0.006 |
| EP10 | -0.007 | -0.005 | -0.003 | -0.011 | 0.093 | 0.071 | 0.043 | 0.016 |
| EP14 | -0.006 | -0.003 | -0.002 | -0.004 | 0.058 | 0.027 | 0.016 | 0.005 |
| EP25 | 0.111 | 0.079 | 0.070 | 0.037 | 0.074 | 0.041 | 0.020 | -0.003 |
| EP15 | -0.009 | -0.009 | -0.005 | 0.008 | 0.539 | 0.514 | 0.473 | 0.319 |
| EP08 | -0.005 | -0.008 | 0.000 | -0.007 | 0.429 | 0.396 | 0.362 | 0.175 |
| EP13 | 0.038 | -0.008 | -0.008 | -0.002 | 0.415 | 0.348 | 0.313 | 0.189 |
| EP27 | 0.184 | 0.135 | 0.110 | 0.056 | 0.189 | 0.170 | 0.122 | 0.037 |
| EP28 | 0.194 | 0.219 | 0.162 | 0.061 | 0.183 | 0.215 | 0.187 | 0.060 |
| EP23 | -0.007 | -0.008 | -0.006 | -0.002 | 0.234 | 0.208 | 0.071 | 0.112 |
| EP05 | -0.001 | -0.005 | 0.004 | -0.008 | 0.263 | 0.209 | 0.164 | 0.056 |
| EP11 | -0.003 | -0.006 | -0.008 | -0.009 | 0.165 | 0.142 | 0.100 | 0.046 |
| EP16 | 0.003 | 0.000 | 0.002 | 0.001 | 0.199 | 0.161 | 0.109 | 0.046 |
| EP02 | -0.019 | -0.026 | -0.022 | -0.021 | -0.029 | -0.042 | -0.021 | -0.019 |
| EP03 | -0.024 | -0.016 | 0.013 | -0.026 | -0.022 | 0.009 | 0.015 | -0.030 |
| EP20 | 0.914 | 0.939 | 0.847 | 0.568 | 0.012 | 0.037 | 0.001 | 0.004 |
| EP12 | -0.007 | -0.026 | -0.016 | -0.019 | 0.773 | 0.701 | 0.658 | 0.433 |
| EP07 | 0.034 | 0.008 | -0.002 | -0.002 | 0.820 | 0.801 | 0.721 | 0.462 |
| EP17 | -0.015 | -0.013 | 0.002 | 0.006 | 0.771 | 0.785 | 0.730 | 0.533 |

FIG. 21-3

SEQUENCE LISTING

```
<160> NUMBER OF SEQ ID NOS: 152

<210> SEQ ID NO 1
<211> LENGTH: 15
<212> TYPE: DNA
<213> ORGANISM: Artificial
<220> FEATURE:
<223> OTHER INFORMATION: An artificially synthesized nucleotide sequence

<400> SEQUENCE: 1
gacacctata tacag                                                    15

<210> SEQ ID NO 2
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 2

Asp Thr Tyr Ile Gln
1               5

<210> SEQ ID NO 3
<211> LENGTH: 51
<212> TYPE: DNA
<213> ORGANISM: Artificial
<220> FEATURE:
<223> OTHER INFORMATION: An artificially synthesized nucleotide sequence

<400> SEQUENCE: 3
aggattgatc ctctgaatgg taatactaaa tatgtcccga agttccaggg c             51

<210> SEQ ID NO 4
<211> LENGTH: 17
<212> TYPE: PRT
<213> ORGANISM: Artificial
<220> FEATURE:
<223> OTHER INFORMATION: An artificially synthesized peptide sequence
```

-continued

<400> SEQUENCE: 4

Arg Ile Asp Pro Leu Asn Gly Asn Thr Lys Tyr Val Pro Lys Phe Gln
1               5                   10                  15

Gly

<210> SEQ ID NO 5
<211> LENGTH: 21
<212> TYPE: DNA
<213> ORGANISM: Artificial
<220> FEATURE:
<223> OTHER INFORMATION: An artificially synthesized nucleotide sequence

<400> SEQUENCE: 5
tctgggaccc tctttgactt c                                          21

<210> SEQ ID NO 6
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 6

Ser Gly Thr Leu Phe Asp Phe
1               5

<210> SEQ ID NO 7
<211> LENGTH: 1413
<212> TYPE: DNA
<213> ORGANISM: Mus musculus
<220> FEATURE:
<221> NAME/KEY: CDS
<222> LOCATION: (1)..(1413)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1413)
<220> FEATURE:
<221> NAME/KEY: V_region
<222> LOCATION: (58)..(405)
<220> FEATURE:
<221> NAME/KEY: C_region
<222> LOCATION: (406)..(1413)

<400> SEQUENCE: 7 atg aaa tgc agc tgg gtt atc ttc ttc ctg atg gca gtg gct aca ggg    48
Met Lys Cys Ser Trp Val Ile Phe Phe Leu Met Ala Val Ala Thr Gly
        -15                 -10                 -5 gtc aat tca gag gat cag ctg cag cag tct ggg gca gag ctt gtg aag    96
Val Asn Ser Glu Asp Gln Leu Gln Gln Ser Gly Ala Glu Leu Val Lys
    -1   1               5                   10 cca ggg gcc tca gtc aag ttg tcc tgc aca gct tct ggc ttc aac att   144
Pro Gly Ala Ser Val Lys Leu Ser Cys Thr Ala Ser Gly Phe Asn Ile
    15                  20                  25 aaa gac acc tat ata cag tgg gtg aag ctg agg cct gaa cag ggc ctg   192
Lys Asp Thr Tyr Ile Gln Trp Val Lys Leu Arg Pro Glu Gln Gly Leu
30                  35                  40                  45 gag tgg att gga agg att gat cct ctg aat ggt aat act aaa tat gtc   240
Glu Trp Ile Gly Arg Ile Asp Pro Leu Asn Gly Asn Thr Lys Tyr Val
                50                  55                  60 ccg aag ttc cag ggc aag gcc act ata aca gca gac aca tcc tcc aat   288
Pro Lys Phe Gln Gly Lys Ala Thr Ile Thr Ala Asp Thr Ser Ser Asn
            65                  70                  75

```
aca gcc tac ctg caa ctc agc agc ctg aca tct gag gac act gcc gtc      336
Thr Ala Tyr Leu Gln Leu Ser Ser Leu Thr Ser Glu Asp Thr Ala Val
        80                  85                  90 tat tac tgt gtt agg tct ggg acc ctc ttt gac ttc tgg ggc caa ggc      384
Tyr Tyr Cys Val Arg Ser Gly Thr Leu Phe Asp Phe Trp Gly Gln Gly
    95                  100                 105 acc act ctc aca gtc tcc tca gcc aaa aca aca ccc cca tca gtc tat      432
Thr Thr Leu Thr Val Ser Ser Ala Lys Thr Thr Pro Pro Ser Val Tyr
110             115                 120                 125 cca ctg gcc cct ggg tgt gga gat aca act ggt tcc tct gtg act ctg      480
Pro Leu Ala Pro Gly Cys Gly Asp Thr Thr Gly Ser Ser Val Thr Leu
                130                 135                 140 gga tgc ctg gtc aag ggc tac ttc cct gag tca gtg act gtg act tgg      528
Gly Cys Leu Val Lys Gly Tyr Phe Pro Glu Ser Val Thr Val Thr Trp
            145                 150                 155 aac tct gga tcc ctg tcc agc agt gtg cac acc ttc cca gct ctc ctg      576
Asn Ser Gly Ser Leu Ser Ser Ser Val His Thr Phe Pro Ala Leu Leu
        160                 165                 170 cag tct gga ctc tac act atg agc agc tca gtg act gtc ccc tcc agc      624
Gln Ser Gly Leu Tyr Thr Met Ser Ser Ser Val Thr Val Pro Ser Ser
    175                 180                 185 act tgg cca agt cag acc gtc acc tgc agc gtt gct cac cca gcc agc      672
Thr Trp Pro Ser Gln Thr Val Thr Cys Ser Val Ala His Pro Ala Ser
190                 195                 200                 205 agc acc acg gtg gac aaa aaa ctt gag ccc agc ggg ccc att tca aca      720
Ser Thr Thr Val Asp Lys Lys Leu Glu Pro Ser Gly Pro Ile Ser Thr
                210                 215                 220 atc aac ccc tgt cct cca tgc aag gag tgt cac aaa tgc cca gct cct      768
Ile Asn Pro Cys Pro Pro Cys Lys Glu Cys His Lys Cys Pro Ala Pro
            225                 230                 235 aac ctc gag ggt gga cca tcc gtc ttc atc ttc cct cca aat atc aag      816
Asn Leu Glu Gly Gly Pro Ser Val Phe Ile Phe Pro Pro Asn Ile Lys
        240                 245                 250 gat gta ctc atg atc tcc ctg aca ccc aag gtc acg tgt gtg gtg gtg      864
Asp Val Leu Met Ile Ser Leu Thr Pro Lys Val Thr Cys Val Val Val
    255                 260                 265 gat gtg agc gag gat gac cca gac gtc cgg atc agc tgg ttt gtg aac      912
Asp Val Ser Glu Asp Asp Pro Asp Val Arg Ile Ser Trp Phe Val Asn
270                 275                 280                 285 aac gtg gaa gta cac aca gct cag aca caa acc cat aga gag gat tac      960
Asn Val Glu Val His Thr Ala Gln Thr Gln Thr His Arg Glu Asp Tyr
                290                 295                 300 aac agt act atc cgg gtg gtc agt gcc ctc ccc atc cag cac cag gac     1008
Asn Ser Thr Ile Arg Val Val Ser Ala Leu Pro Ile Gln His Gln Asp
            305                 310                 315 tgg atg agt ggc aag gag ttc aaa tgc aag gtc aac aac aaa gac ctc     1056
Trp Met Ser Gly Lys Glu Phe Lys Cys Lys Val Asn Asn Lys Asp Leu
        320                 325                 330 cca tca ccc atc gag aga acc atc tca aaa att aaa ggg cta gtc aga     1104
Pro Ser Pro Ile Glu Arg Thr Ile Ser Lys Ile Lys Gly Leu Val Arg
    335                 340                 345 gct cca caa gta tac atc ttg ccg cca cca gca gag cag ttg tcc agg     1152
Ala Pro Gln Val Tyr Ile Leu Pro Pro Ala Glu Gln Leu Ser Arg
350                 355                 360                 365 aaa gat gtc agt ctc act tgc ctg gtc gtg ggc ttc aac cct gga gac     1200
Lys Asp Val Ser Leu Thr Cys Leu Val Val Gly Phe Asn Pro Gly Asp
                370                 375                 380
```

-continued

| | | | |
|---|---|---|---|
| atc agt gtg gag tgg acc agc aat ggg cat aca gag gag aac tac aag<br>Ile Ser Val Glu Trp Thr Ser Asn Gly His Thr Glu Glu Asn Tyr Lys<br>385 390 395 | | | 1248 |
| gac acc gca cca gtc cta gac tct gac ggt tct tac ttc ata tac agc<br>Asp Thr Ala Pro Val Leu Asp Ser Asp Gly Ser Tyr Phe Ile Tyr Ser<br>400 405 410 | | | 1296 |
| aag ctc gat ata aaa aca agc aag tgg gag aaa aca gat tcc ttc tca<br>Lys Leu Asp Ile Lys Thr Ser Lys Trp Glu Lys Thr Asp Ser Phe Ser<br>415 420 425 | | | 1344 |
| tgc aac gtg aga cac gag ggt ctg aaa aat tac tac ctg aag aag acc<br>Cys Asn Val Arg His Glu Gly Leu Lys Asn Tyr Tyr Leu Lys Lys Thr<br>430 435 440 445 | | | 1392 |
| atc tcc cgg tct ccg ggt aaa<br>Ile Ser Arg Ser Pro Gly Lys<br>450 | | | 1413 |

<210> SEQ ID NO 8
<211> LENGTH: 471
<212> TYPE: PRT
<213> ORGANISM: Mus musculus

<400> SEQUENCE: 8

Met Lys Cys Ser Trp Val Ile Phe Phe Leu Met Ala Val Ala Thr Gly
               -15                     -10                   -5

Val Asn Ser Glu Asp Gln Leu Gln Gln Ser Gly Ala Glu Leu Val Lys
 -1  1                 5                         10

Pro Gly Ala Ser Val Lys Leu Ser Cys Thr Ala Ser Gly Phe Asn Ile
      15                 20                 25

Lys Asp Thr Tyr Ile Gln Trp Val Lys Leu Arg Pro Glu Gln Gly Leu
30                    35                 40               45

Glu Trp Ile Gly Arg Ile Asp Pro Leu Asn Gly Asn Thr Lys Tyr Val
           50                 55                 60

Pro Lys Phe Gln Gly Lys Ala Thr Ile Thr Ala Asp Thr Ser Ser Asn
        65                   70                 75

Thr Ala Tyr Leu Gln Leu Ser Ser Leu Thr Ser Glu Asp Thr Ala Val
          80                 85                 90

Tyr Tyr Cys Val Arg Ser Gly Thr Leu Phe Asp Phe Trp Gly Gln Gly
95                  100                105

Thr Thr Leu Thr Val Ser Ser Ala Lys Thr Thr Pro Pro Ser Val Tyr
110                 115               120               125

Pro Leu Ala Pro Gly Cys Gly Asp Thr Thr Gly Ser Ser Val Thr Leu
           130                135               140

Gly Cys Leu Val Lys Gly Tyr Phe Pro Glu Ser Val Thr Val Thr Trp
        145                 150               155

Asn Ser Gly Ser Leu Ser Ser Ser Val His Thr Phe Pro Ala Leu Leu
           160                165               170

Gln Ser Gly Leu Tyr Thr Met Ser Ser Ser Val Thr Val Pro Ser Ser
        175                 180               185

Thr Trp Pro Ser Gln Thr Val Thr Cys Ser Val Ala His Pro Ala Ser
190                 195               200               205

Ser Thr Thr Val Asp Lys Lys Leu Glu Pro Ser Gly Pro Ile Ser Thr
           210                215               220

Ile Asn Pro Cys Pro Pro Cys Lys Glu Cys His Lys Cys Pro Ala Pro
        225                 230                 235

Asn Leu Glu Gly Gly Pro Ser Val Phe Ile Phe Pro Pro Asn Ile Lys
           240                245               250

```
Asp Val Leu Met Ile Ser Leu Thr Pro Lys Val Thr Cys Val Val Val
    255                 260                 265

Asp Val Ser Glu Asp Pro Asp Val Arg Ile Ser Trp Phe Val Asn
270                 275                 280                 285

Asn Val Glu Val His Thr Ala Gln Thr Gln Thr His Arg Glu Asp Tyr
                290                 295                 300

Asn Ser Thr Ile Arg Val Val Ser Ala Leu Pro Ile Gln His Gln Asp
                    305                 310                 315

Trp Met Ser Gly Lys Glu Phe Lys Cys Lys Val Asn Asn Lys Asp Leu
                320                 325                 330

Pro Ser Pro Ile Glu Arg Thr Ile Ser Lys Ile Lys Gly Leu Val Arg
335                 340                 345

Ala Pro Gln Val Tyr Ile Leu Pro Pro Ala Glu Gln Leu Ser Arg
350                 355                 360                 365

Lys Asp Val Ser Leu Thr Cys Leu Val Val Gly Phe Asn Pro Gly Asp
                370                 375                 380

Ile Ser Val Glu Trp Thr Ser Asn Gly His Thr Glu Glu Asn Tyr Lys
                385                 390                 395

Asp Thr Ala Pro Val Leu Asp Ser Asp Gly Ser Tyr Phe Ile Tyr Ser
                400                 405                 410

Lys Leu Asp Ile Lys Thr Ser Lys Trp Glu Lys Thr Asp Ser Phe Ser
415                 420                 425

Cys Asn Val Arg His Glu Gly Leu Lys Asn Tyr Tyr Leu Lys Lys Thr
430                 435                 440                 445

Ile Ser Arg Ser Pro Gly Lys
                450

<210> SEQ ID NO 9
<211> LENGTH: 1398
<212> TYPE: DNA
<213> ORGANISM: Homo sapiens
<220> FEATURE:
<221> NAME/KEY: CDS
<222> LOCATION: (1)..(1395)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1398)
<220> FEATURE:
<221> NAME/KEY: V_region
<222> LOCATION: (58)..(405)
<220> FEATURE:
<221> NAME/KEY: C_region
<222> LOCATION: (406)..(1398)

<400> SEQUENCE: 9 atg aaa tgc agc tgg gtt atc ttc ttc ctg atg gca gtg gct aca ggg      48
Met Lys Cys Ser Trp Val Ile Phe Phe Leu Met Ala Val Ala Thr Gly
            -15                 -10                  -5 gtc aat tca gag gat cag ctg cag cag tct ggg gca gag ctt gtg aag      96
Val Asn Ser Glu Asp Gln Leu Gln Gln Ser Gly Ala Glu Leu Val Lys
     -1   1               5                  10 cca ggg gcc tca gtc aag ttg tcc tgc aca gct tct ggc ttc aac att     144
Pro Gly Ala Ser Val Lys Leu Ser Cys Thr Ala Ser Gly Phe Asn Ile
        15                  20                  25 aaa gac acc tat ata cag tgg gtg aag ctg agg cct gaa cag ggc ctg     192
Lys Asp Thr Tyr Ile Gln Trp Val Lys Leu Arg Pro Glu Gln Gly Leu
 30                  35                  40                  45
```

| | | |
|---|---|---|
| gag tgg att gga agg att gat cct ctg aat ggt aat act aaa tat gtc<br>Glu Trp Ile Gly Arg Ile Asp Pro Leu Asn Gly Asn Thr Lys Tyr Val<br>                    50                       55                     60 | 240 |
| ccg aag ttc cag ggc aag gcc act ata aca gca gac aca tcc tcc aat<br>Pro Lys Phe Gln Gly Lys Ala Thr Ile Thr Ala Asp Thr Ser Ser Asn<br>               65                       70                     75 | 288 |
| aca gcc tac ctg caa ctc agc agc ctg aca tct gag gac act gcc gtc<br>Thr Ala Tyr Leu Gln Leu Ser Ser Leu Thr Ser Glu Asp Thr Ala Val<br>        80                       85                     90 | 336 |
| tat tac tgt gtt agg tct ggg acc ctc ttt gac ttc tgg ggc caa ggc<br>Tyr Tyr Cys Val Arg Ser Gly Thr Leu Phe Asp Phe Trp Gly Gln Gly<br> 95                      100                   105 | 384 |
| acc act ctc aca gtc tcc tca gct agc acc aag ggc cca tcg gtc ttc<br>Thr Thr Leu Thr Val Ser Ser Ala Ser Thr Lys Gly Pro Ser Val Phe<br>110                  115                   120                 125 | 432 |
| ccc ctg gca ccc tcc tcc aag agc acc tct ggg ggc aca gcg gcc ctg<br>Pro Leu Ala Pro Ser Ser Lys Ser Thr Ser Gly Gly Thr Ala Ala Leu<br>                    130                   135                 140 | 480 |
| ggc tgc ctg gtc aag gac tac ttc ccc gaa ccg gtg acg gtg tcg tgg<br>Gly Cys Leu Val Lys Asp Tyr Phe Pro Glu Pro Val Thr Val Ser Trp<br>             145                   150                   155 | 528 |
| aac tca ggc gcc ctg acc agc ggc gtg cac acc ttc ccg gct gtc cta<br>Asn Ser Gly Ala Leu Thr Ser Gly Val His Thr Phe Pro Ala Val Leu<br>160                  165                   170 | 576 |
| cag tcc tca gga ctc tac tcc ctc agc agc gtg gtg acc gtg ccc tcc<br>Gln Ser Ser Gly Leu Tyr Ser Leu Ser Ser Val Val Thr Val Pro Ser<br>             175                   180                   185 | 624 |
| agc agc ttg ggc acc cag acc tac atc tgc aac gtg aat cac aag ccc<br>Ser Ser Leu Gly Thr Gln Thr Tyr Ile Cys Asn Val Asn His Lys Pro<br>190                  195                   200                 205 | 672 |
| agc aac acc aag gtg gac aag aaa gtt gag ccc aaa tct tgt gac aaa<br>Ser Asn Thr Lys Val Asp Lys Lys Val Glu Pro Lys Ser Cys Asp Lys<br>                    210                   215                 220 | 720 |
| act cac aca tgc cca ccg tgc cca gca cct gaa ctc ctg ggg gga ccg<br>Thr His Thr Cys Pro Pro Cys Pro Ala Pro Glu Leu Leu Gly Gly Pro<br>             225                   230                   235 | 768 |
| tca gtc ttc ctc ttc ccc cca aaa ccc aag gac acc ctc atg atc tcc<br>Ser Val Phe Leu Phe Pro Pro Lys Pro Lys Asp Thr Leu Met Ile Ser<br>            240                   245                 250 | 816 |
| cgg acc cct gag gtc aca tgc gtg gtg gtg gac gtg agc cac gaa gac<br>Arg Thr Pro Glu Val Thr Cys Val Val Val Asp Val Ser His Glu Asp<br>255                  260                   265 | 864 |
| cct gag gtc aag ttc aac tgg tac gtg gac ggc gtg gag gtg cat aat<br>Pro Glu Val Lys Phe Asn Trp Tyr Val Asp Gly Val Glu Val His Asn<br>270                  275                   280                 285 | 912 |
| gcc aag aca aag ccg cgg gag gag cag tac aac agc acg tac cgt gtg<br>Ala Lys Thr Lys Pro Arg Glu Glu Gln Tyr Asn Ser Thr Tyr Arg Val<br>                    290                   295                 300 | 960 |
| gtc agc gtc ctc acc gtc ctg cac cag gac tgg ctg aat ggc aag gag<br>Val Ser Val Leu Thr Val Leu His Gln Asp Trp Leu Asn Gly Lys Glu<br>             305                   310                   315 | 1008 |
| tac aag tgc aag gtc tcc aac aaa gcc ctc cca gcc ccc atc gag aaa<br>Tyr Lys Cys Lys Val Ser Asn Lys Ala Leu Pro Ala Pro Ile Glu Lys<br>            320                   325                 330 | 1056 |
| acc atc tcc aaa gcc aaa ggg cag ccc cga gaa cca cag gtg tac acc<br>Thr Ile Ser Lys Ala Lys Gly Gln Pro Arg Glu Pro Gln Val Tyr Thr<br>335                  340                   345 | 1104 |
| ctg ccc cca tcc cgg gat gag ctg acc aag aac cag gtc agc ctg acc<br>Leu Pro Pro Ser Arg Asp Glu Leu Thr Lys Asn Gln Val Ser Leu Thr<br>350                  355                   360                 365 | 1152 |

```
tgc ctg gtc aaa ggc ttc tat ccc agc gac atc gcc gtg gag tgg gag      1200
Cys Leu Val Lys Gly Phe Tyr Pro Ser Asp Ile Ala Val Glu Trp Glu
            370                 375                 380 agc aat ggg cag ccg gag aac aac tac aag acc acg cct ccc gtg ctg      1248
Ser Asn Gly Gln Pro Glu Asn Asn Tyr Lys Thr Thr Pro Pro Val Leu
        385                 390                 395 gac tcc gac ggc tcc ttc ttc ctc tac agc aag ctc acc gtg gac aag      1296
Asp Ser Asp Gly Ser Phe Phe Leu Tyr Ser Lys Leu Thr Val Asp Lys
    400                 405                 410 agc agg tgg cag cag ggg aac gtc ttc tca tgc tcc gtg atg cat gag      1344
Ser Arg Trp Gln Gln Gly Asn Val Phe Ser Cys Ser Val Met His Glu
415                 420                 425 gct ctg cac aac cac tac acg cag aag agc ctc tcc ctg tct ccg ggt      1392
Ala Leu His Asn His Tyr Thr Gln Lys Ser Leu Ser Leu Ser Pro Gly
430                 435                 440                 445 aaa tga                                                              1398
Lys
```

<210> SEQ ID NO 10
<211> LENGTH: 465
<212> TYPE: PRT
<213> ORGANISM: Homo sapiens

<400> SEQUENCE: 10

```
Met Lys Cys Ser Trp Val Ile Phe Phe Leu Met Ala Val Ala Thr Gly
                -15                 -10                  -5

Val Asn Ser Glu Asp Gln Leu Gln Gln Ser Gly Ala Glu Leu Val Lys
         -1   1               5                  10

Pro Gly Ala Ser Val Lys Leu Ser Cys Thr Ala Ser Gly Phe Asn Ile
             15                  20                  25

Lys Asp Thr Tyr Ile Gln Trp Val Lys Leu Arg Pro Glu Gln Gly Leu
 30                  35                  40                  45

Glu Trp Ile Gly Arg Ile Asp Pro Leu Asn Gly Asn Thr Lys Tyr Val
                 50                  55                  60

Pro Lys Phe Gln Gly Lys Ala Thr Ile Thr Ala Asp Thr Ser Ser Asn
             65                  70                  75

Thr Ala Tyr Leu Gln Leu Ser Ser Leu Thr Ser Glu Asp Thr Ala Val
         80                  85                  90

Tyr Tyr Cys Val Arg Ser Gly Thr Leu Phe Asp Phe Trp Gly Gln Gly
     95                 100                 105

Thr Thr Leu Thr Val Ser Ser Ala Ser Thr Lys Gly Pro Ser Val Phe
110                 115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
            145                 150                 155

Asn Ser Gly Ala Leu Thr Ser Gly Val His Thr Phe Pro Ala Val Leu
        160                 165                 170

Gln Ser Ser Gly Leu Tyr Ser Leu Ser Val Val Thr Val Pro Ser
    175                 180                 185

Ser Ser Leu Gly Thr Gln Thr Tyr Ile Cys Asn Val Asn His Lys Pro
190                 195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
            225                 230                 235
```

```
Ser Val Phe Leu Phe Pro Pro Lys Pro Lys Asp Thr Leu Met Ile Ser
        240                 245                 250

Arg Thr Pro Glu Val Thr Cys Val Val Val Asp Val Ser His Glu Asp
    255                 260                 265

Pro Glu Val Lys Phe Asn Trp Tyr Val Asp Gly Val Glu Val His Asn
270                 275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
                305                 310                 315

Tyr Lys Cys Lys Val Ser Asn Lys Ala Leu Pro Ala Pro Ile Glu Lys
        320                 325                 330

Thr Ile Ser Lys Ala Lys Gly Gln Pro Arg Glu Pro Gln Val Tyr Thr
        335                 340                 345

Leu Pro Pro Ser Arg Asp Glu Leu Thr Lys Asn Gln Val Ser Leu Thr
350                 355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
            385                 390                 395

Asp Ser Asp Gly Ser Phe Phe Leu Tyr Ser Lys Leu Thr Val Asp Lys
        400                 405                 410

Ser Arg Trp Gln Gln Gly Asn Val Phe Ser Cys Ser Val Met His Glu
    415                 420                 425

Ala Leu His Asn His Tyr Thr Gln Lys Ser Leu Ser Leu Ser Pro Gly
430                 435                 440                 445

Lys

<210> SEQ ID NO 11
<211> LENGTH: 33
<212> TYPE: DNA
<213> ORGANISM: Artificial
<220> FEATURE:
<223> OTHER INFORMATION: An artificially synthesized nucleotide sequence

<400> SEQUENCE: 11
aaggcaagcc aagacattca caagtatata gct                                 33

<210> SEQ ID NO 12
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 12

Lys Ala Ser Gln Asp Ile His Lys Tyr Ile Ala
1               5                   10

<210> SEQ ID NO 13
<211> LENGTH: 21
<212> TYPE: DNA
<213> ORGANISM: Artificial
<220> FEATURE:
<223> OTHER INFORMATION: An artificially synthesized nucleotide sequence

<400> SEQUENCE: 13
tacacatcta cattacagcc a                                              21
```

<210> SEQ ID NO 14
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 14

Tyr Thr Ser Thr Leu Gln Pro
1               5

<210> SEQ ID NO 15
<211> LENGTH: 24
<212> TYPE: DNA
<213> ORGANISM: Artificial
<220> FEATURE:
<223> OTHER INFORMATION: An artificially synthesized nucleotide sequence

<400> SEQUENCE: 15
ctacagtatg ataatcttcg gacg                                          24

<210> SEQ ID NO 16
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 16

Leu Gln Tyr Asp Asn Leu Arg Thr
1               5

<210> SEQ ID NO 17
<211> LENGTH: 702
<212> TYPE: DNA
<213> ORGANISM: Mus musculus
<220> FEATURE:
<221> NAME/KEY: CDS
<222> LOCATION: (1)..(699)
<220> FEATURE:
<221> NAME/KEY: sig_peptide
<222> LOCATION: (1)..(60)
<220> FEATURE:
<221> NAME/KEY: mat_peptide
<222> LOCATION: (61)..(702)
<220> FEATURE:
<221> NAME/KEY: V_region
<222> LOCATION: (61)..(378)
<220> FEATURE:
<221> NAME/KEY: C_region
<222> LOCATION: (379)..(702)

<400> SEQUENCE: 17 atg aga ccg tct att cag ttc ctg ggg ctc ttg ttg ttc tgg ctt cat        48
Met Arg Pro Ser Ile Gln Phe Leu Gly Leu Leu Leu Phe Trp Leu His
            -20                 -15                 -10             -5 ggt gct cag tgt gac atc cag atg aca cag tct cca tcc tca ctg tct        96
Gly Ala Gln Cys Asp Ile Gln Met Thr Gln Ser Pro Ser Ser Leu Ser
                -1  1               5                  10 gca tct ctg gga ggc aaa gtc acc atc act tgc aag gca agc caa gac       144
Ala Ser Leu Gly Gly Lys Val Thr Ile Thr Cys Lys Ala Ser Gln Asp
            15                  20                  25 att cac aag tat ata gct tgg tac caa cac aag cct gga aaa ggt cct       192
Ile His Lys Tyr Ile Ala Trp Tyr Gln His Lys Pro Gly Lys Gly Pro
    30                  35                  40

| | | | | | | | | | | | | | | | |
|---|---|---|---|---|---|---|---|---|---|---|---|---|---|---|---|
| agg | ctg | ctc | ata | cag | tac | aca | tct | aca | tta | cag | cca | ggc | atc | cca | tca | 240 |
| Arg | Leu | Leu | Ile | Gln | Tyr | Thr | Ser | Thr | Leu | Gln | Pro | Gly | Ile | Pro | Ser | |
| 45 | | | | | 50 | | | | | 55 | | | | | 60 | |

| agg | ttc | agt | gga | agt | ggg | tct | ggg | aga | gat | tat | tcc | ttc | agc | atc | agc | 288 |
| Arg | Phe | Ser | Gly | Ser | Gly | Ser | Gly | Arg | Asp | Tyr | Ser | Phe | Ser | Ile | Ser | |
| | | | | 65 | | | | | 70 | | | | | 75 | | |

| aac | ctg | gag | cct | gaa | gat | att | gca | act | tat | tat | tgt | cta | cag | tat | gat | 336 |
| Asn | Leu | Glu | Pro | Glu | Asp | Ile | Ala | Thr | Tyr | Tyr | Cys | Leu | Gln | Tyr | Asp | |
| | 80 | | | | | 85 | | | | | 90 | | | | | |

| aat | ctt | cgg | acg | ttc | ggt | gga | ggc | acc | aag | ctg | gaa | atc | aaa | cgg | gct | 384 |
| Asn | Leu | Arg | Thr | Phe | Gly | Gly | Gly | Thr | Lys | Leu | Glu | Ile | Lys | Arg | Ala | |
| | 95 | | | | | 100 | | | | | 105 | | | | | |

| gat | gct | gca | cca | act | gta | tcc | atc | ttc | cca | cca | tcc | agt | gag | cag | tta | 432 |
| Asp | Ala | Ala | Pro | Thr | Val | Ser | Ile | Phe | Pro | Pro | Ser | Ser | Glu | Gln | Leu | |
| | 110 | | | | | 115 | | | | | 120 | | | | | |

| aca | tct | gga | ggt | gcc | tca | gtc | gtg | tgc | ttc | ttg | aac | aac | ttc | tac | ccc | 480 |
| Thr | Ser | Gly | Gly | Ala | Ser | Val | Val | Cys | Phe | Leu | Asn | Asn | Phe | Tyr | Pro | |
| 125 | | | | | 130 | | | | | 135 | | | | | 140 | |

| aaa | gac | atc | aat | gtc | aag | tgg | aag | att | gat | ggc | agt | gaa | cga | caa | aat | 528 |
| Lys | Asp | Ile | Asn | Val | Lys | Trp | Lys | Ile | Asp | Gly | Ser | Glu | Arg | Gln | Asn | |
| | | | | 145 | | | | | 150 | | | | | 155 | | |

| ggc | gtc | ctg | aac | agt | tgg | act | gat | cag | gac | agc | aaa | gac | agc | acc | tac | 576 |
| Gly | Val | Leu | Asn | Ser | Trp | Thr | Asp | Gln | Asp | Ser | Lys | Asp | Ser | Thr | Tyr | |
| | | | | 160 | | | | | 165 | | | | | 170 | | |

| agc | atg | agc | agc | acc | ctc | acg | ttg | acc | aag | gac | gag | tat | gaa | cga | cat | 624 |
| Ser | Met | Ser | Ser | Thr | Leu | Thr | Leu | Thr | Lys | Asp | Glu | Tyr | Glu | Arg | His | |
| | | | 175 | | | | | 180 | | | | | 185 | | | |

| aac | agc | tat | acc | tgt | gag | gcc | act | cac | aag | aca | tca | act | tca | ccc | att | 672 |
| Asn | Ser | Tyr | Thr | Cys | Glu | Ala | Thr | His | Lys | Thr | Ser | Thr | Ser | Pro | Ile | |
| | | 190 | | | | | 195 | | | | | 200 | | | | |

| gtc | aag | agc | ttc | aac | agg | aat | gag | tgt | tag | | | | | | | 702 |
| Val | Lys | Ser | Phe | Asn | Arg | Asn | Glu | Cys | | | | | | | | |
| 205 | | | | 210 | | | | | | | | | | | | |

<210> SEQ ID NO 18
<211> LENGTH: 233
<212> TYPE: PRT
<213> ORGANISM: Mus musculus

<400> SEQUENCE: 18

| | | | | | | | | | | |
|---|---|---|---|---|---|---|---|---|---|---|
| Met | Arg | Pro | Ser | Ile | Gln | Phe | Leu | Gly | Leu | Leu | Leu | Phe | Trp | Leu | His |
| | | | -20 | | | | | -15 | | | | | -10 | | -5 |

| Gly | Ala | Gln | Cys | Asp | Ile | Gln | Met | Thr | Gln | Ser | Pro | Ser | Ser | Leu | Ser |
| | | | -1 | 1 | | | | 5 | | | | | 10 | | |

| Ala | Ser | Leu | Gly | Gly | Lys | Val | Thr | Ile | Thr | Cys | Lys | Ala | Ser | Gln | Asp |
| | | | 15 | | | | | 20 | | | | | 25 | | |

| Ile | His | Lys | Tyr | Ile | Ala | Trp | Tyr | Gln | His | Lys | Pro | Gly | Lys | Gly | Pro |
| | | 30 | | | | | 35 | | | | | 40 | | | |

| Arg | Leu | Leu | Ile | Gln | Tyr | Thr | Ser | Thr | Leu | Gln | Pro | Gly | Ile | Pro | Ser |
| 45 | | | | | 50 | | | | | 55 | | | | | 60 |

| Arg | Phe | Ser | Gly | Ser | Gly | Ser | Gly | Arg | Asp | Tyr | Ser | Phe | Ser | Ile | Ser |
| | | | | 65 | | | | | 70 | | | | | 75 | |

| Asn | Leu | Glu | Pro | Glu | Asp | Ile | Ala | Thr | Tyr | Tyr | Cys | Leu | Gln | Tyr | Asp |
| | 80 | | | | | 85 | | | | | 90 | | | | |

| Asn | Leu | Arg | Thr | Phe | Gly | Gly | Gly | Thr | Lys | Leu | Glu | Ile | Lys | Arg | Ala |
| | 95 | | | | | 100 | | | | | 105 | | | | |

| Asp | Ala | Ala | Pro | Thr | Val | Ser | Ile | Phe | Pro | Pro | Ser | Ser | Glu | Gln | Leu |
| | 110 | | | | | 115 | | | | | 120 | | | | |

```
Thr Ser Gly Gly Ala Ser Val Val Cys Phe Leu Asn Asn Phe Tyr Pro
125                 130                 135                 140

Lys Asp Ile Asn Val Lys Trp Lys Ile Asp Gly Ser Glu Arg Gln Asn
            145                 150                 155

Gly Val Leu Asn Ser Trp Thr Asp Gln Asp Ser Lys Asp Ser Thr Tyr
            160                 165                 170

Ser Met Ser Ser Thr Leu Thr Leu Thr Lys Asp Glu Tyr Glu Arg His
        175                 180                 185

Asn Ser Tyr Thr Cys Glu Ala Thr His Lys Thr Ser Thr Ser Pro Ile
        190                 195                 200

Val Lys Ser Phe Asn Arg Asn Glu Cys
205                 210

<210> SEQ ID NO 19
<211> LENGTH: 702
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: sig_peptide
<222> LOCATION: (1)..(60)
<220> FEATURE:
<221> NAME/KEY: mat_peptide
<222> LOCATION: (61)..(702)
<220> FEATURE:
<221> NAME/KEY: V_region
<222> LOCATION: (61)..(378)
<220> FEATURE:
<221> NAME/KEY: C_region
<222> LOCATION: (379)..(702)

<400> SEQUENCE: 19 atg aga ccg tct att cag ttc ctg ggg ctc ttg ttg ttc tgg ctt cat      48
Met Arg Pro Ser Ile Gln Phe Leu Gly Leu Leu Leu Phe Trp Leu His
                -20                 -15                 -10         -5 ggt gct cag tgt gac atc cag atg aca cag tct cca tcc tca ctg tct      96
Gly Ala Gln Cys Asp Ile Gln Met Thr Gln Ser Pro Ser Ser Leu Ser
            -1   1               5                  10 gca tct ctg gga ggc aaa gtc acc atc act tgc aag gca agc caa gac     144
Ala Ser Leu Gly Gly Lys Val Thr Ile Thr Cys Lys Ala Ser Gln Asp
        15                  20                  25 att cac aag tat ata gct tgg tac caa cac aag cct gga aaa ggt cct     192
Ile His Lys Tyr Ile Ala Trp Tyr Gln His Lys Pro Gly Lys Gly Pro
    30                  35                  40 agg ctg ctc ata cag tac aca tct aca tta cag cca ggc atc cca tca     240
Arg Leu Leu Ile Gln Tyr Thr Ser Thr Leu Gln Pro Gly Ile Pro Ser
45                  50                  55                  60 agg ttc agt gga agt ggg tct ggg aga gat tat tcc ttc agc atc agc     288
Arg Phe Ser Gly Ser Gly Ser Gly Arg Asp Tyr Ser Phe Ser Ile Ser
                65                  70                  75 aac ctg gag cct gaa gat att gca act tat tat tgt cta cag tat gat     336
Asn Leu Glu Pro Glu Asp Ile Ala Thr Tyr Tyr Cys Leu Gln Tyr Asp
            80                  85                  90 aat ctt cgg acg ttc ggt gga ggc acc aag ctg gaa atc aaa cgt acg     384
Asn Leu Arg Thr Phe Gly Gly Gly Thr Lys Leu Glu Ile Lys Arg Thr
        95                 100                 105 gtg gct gca cca tct gtc ttc atc ttc ccg cca tct gat gag cag ttg     432
Val Ala Ala Pro Ser Val Phe Ile Phe Pro Pro Ser Asp Glu Gln Leu
    110                 115                 120
```

```
aaa tct gga act gcc tct gtt gtg tgc ctg ctg aat aac ttc tat ccc      480
Lys Ser Gly Thr Ala Ser Val Val Cys Leu Leu Asn Asn Phe Tyr Pro
125             130                 135                 140 aga gag gcc aaa gta cag tgg aag gtg gat aac gcc ctc caa tcg ggt      528
Arg Glu Ala Lys Val Gln Trp Lys Val Asp Asn Ala Leu Gln Ser Gly
            145                 150                 155 aac tcc cag gag agt gtc aca gag cag gac agc aag gac agc acc tac      576
Asn Ser Gln Glu Ser Val Thr Glu Gln Asp Ser Lys Asp Ser Thr Tyr
        160                 165                 170 agc ctc agc agc acc ctg acg ctg agc aaa gca gac tac gag aaa cac      624
Ser Leu Ser Ser Thr Leu Thr Leu Ser Lys Ala Asp Tyr Glu Lys His
    175                 180                 185 aaa gtc tac gcc tgc gaa gtc acc cat cag ggc ctg agc tcg ccc gtc      672
Lys Val Tyr Ala Cys Glu Val Thr His Gln Gly Leu Ser Ser Pro Val
190                 195                 200 aca aag agc ttc aac agg gga gag tgt tga                              702
Thr Lys Ser Phe Asn Arg Gly Glu Cys
205                 210

<210> SEQ ID NO 20
<211> LENGTH: 233
<212> TYPE: PRT
<213> ORGANISM: Homo sapiens

<400> SEQUENCE: 20

Met Arg Pro Ser Ile Gln Phe Leu Gly Leu Leu Leu Phe Trp Leu His
-20                 -15                 -10                 -5

Gly Ala Gln Cys Asp Ile Gln Met Thr Gln Ser Pro Ser Ser Leu Ser
            -1  1               5                   10

Ala Ser Leu Gly Gly Lys Val Thr Ile Thr Cys Lys Ala Ser Gln Asp
        15                  20                  25

Ile His Lys Tyr Ile Ala Trp Tyr Gln His Lys Pro Gly Lys Gly Pro
    30                  35                  40

Arg Leu Leu Ile Gln Tyr Thr Ser Thr Leu Gln Pro Gly Ile Pro Ser
45                  50                  55                  60

Arg Phe Ser Gly Ser Gly Ser Gly Arg Asp Tyr Ser Phe Ser Ile Ser
                65                  70                  75

Asn Leu Glu Pro Glu Asp Ile Ala Thr Tyr Tyr Cys Leu Gln Tyr Asp
            80                  85                  90

Asn Leu Arg Thr Phe Gly Gly Gly Thr Lys Leu Glu Ile Lys Arg Thr
        95                  100                 105

Val Ala Ala Pro Ser Val Phe Ile Phe Pro Pro Ser Asp Glu Gln Leu
    110                 115                 120

Lys Ser Gly Thr Ala Ser Val Val Cys Leu Leu Asn Asn Phe Tyr Pro
125             130                 135                 140

Arg Glu Ala Lys Val Gln Trp Lys Val Asp Asn Ala Leu Gln Ser Gly
            145                 150                 155

Asn Ser Gln Glu Ser Val Thr Glu Gln Asp Ser Lys Asp Ser Thr Tyr
        160                 165                 170

Ser Leu Ser Ser Thr Leu Thr Leu Ser Lys Ala Asp Tyr Glu Lys His
    175                 180                 185

Lys Val Tyr Ala Cys Glu Val Thr His Gln Gly Leu Ser Ser Pro Val
190                 195                 200

Thr Lys Ser Phe Asn Arg Gly Glu Cys
205                 210

<210> SEQ ID NO 21
```

<211> LENGTH: 510
<212> TYPE: DNA
<213> ORGANISM: Homo sapiens
<220> FEATURE:
<221> NAME/KEY: CDS
<222> LOCATION: (1)..(507)

<400> SEQUENCE: 21

```
atg acc gcg ggg agg agg atg gag atg ctc tgt gcc ggc agg gtc cct     48
Met Thr Ala Gly Arg Arg Met Glu Met Leu Cys Ala Gly Arg Val Pro
1               5                   10                  15 gcg ctg ctg ctc tgc ctg ggt ttc cat ctt cta cag gca gtc ctc agt     96
Ala Leu Leu Leu Cys Leu Gly Phe His Leu Leu Gln Ala Val Leu Ser
            20                  25                  30 aca act gtg att cca tca tgt atc cca gga gag tcc agt gat aac tgc    144
Thr Thr Val Ile Pro Ser Cys Ile Pro Gly Glu Ser Ser Asp Asn Cys
        35                  40                  45 aca gct tta gtt cag aca gaa gac aat cca cgt gtg gct caa gtg tca    192
Thr Ala Leu Val Gln Thr Glu Asp Asn Pro Arg Val Ala Gln Val Ser
    50                  55                  60 ata aca aag tgt agc tct gac atg aat ggc tat tgt ttg cat gga cag    240
Ile Thr Lys Cys Ser Ser Asp Met Asn Gly Tyr Cys Leu His Gly Gln
65                  70                  75                  80 tgc atc tat ctg gtg gac atg agt caa aac tac tgc agg tgt gaa gtg    288
Cys Ile Tyr Leu Val Asp Met Ser Gln Asn Tyr Cys Arg Cys Glu Val
                85                  90                  95 ggt tat act ggt gtc cga tgt gaa cac ttc ttt tta acc gtc cac caa    336
Gly Tyr Thr Gly Val Arg Cys Glu His Phe Phe Leu Thr Val His Gln
            100                 105                 110 cct tta agc aaa gag tat gtg gct ttg acc gtg att ctt att att ttg    384
Pro Leu Ser Lys Glu Tyr Val Ala Leu Thr Val Ile Leu Ile Ile Leu
        115                 120                 125 ttt ctt atc aca gtc gtc ggt tcc aca tat tat ttc tgc aga tgg tac    432
Phe Leu Ile Thr Val Val Gly Ser Thr Tyr Tyr Phe Cys Arg Trp Tyr
    130                 135                 140 aga aat cga aaa agt aaa gaa cca aag aag gaa tat gag aga gtt acc    480
Arg Asn Arg Lys Ser Lys Glu Pro Lys Lys Glu Tyr Glu Arg Val Thr
145                 150                 155                 160 tca ggg gat cca gag ttg ccg caa gtc tga                            510
Ser Gly Asp Pro Glu Leu Pro Gln Val
                165
```

<210> SEQ ID NO 22
<211> LENGTH: 169
<212> TYPE: PRT
<213> ORGANISM: Homo sapiens

<400> SEQUENCE: 22

```
Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
    50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95
```

```
Gly Tyr Thr Gly Val Arg Cys Glu His Phe Leu Thr Val His Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165

<210> SEQ ID NO 23
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 23

Gly Gly Gly Ser
1

<210> SEQ ID NO 24
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 24

Ser Gly Gly Gly
1

<210> SEQ ID NO 25
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 25

Gly Gly Gly Gly Ser
1               5

<210> SEQ ID NO 26
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 26

Ser Gly Gly Gly Gly
1               5

<210> SEQ ID NO 27
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 27

Gly Gly Gly Gly Gly Ser
1               5
```

```
<210> SEQ ID NO 28
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 28

Ser Gly Gly Gly Gly Gly
1               5

<210> SEQ ID NO 29
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 29

Gly Gly Gly Gly Gly Gly Ser
1               5

<210> SEQ ID NO 30
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 30

Ser Gly Gly Gly Gly Gly Gly
1               5

<210> SEQ ID NO 31
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 31

Gly Gly Gly Gly Ser
1               5

<210> SEQ ID NO 32
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 32

Ser Gly Gly Gly Gly
1               5

<210> SEQ ID NO 33
<211> LENGTH: 1038
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1035)

<400> SEQUENCE: 33
```

-continued

| | |
|---|---|
| atg gag atg ctc tgt gcc ggc agg gtc cct gcg ctg ctg ctc tgc ctg<br>Met Glu Met Leu Cys Ala Gly Arg Val Pro Ala Leu Leu Leu Cys Leu<br>1                    5                  10               15 | 48 |
| ggt ttc cat ctt cta cag gca gtc ctc agt aca act gtg att cca tca<br>Gly Phe His Leu Leu Gln Ala Val Leu Ser Thr Thr Val Ile Pro Ser<br>           20                    25                   30 | 96 |
| tgt atc cca gga gag tcc agt gat aac tgc aca gct tta gtt cag aca<br>Cys Ile Pro Gly Glu Ser Ser Asp Asn Cys Thr Ala Leu Val Gln Thr<br>        35                    40                   45 | 144 |
| gaa gac aat cca cgt gtg gct caa gtg tca ata aca aag tgt agc tct<br>Glu Asp Asn Pro Arg Val Ala Gln Val Ser Ile Thr Lys Cys Ser Ser<br>50                     55                    60 | 192 |
| gac atg aat ggc tat tgt ttg cat gga cag tgc atc tat ctg gtg gac<br>Asp Met Asn Gly Tyr Cys Leu His Gly Gln Cys Ile Tyr Leu Val Asp<br>65                     70                    75               80 | 240 |
| atg agt caa aac tac tgc agg tgt gaa gtg ggt tat act ggt gtc cga<br>Met Ser Gln Asn Tyr Cys Arg Cys Glu Val Gly Tyr Thr Gly Val Arg<br>                85                    90                   95 | 288 |
| tgt gaa cac ttc ttt tta acc gtc cac caa cct tta agc aaa gag tat<br>Cys Glu His Phe Phe Leu Thr Val His Gln Pro Leu Ser Lys Glu Tyr<br>               100                  105               110 | 336 |
| gtg gct cgc gga ccg aca atc aag ccc tgt cct cca tgc aaa tgc cca<br>Val Ala Arg Gly Pro Thr Ile Lys Pro Cys Pro Pro Cys Lys Cys Pro<br>         115                    120               125 | 384 |
| gca cct aac ctc ttg ggt gga cca tcc gtc ttc atc ttc cct cca aag<br>Ala Pro Asn Leu Leu Gly Gly Pro Ser Val Phe Ile Phe Pro Pro Lys<br>130                   135                  140 | 432 |
| atc aag gat gta ctc atg atc tcc ctg agc ccc ata gtc aca tgt gtg<br>Ile Lys Asp Val Leu Met Ile Ser Leu Ser Pro Ile Val Thr Cys Val<br>145                   150                  155               160 | 480 |
| gtg gtg gat gtg agc gag gat gac cca gat gtc cag atc agc tgg ttt<br>Val Val Asp Val Ser Glu Asp Asp Pro Asp Val Gln Ile Ser Trp Phe<br>               165                  170               175 | 528 |
| gtg aac aac gtg gaa gta cac aca gct cag aca caa acc cat aga gag<br>Val Asn Asn Val Glu Val His Thr Ala Gln Thr Gln Thr His Arg Glu<br>         180                    185               190 | 576 |
| gat tac aac agt act ctc cgg gtg gtc agt gcc ctc ccc atc cag cac<br>Asp Tyr Asn Ser Thr Leu Arg Val Val Ser Ala Leu Pro Ile Gln His<br>               195                  200               205 | 624 |
| cag gac tgg atg agt ggc aag gag ttc aaa tgc aag gtc aac aac aaa<br>Gln Asp Trp Met Ser Gly Lys Glu Phe Lys Cys Lys Val Asn Asn Lys<br>210                   215                  220 | 672 |
| gac ctc cca gcg ccc atc gag aga acc atc tca aaa ccc aaa ggg tca<br>Asp Leu Pro Ala Pro Ile Glu Arg Thr Ile Ser Lys Pro Lys Gly Ser<br>225                   230                  235               240 | 720 |
| gta aga gct cca cag gta tat gtc ttg cct cca cca gaa gaa gag atg<br>Val Arg Ala Pro Gln Val Tyr Val Leu Pro Pro Pro Glu Glu Glu Met<br>               245                  250               255 | 768 |
| act aag aaa cag gtc act ctg acc tgc atg gtc aca gac ttc atg cct<br>Thr Lys Lys Gln Val Thr Leu Thr Cys Met Val Thr Asp Phe Met Pro<br>         260                    265               270 | 816 |
| gaa gac att tac gtg gag tgg acc aac aac ggg aaa aca gag cta aac<br>Glu Asp Ile Tyr Val Glu Trp Thr Asn Asn Gly Lys Thr Glu Leu Asn<br>275                   280                  285 | 864 |
| tac aag aac act gaa cca gtc ctg gac tct gat ggt tct tac ttc atg<br>Tyr Lys Asn Thr Glu Pro Val Leu Asp Ser Asp Gly Ser Tyr Phe Met<br>         290                    295               300 | 912 |
| tac agc aag ctg aga gtg gaa aag aag aac tgg gtg gaa aga aat agc<br>Tyr Ser Lys Leu Arg Val Glu Lys Lys Asn Trp Val Glu Arg Asn Ser<br>305                   310                  315               320 | 960 |

```
tac tcc tgt tca gtg gtc cac gag ggt ctg cac aat cac cac acg act     1008
Tyr Ser Cys Ser Val Val His Glu Gly Leu His Asn His His Thr Thr
            325                 330                 335 aag agc ttc tcc cgg act ccg ggt aaa tga                              1038
Lys Ser Phe Ser Arg Thr Pro Gly Lys
            340                 345
```

<210> SEQ ID NO 34
<211> LENGTH: 345
<212> TYPE: PRT
<213> ORGANISM: Artificial
<220> FEATURE:
<223> OTHER INFORMATION: Synthetic Construct

<400> SEQUENCE: 34

```
Met Glu Met Leu Cys Ala Gly Arg Val Pro Ala Leu Leu Leu Cys Leu
1               5                   10                  15

Gly Phe His Leu Leu Gln Ala Val Leu Ser Thr Thr Val Ile Pro Ser
                20                  25                  30

Cys Ile Pro Gly Glu Ser Ser Asp Asn Cys Thr Ala Leu Val Gln Thr
            35                  40                  45

Glu Asp Asn Pro Arg Val Ala Gln Val Ser Ile Thr Lys Cys Ser Ser
        50                  55                  60

Asp Met Asn Gly Tyr Cys Leu His Gly Gln Cys Ile Tyr Leu Val Asp
65                  70                  75                  80

Met Ser Gln Asn Tyr Cys Arg Cys Glu Val Gly Tyr Thr Gly Val Arg
                85                  90                  95

Cys Glu His Phe Phe Leu Thr Val His Gln Pro Leu Ser Lys Glu Tyr
            100                 105                 110

Val Ala Arg Gly Pro Thr Ile Lys Pro Cys Pro Pro Cys Lys Cys Pro
        115                 120                 125

Ala Pro Asn Leu Leu Gly Gly Pro Ser Val Phe Ile Phe Pro Pro Lys
130                 135                 140

Ile Lys Asp Val Leu Met Ile Ser Leu Ser Pro Ile Val Thr Cys Val
145                 150                 155                 160

Val Val Asp Val Ser Glu Asp Pro Asp Val Gln Ile Ser Trp Phe
                165                 170                 175

Val Asn Asn Val Glu Val His Thr Ala Gln Thr Gln Thr His Arg Glu
            180                 185                 190

Asp Tyr Asn Ser Thr Leu Arg Val Val Ser Ala Leu Pro Ile Gln His
        195                 200                 205

Gln Asp Trp Met Ser Gly Lys Glu Phe Lys Cys Lys Val Asn Asn Lys
    210                 215                 220

Asp Leu Pro Ala Pro Ile Glu Arg Thr Ile Ser Lys Pro Lys Gly Ser
225                 230                 235                 240

Val Arg Ala Pro Gln Val Tyr Val Leu Pro Pro Glu Glu Glu Met
                245                 250                 255

Thr Lys Lys Gln Val Thr Leu Thr Cys Met Val Thr Asp Phe Met Pro
            260                 265                 270

Glu Asp Ile Tyr Val Glu Trp Thr Asn Asn Gly Lys Thr Glu Leu Asn
        275                 280                 285

Tyr Lys Asn Thr Glu Pro Val Leu Asp Ser Asp Gly Ser Tyr Phe Met
    290                 295                 300

Tyr Ser Lys Leu Arg Val Glu Lys Lys Asn Trp Val Glu Arg Asn Ser
305                 310                 315                 320
```

```
Tyr Ser Cys Ser Val His Glu Gly Leu His Asn His His Thr Thr
            325                 330                 335

Lys Ser Phe Ser Arg Thr Pro Gly Lys
            340                 345

<210> SEQ ID NO 35
<211> LENGTH: 3633
<212> TYPE: DNA
<213> ORGANISM: Homo sapiens
<220> FEATURE:
<221> NAME/KEY: CDS
<222> LOCATION: (1)..(3630)

<400> SEQUENCE: 35 atg cga ccc tcc ggg acg gcc ggg gca gcg ctc ctg gcg ctg ctg gct    48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa gtt tgc caa    96
Ala Leu Cys Pro Ala Ser Arg Ala Leu Glu Glu Lys Lys Val Cys Gln
                20                  25                  30 ggc acg agt aac aag ctc acg cag ttg ggc act ttt gaa gat cat ttt   144
Gly Thr Ser Asn Lys Leu Thr Gln Leu Gly Thr Phe Glu Asp His Phe
            35                  40                  45 ctc agc ctc cag agg atg ttc aat aac tgt gag gtg gtc ctt ggg aat   192
Leu Ser Leu Gln Arg Met Phe Asn Asn Cys Glu Val Val Leu Gly Asn
        50                  55                  60 ttg gaa att acc tat gtg cag agg aat tat gat ctt tcc ttc tta aag   240
Leu Glu Ile Thr Tyr Val Gln Arg Asn Tyr Asp Leu Ser Phe Leu Lys
65                  70                  75                  80 acc atc cag gag gtg gct ggt tat gtc ctc att gcc ctc aac aca gtg   288
Thr Ile Gln Glu Val Ala Gly Tyr Val Leu Ile Ala Leu Asn Thr Val
                85                  90                  95 gag cga att cct ttg gaa aac ctg cag atc atc aga gga aat atg tac   336
Glu Arg Ile Pro Leu Glu Asn Leu Gln Ile Ile Arg Gly Asn Met Tyr
            100                 105                 110 tac gaa aat tcc tat gcc tta gca gtc tta tct aac tat gat gca aat   384
Tyr Glu Asn Ser Tyr Ala Leu Ala Val Leu Ser Asn Tyr Asp Ala Asn
        115                 120                 125 aaa acc gga ctg aag gag ctg ccc atg aga aat tta cag gaa atc ctg   432
Lys Thr Gly Leu Lys Glu Leu Pro Met Arg Asn Leu Gln Glu Ile Leu
    130                 135                 140 cat ggc gcc gtg cgg ttc agc aac aac cct gcc ctg tgc aac gtg gag   480
His Gly Ala Val Arg Phe Ser Asn Asn Pro Ala Leu Cys Asn Val Glu
145                 150                 155                 160 agc atc cag tgg cgg gac ata gtc agc agt gac ttt ctc agc aac atg   528
Ser Ile Gln Trp Arg Asp Ile Val Ser Ser Asp Phe Leu Ser Asn Met
                165                 170                 175 tcg atg gac ttc cag aac cac ctg ggc agc tgc caa aag tgt gat cca   576
Ser Met Asp Phe Gln Asn His Leu Gly Ser Cys Gln Lys Cys Asp Pro
            180                 185                 190 agc tgt ccc aat ggg agc tgc tgg ggt gca gga gag gag aac tgc cag   624
Ser Cys Pro Asn Gly Ser Cys Trp Gly Ala Gly Glu Glu Asn Cys Gln
        195                 200                 205 aaa ctg acc aaa atc atc tgt gcc cag cag tgc tcc ggg cgc tgc cgt   672
Lys Leu Thr Lys Ile Ile Cys Ala Gln Gln Cys Ser Gly Arg Cys Arg
    210                 215                 220 ggc aag tcc ccc agt gac tgc tgc cac aac cag tgt gct gca ggc tgc   720
Gly Lys Ser Pro Ser Asp Cys Cys His Asn Gln Cys Ala Ala Gly Cys
225                 230                 235                 240
```

-continued

| | |
|---|---|
| aca ggc ccc cgg gag agc gac tgc ctg gtc tgc cgc aaa ttc cga gac<br>Thr Gly Pro Arg Glu Ser Asp Cys Leu Val Cys Arg Lys Phe Arg Asp<br>              245                      250                      255 | 768 |
| gaa gcc acg tgc aag gac acc tgc ccc cca ctc atg ctc tac aac ccc<br>Glu Ala Thr Cys Lys Asp Thr Cys Pro Pro Leu Met Leu Tyr Asn Pro<br>          260                      265                      270 | 816 |
| acc acg tac cag atg gat gtg aac ccc gag ggc aaa tac agc ttt ggt<br>Thr Thr Tyr Gln Met Asp Val Asn Pro Glu Gly Lys Tyr Ser Phe Gly<br>              275                      280                      285 | 864 |
| gcc acc tgc gtg aag aag tgt ccc cgt aat tat gtg gtg aca gat cac<br>Ala Thr Cys Val Lys Lys Cys Pro Arg Asn Tyr Val Val Thr Asp His<br>290                      295                      300 | 912 |
| ggc tcg tgc gtc cga gcc tgt ggg gcc gac agc tat gag atg gag gaa<br>Gly Ser Cys Val Arg Ala Cys Gly Ala Asp Ser Tyr Glu Met Glu Glu<br>305                      310                      315                      320 | 960 |
| gac ggc gtc cgc aag tgt aag aag tgc gaa ggg cct tgc cgc aaa gtg<br>Asp Gly Val Arg Lys Cys Lys Lys Cys Glu Gly Pro Cys Arg Lys Val<br>                      325                      330                      335 | 1008 |
| tgt aac gga ata ggt att ggt gaa ttt aaa gac tca ctc tcc ata aat<br>Cys Asn Gly Ile Gly Ile Gly Glu Phe Lys Asp Ser Leu Ser Ile Asn<br>              340                      345                      350 | 1056 |
| gct acg aat att aaa cac ttc aaa aac tgc acc tcc atc agt ggc gat<br>Ala Thr Asn Ile Lys His Phe Lys Asn Cys Thr Ser Ile Ser Gly Asp<br>              355                      360                      365 | 1104 |
| ctc cac atc ctg ccg gtg gca ttt agg ggt gac tcc ttc aca cat act<br>Leu His Ile Leu Pro Val Ala Phe Arg Gly Asp Ser Phe Thr His Thr<br>370                      375                      380 | 1152 |
| cct cct ctg gat cca cag gaa ctg gat att ctg aaa acc gta aag gaa<br>Pro Pro Leu Asp Pro Gln Glu Leu Asp Ile Leu Lys Thr Val Lys Glu<br>385                      390                      395                      400 | 1200 |
| atc aca ggg ttt ttg ctg att cag gct tgg cct gaa aac agg acg gac<br>Ile Thr Gly Phe Leu Leu Ile Gln Ala Trp Pro Glu Asn Arg Thr Asp<br>                      405                      410                      415 | 1248 |
| ctc cat gcc ttt gag aac cta gaa atc ata cgc ggc agg acc aag caa<br>Leu His Ala Phe Glu Asn Leu Glu Ile Ile Arg Gly Arg Thr Lys Gln<br>              420                      425                      430 | 1296 |
| cat ggt cag ttt tct ctt gca gtc gtc agc ctg aac ata aca tcc ttg<br>His Gly Gln Phe Ser Leu Ala Val Val Ser Leu Asn Ile Thr Ser Leu<br>              435                      440                      445 | 1344 |
| gga tta cgc tcc ctc aag gag ata agt gat gga gat gtg ata att tca<br>Gly Leu Arg Ser Leu Lys Glu Ile Ser Asp Gly Asp Val Ile Ile Ser<br>450                      455                      460 | 1392 |
| gga aac aaa aat ttg tgc tat gca aat aca ata aac tgg aaa aaa ctg<br>Gly Asn Lys Asn Leu Cys Tyr Ala Asn Thr Ile Asn Trp Lys Lys Leu<br>465                      470                      475                      480 | 1440 |
| ttt ggg acc tcc ggt cag aaa acc aaa att ata agc aac aga ggt gaa<br>Phe Gly Thr Ser Gly Gln Lys Thr Lys Ile Ile Ser Asn Arg Gly Glu<br>                      485                      490                      495 | 1488 |
| aac agc tgc aag gcc aca ggc cag gtc tgc cat gcc ttg tgc tcc ccc<br>Asn Ser Cys Lys Ala Thr Gly Gln Val Cys His Ala Leu Cys Ser Pro<br>          500                      505                      510 | 1536 |
| gag ggc tgc tgg ggc ccg gag ccc agg gac tgc gtc tct tgc cgg aat<br>Glu Gly Cys Trp Gly Pro Glu Pro Arg Asp Cys Val Ser Cys Arg Asn<br>              515                      520                      525 | 1584 |
| gtc agc cga ggc agg gaa tgc gtg gac aag tgc aac ctt ctg gag ggt<br>Val Ser Arg Gly Arg Glu Cys Val Asp Lys Cys Asn Leu Leu Glu Gly<br>          530                      535                      540 | 1632 |
| gag cca agg gag ttt gtg gag aac tct gag tgc ata cag tgc cac cca<br>Glu Pro Arg Glu Phe Val Glu Asn Ser Glu Cys Ile Gln Cys His Pro<br>545                      550                      555                      560 | 1680 |

```
gag tgc ctg cct cag gcc atg aac atc acc tgc aca gga cgg gga cca    1728
Glu Cys Leu Pro Gln Ala Met Asn Ile Thr Cys Thr Gly Arg Gly Pro
            565                 570                 575 gac aac tgt atc cag tgt gcc cac tac att gac ggc ccc cac tgc gtc    1776
Asp Asn Cys Ile Gln Cys Ala His Tyr Ile Asp Gly Pro His Cys Val
        580                 585                 590 aag acc tgc ccg gca gga gtc atg gga gaa aac aac acc ctg gtc tgg    1824
Lys Thr Cys Pro Ala Gly Val Met Gly Glu Asn Asn Thr Leu Val Trp
    595                 600                 605 aag tac gca gac gcc ggc cat gtg tgc cac ctg tgc cat cca aac tgc    1872
Lys Tyr Ala Asp Ala Gly His Val Cys His Leu Cys His Pro Asn Cys
610                 615                 620 acc tac gga tgc act ggg cca ggt ctt gaa ggc tgt cca acg aat ggg    1920
Thr Tyr Gly Cys Thr Gly Pro Gly Leu Glu Gly Cys Pro Thr Asn Gly
625                 630                 635                 640 cct aag atc ccg tcc atc gcc act ggg atg gtg ggg gcc ctc ctc ttg    1968
Pro Lys Ile Pro Ser Ile Ala Thr Gly Met Val Gly Ala Leu Leu Leu
            645                 650                 655 ctg ctg gtg gtg gcc ctg ggg atc ggc ctc ttc atg cga agg cgc cac    2016
Leu Leu Val Val Ala Leu Gly Ile Gly Leu Phe Met Arg Arg Arg His
        660                 665                 670 atc gtt cgg aag cgc acg ctg cgg agg ctg ctg cag gag agg gag ctt    2064
Ile Val Arg Lys Arg Thr Leu Arg Arg Leu Leu Gln Glu Arg Glu Leu
    675                 680                 685 gtg gag cct ctt aca ccc agt gga gaa gct ccc aac caa gct ctc ttg    2112
Val Glu Pro Leu Thr Pro Ser Gly Glu Ala Pro Asn Gln Ala Leu Leu
690                 695                 700 agg atc ttg aag gaa act gaa ttc aaa aag atc aaa gtg ctg ggc tcc    2160
Arg Ile Leu Lys Glu Thr Glu Phe Lys Lys Ile Lys Val Leu Gly Ser
705                 710                 715                 720 ggt gcg ttc ggc acg gtg tat aag gga ctc tgg atc cca gaa ggt gag    2208
Gly Ala Phe Gly Thr Val Tyr Lys Gly Leu Trp Ile Pro Glu Gly Glu
            725                 730                 735 aaa gtt aaa att ccc gtc gct atc aag gaa tta aga gaa gca aca tct    2256
Lys Val Lys Ile Pro Val Ala Ile Lys Glu Leu Arg Glu Ala Thr Ser
        740                 745                 750 ccg aaa gcc aac aag gaa atc ctc gat gaa gcc tac gtg atg gcc agc    2304
Pro Lys Ala Asn Lys Glu Ile Leu Asp Glu Ala Tyr Val Met Ala Ser
    755                 760                 765 gtg gac aac ccc cac gtg tgc cgc ctg ctg ggc atc tgc ctc acc tcc    2352
Val Asp Asn Pro His Val Cys Arg Leu Leu Gly Ile Cys Leu Thr Ser
770                 775                 780 acc gtg cag ctc atc acg cag ctc atg ccc ttc ggc tgc ctc ctg gac    2400
Thr Val Gln Leu Ile Thr Gln Leu Met Pro Phe Gly Cys Leu Leu Asp
785                 790                 795                 800 tat gtc cgg gaa cac aaa gac aat att ggc tcc cag tac ctg ctc aac    2448
Tyr Val Arg Glu His Lys Asp Asn Ile Gly Ser Gln Tyr Leu Leu Asn
            805                 810                 815 tgg tgt gtg cag atc gca aag ggc atg aac tac ttg gag gac cgt cgc    2496
Trp Cys Val Gln Ile Ala Lys Gly Met Asn Tyr Leu Glu Asp Arg Arg
        820                 825                 830 ttg gtg cac cgc gac ctg gca gcc agg aac gta ctg gtg aaa aca ccg    2544
Leu Val His Arg Asp Leu Ala Ala Arg Asn Val Leu Val Lys Thr Pro
    835                 840                 845 cag cat gtc aag atc aca gat ttt ggg ctg gcc aaa ctg ctg ggt gcg    2592
Gln His Val Lys Ile Thr Asp Phe Gly Leu Ala Lys Leu Leu Gly Ala
850                 855                 860
```

-continued

| | |
|---|---|
| gaa gag aaa gaa tac cat gca gaa gga ggc aaa gtg cct atc aag tgg<br>Glu Glu Lys Glu Tyr His Ala Glu Gly Gly Lys Val Pro Ile Lys Trp<br>865                   870                875                  880 | 2640 |
| atg gca ttg gaa tca att tta cac aga atc tat acc cac cag agt gat<br>Met Ala Leu Glu Ser Ile Leu His Arg Ile Tyr Thr His Gln Ser Asp<br>                         885                890                  895 | 2688 |
| gtc tgg agc tac ggg gtg acc gtt tgg gag ttg atg acc ttt gga tcc<br>Val Trp Ser Tyr Gly Val Thr Val Trp Glu Leu Met Thr Phe Gly Ser<br>           900                  905                910 | 2736 |
| aag cca tat gac gga atc cct gcc agc gag atc tcc tcc atc ctg gag<br>Lys Pro Tyr Asp Gly Ile Pro Ala Ser Glu Ile Ser Ser Ile Leu Glu<br>915                   920                925 | 2784 |
| aaa gga gaa cgc ctc cct cag cca ccc ata tgt acc atc gat gtc tac<br>Lys Gly Glu Arg Leu Pro Gln Pro Pro Ile Cys Thr Ile Asp Val Tyr<br>           930                  935                940 | 2832 |
| atg atc atg gtc aag tgc tgg atg ata gac gca gat agt cgc cca aag<br>Met Ile Met Val Lys Cys Trp Met Ile Asp Ala Asp Ser Arg Pro Lys<br>945                   950                955                  960 | 2880 |
| ttc cgt gag ttg atc atc gaa ttc tcc aaa atg gcc cga gac ccc cag<br>Phe Arg Glu Leu Ile Ile Glu Phe Ser Lys Met Ala Arg Asp Pro Gln<br>                         965                970                  975 | 2928 |
| cgc tac ctt gtc att cag ggg gat gaa aga atg cat ttg cca agt cct<br>Arg Tyr Leu Val Ile Gln Gly Asp Glu Arg Met His Leu Pro Ser Pro<br>           980                  985                990 | 2976 |
| aca gac tcc aac ttc tac cgt gcc ctg atg gat gaa gaa gac atg gac<br>Thr Asp Ser Asn Phe Tyr Arg Ala Leu Met Asp Glu Glu Asp Met Asp<br>                         995                1000              1005 | 3024 |
| gac gtg gtg gat gcc gac gag tac ctc atc cca cag cag ggc ttc<br>Asp Val Val Asp Ala Asp Glu Tyr Leu Ile Pro Gln Gln Gly Phe<br>          1010                1015              1020 | 3069 |
| ttc agc agc ccc tcc acg tca cgg act ccc ctc ctg agc tct ctg<br>Phe Ser Ser Pro Ser Thr Ser Arg Thr Pro Leu Leu Ser Ser Leu<br>1025                  1030              1035 | 3114 |
| agt gca acc agc aac aat tcc acc gtg gct tgc att gat aga aat<br>Ser Ala Thr Ser Asn Asn Ser Thr Val Ala Cys Ile Asp Arg Asn<br>          1040              1045              1050 | 3159 |
| ggg ctg caa agc tgt ccc atc aag gaa gac agc ttc ttg cag cga<br>Gly Leu Gln Ser Cys Pro Ile Lys Glu Asp Ser Phe Leu Gln Arg<br>1055                1060              1065 | 3204 |
| tac agc tca gac ccc aca ggc gcc ttg act gag gac agc ata gac<br>Tyr Ser Ser Asp Pro Thr Gly Ala Leu Thr Glu Asp Ser Ile Asp<br>          1070              1075              1080 | 3249 |
| gac acc ttc ctc cca gtg cct gaa tac ata aac cag tcc gtt ccc<br>Asp Thr Phe Leu Pro Val Pro Glu Tyr Ile Asn Gln Ser Val Pro<br>1085                1090              1095 | 3294 |
| aaa agg ccc gct ggc tct gtg cag aat cct gtc tat cac aat cag<br>Lys Arg Pro Ala Gly Ser Val Gln Asn Pro Val Tyr His Asn Gln<br>          1100              1105              1110 | 3339 |
| cct ctg aac ccc gcg ccc agc aga gac cca cac tac cag gac ccc<br>Pro Leu Asn Pro Ala Pro Ser Arg Asp Pro His Tyr Gln Asp Pro<br>1115                1120              1125 | 3384 |
| cac agc act gca gtg ggc aac ccc gag tat ctc aac act gtc cag<br>His Ser Thr Ala Val Gly Asn Pro Glu Tyr Leu Asn Thr Val Gln<br>          1130              1135              1140 | 3429 |
| ccc acc tgt gtc aac agc aca ttc gac agc cct gcc cac tgg gcc<br>Pro Thr Cys Val Asn Ser Thr Phe Asp Ser Pro Ala His Trp Ala<br>1145                1150              1155 | 3474 |
| cag aaa ggc agc cac caa att agc ctg gac aac cct gac tac cag<br>Gln Lys Gly Ser His Gln Ile Ser Leu Asp Asn Pro Asp Tyr Gln<br>          1160              1165              1170 | 3519 |

-continued

| cag | gac | ttc | ttt | ccc | aag | gaa | gcc | aag | cca | aat | ggc | atc | ttt | aag | 3564 |
| Gln | Asp | Phe | Phe | Pro | Lys | Glu | Ala | Lys | Pro | Asn | Gly | Ile | Phe | Lys | |
| | 1175 | | | | 1180 | | | | | 1185 | | | | | |

| ggc | tcc | aca | gct | gaa | aat | gca | gaa | tac | cta | agg | gtc | gcg | cca | caa | 3609 |
| Gly | Ser | Thr | Ala | Glu | Asn | Ala | Glu | Tyr | Leu | Arg | Val | Ala | Pro | Gln | |
| 1190 | | | | | 1195 | | | | | 1200 | | | | | |

| agc | agt | gaa | ttt | att | gga | gca | tga | | | | | | | | 3633 |
| Ser | Ser | Glu | Phe | Ile | Gly | Ala | | | | | | | | | |
| 1205 | | | | | 1210 | | | | | | | | | | |

<210> SEQ ID NO 36
<211> LENGTH: 1210
<212> TYPE: PRT
<213> ORGANISM: Homo sapiens

<400> SEQUENCE: 36

Met Arg Pro Ser Gly Thr Ala Gly Ala Ala Leu Leu Ala Leu Leu Ala
1               5                  10                 15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

```
Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720
```

```
Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125
```

| His | Ser | Thr | Ala | Val | Gly | Asn | Pro | Glu | Tyr | Leu | Asn | Thr | Val | Gln |
|---|---|---|---|---|---|---|---|---|---|---|---|---|---|---|
| | 1130 | | | | 1135 | | | | 1140 | | | | | |

| Pro | Thr | Cys | Val | Asn | Ser | Thr | Phe | Asp | Ser | Pro | Ala | His | Trp | Ala |
|---|---|---|---|---|---|---|---|---|---|---|---|---|---|---|
| 1145 | | | | | 1150 | | | | | 1155 | | | | |

| Gln | Lys | Gly | Ser | His | Gln | Ile | Ser | Leu | Asp | Asn | Pro | Asp | Tyr | Gln |
|---|---|---|---|---|---|---|---|---|---|---|---|---|---|---|
| | 1160 | | | | 1165 | | | | 1170 | | | | | |

| Gln | Asp | Phe | Phe | Pro | Lys | Glu | Ala | Lys | Pro | Asn | Gly | Ile | Phe | Lys |
|---|---|---|---|---|---|---|---|---|---|---|---|---|---|---|
| 1175 | | | | | 1180 | | | | | 1185 | | | | |

| Gly | Ser | Thr | Ala | Glu | Asn | Ala | Glu | Tyr | Leu | Arg | Val | Ala | Pro | Gln |
|---|---|---|---|---|---|---|---|---|---|---|---|---|---|---|
| | 1190 | | | | 1195 | | | | 1200 | | | | | |

| Ser | Ser | Glu | Phe | Ile | Gly | Ala |
|---|---|---|---|---|---|---|
| | 1205 | | | | 1210 | |

<210> SEQ ID NO 37
<211> LENGTH: 2514
<212> TYPE: DNA
<213> ORGANISM: Mus musculus
<220> FEATURE:
<221> NAME/KEY: CDS
<222> LOCATION: (1)..(2511)

<400> SEQUENCE: 37

```
atg gta ggg ctg gga gcc tgc acc ctg act gga gtt acc ctg atc ttc         48
Met Val Gly Leu Gly Ala Cys Thr Leu Thr Gly Val Thr Leu Ile Phe
1               5                   10                  15 ttg cta ctc ccc aga agt ctg gag agc tgt gga cac atc gag att tca         96
Leu Leu Leu Pro Arg Ser Leu Glu Ser Cys Gly His Ile Glu Ile Ser
                20                  25                  30 ccc cct gtt gtc cgc ctg ggg gac cct gtc ctg gcc tct tgc acc atc        144
Pro Pro Val Val Arg Leu Gly Asp Pro Val Leu Ala Ser Cys Thr Ile
            35                  40                  45 agc cca aac tgc agc aaa ctg gac caa cag gca aag atc tta tgg aga        192
Ser Pro Asn Cys Ser Lys Leu Asp Gln Gln Ala Lys Ile Leu Trp Arg
        50                  55                  60 ctg caa gat gag ccc atc caa cct ggg gac aga cag cat cat ctg cct        240
Leu Gln Asp Glu Pro Ile Gln Pro Gly Asp Arg Gln His His Leu Pro
65                  70                  75                  80 gat ggg acc caa gag tcc ctc atc act ctg cct cac ttg aac tac acc        288
Asp Gly Thr Gln Glu Ser Leu Ile Thr Leu Pro His Leu Asn Tyr Thr
                85                  90                  95 cag gcc ttc ctc ttc tgc tta gtg cca tgg gaa gac agc gtc caa ctc        336
Gln Ala Phe Leu Phe Cys Leu Val Pro Trp Glu Asp Ser Val Gln Leu
                100                 105                 110 ctg gat caa gct gag ctt cac gca ggc tat ccc cct gcc agc ccc tca        384
Leu Asp Gln Ala Glu Leu His Ala Gly Tyr Pro Pro Ala Ser Pro Ser
            115                 120                 125 aac cta tcc tgc ctc atg cac ctc acc acc aac agc ctg gtc tgc cag        432
Asn Leu Ser Cys Leu Met His Leu Thr Thr Asn Ser Leu Val Cys Gln
        130                 135                 140 tgg gag cca ggt cct gag acc cac ctg ccc acc agc ttc atc cta aag        480
Trp Glu Pro Gly Pro Glu Thr His Leu Pro Thr Ser Phe Ile Leu Lys
145                 150                 155                 160 agc ttc agg agc cgc gcc gac tgt cag tac caa ggg gac acc atc ccg        528
Ser Phe Arg Ser Arg Ala Asp Cys Gln Tyr Gln Gly Asp Thr Ile Pro
                165                 170                 175 gat tgt gtg gca aag aag agg cag aac aac tgc tcc atc ccc cga aaa        576
Asp Cys Val Ala Lys Lys Arg Gln Asn Asn Cys Ser Ile Pro Arg Lys
            180                 185                 190
```

-continued

| | | |
|---|---|---|
| aac ttg ctc ctg tac cag tat atg gcc atc tgg gtg caa gca gag aat<br>Asn Leu Leu Leu Tyr Gln Tyr Met Ala Ile Trp Val Gln Ala Glu Asn<br>195                    200                    205 | | 624 |
| atg cta ggg tcc agc gag tcc cca aag ctg tgc ctc gac ccc atg gat<br>Met Leu Gly Ser Ser Glu Ser Pro Lys Leu Cys Leu Asp Pro Met Asp<br>210                    215                    220 | | 672 |
| gtt gtg aaa ttg gag cct ccc atg ctg cag gcc ctg gac att ggc cct<br>Val Val Lys Leu Glu Pro Pro Met Leu Gln Ala Leu Asp Ile Gly Pro<br>225                    230                    235                    240 | | 720 |
| gat gta gtc tct cac cag cct ggc tgc ctg tgg ctg agc tgg aag cca<br>Asp Val Val Ser His Gln Pro Gly Cys Leu Trp Leu Ser Trp Lys Pro<br>                    245                    250                    255 | | 768 |
| tgg aag ccc agt gag tac atg gaa cag gag tgt gaa ctt cgc tac cag<br>Trp Lys Pro Ser Glu Tyr Met Glu Gln Glu Cys Glu Leu Arg Tyr Gln<br>260                    265                    270 | | 816 |
| cca cag ctc aaa gga gcc aac tgg act ctg gtg ttc cac ctg cct tcc<br>Pro Gln Leu Lys Gly Ala Asn Trp Thr Leu Val Phe His Leu Pro Ser<br>                    275                    280                    285 | | 864 |
| agc aag gac cag ttt gag ctc tgc ggg ctc cat cag gcc cca gtc tac<br>Ser Lys Asp Gln Phe Glu Leu Cys Gly Leu His Gln Ala Pro Val Tyr<br>290                    295                    300 | | 912 |
| acc cta cag atg cga tgc att cgc tca tct ctg cct gga ttc tgg agc<br>Thr Leu Gln Met Arg Cys Ile Arg Ser Ser Leu Pro Gly Phe Trp Ser<br>305                    310                    315                    320 | | 960 |
| ccc tgg agc ccc ggc ctg cag ctg agg cct acc atg aag gcc ccc acc<br>Pro Trp Ser Pro Gly Leu Gln Leu Arg Pro Thr Met Lys Ala Pro Thr<br>                    325                    330                    335 | | 1008 |
| atc aga ctg gac acg tgg tgt cag aag aag caa cta gat cca ggg aca<br>Ile Arg Leu Asp Thr Trp Cys Gln Lys Lys Gln Leu Asp Pro Gly Thr<br>340                    345                    350 | | 1056 |
| gtg agt gtg cag ctg ttc tgg aag cca acg ccc ctg cag gaa gac agt<br>Val Ser Val Gln Leu Phe Trp Lys Pro Thr Pro Leu Gln Glu Asp Ser<br>                    355                    360                    365 | | 1104 |
| gga cag atc cag ggc tac ctg ctg tcc tgg aat tcc cca gat cat caa<br>Gly Gln Ile Gln Gly Tyr Leu Leu Ser Trp Asn Ser Pro Asp His Gln<br>370                    375                    380 | | 1152 |
| ggg cag gac ata cac ctt tgc aac acc acg cag ctc agc tgt atc ttc<br>Gly Gln Asp Ile His Leu Cys Asn Thr Thr Gln Leu Ser Cys Ile Phe<br>385                    390                    395                    400 | | 1200 |
| ctc ctg ccc tca gag gcc cag aac gtg acc ctt gtg gcc tac aac aaa<br>Leu Leu Pro Ser Glu Ala Gln Asn Val Thr Leu Val Ala Tyr Asn Lys<br>                    405                    410                    415 | | 1248 |
| gca ggg acc tct tca cct act aca gtg gtt ttc ctg gag aac gaa ggt<br>Ala Gly Thr Ser Ser Pro Thr Thr Val Val Phe Leu Glu Asn Glu Gly<br>420                    425                    430 | | 1296 |
| cca gct gtg acc gga ctc cat gcc atg gcc caa gac ctt aac acc atc<br>Pro Ala Val Thr Gly Leu His Ala Met Ala Gln Asp Leu Asn Thr Ile<br>                    435                    440                    445 | | 1344 |
| tgg gta gac tgg gaa gcc ccc agc ctt ctg cct cag ggc tat ctc att<br>Trp Val Asp Trp Glu Ala Pro Ser Leu Leu Pro Gln Gly Tyr Leu Ile<br>450                    455                    460 | | 1392 |
| gag tgg gaa atg agt tct ccc agc tac aat aac agc tat aag tcc tgg<br>Glu Trp Glu Met Ser Ser Pro Ser Tyr Asn Asn Ser Tyr Lys Ser Trp<br>465                    470                    475                    480 | | 1440 |
| atg ata gaa cct aac ggg aac atc act gga att ctg tta aag gac aac<br>Met Ile Glu Pro Asn Gly Asn Ile Thr Gly Ile Leu Leu Lys Asp Asn<br>                    485                    490                    495 | | 1488 |
| ata aat ccc ttt cag ctc tac aga att aca gtg gct ccc ctg tac cca<br>Ile Asn Pro Phe Gln Leu Tyr Arg Ile Thr Val Ala Pro Leu Tyr Pro<br>500                    505                    510 | | 1536 |

```
ggc atc gtg gga ccc cct gta aat gtc tac acc ttc gct gga gag aga      1584
Gly Ile Val Gly Pro Pro Val Asn Val Tyr Thr Phe Ala Gly Glu Arg
            515                 520                 525 gct cct cct cat gct cca gcg ctg cat cta aag cat gtt ggc aca acc      1632
Ala Pro Pro His Ala Pro Ala Leu His Leu Lys His Val Gly Thr Thr
        530                 535                 540 tgg gca cag ctg gag tgg gta cct gag gcc cct agg ctg ggg atg ata      1680
Trp Ala Gln Leu Glu Trp Val Pro Glu Ala Pro Arg Leu Gly Met Ile
545                 550                 555                 560 ccc ctc acc cac tac acc atc ttc tgg gcc gat gct ggg gac cac tcc      1728
Pro Leu Thr His Tyr Thr Ile Phe Trp Ala Asp Ala Gly Asp His Ser
                565                 570                 575 ttc tcc gtc acc cta aac atc tcc ctc cat gac ttt gtc ctg aag cac      1776
Phe Ser Val Thr Leu Asn Ile Ser Leu His Asp Phe Val Leu Lys His
            580                 585                 590 ctg gag ccc gcc agt ttg tat cat gtc tac ctc atg gcc acc agt cga      1824
Leu Glu Pro Ala Ser Leu Tyr His Val Tyr Leu Met Ala Thr Ser Arg
        595                 600                 605 gca ggg tcc acc aat agt aca ggc ctt acc ctg agg acc cta gat cca      1872
Ala Gly Ser Thr Asn Ser Thr Gly Leu Thr Leu Arg Thr Leu Asp Pro
    610                 615                 620 tct gac tta aac att ttc ctg ggc ata ctt tgc tta gta ctc ttg tcc      1920
Ser Asp Leu Asn Ile Phe Leu Gly Ile Leu Cys Leu Val Leu Leu Ser
625                 630                 635                 640 act acc tgt gta gtg acc tgg ctc tgc tgc aaa cgc aga gga aag act      1968
Thr Thr Cys Val Val Thr Trp Leu Cys Cys Lys Arg Arg Gly Lys Thr
                645                 650                 655 tcc ttc tgg tca gat gtg cca gac cca gcc cac agt agc ctg agc tcc      2016
Ser Phe Trp Ser Asp Val Pro Asp Pro Ala His Ser Ser Leu Ser Ser
            660                 665                 670 tgg ttg ccc acc atc atg aca gag gaa acc ttc cag tta ccc agc ttc      2064
Trp Leu Pro Thr Ile Met Thr Glu Glu Thr Phe Gln Leu Pro Ser Phe
        675                 680                 685 tgg gac tcc agc gtg cca tca atc acc aag atc act gaa ctg gag gaa      2112
Trp Asp Ser Ser Val Pro Ser Ile Thr Lys Ile Thr Glu Leu Glu Glu
    690                 695                 700 gac aag aaa ccg acc cac tgg gat tcc gaa agc tct ggg aat ggt agc      2160
Asp Lys Lys Pro Thr His Trp Asp Ser Glu Ser Ser Gly Asn Gly Ser
705                 710                 715                 720 ctt cca gcc ctg gtt cag gcc tat gtg ctc caa gga gat cca aga gaa      2208
Leu Pro Ala Leu Val Gln Ala Tyr Val Leu Gln Gly Asp Pro Arg Glu
                725                 730                 735 att tcc aac cag tcc cag cct ccc tct cgc act ggt gac cag gtc ctc      2256
Ile Ser Asn Gln Ser Gln Pro Pro Ser Arg Thr Gly Asp Gln Val Leu
            740                 745                 750 tat ggt cag gtg ctt gag agc ccc acc agc cca gga gta atg cag tac      2304
Tyr Gly Gln Val Leu Glu Ser Pro Thr Ser Pro Gly Val Met Gln Tyr
        755                 760                 765 att cgc tct gac tcc act cag ccc ctc ttg ggg ggc ccc acc cct agc      2352
Ile Arg Ser Asp Ser Thr Gln Pro Leu Leu Gly Gly Pro Thr Pro Ser
    770                 775                 780 cct aaa tct tat gaa aac atc tgg ttc cat tca aga ccc cag gag acc      2400
Pro Lys Ser Tyr Glu Asn Ile Trp Phe His Ser Arg Pro Gln Glu Thr
785                 790                 795                 800 ttt gtg ccc caa cct cca aac cag gaa gat gac tgt gtc ttt ggg cct      2448
Phe Val Pro Gln Pro Pro Asn Gln Glu Asp Asp Cys Val Phe Gly Pro
                805                 810                 815
```

```
cca ttt gat ttt ccc ctc ttt cag ggg ctc cag gtc cat gga gtt gaa         2496
Pro Phe Asp Phe Pro Leu Phe Gln Gly Leu Gln Val His Gly Val Glu
            820                 825                 830 gaa caa ggg ggt ttc tag                                                 2514
Glu Gln Gly Gly Phe
835
```

<210> SEQ ID NO 38
<211> LENGTH: 837
<212> TYPE: PRT
<213> ORGANISM: Mus musculus

<400> SEQUENCE: 38

```
Met Val Gly Leu Gly Ala Cys Thr Leu Thr Gly Val Thr Leu Ile Phe
1               5                   10                  15

Leu Leu Leu Pro Arg Ser Leu Glu Ser Cys Gly His Ile Glu Ile Ser
            20                  25                  30

Pro Pro Val Val Arg Leu Gly Asp Pro Val Leu Ala Ser Cys Thr Ile
        35                  40                  45

Ser Pro Asn Cys Ser Lys Leu Asp Gln Gln Ala Lys Ile Leu Trp Arg
    50                  55                  60

Leu Gln Asp Glu Pro Ile Gln Pro Gly Asp Arg Gln His His Leu Pro
65                  70                  75                  80

Asp Gly Thr Gln Glu Ser Leu Ile Thr Leu Pro His Leu Asn Tyr Thr
                85                  90                  95

Gln Ala Phe Leu Phe Cys Leu Val Pro Trp Glu Asp Ser Val Gln Leu
            100                 105                 110

Leu Asp Gln Ala Glu Leu His Ala Gly Tyr Pro Pro Ala Ser Pro Ser
        115                 120                 125

Asn Leu Ser Cys Leu Met His Leu Thr Thr Asn Ser Leu Val Cys Gln
    130                 135                 140

Trp Glu Pro Gly Pro Glu Thr His Leu Pro Thr Ser Phe Ile Leu Lys
145                 150                 155                 160

Ser Phe Arg Ser Arg Ala Asp Cys Gln Tyr Gln Gly Asp Thr Ile Pro
                165                 170                 175

Asp Cys Val Ala Lys Lys Arg Gln Asn Asn Cys Ser Ile Pro Arg Lys
            180                 185                 190

Asn Leu Leu Leu Tyr Gln Tyr Met Ala Ile Trp Val Gln Ala Glu Asn
        195                 200                 205

Met Leu Gly Ser Ser Glu Ser Pro Lys Leu Cys Leu Asp Pro Met Asp
    210                 215                 220

Val Val Lys Leu Glu Pro Pro Met Leu Gln Ala Leu Asp Ile Gly Pro
225                 230                 235                 240

Asp Val Val Ser His Gln Pro Gly Cys Leu Trp Leu Ser Trp Lys Pro
                245                 250                 255

Trp Lys Pro Ser Glu Tyr Met Glu Gln Glu Cys Glu Leu Arg Tyr Gln
            260                 265                 270

Pro Gln Leu Lys Gly Ala Asn Trp Thr Leu Val Phe His Leu Pro Ser
        275                 280                 285

Ser Lys Asp Gln Phe Glu Leu Cys Gly Leu His Gln Ala Pro Val Tyr
    290                 295                 300

Thr Leu Gln Met Arg Cys Ile Arg Ser Ser Leu Pro Gly Phe Trp Ser
305                 310                 315                 320

Pro Trp Ser Pro Gly Leu Gln Leu Arg Pro Thr Met Lys Ala Pro Thr
                325                 330                 335
```

```
Ile Arg Leu Asp Thr Trp Cys Gln Lys Lys Gln Leu Asp Pro Gly Thr
            340                 345                 350
Val Ser Val Gln Leu Phe Trp Lys Pro Thr Pro Leu Gln Glu Asp Ser
        355                 360                 365
Gly Gln Ile Gln Gly Tyr Leu Leu Ser Trp Asn Ser Pro Asp His Gln
    370                 375                 380
Gly Gln Asp Ile His Leu Cys Asn Thr Thr Gln Leu Ser Cys Ile Phe
385                 390                 395                 400
Leu Leu Pro Ser Glu Ala Gln Asn Val Thr Leu Val Ala Tyr Asn Lys
                405                 410                 415
Ala Gly Thr Ser Ser Pro Thr Thr Val Val Phe Leu Glu Asn Glu Gly
            420                 425                 430
Pro Ala Val Thr Gly Leu His Ala Met Ala Gln Asp Leu Asn Thr Ile
        435                 440                 445
Trp Val Asp Trp Glu Ala Pro Ser Leu Leu Pro Gln Gly Tyr Leu Ile
    450                 455                 460
Glu Trp Glu Met Ser Ser Pro Ser Tyr Asn Asn Ser Tyr Lys Ser Trp
465                 470                 475                 480
Met Ile Glu Pro Asn Gly Asn Ile Thr Gly Ile Leu Leu Lys Asp Asn
                485                 490                 495
Ile Asn Pro Phe Gln Leu Tyr Arg Ile Thr Val Ala Pro Leu Tyr Pro
            500                 505                 510
Gly Ile Val Gly Pro Pro Val Asn Val Tyr Thr Phe Ala Gly Glu Arg
        515                 520                 525
Ala Pro Pro His Ala Pro Ala Leu His Leu Lys His Val Gly Thr Thr
    530                 535                 540
Trp Ala Gln Leu Glu Trp Val Pro Glu Ala Pro Arg Leu Gly Met Ile
545                 550                 555                 560
Pro Leu Thr His Tyr Thr Ile Phe Trp Ala Asp Ala Gly Asp His Ser
                565                 570                 575
Phe Ser Val Thr Leu Asn Ile Ser Leu His Asp Phe Val Leu Lys His
            580                 585                 590
Leu Glu Pro Ala Ser Leu Tyr His Val Tyr Leu Met Ala Thr Ser Arg
        595                 600                 605
Ala Gly Ser Thr Asn Ser Thr Gly Leu Thr Leu Arg Thr Leu Asp Pro
    610                 615                 620
Ser Asp Leu Asn Ile Phe Leu Gly Ile Leu Cys Leu Val Leu Leu Ser
625                 630                 635                 640
Thr Thr Cys Val Val Thr Trp Leu Cys Cys Lys Arg Arg Gly Lys Thr
                645                 650                 655
Ser Phe Trp Ser Asp Val Pro Asp Pro Ala His Ser Ser Leu Ser Ser
            660                 665                 670
Trp Leu Pro Thr Ile Met Thr Glu Glu Thr Phe Gln Leu Pro Ser Phe
        675                 680                 685
Trp Asp Ser Ser Val Pro Ser Ile Thr Lys Ile Thr Glu Leu Glu Glu
    690                 695                 700
Asp Lys Lys Pro Thr His Trp Asp Ser Glu Ser Ser Gly Asn Gly Ser
705                 710                 715                 720
Leu Pro Ala Leu Val Gln Ala Tyr Val Leu Gln Gly Asp Pro Arg Glu
                725                 730                 735
Ile Ser Asn Gln Ser Gln Pro Pro Ser Arg Thr Gly Asp Gln Val Leu
            740                 745                 750
```

```
Tyr Gly Gln Val Leu Glu Ser Pro Thr Ser Pro Gly Val Met Gln Tyr
            755                 760                 765

Ile Arg Ser Asp Ser Thr Gln Pro Leu Leu Gly Gly Pro Thr Pro Ser
770                 775                 780

Pro Lys Ser Tyr Glu Asn Ile Trp Phe His Ser Arg Pro Gln Glu Thr
785                 790                 795                 800

Phe Val Pro Gln Pro Pro Asn Gln Glu Asp Asp Cys Val Phe Gly Pro
                805                 810                 815

Pro Phe Asp Pro Leu Phe Gln Gly Leu Gln Val His Gly Val Glu
            820                 825                 830

Glu Gln Gly Gly Phe
            835

<210> SEQ ID NO 39
<211> LENGTH: 2583
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(2580)

<400> SEQUENCE: 39 atg cga cct tcc ggg acg gcc ggg gca gcg ctc ctg gcg ctg ctg gct    48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa gtt tgc caa    96
Ala Leu Cys Pro Ala Ser Arg Ala Leu Glu Glu Lys Lys Val Cys Gln
                20                  25                  30 ggc acg agt aac aag ctc acg cag ttg ggc act ttt gaa gat cat ttt   144
Gly Thr Ser Asn Lys Leu Thr Gln Leu Gly Thr Phe Glu Asp His Phe
            35                  40                  45 ctc agc ctc cag agg atg ttc aat aac tgt gag gtg gtc ctt ggg aat   192
Leu Ser Leu Gln Arg Met Phe Asn Asn Cys Glu Val Val Leu Gly Asn
    50                  55                  60 ttg gaa att acc tat gtg cag agg aat tat gat ctt tcc ttc tta aag   240
Leu Glu Ile Thr Tyr Val Gln Arg Asn Tyr Asp Leu Ser Phe Leu Lys
65                  70                  75                  80 acc atc cag gag gtg gct ggt tat gtc ctc att gcc ctc aac aca gtg   288
Thr Ile Gln Glu Val Ala Gly Tyr Val Leu Ile Ala Leu Asn Thr Val
                85                  90                  95 gag cga att cct ttg gaa aac ctg cag atc atc aga gga aat atg tac   336
Glu Arg Ile Pro Leu Glu Asn Leu Gln Ile Ile Arg Gly Asn Met Tyr
                100                 105                 110 tac gaa aat tcc tat gcc tta gca gtc tta tct aac tat gat gca aat   384
Tyr Glu Asn Ser Tyr Ala Leu Ala Val Leu Ser Asn Tyr Asp Ala Asn
            115                 120                 125 aaa acc gga ctg aag gag ctg ccc atg aga aat tta cag gaa atc ctg   432
Lys Thr Gly Leu Lys Glu Leu Pro Met Arg Asn Leu Gln Glu Ile Leu
    130                 135                 140 cat ggc gcc gtg cgg ttc agc aac aac cct gcc ctg tgc aat gtg gag   480
His Gly Ala Val Arg Phe Ser Asn Asn Pro Ala Leu Cys Asn Val Glu
145                 150                 155                 160 agc atc cag tgg cgg gac ata gtc agc agt gac ttt ctc agc aac atg   528
Ser Ile Gln Trp Arg Asp Ile Val Ser Ser Asp Phe Leu Ser Asn Met
                165                 170                 175 tcg atg gac ttc cag aac cac ctg ggc agc tgc caa aag tgt gat cca   576
Ser Met Asp Phe Gln Asn His Leu Gly Ser Cys Gln Lys Cys Asp Pro
                180                 185                 190
```

| | |
|---|---|
| agc tgt ccc aat ggg agc tgc tgg ggt gca gga gag gag aac tgc cag<br>Ser Cys Pro Asn Gly Ser Cys Trp Gly Ala Gly Glu Glu Asn Cys Gln<br>     195                          200                   205 | 624 |
| aaa ctg acc aaa atc atc tgt gcc cag cag tgc tcc ggg cgc tgc cgt<br>Lys Leu Thr Lys Ile Ile Cys Ala Gln Gln Cys Ser Gly Arg Cys Arg<br>     210                          215                   220 | 672 |
| ggc aag tcc ccc agt gac tgc tgc cac aac cag tgt gct gca ggc tgc<br>Gly Lys Ser Pro Ser Asp Cys Cys His Asn Gln Cys Ala Ala Gly Cys<br>225                   230                   235                   240 | 720 |
| aca ggc ccc cgg gag agc gac tgc ctg gtc tgc cgc aaa ttc cga gac<br>Thr Gly Pro Arg Glu Ser Asp Cys Leu Val Cys Arg Lys Phe Arg Asp<br>                     245                   250                   255 | 768 |
| gaa gcc acg tgc aag gac acc tgc ccc cca ctc atg ctc tac aac ccc<br>Glu Ala Thr Cys Lys Asp Thr Cys Pro Pro Leu Met Leu Tyr Asn Pro<br>         260                          265                   270 | 816 |
| acc acg tac cag atg gat gtg aac ccc gag ggc aaa tac agc ttt ggt<br>Thr Thr Tyr Gln Met Asp Val Asn Pro Glu Gly Lys Tyr Ser Phe Gly<br>             275                   280                   285 | 864 |
| gcc acc tgc gtg aag aag tgt ccc cgt aat tat gtg gtg aca gat cac<br>Ala Thr Cys Val Lys Lys Cys Pro Arg Asn Tyr Val Val Thr Asp His<br>     290                          295                   300 | 912 |
| ggc tcg tgc gtc cga gcc tgt ggg gcc gac agc tat gag atg gag gaa<br>Gly Ser Cys Val Arg Ala Cys Gly Ala Asp Ser Tyr Glu Met Glu Glu<br>305                   310                   315                   320 | 960 |
| gac ggc gtc cgc aag tgt aag aag tgc gaa ggg cct tgc cgc aaa gtg<br>Asp Gly Val Arg Lys Cys Lys Lys Cys Glu Gly Pro Cys Arg Lys Val<br>                   325                   330                   335 | 1008 |
| tgt aac gga ata ggt att ggt gaa ttt aaa gac tca ctc tcc ata aat<br>Cys Asn Gly Ile Gly Ile Gly Glu Phe Lys Asp Ser Leu Ser Ile Asn<br>             340                   345                   350 | 1056 |
| gct acg aat att aaa cac ttc aaa aac tgc acc tcc atc agt ggc gat<br>Ala Thr Asn Ile Lys His Phe Lys Asn Cys Thr Ser Ile Ser Gly Asp<br>     355                          360                   365 | 1104 |
| ctc cac atc ctg ccg gtg gca ttt agg ggt gac tcc ttc aca cat act<br>Leu His Ile Leu Pro Val Ala Phe Arg Gly Asp Ser Phe Thr His Thr<br>370                   375                   380 | 1152 |
| cct cct ctg gat cca cag gaa ctg gat att ctg aaa acc gta aag gaa<br>Pro Pro Leu Asp Pro Gln Glu Leu Asp Ile Leu Lys Thr Val Lys Glu<br>385                   390                   395                   400 | 1200 |
| atc aca ggg ttt ttg ctg att cag gct tgg cct gaa aac agg acg gac<br>Ile Thr Gly Phe Leu Leu Ile Gln Ala Trp Pro Glu Asn Arg Thr Asp<br>                     405                   410                   415 | 1248 |
| ctc cat gcc ttt gag aac cta gaa atc ata cgc ggc agg acc aag caa<br>Leu His Ala Phe Glu Asn Leu Glu Ile Ile Arg Gly Arg Thr Lys Gln<br>         420                          425                   430 | 1296 |
| cat ggt cag ttt tct ctt gca gtc gtc agc ctg aac ata aca tcc ttg<br>His Gly Gln Phe Ser Leu Ala Val Val Ser Leu Asn Ile Thr Ser Leu<br>             435                   440                   445 | 1344 |
| gga tta cgc tcc ctc aag gag ata agt gat gga gat gtg ata att tca<br>Gly Leu Arg Ser Leu Lys Glu Ile Ser Asp Gly Asp Val Ile Ile Ser<br>     450                          455                   460 | 1392 |
| gga aac aaa aat ttg tgc tat gca aat aca ata aac tgg aaa aaa ctg<br>Gly Asn Lys Asn Leu Cys Tyr Ala Asn Thr Ile Asn Trp Lys Lys Leu<br>465                   470                   475                   480 | 1440 |
| ttt ggg acc tcc ggt cag aaa acc aaa att ata agc aac aga ggt gaa<br>Phe Gly Thr Ser Gly Gln Lys Thr Lys Ile Ile Ser Asn Arg Gly Glu<br>                     485                   490                   495 | 1488 |
| aac agc tgc aag gcc aca ggc cag gtc tgc cat gcc ttg tgc tcc ccc<br>Asn Ser Cys Lys Ala Thr Gly Gln Val Cys His Ala Leu Cys Ser Pro<br>         500                          505                   510 | 1536 |

```
gag ggc tgc tgg ggc ccg gag ccc agg gac tgc gtc tct tgc cgg aat    1584
Glu Gly Cys Trp Gly Pro Glu Pro Arg Asp Cys Val Ser Cys Arg Asn
            515                 520                 525 gtc agc cga ggc agg gaa tgc gtg gac aag tgc aac ctt ctg gag ggt    1632
Val Ser Arg Gly Arg Glu Cys Val Asp Lys Cys Asn Leu Leu Glu Gly
        530                 535                 540 gag cca agg gag ttt gtg gag aac tct gag tgc ata cag tgc cac cca    1680
Glu Pro Arg Glu Phe Val Glu Asn Ser Glu Cys Ile Gln Cys His Pro
545                 550                 555                 560 gag tgc ctg cct cag gcc atg aac atc acc tgc aca gga cgg gga cca    1728
Glu Cys Leu Pro Gln Ala Met Asn Ile Thr Cys Thr Gly Arg Gly Pro
                565                 570                 575 gac aac tgt atc cag tgt gcc cac tac att gac ggc ccc cac tgc gtc    1776
Asp Asn Cys Ile Gln Cys Ala His Tyr Ile Asp Gly Pro His Cys Val
            580                 585                 590 aag acc tgc ccg gca gga gtc atg gga gaa aac aac acc ctg gtc tgg    1824
Lys Thr Cys Pro Ala Gly Val Met Gly Glu Asn Asn Thr Leu Val Trp
        595                 600                 605 aag tac gca gac gcc ggc cat gtg tgc cac ctg tgc cat cca aac tgc    1872
Lys Tyr Ala Asp Ala Gly His Val Cys His Leu Cys His Pro Asn Cys
    610                 615                 620 acc tac gga tgc act ggg cca ggt ctt gaa ggc tgt cca acg aat ggg    1920
Thr Tyr Gly Cys Thr Gly Pro Gly Leu Glu Gly Cys Pro Thr Asn Gly
625                 630                 635                 640 cct aag atc ccg tcc gat cca tct gac tta aac att ttc ctg gag atc    1968
Pro Lys Ile Pro Ser Asp Pro Ser Asp Leu Asn Ile Phe Leu Glu Ile
                645                 650                 655 ctt tgc tta gta ctc ttg tcc act acc tgt gta gtg acc tgg ctc tgc    2016
Leu Cys Leu Val Leu Leu Ser Thr Thr Cys Val Val Thr Trp Leu Cys
            660                 665                 670 tgc aaa cgc aga gga aag act tcc ttc tgg tca gat gtg cca gac cca    2064
Cys Lys Arg Arg Gly Lys Thr Ser Phe Trp Ser Asp Val Pro Asp Pro
        675                 680                 685 gcc cac agt agc ctg agc tcc tgg ttg ccc acc atc atg aca gag gaa    2112
Ala His Ser Ser Leu Ser Ser Trp Leu Pro Thr Ile Met Thr Glu Glu
    690                 695                 700 acc ttc cag tta ccc agc ttc tgg gac tcc agc gtg cca tca atc acc    2160
Thr Phe Gln Leu Pro Ser Phe Trp Asp Ser Ser Val Pro Ser Ile Thr
705                 710                 715                 720 aag atc act gaa ctg gag gaa gac aag aaa ccg acc cac tgg gat tcc    2208
Lys Ile Thr Glu Leu Glu Glu Asp Lys Lys Pro Thr His Trp Asp Ser
                725                 730                 735 gaa agc tct ggg aat ggt agc ctt cca gcc ctg gtt cag gcc tat gtg    2256
Glu Ser Ser Gly Asn Gly Ser Leu Pro Ala Leu Val Gln Ala Tyr Val
            740                 745                 750 ctc caa gga gat cca aga gaa att tcc aac cag tcc cag cct ccc tct    2304
Leu Gln Gly Asp Pro Arg Glu Ile Ser Asn Gln Ser Gln Pro Pro Ser
        755                 760                 765 cgc act ggt gac cag gtc ctc tat ggt cag gtg ctt gag agc ccc acc    2352
Arg Thr Gly Asp Gln Val Leu Tyr Gly Gln Val Leu Glu Ser Pro Thr
    770                 775                 780 agc cca gga gta atg cag tac att cgc tct gac tcc act cag ccc ctc    2400
Ser Pro Gly Val Met Gln Tyr Ile Arg Ser Asp Ser Thr Gln Pro Leu
785                 790                 795                 800 ttg ggg ggc ccc acc cct agc cct aaa tct tat gaa aac atc tgg ttc    2448
Leu Gly Gly Pro Thr Pro Ser Pro Lys Ser Tyr Glu Asn Ile Trp Phe
                805                 810                 815
```

```
cat tca aga ccc cag gag acc ttt gtg ccc caa cct cca aac cag gaa    2496
His Ser Arg Pro Gln Glu Thr Phe Val Pro Gln Pro Pro Asn Gln Glu
            820                 825                 830 gat gac tgt gtc ttt ggg cct cca ttt gat ttt ccc ctc ttt cag ggg    2544
Asp Asp Cys Val Phe Gly Pro Pro Phe Asp Phe Pro Leu Phe Gln Gly
            835                 840                 845 ctc cag gtc cat gga gtt gaa gaa caa ggg ggt ttc tag               2583
Leu Gln Val His Gly Val Glu Glu Gln Gly Gly Phe
            850                 855             860

<210> SEQ ID NO 40
<211> LENGTH: 860
<212> TYPE: PRT
<213> ORGANISM: Artificial
<220> FEATURE:
<223> OTHER INFORMATION: Synthetic Construct

<400> SEQUENCE: 40

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
290                 295                 300
```

```
Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Asp Pro Ser Asp Leu Asn Ile Phe Leu Glu Ile
                645                 650                 655

Leu Cys Leu Val Leu Leu Ser Thr Thr Cys Val Val Thr Trp Leu Cys
                660                 665                 670

Cys Lys Arg Arg Gly Lys Thr Ser Phe Trp Ser Asp Val Pro Asp Pro
            675                 680                 685

Ala His Ser Ser Leu Ser Ser Trp Leu Pro Thr Ile Met Thr Glu Glu
        690                 695                 700

Thr Phe Gln Leu Pro Ser Phe Trp Asp Ser Ser Val Pro Ser Ile Thr
705                 710                 715                 720
```

```
Lys Ile Thr Glu Leu Glu Glu Asp Lys Lys Pro Thr His Trp Asp Ser
            725                 730                 735

Glu Ser Ser Gly Asn Gly Ser Leu Pro Ala Leu Val Gln Ala Tyr Val
        740                 745                 750

Leu Gln Gly Asp Pro Arg Glu Ile Ser Asn Gln Ser Gln Pro Pro Ser
    755                 760                 765

Arg Thr Gly Asp Gln Val Leu Tyr Gly Gln Val Leu Glu Ser Pro Thr
770                 775                 780

Ser Pro Gly Val Met Gln Tyr Ile Arg Ser Asp Ser Thr Gln Pro Leu
785                 790                 795                 800

Leu Gly Gly Pro Thr Pro Ser Pro Lys Ser Tyr Glu Asn Ile Trp Phe
            805                 810                 815

His Ser Arg Pro Gln Glu Thr Phe Val Pro Gln Pro Asn Gln Glu
        820                 825                 830

Asp Asp Cys Val Phe Gly Pro Pro Phe Asp Phe Pro Leu Phe Gln Gly
    835                 840                 845

Leu Gln Val His Gly Val Glu Glu Gln Gly Gly Phe
    850                 855                 860

<210> SEQ ID NO 41
<211> LENGTH: 24
<212> TYPE: DNA
<213> ORGANISM: Artificial
<220> FEATURE:
<223> OTHER INFORMATION: An artificially synthesized oligonucleotide
      sequence

<400> SEQUENCE: 41 cagggccag tggatagacc gatg                                          24

<210> SEQ ID NO 42
<211> LENGTH: 23
<212> TYPE: DNA
<213> ORGANISM: Artificial
<220> FEATURE:
<223> OTHER INFORMATION: An artificially synthesized oligonucleotide
      sequence

<400> SEQUENCE: 42
gctcactgga tggtgggaag atg                                          23

<210> SEQ ID NO 43
<211> LENGTH: 348
<212> TYPE: DNA
<213> ORGANISM: Mus musculus
<220> FEATURE:
<221> NAME/KEY: CDS
<222> LOCATION: (1)..(348)
<220> FEATURE:
<221> NAME/KEY: V_region
<222> LOCATION: (1)..(348)

<400> SEQUENCE: 43 gag gat cag ctg cag cag tct ggg gca gag ctt gtg aag cca ggg gcc    48
Glu Asp Gln Leu Gln Gln Ser Gly Ala Glu Leu Val Lys Pro Gly Ala
1               5                   10                  15 tca gtc aag ttg tcc tgc aca gct tct ggc ttc aac att aaa gac acc    96
Ser Val Lys Leu Ser Cys Thr Ala Ser Gly Phe Asn Ile Lys Asp Thr
            20                  25                  30 tat ata cag tgg gtg aag ctg agg cct gaa cag ggc ctg gag tgg att   144
Tyr Ile Gln Trp Val Lys Leu Arg Pro Glu Gln Gly Leu Glu Trp Ile
        35                  40                  45
```

```
gga agg att gat cct ctg aat ggt aat act aaa tat gtc ccg aag ttc      192
Gly Arg Ile Asp Pro Leu Asn Gly Asn Thr Lys Tyr Val Pro Lys Phe
    50                  55                  60 cag ggc aag gcc act ata aca gca gac aca tcc tcc aat aca gcc tac      240
Gln Gly Lys Ala Thr Ile Thr Ala Asp Thr Ser Ser Asn Thr Ala Tyr
65                  70                  75                  80 ctg caa ctc agc agc ctg aca tct gag gac act gcc gtc tat tac tgt      288
Leu Gln Leu Ser Ser Leu Thr Ser Glu Asp Thr Ala Val Tyr Tyr Cys
                85                  90                  95 gtt agg tct ggg acc ctc ttt gac ttc tgg ggc caa ggc acc act ctc      336
Val Arg Ser Gly Thr Leu Phe Asp Phe Trp Gly Gln Gly Thr Thr Leu
            100                 105                 110 aca gtc tcc tca                                                      348
Thr Val Ser Ser
        115

<210> SEQ ID NO 44
<211> LENGTH: 116
<212> TYPE: PRT
<213> ORGANISM: Mus musculus

<400> SEQUENCE: 44

Glu Asp Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Gln Trp Val Lys Leu Arg Pro Glu Gln Gly Leu Glu Trp Ile
        35                  40                  45

Gly Arg Ile Asp Pro Leu Asn Gly Asn Thr Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Ser Gly Thr Leu Phe Asp Phe Trp Gly Gln Gly Thr Thr Leu
            100                 105                 110

Thr Val Ser Ser
        115

<210> SEQ ID NO 45
<211> LENGTH: 318
<212> TYPE: DNA
<213> ORGANISM: Mus musculus
<220> FEATURE:
<221> NAME/KEY: CDS
<222> LOCATION: (1)..(318)
<220> FEATURE:
<221> NAME/KEY: V_region
<222> LOCATION: (1)..(318)

<400> SEQUENCE: 45 gac atc cag atg aca cag tct cca tcc tca ctg tct gca tct ctg gga      48
Asp Ile Gln Met Thr Gln Ser Pro Ser Ser Leu Ser Ala Ser Leu Gly
1               5                   10                  15 ggc aaa gtc acc atc act tgc aag gca agc caa gac att cac aag tat      96
Gly Lys Val Thr Ile Thr Cys Lys Ala Ser Gln Asp Ile His Lys Tyr
            20                  25                  30 ata gct tgg tac caa cac aag cct gga aaa ggt cct agg ctg ctc ata     144
Ile Ala Trp Tyr Gln His Lys Pro Gly Lys Gly Pro Arg Leu Leu Ile
        35                  40                  45
```

```
cag tac aca tct aca tta cag cca ggc atc cca tca agg ttc agt gga    192
Gln Tyr Thr Ser Thr Leu Gln Pro Gly Ile Pro Ser Arg Phe Ser Gly
     50                  55                  60 agt ggg tct ggg aga gat tat tcc ttc agc atc agc aac ctg gag cct    240
Ser Gly Ser Gly Arg Asp Tyr Ser Phe Ser Ile Ser Asn Leu Glu Pro
 65                  70                  75                  80 gaa gat att gca act tat tat tgt cta cag tat gat aat ctt cgg acg    288
Glu Asp Ile Ala Thr Tyr Tyr Cys Leu Gln Tyr Asp Asn Leu Arg Thr
                 85                  90                  95 ttc ggt gga ggc acc aag ctg gaa atc aaa                            318
Phe Gly Gly Gly Thr Lys Leu Glu Ile Lys
            100                 105

<210> SEQ ID NO 46
<211> LENGTH: 106
<212> TYPE: PRT
<213> ORGANISM: Mus musculus

<400> SEQUENCE: 46

Asp Ile Gln Met Thr Gln Ser Pro Ser Ser Leu Ser Ala Ser Leu Gly
 1               5                   10                  15

Gly Lys Val Thr Ile Thr Cys Lys Ala Ser Gln Asp Ile His Lys Tyr
             20                  25                  30

Ile Ala Trp Tyr Gln His Lys Pro Gly Lys Gly Pro Arg Leu Leu Ile
         35                  40                  45

Gln Tyr Thr Ser Thr Leu Gln Pro Gly Ile Pro Ser Arg Phe Ser Gly
     50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Arg Thr
                 85                  90                  95

Phe Gly Gly Gly Thr Lys Leu Glu Ile Lys
            100                 105

<210> SEQ ID NO 47
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 47
ccatggagtt agtttgggca gcagatcc                                      28

<210> SEQ ID NO 48
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 48 aac tac tgg atg aac                                                 15
Asn Tyr Trp Met Asn
 1               5

<210> SEQ ID NO 49
<211> LENGTH: 5
<212> TYPE: PRT
<213> ORGANISM: Mus musculus

<400> SEQUENCE: 49
```

```
Asn Tyr Trp Met Asn
1               5

<210> SEQ ID NO 50
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 50 agg att cat cct tct gat agt gaa act cac tac aat caa aag ttc aag      48
Arg Ile His Pro Ser Asp Ser Glu Thr His Tyr Asn Gln Lys Phe Lys
1               5                   10                  15 aac                                                                  51
Asn

<210> SEQ ID NO 51
<211> LENGTH: 17
<212> TYPE: PRT
<213> ORGANISM: Mus musculus

<400> SEQUENCE: 51

Arg Ile His Pro Ser Asp Ser Glu Thr His Tyr Asn Gln Lys Phe Lys
1               5                   10                  15

Asn

<210> SEQ ID NO 52
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 52 tta tat tac tat act atg gac tac                                      24
Leu Tyr Tyr Tyr Thr Met Asp Tyr
1               5

<210> SEQ ID NO 53
<211> LENGTH: 8
<212> TYPE: PRT
<213> ORGANISM: Mus musculus

<400> SEQUENCE: 53

Leu Tyr Tyr Tyr Thr Met Asp Tyr
1               5

<210> SEQ ID NO 54
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 54 aag gca agc caa gac att aac aag aat ata gct                          33
Lys Ala Ser Gln Asp Ile Asn Lys Asn Ile Ala
1               5                   10

<210> SEQ ID NO 55
<211> LENGTH: 11
```

<212> TYPE: PRT
<213> ORGANISM: Mus musculus

<400> SEQUENCE: 55

Lys Ala Ser Gln Asp Ile Asn Lys Asn Ile Ala
1               5                   10

<210> SEQ ID NO 56
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 56 tac aca tct aca tta cag cca                                          21
Tyr Thr Ser Thr Leu Gln Pro
1               5

<210> SEQ ID NO 57
<211> LENGTH: 7
<212> TYPE: PRT
<213> ORGANISM: Mus musculus

<400> SEQUENCE: 57

Tyr Thr Ser Thr Leu Gln Pro
1               5

<210> SEQ ID NO 58
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 58 cta cag tat gat aat ctt ccg tat acg                                  27
Leu Gln Tyr Asp Asn Leu Pro Tyr Thr
1               5

<210> SEQ ID NO 59
<211> LENGTH: 9
<212> TYPE: PRT
<213> ORGANISM: Mus musculus

<400> SEQUENCE: 59

Leu Gln Tyr Asp Asn Leu Pro Tyr Thr
1               5

<210> SEQ ID NO 60
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 60 agc tac tgg atg cac                                                  15
Ser Tyr Trp Met His
1               5

<210> SEQ ID NO 61
<211> LENGTH: 5
<212> TYPE: PRT

<213> ORGANISM: Mus musculus

<400> SEQUENCE: 61

Ser Tyr Trp Met His
1               5

<210> SEQ ID NO 62
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 62 gag att aat cct tac aat ggt ggt act aac tac aat gag aag ttc aag      48
Glu Ile Asn Pro Tyr Asn Gly Gly Thr Asn Tyr Asn Glu Lys Phe Lys
1               5                   10                  15 agc                                                                  51
Ser

<210> SEQ ID NO 63
<211> LENGTH: 17
<212> TYPE: PRT
<213> ORGANISM: Mus musculus

<400> SEQUENCE: 63

Glu Ile Asn Pro Tyr Asn Gly Gly Thr Asn Tyr Asn Glu Lys Phe Lys
1               5                   10                  15

Ser

<210> SEQ ID NO 64
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 64 tgg aag ttg ggg act tac                                              18
Trp Lys Leu Gly Thr Tyr
1               5

<210> SEQ ID NO 65
<211> LENGTH: 6
<212> TYPE: PRT
<213> ORGANISM: Mus musculus

<400> SEQUENCE: 65

Trp Lys Leu Gly Thr Tyr
1               5

<210> SEQ ID NO 66
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 66 cgg gca agt cag gaa att agt ggt tac tta agc                          33
Arg Ala Ser Gln Glu Ile Ser Gly Tyr Leu Ser
1               5                   10

```
<210> SEQ ID NO 67
<211> LENGTH: 11
<212> TYPE: PRT
<213> ORGANISM: Mus musculus

<400> SEQUENCE: 67

Arg Ala Ser Gln Glu Ile Ser Gly Tyr Leu Ser
1               5                   10

<210> SEQ ID NO 68
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 68 gcc gca tcc act tta gat tct                                          21
Ala Ala Ser Thr Leu Asp Ser
1               5

<210> SEQ ID NO 69
<211> LENGTH: 7
<212> TYPE: PRT
<213> ORGANISM: Mus musculus

<400> SEQUENCE: 69

Ala Ala Ser Thr Leu Asp Ser
1               5

<210> SEQ ID NO 70
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 70 cta caa tat gct agt tat cct cgg acg                                  27
Leu Gln Tyr Ala Ser Tyr Pro Arg Thr
1               5

<210> SEQ ID NO 71
<211> LENGTH: 9
<212> TYPE: PRT
<213> ORGANISM: Mus musculus

<400> SEQUENCE: 71

Leu Gln Tyr Ala Ser Tyr Pro Arg Thr
1               5

<210> SEQ ID NO 72
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 72 gtt tat tct ttg cac                                                  15
Val Tyr Ser Leu His
1               5
```

<210> SEQ ID NO 73
<211> LENGTH: 5
<212> TYPE: PRT
<213> ORGANISM: Mus musculus

<400> SEQUENCE: 73

Val Tyr Ser Leu His
1               5

<210> SEQ ID NO 74
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 74 gtt att agt act tac tat ggt gat gct atc tac aac cag aag ttc aag      48
Val Ile Ser Thr Tyr Tyr Gly Asp Ala Ile Tyr Asn Gln Lys Phe Lys
1               5                   10                  15 ggc                                                                  51
Gly

<210> SEQ ID NO 75
<211> LENGTH: 17
<212> TYPE: PRT
<213> ORGANISM: Mus musculus

<400> SEQUENCE: 75

Val Ile Ser Thr Tyr Tyr Gly Asp Ala Ile Tyr Asn Gln Lys Phe Lys
1               5                   10                  15

Gly

<210> SEQ ID NO 76
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 76 gag ggg aat ggt aac ccc ctt gac tac                                  27
Glu Gly Asn Gly Asn Pro Leu Asp Tyr
1               5

<210> SEQ ID NO 77
<211> LENGTH: 9
<212> TYPE: PRT
<213> ORGANISM: Mus musculus

<400> SEQUENCE: 77

Glu Gly Asn Gly Asn Pro Leu Asp Tyr
1               5

<210> SEQ ID NO 78
<211> LENGTH: 36
<212> TYPE: DNA
<213> ORGANISM: Mus musculus
<220> FEATURE:
<221> NAME/KEY: CDS
<222> LOCATION: (1)..(36)

<400> SEQUENCE: 78 act gcc agc tca agt gta agt tcc agt tac ttg cac                      36

Thr Ala Ser Ser Ser Val Ser Ser Ser Tyr Leu His
1               5                   10

<210> SEQ ID NO 79
<211> LENGTH: 12
<212> TYPE: PRT
<213> ORGANISM: Mus musculus

<400> SEQUENCE: 79

Thr Ala Ser Ser Ser Val Ser Ser Ser Tyr Leu His
1               5                   10

<210> SEQ ID NO 80
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 80 agc aca tcc aac ctg gct tct                                      21
Ser Thr Ser Asn Leu Ala Ser
1               5

<210> SEQ ID NO 81
<211> LENGTH: 7
<212> TYPE: PRT
<213> ORGANISM: Mus musculus

<400> SEQUENCE: 81

Ser Thr Ser Asn Leu Ala Ser
1               5

<210> SEQ ID NO 82
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 82 cac cag tat cat cgt tcc ccg ctc acg                              27
His Gln Tyr His Arg Ser Pro Leu Thr
1               5

<210> SEQ ID NO 83
<211> LENGTH: 9
<212> TYPE: PRT
<213> ORGANISM: Mus musculus

<400> SEQUENCE: 83

His Gln Tyr His Arg Ser Pro Leu Thr
1               5

<210> SEQ ID NO 84
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 84

```
agt tat ggt gta cac                                              15
Ser Tyr Gly Val His
1               5
```

<210> SEQ ID NO 85
<211> LENGTH: 5
<212> TYPE: PRT
<213> ORGANISM: Mus musculus

<400> SEQUENCE: 85

```
Ser Tyr Gly Val His
1               5
```

<210> SEQ ID NO 86
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 86

```
gtg ata tgg agg gat gga agc aca acc tat aat tca gct ctc aaa tcc   48
Val Ile Trp Arg Asp Gly Ser Thr Thr Tyr Asn Ser Ala Leu Lys Ser
1               5                   10                  15
```

<210> SEQ ID NO 87
<211> LENGTH: 16
<212> TYPE: PRT
<213> ORGANISM: Mus musculus

<400> SEQUENCE: 87

```
Val Ile Trp Arg Asp Gly Ser Thr Thr Tyr Asn Ser Ala Leu Lys Ser
1               5                   10                  15
```

<210> SEQ ID NO 88
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 88

```
aat tgg aat ggt ctt atg gac tac                                  24
Asn Trp Asn Gly Leu Met Asp Tyr
1               5
```

<210> SEQ ID NO 89
<211> LENGTH: 8
<212> TYPE: PRT
<213> ORGANISM: Mus musculus

<400> SEQUENCE: 89

```
Asn Trp Asn Gly Leu Met Asp Tyr
1               5
```

<210> SEQ ID NO 90
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 90

-continued

```
agg gca agt cag gac att agc tat tat tta aac                              33
Arg Ala Ser Gln Asp Ile Ser Tyr Tyr Leu Asn
1               5                   10

<210> SEQ ID NO 91
<211> LENGTH: 11
<212> TYPE: PRT
<213> ORGANISM: Mus musculus

<400> SEQUENCE: 91

Arg Ala Ser Gln Asp Ile Ser Tyr Tyr Leu Asn
1               5                   10

<210> SEQ ID NO 92
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 92 tac aca tca aga tta cac tca                                              21
Tyr Thr Ser Arg Leu His Ser
1               5

<210> SEQ ID NO 93
<211> LENGTH: 7
<212> TYPE: PRT
<213> ORGANISM: Mus musculus

<400> SEQUENCE: 93

Tyr Thr Ser Arg Leu His Ser
1               5

<210> SEQ ID NO 94
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 94 caa cag ggt cat acg gtt ccg tgg acg                                      27
Gln Gln Gly His Thr Val Pro Trp Thr
1               5

<210> SEQ ID NO 95
<211> LENGTH: 9
<212> TYPE: PRT
<213> ORGANISM: Mus musculus

<400> SEQUENCE: 95

Gln Gln Gly His Thr Val Pro Trp Thr
1               5

<210> SEQ ID NO 96
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 96 agc tac tgg atg cac                                                      15
```

Ser Tyr Trp Met His
1               5

<210> SEQ ID NO 97
<211> LENGTH: 5
<212> TYPE: PRT
<213> ORGANISM: Mus musculus

<400> SEQUENCE: 97

Ser Tyr Trp Met His
1               5

<210> SEQ ID NO 98
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 98 gct att tat cct gga aac agt gat agc tac aac cag aag ttc aag ggc      48
Ala Ile Tyr Pro Gly Asn Ser Asp Ser Tyr Asn Gln Lys Phe Lys Gly
1               5                   10                  15

<210> SEQ ID NO 99
<211> LENGTH: 16
<212> TYPE: PRT
<213> ORGANISM: Mus musculus

<400> SEQUENCE: 99

Ala Ile Tyr Pro Gly Asn Ser Asp Ser Tyr Asn Gln Lys Phe Lys Gly
1               5                   10                  15

<210> SEQ ID NO 100
<211> LENGTH: 12
<212> TYPE: DNA
<213> ORGANISM: Mus musculus
<220> FEATURE:
<221> NAME/KEY: CDS
<222> LOCATION: (1)..(12)

<400> SEQUENCE: 100 gtt atg gcc tac                                                      12
Val Met Ala Tyr
1

<210> SEQ ID NO 101
<211> LENGTH: 4
<212> TYPE: PRT
<213> ORGANISM: Mus musculus

<400> SEQUENCE: 101

Val Met Ala Tyr
1

<210> SEQ ID NO 102
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 102

```
cgg gca agt cag gac att ggt aat agc tta aac                          33
Arg Ala Ser Gln Asp Ile Gly Asn Ser Leu Asn
1               5                   10
```

<210> SEQ ID NO 103
<211> LENGTH: 11
<212> TYPE: PRT
<213> ORGANISM: Mus musculus

<400> SEQUENCE: 103

```
Arg Ala Ser Gln Asp Ile Gly Asn Ser Leu Asn
1               5                   10
```

<210> SEQ ID NO 104
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 104

```
gcc aca tcc aat tta gat tct                                          21
Ala Thr Ser Asn Leu Asp Ser
1               5
```

<210> SEQ ID NO 105
<211> LENGTH: 7
<212> TYPE: PRT
<213> ORGANISM: Mus musculus

<400> SEQUENCE: 105

```
Ala Thr Ser Asn Leu Asp Ser
1               5
```

<210> SEQ ID NO 106
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 106

```
cta caa tat gct agt tct ccg tgg acg                                  27
Leu Gln Tyr Ala Ser Ser Pro Trp Thr
1               5
```

<210> SEQ ID NO 107
<211> LENGTH: 9
<212> TYPE: PRT
<213> ORGANISM: Mus musculus

<400> SEQUENCE: 107

```
Leu Gln Tyr Ala Ser Ser Pro Trp Thr
1               5
```

<210> SEQ ID NO 108
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 108

| | | |
|---|---|---|
| cag gtc caa ctg cag cag cct ggg gct gaa ctg gtg aag cct ggg gct | | 48 |
| Gln Val Gln Leu Gln Gln Pro Gly Ala Glu Leu Val Lys Pro Gly Ala | | |
| 1               5                   10                  15 | | |
| tca gtg aag ctg tcc tgc aag gct tct ggc tac act ttc acc aac tac | | 96 |
| Ser Val Lys Leu Ser Cys Lys Ala Ser Gly Tyr Thr Phe Thr Asn Tyr | | |
|         20                  25                  30 | | |
| tgg atg aac tgg gtg aag cag agg cct gga cga ggc ctc gag tgg att | | 144 |
| Trp Met Asn Trp Val Lys Gln Arg Pro Gly Arg Gly Leu Glu Trp Ile | | |
|         35                  40                  45 | | |
| gga agg att cat cct tct gat agt gaa act cac tac aat caa aag ttc | | 192 |
| Gly Arg Ile His Pro Ser Asp Ser Glu Thr His Tyr Asn Gln Lys Phe | | |
| 50                  55                  60 | | |
| aag aac aag gcc aca ctg act gta gac aaa tcc tcc agc aca gcc tac | | 240 |
| Lys Asn Lys Ala Thr Leu Thr Val Asp Lys Ser Ser Ser Thr Ala Tyr | | |
| 65                  70                  75                  80 | | |
| atc caa ctc agc agc ctg aca tct gag gac tct gcg gtc tat tat tgt | | 288 |
| Ile Gln Leu Ser Ser Leu Thr Ser Glu Asp Ser Ala Val Tyr Tyr Cys | | |
|                 85                  90                  95 | | |
| gca aat tta tat tac tat act atg gac tac tgg ggt caa gga acc tca | | 336 |
| Ala Asn Leu Tyr Tyr Tyr Thr Met Asp Tyr Trp Gly Gln Gly Thr Ser | | |
|                 100                 105                 110 | | |
| gtc acc gtc tcc tca | | 351 |
| Val Thr Val Ser Ser | | |
|         115 | | |

```
<210> SEQ ID NO 109
<211> LENGTH: 117
<212> TYPE: PRT
<213> ORGANISM: Mus musculus

<400> SEQUENCE: 109
```

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Lys Phe
    50                  55                  60

Lys Asn Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Asn Leu Tyr Tyr Tyr Thr Met Asp Tyr Trp Gly Gln Gly Thr Ser
            100                 105                 110

Val Thr Val Ser Ser
        115

```
<210> SEQ ID NO 110
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 110
```

| | | |
|---|---|---|
| gac atc cag atg aca cag tct cca tcc tca ctg tct gca tct ctg gga | | 48 |
| Asp Ile Gln Met Thr Gln Ser Pro Ser Ser Leu Ser Ala Ser Leu Gly | | |
| 1               5                   10                  15 | | |

```
ggc aaa gtc acc atc act tgc aag gca agc caa gac att aac aag aat      96
Gly Lys Val Thr Ile Thr Cys Lys Ala Ser Gln Asp Ile Asn Lys Asn
         20                  25                  30 ata gct tgg cac caa cac aag cct gga aaa ggt cct agg ctg ctc ata     144
Ile Ala Trp His Gln His Lys Pro Gly Lys Gly Pro Arg Leu Leu Ile
             35                  40                  45 tgg tac aca tct aca tta cag cca ggc atc cca tca agg ttc agt gga     192
Trp Tyr Thr Ser Thr Leu Gln Pro Gly Ile Pro Ser Arg Phe Ser Gly
     50                  55                  60 agt ggg tct ggg aga gat tat tcc ttc agc atc agc aac ctg gag cct     240
Ser Gly Ser Gly Arg Asp Tyr Ser Phe Ser Ile Ser Asn Leu Glu Pro
 65                  70                  75                  80 gaa gat att gca act tat tac tgt cta cag tat gat aat ctt ccg tat     288
Glu Asp Ile Ala Thr Tyr Tyr Cys Leu Gln Tyr Asp Asn Leu Pro Tyr
                 85                  90                  95 acg ttc gga tcg ggg acc aag ctg gaa ata aaa                         321
Thr Phe Gly Ser Gly Thr Lys Leu Glu Ile Lys
            100                 105

<210> SEQ ID NO 111
<211> LENGTH: 107
<212> TYPE: PRT
<213> ORGANISM: Mus musculus

<400> SEQUENCE: 111

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Asn
            20                  25                  30

Ile Ala Trp His Gln His Lys Pro Gly Lys Gly Pro Arg Leu Leu Ile
        35                  40                  45

Trp Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Pro Tyr
                85                  90                  95

Thr Phe Gly Ser Gly Thr Lys Leu Glu Ile Lys
            100                 105

<210> SEQ ID NO 112
<211> LENGTH: 345
<212> TYPE: DNA
<213> ORGANISM: Mus musculus
<220> FEATURE:
<221> NAME/KEY: CDS
<222> LOCATION: (1)..(345)

<400> SEQUENCE: 112 cag gtc caa ctg cag cag cct ggg gct gag ctt gtg aag cct ggg gct      48
Gln Val Gln Leu Gln Gln Pro Gly Ala Glu Leu Val Lys Pro Gly Ala
1               5                   10                  15 tca gtg aag ttg tcc tgc aag gct tct ggc tac acc ttc acc agc tac      96
Ser Val Lys Leu Ser Cys Lys Ala Ser Gly Tyr Thr Phe Thr Ser Tyr
            20                  25                  30 tgg atg cac tgg gtg aag cag agg cct gga caa ggc ctt gag tgg att     144
Trp Met His Trp Val Lys Gln Arg Pro Gly Gln Gly Leu Glu Trp Ile
        35                  40                  45 gga gag att aat cct tac aat ggt ggt act aac tac aat gag aag ttc     192
Gly Glu Ile Asn Pro Tyr Asn Gly Gly Thr Asn Tyr Asn Glu Lys Phe
    50                  55                  60
```

```
aag agc aag gcc aca ctg act gta gac aaa tcc tcc agc aca gcc tac      240
Lys Ser Lys Ala Thr Leu Thr Val Asp Lys Ser Ser Ser Thr Ala Tyr
 65                  70                  75                  80 atg caa ctc agc agc ctg aca tct gag gac tct gcg gtc tat tac tgt      288
Met Gln Leu Ser Ser Leu Thr Ser Glu Asp Ser Ala Val Tyr Tyr Cys
                 85                  90                  95 aca ata tgg aag ttg ggg act tac tgg ggc caa ggg act ctg gtc act      336
Thr Ile Trp Lys Leu Gly Thr Tyr Trp Gly Gln Gly Thr Leu Val Thr
            100                 105                 110 gtc tct gca                                                          345
Val Ser Ala
    115

<210> SEQ ID NO 113
<211> LENGTH: 115
<212> TYPE: PRT
<213> ORGANISM: Mus musculus

<400> SEQUENCE: 113

Gln Val Gln Leu Gln Gln Pro Gly Ala Glu Leu Val Lys Pro Gly Ala
  1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Glu Ile Asn Pro Tyr Asn Gly Gly Thr Asn Tyr Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Ile Trp Lys Leu Gly Thr Tyr Trp Gly Gln Gly Thr Leu Val Thr
            100                 105                 110

Val Ser Ala
    115

<210> SEQ ID NO 114
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 114 gac atc cag atg acc cag tct cca tcc tcc tta tct gcc tct ctg gga      48
Asp Ile Gln Met Thr Gln Ser Pro Ser Ser Leu Ser Ala Ser Leu Gly
  1               5                  10                  15 gaa aga gtc agt ctc act tgt cgg gca agt cag gaa att agt ggt tac      96
Glu Arg Val Ser Leu Thr Cys Arg Ala Ser Gln Glu Ile Ser Gly Tyr
             20                  25                  30 tta agc tgg ctt cag cag aaa cca gat gga act att aaa cgc ctg atc      144
Leu Ser Trp Leu Gln Gln Lys Pro Asp Gly Thr Ile Lys Arg Leu Ile
         35                  40                  45 tac gcc gca tcc act tta gat tct ggt gtc cca aaa agg ttc agt ggc      192
Tyr Ala Ala Ser Thr Leu Asp Ser Gly Val Pro Lys Arg Phe Ser Gly
     50                  55                  60 agt agg tct ggg tca gat tat tct ctc acc atc agc agc ctt gag tct      240
Ser Arg Ser Gly Ser Asp Tyr Ser Leu Thr Ile Ser Ser Leu Glu Ser
 65                  70                  75                  80
```

```
gaa gat ttt gca gac tat tac tgt cta caa tat gct agt tat cct cgg      288
Glu Asp Phe Ala Asp Tyr Tyr Cys Leu Gln Tyr Ala Ser Tyr Pro Arg
                85                  90                  95 acg ttc ggt gga ggc acc aag ctg gaa atc aaa                          321
Thr Phe Gly Gly Gly Thr Lys Leu Glu Ile Lys
            100                 105
```

<210> SEQ ID NO 115
<211> LENGTH: 107
<212> TYPE: PRT
<213> ORGANISM: Mus musculus

<400> SEQUENCE: 115

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105
```

<210> SEQ ID NO 116
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 116

```
cag gtc cag ctg cag cag tct ggg gct gag ctg gtg agg cct ggg gtc      48
Gln Val Gln Leu Gln Gln Ser Gly Ala Glu Leu Val Arg Pro Gly Val
1               5                   10                  15 tca gtg aag att tcc tgc aag ggt tct ggc tac aca ttc act gtt tat      96
Ser Val Lys Ile Ser Cys Lys Gly Ser Gly Tyr Thr Phe Thr Val Tyr
            20                  25                  30 tct ttg cac tgg gtg aag cag agt cat gca agg agt cta gag tgg att      144
Ser Leu His Trp Val Lys Gln Ser His Ala Arg Ser Leu Glu Trp Ile
        35                  40                  45 gga gtt att agt act tac tat ggt gat gct atc tac aac cag aag ttc      192
Gly Val Ile Ser Thr Tyr Tyr Gly Asp Ala Ile Tyr Asn Gln Lys Phe
    50                  55                  60 aag ggc aag gcc aca atg act gta gac aaa tcc tcc agc aca gcc tat      240
Lys Gly Lys Ala Thr Met Thr Val Asp Lys Ser Ser Ser Thr Ala Tyr
65                  70                  75                  80 atg gaa ctt gcc aga ctg aca tct gag gat tct gcc atc tat tac tgt      288
Met Glu Leu Ala Arg Leu Thr Ser Glu Asp Ser Ala Ile Tyr Tyr Cys
                85                  90                  95 gca aga gag ggg aat ggt aac ccc ctt gac tac tgg ggc caa ggc acc      336
Ala Arg Glu Gly Asn Gly Asn Pro Leu Asp Tyr Trp Gly Gln Gly Thr
            100                 105                 110
```

```
act ctc aca gtc tcc tca                                                      354
Thr Leu Thr Val Ser Ser
        115

<210> SEQ ID NO 117
<211> LENGTH: 118
<212> TYPE: PRT
<213> ORGANISM: Mus musculus

<400> SEQUENCE: 117

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Val Tyr
            20                  25                  30

Ser Leu His Trp Val Lys Gln Ser His Ala Arg Ser Leu Glu Trp Ile
        35                  40                  45

Gly Val Ile Ser Thr Tyr Tyr Gly Asp Ala Ile Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Gly Asn Gly Asn Pro Leu Asp Tyr Trp Gly Gln Gly Thr
            100                 105                 110

Thr Leu Thr Val Ser Ser
        115

<210> SEQ ID NO 118
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 118 caa att gtt ctc acc cag tct cca gca atc atg tct gca tct cta ggg          48
Gln Ile Val Leu Thr Gln Ser Pro Ala Ile Met Ser Ala Ser Leu Gly
1               5                   10                  15 gaa cgg gtc acc atg acc tgc act gcc agc tca agt gta agt tcc agt          96
Glu Arg Val Thr Met Thr Cys Thr Ala Ser Ser Ser Val Ser Ser Ser
            20                  25                  30 tac ttg cac tgg tac cag cag aag cca gga tcc tcc ccc aaa ctc tgg         144
Tyr Leu His Trp Tyr Gln Gln Lys Pro Gly Ser Ser Pro Lys Leu Trp
        35                  40                  45 att tat agc aca tcc aac ctg gct tct gga gtc cca gct cgc ttc agt         192
Ile Tyr Ser Thr Ser Asn Leu Ala Ser Gly Val Pro Ala Arg Phe Ser
    50                  55                  60 ggc agt ggg tct ggg acc tct tac tct ctc aca atc acc aac atg gag         240
Gly Ser Gly Ser Gly Thr Ser Tyr Ser Leu Thr Ile Thr Asn Met Glu
65                  70                  75                  80 gct gaa gat tct gcc act tat tac tgc cac cag tat cat cgt tcc ccg         288
Ala Glu Asp Ser Ala Thr Tyr Tyr Cys His Gln Tyr His Arg Ser Pro
                85                  90                  95 ctc acg ttc ggt gct ggg acc aag ctg gag ctg aaa                         324
Leu Thr Phe Gly Ala Gly Thr Lys Leu Glu Leu Lys
            100                 105

<210> SEQ ID NO 119
<211> LENGTH: 108
<212> TYPE: PRT
```

<213> ORGANISM: Mus musculus

<400> SEQUENCE: 119

| Gln | Ile | Val | Leu | Thr | Gln | Ser | Pro | Ala | Ile | Met | Ser | Ala | Ser | Leu | Gly |
|---|---|---|---|---|---|---|---|---|---|---|---|---|---|---|---|
| 1 | | | | 5 | | | | | 10 | | | | | 15 | |

| Glu | Arg | Val | Thr | Met | Thr | Cys | Thr | Ala | Ser | Ser | Val | Ser | Ser |
|---|---|---|---|---|---|---|---|---|---|---|---|---|---|
| | | | 20 | | | | | 25 | | | | | 30 |

| Tyr | Leu | His | Trp | Tyr | Gln | Gln | Lys | Pro | Gly | Ser | Ser | Pro | Lys | Leu | Trp |
|---|---|---|---|---|---|---|---|---|---|---|---|---|---|---|---|
| | | 35 | | | | | 40 | | | | | 45 | | | |

| Ile | Tyr | Ser | Thr | Ser | Asn | Leu | Ala | Ser | Gly | Val | Pro | Ala | Arg | Phe | Ser |
|---|---|---|---|---|---|---|---|---|---|---|---|---|---|---|---|
| | 50 | | | | | 55 | | | | | 60 | | | | |

| Gly | Ser | Gly | Ser | Gly | Thr | Ser | Tyr | Ser | Leu | Thr | Ile | Thr | Asn | Met | Glu |
|---|---|---|---|---|---|---|---|---|---|---|---|---|---|---|---|
| 65 | | | | | 70 | | | | | 75 | | | | | 80 |

| Ala | Glu | Asp | Ser | Ala | Thr | Tyr | Tyr | Cys | His | Gln | Tyr | His | Arg | Ser | Pro |
|---|---|---|---|---|---|---|---|---|---|---|---|---|---|---|---|
| | | | 85 | | | | | 90 | | | | | 95 | | |

| Leu | Thr | Phe | Gly | Ala | Gly | Thr | Lys | Leu | Glu | Leu | Lys |
|---|---|---|---|---|---|---|---|---|---|---|---|
| | | | 100 | | | | | 105 | | | |

<210> SEQ ID NO 120
<211> LENGTH: 348
<212> TYPE: DNA
<213> ORGANISM: Mus musculus
<220> FEATURE:
<221> NAME/KEY: CDS
<222> LOCATION: (1)..(348)

<400> SEQUENCE: 120

| cag | gtg | cag | ctg | aag | gag | tca | gga | cct | ggc | ctg | gtg | gcg | ccc | tca | cag | 48 |
|---|---|---|---|---|---|---|---|---|---|---|---|---|---|---|---|---|
| Gln | Val | Gln | Leu | Lys | Glu | Ser | Gly | Pro | Gly | Leu | Val | Ala | Pro | Ser | Gln | |
| 1 | | | | 5 | | | | | 10 | | | | | 15 | | |

| agc | ctg | tcc | atc | aca | tgc | acc | gtc | tca | gga | ttc | tca | tta | agt | agt | tat | 96 |
|---|---|---|---|---|---|---|---|---|---|---|---|---|---|---|---|---|
| Ser | Leu | Ser | Ile | Thr | Cys | Thr | Val | Ser | Gly | Phe | Ser | Leu | Ser | Ser | Tyr | |
| | | | 20 | | | | | 25 | | | | | 30 | | | |

| ggt | gta | cac | tgg | gtt | cgc | cag | cct | cca | gga | aag | ggt | ctg | gag | tgg | ctg | 144 |
|---|---|---|---|---|---|---|---|---|---|---|---|---|---|---|---|---|
| Gly | Val | His | Trp | Val | Arg | Gln | Pro | Pro | Gly | Lys | Gly | Leu | Glu | Trp | Leu | |
| | | 35 | | | | | 40 | | | | | 45 | | | | |

| gga | gtg | ata | tgg | agg | gat | gga | agc | aca | acc | tat | aat | tca | gct | ctc | aaa | 192 |
|---|---|---|---|---|---|---|---|---|---|---|---|---|---|---|---|---|
| Gly | Val | Ile | Trp | Arg | Asp | Gly | Ser | Thr | Thr | Tyr | Asn | Ser | Ala | Leu | Lys | |
| | 50 | | | | | 55 | | | | | 60 | | | | | |

| tcc | aga | ctg | agc | atc | agc | aag | gac | ggc | tcc | aag | agc | caa | gtt | ttc | tta | 240 |
|---|---|---|---|---|---|---|---|---|---|---|---|---|---|---|---|---|
| Ser | Arg | Leu | Ser | Ile | Ser | Lys | Asp | Gly | Ser | Lys | Ser | Gln | Val | Phe | Leu | |
| 65 | | | | | 70 | | | | | 75 | | | | | 80 | |

| aaa | atg | aac | agt | ctc | caa | act | gat | gac | aca | gcc | atg | tac | tac | tgt | gcc | 288 |
|---|---|---|---|---|---|---|---|---|---|---|---|---|---|---|---|---|
| Lys | Met | Asn | Ser | Leu | Gln | Thr | Asp | Asp | Thr | Ala | Met | Tyr | Tyr | Cys | Ala | |
| | | | | 85 | | | | | 90 | | | | | 95 | | |

| aga | aat | tgg | aat | ggt | ctt | atg | gac | tac | tgg | ggt | caa | gga | acc | tca | gtc | 336 |
|---|---|---|---|---|---|---|---|---|---|---|---|---|---|---|---|---|
| Arg | Asn | Trp | Asn | Gly | Leu | Met | Asp | Tyr | Trp | Gly | Gln | Gly | Thr | Ser | Val | |
| | | | 100 | | | | | 105 | | | | | 110 | | | |

| acc | gtc | tcc | tca | 348 |
|---|---|---|---|---|
| Thr | Val | Ser | Ser | |
| | | 115 | | |

<210> SEQ ID NO 121
<211> LENGTH: 116
<212> TYPE: PRT
<213> ORGANISM: Mus musculus

<400> SEQUENCE: 121

| Gln | Val | Gln | Leu | Lys | Glu | Ser | Gly | Pro | Gly | Leu | Val | Ala | Pro | Ser | Gln |
|---|---|---|---|---|---|---|---|---|---|---|---|---|---|---|---|
| 1 | | | | 5 | | | | | 10 | | | | | 15 | |

```
Ser Leu Ser Ile Thr Cys Thr Val Ser Gly Phe Ser Leu Ser Ser Tyr
            20                  25                  30

Gly Val His Trp Val Arg Gln Pro Gly Lys Gly Leu Glu Trp Leu
        35                  40                  45

Gly Val Ile Trp Arg Asp Gly Ser Thr Thr Tyr Asn Ser Ala Leu Lys
50                  55                  60

Ser Arg Leu Ser Ile Ser Lys Asp Gly Ser Lys Ser Gln Val Phe Leu
65                  70                  75                  80

Lys Met Asn Ser Leu Gln Thr Asp Thr Ala Met Tyr Tyr Cys Ala
                85                  90                  95

Arg Asn Trp Asn Gly Leu Met Asp Tyr Trp Gly Gln Gly Thr Ser Val
            100                 105                 110

Thr Val Ser Ser
        115

<210> SEQ ID NO 122
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 122 gat atc cag atg aca cag act aca tcc tcc ctg tct gcc tct ctg gga      48
Asp Ile Gln Met Thr Gln Thr Thr Ser Ser Leu Ser Ala Ser Leu Gly
1               5                   10                  15 gac aga gtc acc atc agt tgc agg gca agt cag gac att agc tat tat      96
Asp Arg Val Thr Ile Ser Cys Arg Ala Ser Gln Asp Ile Ser Tyr Tyr
            20                  25                  30 tta aac tgg tat cag cag aga cca gat gga act gtt aaa ctc ctg atc     144
Leu Asn Trp Tyr Gln Gln Arg Pro Asp Gly Thr Val Lys Leu Leu Ile
        35                  40                  45 tac tac aca tca aga tta cac tca gga gtc cca tca agg ttc agt ggc     192
Tyr Tyr Thr Ser Arg Leu His Ser Gly Val Pro Ser Arg Phe Ser Gly
50                  55                  60 agt ggg tct gga aca gaa tct tct ctc acc att agc aat ctg gaa caa     240
Ser Gly Ser Gly Thr Glu Ser Ser Leu Thr Ile Ser Asn Leu Glu Gln
65                  70                  75                  80 gaa gat att gcc act tac ttt tgc caa cag ggt cat acg gtt ccg tgg     288
Glu Asp Ile Ala Thr Tyr Phe Cys Gln Gln Gly His Thr Val Pro Trp
                85                  90                  95 acg ttc ggt gga ggc acc aag ctg gaa atc aaa                         321
Thr Phe Gly Gly Gly Thr Lys Leu Glu Ile Lys
            100                 105

<210> SEQ ID NO 123
<211> LENGTH: 107
<212> TYPE: PRT
<213> ORGANISM: Mus musculus

<400> SEQUENCE: 123

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Tyr Tyr
            20                  25                  30

Leu Asn Trp Tyr Gln Gln Arg Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60
```

```
Ser Gly Ser Gly Thr Glu Ser Leu Thr Ile Ser Asn Leu Glu Gln
 65                  70                  75                  80

Glu Asp Ile Ala Thr Tyr Phe Cys Gln Gln Gly His Thr Val Pro Trp
                 85                  90                  95

Thr Phe Gly Gly Gly Thr Lys Leu Glu Ile Lys
            100                 105
```

<210> SEQ ID NO 124
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 124

```
gag gtt cag ctc cag cag tct ggg act gtg ctg gca agg cct ggg gct      48
Glu Val Gln Leu Gln Gln Ser Gly Thr Val Leu Ala Arg Pro Gly Ala
  1               5                  10                  15 tca gtg aag atg tcc tgc aag gct tct ggc tac acc ttt acc agc tac      96
Ser Val Lys Met Ser Cys Lys Ala Ser Gly Tyr Thr Phe Thr Ser Tyr
             20                  25                  30 tgg atg cac tgg gtg aaa cag agg cct gga cag ggt ctg gaa tgg att    144
Trp Met His Trp Val Lys Gln Arg Pro Gly Gln Gly Leu Glu Trp Ile
         35                  40                  45 ggc gct att tat cct gga aac agt gat agc tac aac cag aag ttc aag    192
Gly Ala Ile Tyr Pro Gly Asn Ser Asp Ser Tyr Asn Gln Lys Phe Lys
     50                  55                  60 ggc aag gcc aaa ctg act gca gtc aca tcc acc agc act gcc tac atg    240
Gly Lys Ala Lys Leu Thr Ala Val Thr Ser Thr Ser Thr Ala Tyr Met
 65                  70                  75                  80 gag ctc agc agc ctg aca aat gag gac tct gcg gtc tat tac tgt aca    288
Glu Leu Ser Ser Leu Thr Asn Glu Asp Ser Ala Val Tyr Tyr Cys Thr
                 85                  90                  95 agt gtt atg gcc tac tgg ggt caa gga acc tca gtc acc gtc tcc tca    336
Ser Val Met Ala Tyr Trp Gly Gln Gly Thr Ser Val Thr Val Ser Ser
            100                 105                 110
```

<210> SEQ ID NO 125
<211> LENGTH: 112
<212> TYPE: PRT
<213> ORGANISM: Mus musculus

<400> SEQUENCE: 125

```
Glu Val Gln Leu Gln Gln Ser Gly Thr Val Leu Ala Arg Pro Gly Ala
  1               5                  10                  15

Ser Val Lys Met Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Ala Ile Tyr Pro Gly Asn Ser Asp Ser Tyr Asn Gln Lys Phe Lys
     50                  55                  60

Gly Lys Ala Lys Leu Thr Ala Val Thr Ser Thr Ser Thr Ala Tyr Met
 65                  70                  75                  80

Glu Leu Ser Ser Leu Thr Asn Glu Asp Ser Ala Val Tyr Tyr Cys Thr
                 85                  90                  95

Ser Val Met Ala Tyr Trp Gly Gln Gly Thr Ser Val Thr Val Ser Ser
            100                 105                 110
```

```
<210> SEQ ID NO 126
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 126 gac atc cag atg acc cag tct cca tcc tcc tta tct gcc tct ctg gga      48
Asp Ile Gln Met Thr Gln Ser Pro Ser Ser Leu Ser Ala Ser Leu Gly
1               5                   10                  15 gaa aga gtc agt ctc act tgt cgg gca agt cag gac att ggt aat agc      96
Glu Arg Val Ser Leu Thr Cys Arg Ala Ser Gln Asp Ile Gly Asn Ser
            20                  25                  30 tta aac tgg ctt cag cag gaa cca gat gga act att aaa cgc ctg atc     144
Leu Asn Trp Leu Gln Gln Glu Pro Asp Gly Thr Ile Lys Arg Leu Ile
        35                  40                  45 tac gcc aca tcc aat tta gat tct ggt gtc tcc aaa agg ttc agt ggc     192
Tyr Ala Thr Ser Asn Leu Asp Ser Gly Val Ser Lys Arg Phe Ser Gly
    50                  55                  60 agt agg tct ggg tca gat tat tct ctc acc atc agc agc ctt gag tct     240
Ser Arg Ser Gly Ser Asp Tyr Ser Leu Thr Ile Ser Ser Leu Glu Ser
65                  70                  75                  80 gaa gat ttt gta gac tat tac tgt cta caa tat gct agt tct ccg tgg     288
Glu Asp Phe Val Asp Tyr Tyr Cys Leu Gln Tyr Ala Ser Ser Pro Trp
                85                  90                  95 acg ttc ggt gga ggc acc aag ctg gaa atc aag                          321
Thr Phe Gly Gly Gly Thr Lys Leu Glu Ile Lys
                100                 105

<210> SEQ ID NO 127
<211> LENGTH: 107
<212> TYPE: PRT
<213> ORGANISM: Mus musculus

<400> SEQUENCE: 127

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asn Ser
            20                  25                  30

Leu Asn Trp Leu Gln Gln Glu Pro Asp Gly Thr Ile Lys Arg Leu Ile
        35                  40                  45

Tyr Ala Thr Ser Asn Leu Asp Ser Gly Val Ser Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95

Thr Phe Gly Gly Gly Thr Lys Leu Glu Ile Lys
                100                 105

<210> SEQ ID NO 128
<211> LENGTH: 1401
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1401)

<400> SEQUENCE: 128
```

```
atg gga tgg agc tgt atc atc ctc ttc ttg gta gca gca gct aca ggt      48
Met Gly Trp Ser Cys Ile Ile Leu Phe Leu Val Ala Ala Ala Thr Gly
1               5                   10                  15 gtc cac tcc cag gtc caa ctg cag cag cct ggg gct gaa ctg gtg aag      96
Val His Ser Gln Val Gln Leu Gln Gln Pro Gly Ala Glu Leu Val Lys
                20                  25                  30 cct ggg gct tca gtg aag ctg tcc tgc aag gct tct ggc tac act ttc     144
Pro Gly Ala Ser Val Lys Leu Ser Cys Lys Ala Ser Gly Tyr Thr Phe
            35                  40                  45 acc aac tac tgg atg aac tgg gtg aag cag agg cct gga cga ggc ctc     192
Thr Asn Tyr Trp Met Asn Trp Val Lys Gln Arg Pro Gly Arg Gly Leu
50                  55                  60 gag tgg att gga agg att cat cct tct gat agt gaa act cac tac aat     240
Glu Trp Ile Gly Arg Ile His Pro Ser Asp Ser Glu Thr His Tyr Asn
65                  70                  75                  80 caa aag ttc aag aac aag gcc aca ctg act gta gac aaa tcc tcc agc     288
Gln Lys Phe Lys Asn Lys Ala Thr Leu Thr Val Asp Lys Ser Ser Ser
                85                  90                  95 aca gcc tac atc caa ctc agc agc ctg aca tct gag gac tct gcg gtc     336
Thr Ala Tyr Ile Gln Leu Ser Ser Leu Thr Ser Glu Asp Ser Ala Val
            100                 105                 110 tat tat tgt gca aat tta tat tac tat act atg gac tac tgg ggt caa     384
Tyr Tyr Cys Ala Asn Leu Tyr Tyr Tyr Thr Met Asp Tyr Trp Gly Gln
        115                 120                 125 gga acc tca gtc acc gtc tcc tca gct agc acc aag ggc cca tcg gtc     432
Gly Thr Ser Val Thr Val Ser Ser Ala Ser Thr Lys Gly Pro Ser Val
    130                 135                 140 ttc ccc ctg gca ccc tcc tcc aag agc acc tct ggg ggc aca gcg gcc     480
Phe Pro Leu Ala Pro Ser Ser Lys Ser Thr Ser Gly Gly Thr Ala Ala
145                 150                 155                 160 ctg ggc tgc ctg gtc aag gac tac ttc ccc gaa ccg gtg acg gtg tcg     528
Leu Gly Cys Leu Val Lys Asp Tyr Phe Pro Glu Pro Val Thr Val Ser
                165                 170                 175 tgg aac tca ggc gcc ctg acc agc ggc gtg cac acc ttc ccg gct gtc     576
Trp Asn Ser Gly Ala Leu Thr Ser Gly Val His Thr Phe Pro Ala Val
            180                 185                 190 cta cag tcc tca gga ctc tac tcc ctc agc agc gtg gtg acc gtg ccc     624
Leu Gln Ser Ser Gly Leu Tyr Ser Leu Ser Ser Val Val Thr Val Pro
        195                 200                 205 tcc agc agc ttg ggc acc cag acc tac atc tgc aac gtg aat cac aag     672
Ser Ser Ser Leu Gly Thr Gln Thr Tyr Ile Cys Asn Val Asn His Lys
    210                 215                 220 ccc agc aac acc aag gtg gac aag aaa gtt gag ccc aaa tct tgt gac     720
Pro Ser Asn Thr Lys Val Asp Lys Lys Val Glu Pro Lys Ser Cys Asp
225                 230                 235                 240 aaa act cac aca tgc cca ccg tgc cca gca cct gaa ctc ctg ggg gga     768
Lys Thr His Thr Cys Pro Pro Cys Pro Ala Pro Glu Leu Leu Gly Gly
                245                 250                 255 ccg tca gtc ttc ctc ttc ccc cca aaa ccc aag gac acc ctc atg atc     816
Pro Ser Val Phe Leu Phe Pro Pro Lys Pro Lys Asp Thr Leu Met Ile
            260                 265                 270 tcc cgg acc cct gag gtc aca tgc gtg gtg gtg gac gtg agc cac gaa     864
Ser Arg Thr Pro Glu Val Thr Cys Val Val Val Asp Val Ser His Glu
        275                 280                 285 gac cct gag gtc aag ttc aac tgg tac gtg gac ggc gtg gag gtg cat     912
Asp Pro Glu Val Lys Phe Asn Trp Tyr Val Asp Gly Val Glu Val His
    290                 295                 300
```

```
aat gcc aag aca aag ccg cgg gag gag cag tac aac agc acg tac cgt    960
Asn Ala Lys Thr Lys Pro Arg Glu Glu Gln Tyr Asn Ser Thr Tyr Arg
305             310                 315                 320 gtg gtc agc gtc ctc acc gtc ctg cac cag gac tgg ctg aat ggc aag   1008
Val Val Ser Val Leu Thr Val Leu His Gln Asp Trp Leu Asn Gly Lys
            325                 330                 335 gag tac aag tgc aag gtc tcc aac aaa gcc ctc cca gcc ccc atc gag   1056
Glu Tyr Lys Cys Lys Val Ser Asn Lys Ala Leu Pro Ala Pro Ile Glu
        340                 345                 350 aaa acc atc tcc aaa gcc aaa ggg cag ccc cga gaa cca cag gtg tac   1104
Lys Thr Ile Ser Lys Ala Lys Gly Gln Pro Arg Glu Pro Gln Val Tyr
    355                 360                 365 acc ctg ccc cca tcc cgg gat gag ctg acc aag aac cag gtc agc ctg   1152
Thr Leu Pro Pro Ser Arg Asp Glu Leu Thr Lys Asn Gln Val Ser Leu
370                 375                 380 acc tgc ctg gtc aaa ggc ttc tat ccc agc gac atc gcc gtg gag tgg   1200
Thr Cys Leu Val Lys Gly Phe Tyr Pro Ser Asp Ile Ala Val Glu Trp
385                 390                 395                 400 gag agc aat ggg cag ccg gag aac aac tac aag acc acg cct ccc gtg   1248
Glu Ser Asn Gly Gln Pro Glu Asn Asn Tyr Lys Thr Thr Pro Pro Val
            405                 410                 415 ctg gac tcc gac ggc tcc ttc ttc ctc tac agc aag ctc acc gtg gac   1296
Leu Asp Ser Asp Gly Ser Phe Phe Leu Tyr Ser Lys Leu Thr Val Asp
        420                 425                 430 aag agc agg tgg cag cag ggg aac gtc ttc tca tgc tcc gtg atg cat   1344
Lys Ser Arg Trp Gln Gln Gly Asn Val Phe Ser Cys Ser Val Met His
    435                 440                 445 gag gct ctg cac aac cac tac acg cag aag agc ctc tcc ctg tct ccg   1392
Glu Ala Leu His Asn His Tyr Thr Gln Lys Ser Leu Ser Leu Ser Pro
450                 455                 460 ggt aaa tga                                                       1401
Gly Lys
465

<210> SEQ ID NO 129
<211> LENGTH: 466
<212> TYPE: PRT
<213> ORGANISM: Artificial
<220> FEATURE:
<223> OTHER INFORMATION: Synthetic Construct

<400> SEQUENCE: 129

Met Gly Trp Ser Cys Ile Ile Leu Phe Leu Val Ala Ala Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Met Asn Trp Val Lys Gln Arg Pro Gly Arg Gly Leu
    50                  55                  60

Glu Trp Ile Gly Arg Ile His Pro Ser Asp Ser Glu Thr His Tyr Asn
65                  70                  75                  80

Gln Lys Phe Lys Asn Lys Ala Thr Leu Thr Val Asp Lys Ser Ser Ser
                85                  90                  95

Thr Ala Tyr Ile Gln Leu Ser Ser Leu Thr Ser Glu Asp Ser Ala Val
            100                 105                 110

Tyr Tyr Cys Ala Asn Leu Tyr Tyr Tyr Thr Met Asp Tyr Trp Gly Gln
        115                 120                 125
```

Gly Thr Ser Val Thr Val Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 130
<211> LENGTH: 705
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(705)

<400> SEQUENCE: 130

```
atg aga ccc tcc att cag ttc ctg ggg ctc ttg ttg ttc tgg ctt cat       48
Met Arg Pro Ser Ile Gln Phe Leu Gly Leu Leu Leu Phe Trp Leu His
1               5                   10                  15 ggt gct cag tgt gac atc cag atg aca cag tct cca tcc tca ctg tct       96
Gly Ala Gln Cys Asp Ile Gln Met Thr Gln Ser Pro Ser Ser Leu Ser
            20                  25                  30 gca tct ctg gga ggc aaa gtc acc atc act tgc aag gca agc caa gac      144
Ala Ser Leu Gly Gly Lys Val Thr Ile Thr Cys Lys Ala Ser Gln Asp
        35                  40                  45 att aac aag aat ata gct tgg cac caa cac aag cct gga aaa ggt cct      192
Ile Asn Lys Asn Ile Ala Trp His Gln His Lys Pro Gly Lys Gly Pro
    50                  55                  60 agg ctg ctc ata tgg tac aca tct aca tta cag cca ggc atc cca tca      240
Arg Leu Leu Ile Trp Tyr Thr Ser Thr Leu Gln Pro Gly Ile Pro Ser
65                  70                  75                  80 agg ttc agt gga agt ggg tct ggg aga gat tat tcc ttc agc atc agc      288
Arg Phe Ser Gly Ser Gly Ser Gly Arg Asp Tyr Ser Phe Ser Ile Ser
                85                  90                  95 aac ctg gag cct gaa gat att gca act tat tac tgt cta cag tat gat      336
Asn Leu Glu Pro Glu Asp Ile Ala Thr Tyr Tyr Cys Leu Gln Tyr Asp
            100                 105                 110 aat ctt ccg tat acg ttc gga tcg ggg acc aag ctg gaa ata aaa cgt      384
Asn Leu Pro Tyr Thr Phe Gly Ser Gly Thr Lys Leu Glu Ile Lys Arg
        115                 120                 125 acg gtg gct gca cca tct gtc ttc atc ttc ccg cca tct gat gag cag      432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat      480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg      528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc      576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa      624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc      672
His Lys Val Tyr Ala Cys Glu Val Thr His Gln Gly Leu Ser Ser Pro
    210                 215                 220 gtc aca aag agc ttc aac agg gga gag tgt tga                          705
Val Thr Lys Ser Phe Asn Arg Gly Glu Cys
225                 230
```

<210> SEQ ID NO 131
<211> LENGTH: 234
<212> TYPE: PRT
<213> ORGANISM: Artificial
<220> FEATURE:
<223> OTHER INFORMATION: Synthetic Construct

<400> SEQUENCE: 131

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45
```

```
Ile Asn Lys Asn Ile Ala Trp His Gln His Lys Pro Gly Lys Gly Pro
        50                  55                  60

Arg Leu Leu Ile Trp Tyr Thr Ser Thr Leu Gln Pro Gly Ile Pro Ser
 65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Pro Tyr Thr Phe Gly Ser Gly Thr Lys Leu Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```

<210> SEQ ID NO 132
<211> LENGTH: 1395
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1395)

<400> SEQUENCE: 132

```
atg gga tgg agc tat atc atc ctc ttt ttg gta gca aca gtt aca gat      48
Met Gly Trp Ser Tyr Ile Ile Leu Phe Leu Val Ala Thr Val Thr Asp
 1               5                  10                  15 gtc cac tcc cag gtc caa ctg cag cag cct ggg gct gag ctt gtg aag      96
Val His Ser Gln Val Gln Leu Gln Gln Pro Gly Ala Glu Leu Val Lys
                20                  25                  30 cct ggg gct tca gtg aag ttg tcc tgc aag gct tct ggc tac acc ttc     144
Pro Gly Ala Ser Val Lys Leu Ser Cys Lys Ala Ser Gly Tyr Thr Phe
            35                  40                  45 acc agc tac tgg atg cac tgg gtg aag cag agg cct gga caa ggc ctt     192
Thr Ser Tyr Trp Met His Trp Val Lys Gln Arg Pro Gly Gln Gly Leu
        50                  55                  60 gag tgg att gga gag att aat cct tac aat ggt ggt act aac tac aat     240
Glu Trp Ile Gly Glu Ile Asn Pro Tyr Asn Gly Gly Thr Asn Tyr Asn
 65                  70                  75                  80 gag aag ttc aag agc aag gcc aca ctg act gta gac aaa tcc tcc agc     288
Glu Lys Phe Lys Ser Lys Ala Thr Leu Thr Val Asp Lys Ser Ser Ser
                85                  90                  95 aca gcc tac atg caa ctc agc agc ctg aca tct gag gac tct gcg gtc     336
Thr Ala Tyr Met Gln Leu Ser Ser Leu Thr Ser Glu Asp Ser Ala Val
            100                 105                 110
```

| | | |
|---|---|---|
| tat tac tgt aca ata tgg aag ttg ggg act tac tgg ggc caa ggg act<br>Tyr Tyr Cys Thr Ile Trp Lys Leu Gly Thr Tyr Trp Gly Gln Gly Thr<br>         115                        120                        125 | 384 | |
| ctg gtc act gtc tct gca gct agc acc aag ggc cca tcg gtc ttc ccc<br>Leu Val Thr Val Ser Ala Ala Ser Thr Lys Gly Pro Ser Val Phe Pro<br>130                       135                       140 | 432 | |
| ctg gca ccc tcc tcc aag agc acc tct ggg ggc aca gcg gcc ctg ggc<br>Leu Ala Pro Ser Ser Lys Ser Thr Ser Gly Gly Thr Ala Ala Leu Gly<br>145                     150                     155                   160 | 480 | |
| tgc ctg gtc aag gac tac ttc ccc gaa ccg gtg acg gtg tcg tgg aac<br>Cys Leu Val Lys Asp Tyr Phe Pro Glu Pro Val Thr Val Ser Trp Asn<br>                   165                       170                     175 | 528 | |
| tca ggc gcc ctg acc agc ggc gtg cac acc ttc ccg gct gtc cta cag<br>Ser Gly Ala Leu Thr Ser Gly Val His Thr Phe Pro Ala Val Leu Gln<br>                  180                      185                     190 | 576 | |
| tcc tca gga ctc tac tcc ctc agc agc gtg gtg acc gtg ccc tcc agc<br>Ser Ser Gly Leu Tyr Ser Leu Ser Ser Val Val Thr Val Pro Ser Ser<br>         195                       200                     205 | 624 | |
| agc ttg ggc acc cag acc tac atc tgc aac gtg aat cac aag ccc agc<br>Ser Leu Gly Thr Gln Thr Tyr Ile Cys Asn Val Asn His Lys Pro Ser<br>210                       215                       220 | 672 | |
| aac acc aag gtg gac aag aaa gtt gag ccc aaa tct tgt gac aaa act<br>Asn Thr Lys Val Asp Lys Lys Val Glu Pro Lys Ser Cys Asp Lys Thr<br>225                     230                     235                   240 | 720 | |
| cac aca tgc cca ccg tgc cca gca cct gaa ctc ctg ggg gga ccg tca<br>His Thr Cys Pro Pro Cys Pro Ala Pro Glu Leu Leu Gly Gly Pro Ser<br>                  245                      250                     255 | 768 | |
| gtc ttc ctc ttc ccc cca aaa ccc aag gac acc ctc atg atc tcc cgg<br>Val Phe Leu Phe Pro Pro Lys Pro Lys Asp Thr Leu Met Ile Ser Arg<br>                 260                       265                     270 | 816 | |
| acc cct gag gtc aca tgc gtg gtg gtg gac gtg agc cac gaa gac cct<br>Thr Pro Glu Val Thr Cys Val Val Val Asp Val Ser His Glu Asp Pro<br>              275                     280                     285 | 864 | |
| gag gtc aag ttc aac tgg tac gtg gac ggc gtg gag gtg cat aat gcc<br>Glu Val Lys Phe Asn Trp Tyr Val Asp Gly Val Glu Val His Asn Ala<br>290                     295                     300 | 912 | |
| aag aca aag ccg cgg gag gag cag tac aac agc acg tac cgt gtg gtc<br>Lys Thr Lys Pro Arg Glu Glu Gln Tyr Asn Ser Thr Tyr Arg Val Val<br>305                     310                     315                   320 | 960 | |
| agc gtc ctc acc gtc ctg cac cag gac tgg ctg aat ggc aag gag tac<br>Ser Val Leu Thr Val Leu His Gln Asp Trp Leu Asn Gly Lys Glu Tyr<br>                  325                      330                     335 | 1008 | |
| aag tgc aag gtc tcc aac aaa gcc ctc cca gcc ccc atc gag aaa acc<br>Lys Cys Lys Val Ser Asn Lys Ala Leu Pro Ala Pro Ile Glu Lys Thr<br>                 340                      345                     350 | 1056 | |
| atc tcc aaa gcc aaa ggg cag ccc cga gaa cca cag gtg tac acc ctg<br>Ile Ser Lys Ala Lys Gly Gln Pro Arg Glu Pro Gln Val Tyr Thr Leu<br>         355                       360                     365 | 1104 | |
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>370                       375                     380 | 1152 | |
| ctg gtc aaa ggc ttc tat ccc agc gac atc gcc gtg gag tgg gag agc<br>Leu Val Lys Gly Phe Tyr Pro Ser Asp Ile Ala Val Glu Trp Glu Ser<br>385                     390                     395                   400 | 1200 | |
| aat ggg cag ccg gag aac aac tac aag acc acg cct ccc gtg ctg gac<br>Asn Gly Gln Pro Glu Asn Asn Tyr Lys Thr Thr Pro Pro Val Leu Asp<br>                  405                      410                     415 | 1248 | |
| tcc gac ggc tcc ttc ttc ctc tac agc aag ctc acc gtg gac aag agc<br>Ser Asp Gly Ser Phe Phe Leu Tyr Ser Lys Leu Thr Val Asp Lys Ser<br>                 420                     425                     430 | 1296 | |

```
agg tgg cag cag ggg aac gtc ttc tca tgc tcc gtg atg cat gag gct    1344
Arg Trp Gln Gln Gly Asn Val Phe Ser Cys Ser Val Met His Glu Ala
        435                 440                 445 ctg cac aac cac tac acg cag aag agc ctc tcc ctg tct ccg ggt aaa    1392
Leu His Asn His Tyr Thr Gln Lys Ser Leu Ser Leu Ser Pro Gly Lys
    450                 455                 460 tga                                                                1395
```

<210> SEQ ID NO 133
<211> LENGTH: 464
<212> TYPE: PRT
<213> ORGANISM: Artificial
<220> FEATURE:
<223> OTHER INFORMATION: Synthetic Construct

<400> SEQUENCE: 133

```
Met Gly Trp Ser Tyr Ile Ile Leu Phe Leu Val Ala Thr Val Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Tyr Asn Gly Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Ile Trp Lys Leu Gly Thr Tyr Trp Gly Gln Gly Thr
        115                 120                 125

Leu Val Thr Val Ser Ala Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300
```

```
Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 134
<211> LENGTH: 711
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(711)

<400> SEQUENCE: 134 atg gac atg agg gtt cct gct cac gtt ttt ggc ttc ttg ttg ctc tgg      48
Met Asp Met Arg Val Pro Ala His Val Phe Gly Phe Leu Leu Leu Trp
1               5                   10                  15 ttt cca ggt acc aga tgt gac atc cag atg acc cag tct cca tcc tcc      96
Phe Pro Gly Thr Arg Cys Asp Ile Gln Met Thr Gln Ser Pro Ser Ser
            20                  25                  30 tta tct gcc tct ctg gga gaa aga gtc agt ctc act tgt cgg gca agt     144
Leu Ser Ala Ser Leu Gly Glu Arg Val Ser Leu Thr Cys Arg Ala Ser
        35                  40                  45 cag gaa att agt ggt tac tta agc tgg ctt cag cag aaa cca gat gga     192
Gln Glu Ile Ser Gly Tyr Leu Ser Trp Leu Gln Gln Lys Pro Asp Gly
    50                  55                  60 act att aaa cgc ctg atc tac gcc gca tcc act tta gat tct ggt gtc     240
Thr Ile Lys Arg Leu Ile Tyr Ala Ala Ser Thr Leu Asp Ser Gly Val
65                  70                  75                  80 cca aaa agg ttc agt ggc agt agg tct ggg tca gat tat tct ctc acc     288
Pro Lys Arg Phe Ser Gly Ser Arg Ser Gly Ser Asp Tyr Ser Leu Thr
                85                  90                  95 atc agc agc ctt gag tct gaa gat ttt gca gac tat tac tgt cta caa     336
Ile Ser Ser Leu Glu Ser Glu Asp Phe Ala Asp Tyr Tyr Cys Leu Gln
            100                 105                 110 tat gct agt tat cct cgg acg ttc ggt gga ggc acc aag ctg gaa atc     384
Tyr Ala Ser Tyr Pro Arg Thr Phe Gly Gly Gly Thr Lys Leu Glu Ile
        115                 120                 125 aaa cgt acg gtg gct gca cca tct gtc ttc atc ttc ccg cca tct gat     432
Lys Arg Thr Val Ala Ala Pro Ser Val Phe Ile Phe Pro Pro Ser Asp
    130                 135                 140
```

```
gag cag ttg aaa tct gga act gcc tct gtt gtg tgc ctg ctg aat aac      480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc      528
Phe Tyr Pro Arg Glu Ala Lys Val Gln Trp Lys Val Asp Asn Ala Leu
            165                 170                 175 caa tcg ggt aac tcc cag gag agt gtc aca gag cag gac agc aag gac      576
Gln Ser Gly Asn Ser Gln Glu Ser Val Thr Glu Gln Asp Ser Lys Asp
        180                 185                 190 agc acc tac agc ctc agc agc acc ctg acg ctg agc aaa gca gac tac      624
Ser Thr Tyr Ser Leu Ser Ser Thr Leu Thr Leu Ser Lys Ala Asp Tyr
    195                 200                 205 gag aaa cac aaa gtc tac gcc tgc gaa gtc acc cat cag ggc ctg agc      672
Glu Lys His Lys Val Tyr Ala Cys Glu Val Thr His Gln Gly Leu Ser
210                 215                 220 tcg ccc gtc aca aag agc ttc aac agg gga gag tgt tga                  711
Ser Pro Val Thr Lys Ser Phe Asn Arg Gly Glu Cys
225                 230                 235
```

<210> SEQ ID NO 135
<211> LENGTH: 236
<212> TYPE: PRT
<213> ORGANISM: Artificial
<220> FEATURE:
<223> OTHER INFORMATION: Synthetic Construct

<400> SEQUENCE: 135

```
Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Glu Ile Ser Gly Tyr Leu Ser Trp Leu Gln Gln Lys Pro Asp Gly
    50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Tyr Ala Ser Tyr Pro Arg Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

```
<210> SEQ ID NO 136
<211> LENGTH: 1404
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1404)

<400> SEQUENCE: 136 atg ggt tgg agc tgt atc atc ttc ttt ctg gta gca aca gct aca ggt      48
Met Gly Trp Ser Cys Ile Ile Phe Phe Leu Val Ala Thr Ala Thr Gly
1               5                   10                  15 gtg cac tcc cag gtc cag ctg cag cag tct ggg gct gag ctg gtg agg      96
Val His Ser Gln Val Gln Leu Gln Gln Ser Gly Ala Glu Leu Val Arg
            20                  25                  30 cct ggg gtc tca gtg aag att tcc tgc aag ggt tct ggc tac aca ttc     144
Pro Gly Val Ser Val Lys Ile Ser Cys Lys Gly Ser Gly Tyr Thr Phe
        35                  40                  45 act gtt tat tct ttg cac tgg gtg aag cag agt cat gca agg agt cta     192
Thr Val Tyr Ser Leu His Trp Val Lys Gln Ser His Ala Arg Ser Leu
    50                  55                  60 gag tgg att gga gtt att agt act tac tat ggt gat gct atc tac aac     240
Glu Trp Ile Gly Val Ile Ser Thr Tyr Tyr Gly Asp Ala Ile Tyr Asn
65                  70                  75                  80 cag aag ttc aag ggc aag gcc aca atg act gta gac aaa tcc tcc agc     288
Gln Lys Phe Lys Gly Lys Ala Thr Met Thr Val Asp Lys Ser Ser Ser
                85                  90                  95 aca gcc tat atg gaa ctt gcc aga ctg aca tct gag gat tct gcc atc     336
Thr Ala Tyr Met Glu Leu Ala Arg Leu Thr Ser Glu Asp Ser Ala Ile
            100                 105                 110 tat tac tgt gca aga gag ggg aat ggt aac ccc ctt gac tac tgg ggc     384
Tyr Tyr Cys Ala Arg Glu Gly Asn Gly Asn Pro Leu Asp Tyr Trp Gly
        115                 120                 125 caa ggc acc act ctc aca gtc tcc tca gct agc acc aag ggc cca tcg     432
Gln Gly Thr Thr Leu Thr Val Ser Ser Ala Ser Thr Lys Gly Pro Ser
    130                 135                 140 gtc ttc ccc ctg gca ccc tcc tcc aag agc acc tct ggg ggc aca gcg     480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccg gtg acg gtg     528
Ala Leu Gly Cys Leu Val Lys Asp Tyr Phe Pro Glu Pro Val Thr Val
                165                 170                 175 tcg tgg aac tca ggc gcc ctg acc agc ggc gtg cac acc ttc ccg gct     576
Ser Trp Asn Ser Gly Ala Leu Thr Ser Gly Val His Thr Phe Pro Ala
            180                 185                 190 gtc cta cag tcc tca gga ctc tac tcc ctc agc agc gtg gtg acc gtg     624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac     672
Pro Ser Ser Ser Leu Gly Thr Gln Thr Tyr Ile Cys Asn Val Asn His
    210                 215                 220 aag ccc agc aac acc aag gtg gac aag aaa gtt gag ccc aaa tct tgt     720
Lys Pro Ser Asn Thr Lys Val Asp Lys Lys Val Glu Pro Lys Ser Cys
225                 230                 235                 240 gac aaa act cac aca tgc cca ccg tgc cca gca cct gaa ctc ctg ggg     768
Asp Lys Thr His Thr Cys Pro Pro Cys Pro Ala Pro Glu Leu Leu Gly
                245                 250                 255
```

```
gga ccg tca gtc ttc ctc ttc ccc cca aaa ccc aag gac acc ctc atg    816
Gly Pro Ser Val Phe Leu Phe Pro Pro Lys Pro Lys Asp Thr Leu Met
        260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
    275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
290                 295                 300 cat aat gcc aag aca aag ccg cgg gag gag cag tac aac agc acg tac    960
His Asn Ala Lys Thr Lys Pro Arg Glu Glu Gln Tyr Asn Ser Thr Tyr
305                 310                 315                 320 cgt gtg gtc agc gtc ctc acc gtc ctg cac cag gac tgg ctg aat ggc   1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc   1056
Lys Glu Tyr Lys Cys Lys Val Ser Asn Lys Ala Leu Pro Ala Pro Ile
            340                 345                 350 gag aaa acc atc tcc aaa gcc aaa ggg cag ccc cga gaa cca cag gtg   1104
Glu Lys Thr Ile Ser Lys Ala Lys Gly Gln Pro Arg Glu Pro Gln Val
        355                 360                 365 tac acc ctg ccc cca tcc cgg gat gag ctg acc aag aac cag gtc agc   1152
Tyr Thr Leu Pro Pro Ser Arg Asp Glu Leu Thr Lys Asn Gln Val Ser
370                 375                 380 ctg acc tgc ctg gtc aaa ggc ttc tat ccc agc gac atc gcc gtg gag   1200
Leu Thr Cys Leu Val Lys Gly Phe Tyr Pro Ser Asp Ile Ala Val Glu
385                 390                 395                 400 tgg gag agc aat ggg cag ccg gag aac aac tac aag acc acg cct ccc   1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg   1296
Val Leu Asp Ser Asp Gly Ser Phe Phe Leu Tyr Ser Lys Leu Thr Val
            420                 425                 430 gac aag agc agg tgg cag cag ggg aac gtc ttc tca tgc tcc gtg atg   1344
Asp Lys Ser Arg Trp Gln Gln Gly Asn Val Phe Ser Cys Ser Val Met
        435                 440                 445 cat gag gct ctg cac aac cac tac acg cag aag agc ctc tcc ctg tct   1392
His Glu Ala Leu His Asn His Tyr Thr Gln Lys Ser Leu Ser Leu Ser
450                 455                 460 ccg ggt aaa tga                                                    1404
Pro Gly Lys
465

<210> SEQ ID NO 137
<211> LENGTH: 467
<212> TYPE: PRT
<213> ORGANISM: Artificial
<220> FEATURE:
<223> OTHER INFORMATION: Synthetic Construct

<400> SEQUENCE: 137

Met Gly Trp Ser Cys Ile Ile Phe Phe Leu Val Ala Thr Ala Thr Gly
1               5                   10                  15

Val His Ser Gln Val Gln Leu Gln Gln Ser Gly Ala Glu Leu Val Arg
            20                  25                  30

Pro Gly Val Ser Val Lys Ile Ser Cys Lys Gly Ser Gly Tyr Thr Phe
        35                  40                  45

Thr Val Tyr Ser Leu His Trp Val Lys Gln Ser His Ala Arg Ser Leu
    50                  55                  60
```

```
Glu Trp Ile Gly Val Ile Ser Thr Tyr Tyr Gly Asp Ala Ile Tyr Asn
 65                  70                  75                  80

Gln Lys Phe Lys Gly Lys Ala Thr Met Thr Val Asp Lys Ser Ser Ser
                 85                  90                  95

Thr Ala Tyr Met Glu Leu Ala Arg Leu Thr Ser Glu Asp Ser Ala Ile
            100                 105                 110

Tyr Tyr Cys Ala Arg Glu Gly Asn Gly Asn Pro Leu Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 138
<211> LENGTH: 714
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(714)

<400> SEQUENCE: 138

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tcc aga gga caa att gtt ctc acc cag tct cca gca atc      96
Val Ile Met Ser Arg Gly Gln Ile Val Leu Thr Gln Ser Pro Ala Ile
            20                  25                  30 atg tct gca tct cta ggg gaa cgg gtc acc atg acc tgc act gcc agc     144
Met Ser Ala Ser Leu Gly Glu Arg Val Thr Met Thr Cys Thr Ala Ser
        35                  40                  45 tca agt gta agt tcc agt tac ttg cac tgg tac cag cag aag cca gga     192
Ser Ser Val Ser Ser Ser Tyr Leu His Trp Tyr Gln Gln Lys Pro Gly
    50                  55                  60 tcc tcc ccc aaa ctc tgg att tat agc aca tcc aac ctg gct tct gga     240
Ser Ser Pro Lys Leu Trp Ile Tyr Ser Thr Ser Asn Leu Ala Ser Gly
65                  70                  75                  80 gtc cca gct cgc ttc agt ggc agt ggg tct ggg acc tct tac tct ctc     288
Val Pro Ala Arg Phe Ser Gly Ser Gly Ser Gly Thr Ser Tyr Ser Leu
                85                  90                  95 aca atc acc aac atg gag gct gaa gat tct gcc act tat tac tgc cac     336
Thr Ile Thr Asn Met Glu Ala Glu Asp Ser Ala Thr Tyr Tyr Cys His
            100                 105                 110 cag tat cat cgt tcc ccg ctc acg ttc ggt gct ggg acc aag ctg gag     384
Gln Tyr His Arg Ser Pro Leu Thr Phe Gly Ala Gly Thr Lys Leu Glu
        115                 120                 125 ctg aaa cgt acg gtg gct gca cca tct gtc ttc atc ttc ccg cca tct     432
Leu Lys Arg Thr Val Ala Ala Pro Ser Val Phe Ile Phe Pro Pro Ser
    130                 135                 140 gat gag cag ttg aaa tct gga act gcc tct gtt gtg tgc ctg ctg aat     480
Asp Glu Gln Leu Lys Ser Gly Thr Ala Ser Val Val Cys Leu Leu Asn
145                 150                 155                 160 aac ttc tat ccc aga gag gcc aaa gta cag tgg aag gtg gat aac gcc     528
Asn Phe Tyr Pro Arg Glu Ala Lys Val Gln Trp Lys Val Asp Asn Ala
                165                 170                 175 ctc caa tcg ggt aac tcc cag gag agt gtc aca gag cag gac agc aag     576
Leu Gln Ser Gly Asn Ser Gln Glu Ser Val Thr Glu Gln Asp Ser Lys
            180                 185                 190 gac agc acc tac agc ctc agc agc acc ctg acg ctg agc aaa gca gac     624
Asp Ser Thr Tyr Ser Leu Ser Ser Thr Leu Thr Leu Ser Lys Ala Asp
        195                 200                 205 tac gag aaa cac aaa gtc tac gcc tgc gaa gtc acc cat cag ggc ctg     672
Tyr Glu Lys His Lys Val Tyr Ala Cys Glu Val Thr His Gln Gly Leu
    210                 215                 220 agc tcg ccc gtc aca aag agc ttc aac agg gga gag tgt tga             714
Ser Ser Pro Val Thr Lys Ser Phe Asn Arg Gly Glu Cys
225                 230                 235
```

<210> SEQ ID NO 139
<211> LENGTH: 237
<212> TYPE: PRT
<213> ORGANISM: Artificial
<220> FEATURE:
<223> OTHER INFORMATION: Synthetic Construct

<400> SEQUENCE: 139

| | | | | | | | | | | | | | | | |
|---|---|---|---|---|---|---|---|---|---|---|---|---|---|---|---|
| Met | Asp | Phe | Gln | Val | Gln | Ile | Phe | Ser | Phe | Leu | Leu | Ile | Ser | Ala | Ser |
| 1 | | | | 5 | | | | | 10 | | | | | 15 | |
| Val | Ile | Met | Ser | Arg | Gly | Gln | Ile | Val | Leu | Thr | Gln | Ser | Pro | Ala | Ile |
| | | | 20 | | | | | 25 | | | | | 30 | | |
| Met | Ser | Ala | Ser | Leu | Gly | Glu | Arg | Val | Thr | Met | Thr | Cys | Thr | Ala | Ser |
| | | | 35 | | | | | 40 | | | | | 45 | | |
| Ser | Ser | Val | Ser | Ser | Ser | Tyr | Leu | His | Trp | Tyr | Gln | Gln | Lys | Pro | Gly |
| | 50 | | | | | 55 | | | | | 60 | | | | |
| Ser | Ser | Pro | Lys | Leu | Trp | Ile | Tyr | Ser | Thr | Ser | Asn | Leu | Ala | Ser | Gly |
| 65 | | | | | 70 | | | | | 75 | | | | | 80 |
| Val | Pro | Ala | Arg | Phe | Ser | Gly | Ser | Gly | Ser | Gly | Thr | Ser | Tyr | Ser | Leu |
| | | | | 85 | | | | | 90 | | | | | 95 | |
| Thr | Ile | Thr | Asn | Met | Glu | Ala | Glu | Asp | Ser | Ala | Thr | Tyr | Tyr | Cys | His |
| | | | 100 | | | | | 105 | | | | | 110 | | |
| Gln | Tyr | His | Arg | Ser | Pro | Leu | Thr | Phe | Gly | Ala | Gly | Thr | Lys | Leu | Glu |
| | | | 115 | | | | | 120 | | | | | 125 | | |
| Leu | Lys | Arg | Thr | Val | Ala | Ala | Pro | Ser | Val | Phe | Ile | Phe | Pro | Pro | Ser |
| 130 | | | | | 135 | | | | | 140 | | | | | |
| Asp | Glu | Gln | Leu | Lys | Ser | Gly | Thr | Ala | Ser | Val | Val | Cys | Leu | Leu | Asn |
| 145 | | | | | 150 | | | | | 155 | | | | | 160 |
| Asn | Phe | Tyr | Pro | Arg | Glu | Ala | Lys | Val | Gln | Trp | Lys | Val | Asp | Asn | Ala |
| | | | | 165 | | | | | 170 | | | | | 175 | |
| Leu | Gln | Ser | Gly | Asn | Ser | Gln | Glu | Ser | Val | Thr | Glu | Gln | Asp | Ser | Lys |
| | | | 180 | | | | | 185 | | | | | 190 | | |
| Asp | Ser | Thr | Tyr | Ser | Leu | Ser | Ser | Thr | Leu | Thr | Leu | Ser | Lys | Ala | Asp |
| | | | 195 | | | | | 200 | | | | | 205 | | |
| Tyr | Glu | Lys | His | Lys | Val | Tyr | Ala | Cys | Glu | Val | Thr | His | Gln | Gly | Leu |
| | | | 210 | | | | | 215 | | | | | 220 | | |
| Ser | Ser | Pro | Val | Thr | Lys | Ser | Phe | Asn | Arg | Gly | Glu | Cys | | | |
| 225 | | | | | 230 | | | | | 235 | | | | | |

<210> SEQ ID NO 140
<211> LENGTH: 1398
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1398)

<400> SEQUENCE: 140

| atg | gct | gtc | ctg | ggg | ctg | ctt | ctc | tgc | ctg | gtg | act | ttc | cca | agc | tgt | 48 |
|---|---|---|---|---|---|---|---|---|---|---|---|---|---|---|---|---|
| Met | Ala | Val | Leu | Gly | Leu | Leu | Leu | Cys | Leu | Val | Thr | Phe | Pro | Ser | Cys | |
| 1 | | | | 5 | | | | | 10 | | | | | 15 | | |

| gcc | ctg | tcc | cag | gtg | cag | ctg | aag | gag | tca | gga | cct | ggc | ctg | gtg | gcg | 96 |
|---|---|---|---|---|---|---|---|---|---|---|---|---|---|---|---|---|
| Ala | Leu | Ser | Gln | Val | Gln | Leu | Lys | Glu | Ser | Gly | Pro | Gly | Leu | Val | Ala | |
| | | | 20 | | | | | 25 | | | | | 30 | | | |

| ccc | tca | cag | agc | ctg | tcc | atc | aca | tgc | acc | gtc | tca | gga | ttc | tca | tta | 144 |
|---|---|---|---|---|---|---|---|---|---|---|---|---|---|---|---|---|
| Pro | Ser | Gln | Ser | Leu | Ser | Ile | Thr | Cys | Thr | Val | Ser | Gly | Phe | Ser | Leu | |
| | | | 35 | | | | | 40 | | | | | 45 | | | |

| agt | agt | tat | ggt | gta | cac | tgg | gtt | cgc | cag | cct | cca | gga | aag | ggt | ctg | 192 |
|---|---|---|---|---|---|---|---|---|---|---|---|---|---|---|---|---|
| Ser | Ser | Tyr | Gly | Val | His | Trp | Val | Arg | Gln | Pro | Pro | Gly | Lys | Gly | Leu | |
| | 50 | | | | | 55 | | | | | 60 | | | | | |

-continued

| | | |
|---|---|---|
| gag tgg ctg gga gtg ata tgg agg gat gga agc aca acc tat aat tca<br>Glu Trp Leu Gly Val Ile Trp Arg Asp Gly Ser Thr Thr Tyr Asn Ser<br>65                           70                     75                    80 | 240 | |
| gct ctc aaa tcc aga ctg agc atc agc aag gac ggc tcc aag agc caa<br>Ala Leu Lys Ser Arg Leu Ser Ile Ser Lys Asp Gly Ser Lys Ser Gln<br>                    85                     90                    95 | 288 | |
| gtt ttc tta aaa atg aac agt ctc caa act gat gac aca gcc atg tac<br>Val Phe Leu Lys Met Asn Ser Leu Gln Thr Asp Asp Thr Ala Met Tyr<br>100                         105                   110 | 336 | |
| tac tgt gcc aga aat tgg aat ggt ctt atg gac tac tgg ggt caa gga<br>Tyr Cys Ala Arg Asn Trp Asn Gly Leu Met Asp Tyr Trp Gly Gln Gly<br>               115                   120                   125 | 384 | |
| acc tca gtc acc gtc tcc tca gct agc acc aag ggc cca tcg gtc ttc<br>Thr Ser Val Thr Val Ser Ser Ala Ser Thr Lys Gly Pro Ser Val Phe<br>130                         135                   140 | 432 | |
| ccc ctg gca ccc tcc tcc aag agc acc tct ggg ggc aca gcg gcc ctg<br>Pro Leu Ala Pro Ser Ser Lys Ser Thr Ser Gly Gly Thr Ala Ala Leu<br>145                       150                   155                  160 | 480 | |
| ggc tgc ctg gtc aag gac tac ttc ccc gaa ccg gtg acg gtg tcg tgg<br>Gly Cys Leu Val Lys Asp Tyr Phe Pro Glu Pro Val Thr Val Ser Trp<br>               165                   170                   175 | 528 | |
| aac tca ggc gcc ctg acc agc ggc gtg cac acc ttc ccg gct gtc cta<br>Asn Ser Gly Ala Leu Thr Ser Gly Val His Thr Phe Pro Ala Val Leu<br>                    180                     185                   190 | 576 | |
| cag tcc tca gga ctc tac tcc ctc agc agc gtg gtg acc gtg ccc tcc<br>Gln Ser Ser Gly Leu Tyr Ser Leu Ser Ser Val Val Thr Val Pro Ser<br>               195                   200                   205 | 624 | |
| agc agc ttg ggc acc cag acc tac atc tgc aac gtg aat cac aag ccc<br>Ser Ser Leu Gly Thr Gln Thr Tyr Ile Cys Asn Val Asn His Lys Pro<br>210                         215                     220 | 672 | |
| agc aac acc aag gtg gac aag aaa gtt gag ccc aaa tct tgt gac aaa<br>Ser Asn Thr Lys Val Asp Lys Lys Val Glu Pro Lys Ser Cys Asp Lys<br>225                       230                   235                  240 | 720 | |
| act cac aca tgc cca ccg tgc cca gca cct gaa ctc ctg ggg gga ccg<br>Thr His Thr Cys Pro Pro Cys Pro Ala Pro Glu Leu Leu Gly Gly Pro<br>                    245                     250                   255 | 768 | |
| tca gtc ttc ctc ttc ccc cca aaa ccc aag gac acc ctc atg atc tcc<br>Ser Val Phe Leu Phe Pro Pro Lys Pro Lys Asp Thr Leu Met Ile Ser<br>260                         265                     270 | 816 | |
| cgg acc cct gag gtc aca tgc gtg gtg gtg gac gtg agc cac gaa gac<br>Arg Thr Pro Glu Val Thr Cys Val Val Val Asp Val Ser His Glu Asp<br>               275                   280                   285 | 864 | |
| cct gag gtc aag ttc aac tgg tac gtg gac ggc gtg gag gtg cat aat<br>Pro Glu Val Lys Phe Asn Trp Tyr Val Asp Gly Val Glu Val His Asn<br>290                         295                     300 | 912 | |
| gcc aag aca aag ccg cgg gag gag cag tac aac agc acg tac cgt gtg<br>Ala Lys Thr Lys Pro Arg Glu Glu Gln Tyr Asn Ser Thr Tyr Arg Val<br>305                       310                   315                  320 | 960 | |
| gtc agc gtc ctc acc gtc ctg cac cag gac tgg ctg aat ggc aag gag<br>Val Ser Val Leu Thr Val Leu His Gln Asp Trp Leu Asn Gly Lys Glu<br>               325                   330                   335 | 1008 | |
| tac aag tgc aag gtc tcc aac aaa gcc ctc cca gcc ccc atc gag aaa<br>Tyr Lys Cys Lys Val Ser Asn Lys Ala Leu Pro Ala Pro Ile Glu Lys<br>                    340                     345                   350 | 1056 | |
| acc atc tcc aaa gcc aaa ggg cag ccc cga gaa cca cag gtg tac acc<br>Thr Ile Ser Lys Ala Lys Gly Gln Pro Arg Glu Pro Gln Val Tyr Thr<br>               355                   360                   365 | 1104 | |
| ctg ccc cca tcc cgg gat gag ctg acc aag aac cag gtc agc ctg acc<br>Leu Pro Pro Ser Arg Asp Glu Leu Thr Lys Asn Gln Val Ser Leu Thr<br>370                         375                     380 | 1152 | |

```
tgc ctg gtc aaa ggc ttc tat ccc agc gac atc gcc gtg gag tgg gag      1200
Cys Leu Val Lys Gly Phe Tyr Pro Ser Asp Ile Ala Val Glu Trp Glu
385                 390                 395                 400 agc aat ggg cag ccg gag aac aac tac aag acc acg cct ccc gtg ctg      1248
Ser Asn Gly Gln Pro Glu Asn Asn Tyr Lys Thr Thr Pro Pro Val Leu
            405                 410                 415 gac tcc gac ggc tcc ttc ttc ctc tac agc aag ctc acc gtg gac aag      1296
Asp Ser Asp Gly Ser Phe Phe Leu Tyr Ser Lys Leu Thr Val Asp Lys
420                 425                 430 agc agg tgg cag cag ggg aac gtc ttc tca tgc tcc gtg atg cat gag      1344
Ser Arg Trp Gln Gln Gly Asn Val Phe Ser Cys Ser Val Met His Glu
        435                 440                 445 gct ctg cac aac cac tac acg cag aag agc ctc tcc ctg tct ccg ggt      1392
Ala Leu His Asn His Tyr Thr Gln Lys Ser Leu Ser Leu Ser Pro Gly
        450                 455                 460 aaa tga                                                              1398
Lys
465

<210> SEQ ID NO 141
<211> LENGTH: 465
<212> TYPE: PRT
<213> ORGANISM: Artificial
<220> FEATURE:
<223> OTHER INFORMATION: Synthetic Construct

<400> SEQUENCE: 141

Met Ala Val Leu Gly Leu Leu Leu Cys Leu Val Thr Phe Pro Ser Cys
1               5                   10                  15

Ala Leu Ser Gln Val Gln Leu Lys Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Ser Ser Tyr Gly Val His Trp Val Arg Gln Pro Pro Gly Lys Gly Leu
        50                  55                  60

Glu Trp Leu Gly Val Ile Trp Arg Asp Gly Ser Thr Thr Tyr Asn Ser
65                  70                  75                  80

Ala Leu Lys Ser Arg Leu Ser Ile Ser Lys Asp Gly Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Asn Trp Asn Gly Leu Met Asp Tyr Trp Gly Gln Gly
        115                 120                 125

Thr Ser Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240
```

-continued

```
Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
450                 455                 460

Lys
465

<210> SEQ ID NO 142
<211> LENGTH: 705
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(705)

<400> SEQUENCE: 142 atg atg tcc tct gct cag ttc ctt ggt ctc ctg ttg ctc tgt ttt caa      48
Met Met Ser Ser Ala Gln Phe Leu Gly Leu Leu Leu Leu Cys Phe Gln
1               5                   10                  15 ggt acc aga tgt gat atc cag atg aca cag act aca tcc tcc ctg tct      96
Gly Thr Arg Cys Asp Ile Gln Met Thr Gln Thr Thr Ser Ser Leu Ser
                20                  25                  30 gcc tct ctg gga gac aga gtc acc atc agt tgc agg gca agt cag gac     144
Ala Ser Leu Gly Asp Arg Val Thr Ile Ser Cys Arg Ala Ser Gln Asp
            35                  40                  45 att agc tat tat tta aac tgg tat cag cag aga cca gat gga act gtt     192
Ile Ser Tyr Tyr Leu Asn Trp Tyr Gln Gln Arg Pro Asp Gly Thr Val
        50                  55                  60 aaa ctc ctg atc tac tac aca tca aga tta cac tca gga gtc cca tca     240
Lys Leu Leu Ile Tyr Tyr Thr Ser Arg Leu His Ser Gly Val Pro Ser
65                  70                  75                  80
```

```
agg ttc agt ggc agt ggg tct gga aca gaa tct tct ctc acc att agc        288
Arg Phe Ser Gly Ser Gly Ser Gly Thr Glu Ser Ser Leu Thr Ile Ser
                85                  90                  95 aat ctg gaa caa gaa gat att gcc act tac ttt tgc caa cag ggt cat        336
Asn Leu Glu Gln Glu Asp Ile Ala Thr Tyr Phe Cys Gln Gln Gly His
            100                 105                 110 acg gtt ccg tgg acg ttc ggt gga ggc acc aag ctg gaa atc aaa cgt        384
Thr Val Pro Trp Thr Phe Gly Gly Gly Thr Lys Leu Glu Ile Lys Arg
        115                 120                 125 acg gtg gct gca cca tct gtc ttc atc ttc ccg cca tct gat gag cag        432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat        480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg        528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc        576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa        624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc        672
His Lys Val Tyr Ala Cys Glu Val Thr His Gln Gly Leu Ser Ser Pro
    210                 215                 220 gtc aca aag agc ttc aac agg gga gag tgt tga                            705
Val Thr Lys Ser Phe Asn Arg Gly Glu Cys
225                 230

<210> SEQ ID NO 143
<211> LENGTH: 234
<212> TYPE: PRT
<213> ORGANISM: Artificial
<220> FEATURE:
<223> OTHER INFORMATION: Synthetic Construct

<400> SEQUENCE: 143

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Tyr Tyr Leu Asn Trp Tyr Gln Gln Arg Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Glu Ser Ser Leu Thr Ile Ser
                85                  90                  95

Asn Leu Glu Gln Glu Asp Ile Ala Thr Tyr Phe Cys Gln Gln Gly His
            100                 105                 110

Thr Val Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160
```

```
Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
        180                 185                 190

Tyr Ser Leu Ser Ser Thr Leu Thr Leu Ser Lys Ala Asp Tyr Glu Lys
    195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 144
<211> LENGTH: 1386
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1386)

<400> SEQUENCE: 144 atg gaa tgt aac tgg ata ctt cct ttt att ctg tcg gta act tca ggg      48
Met Glu Cys Asn Trp Ile Leu Pro Phe Ile Leu Ser Val Thr Ser Gly
1               5                   10                  15 gtc tac tca gag gtt cag ctc cag cag tct ggg act gtg ctg gca agg      96
Val Tyr Ser Glu Val Gln Leu Gln Gln Ser Gly Thr Val Leu Ala Arg
            20                  25                  30 cct ggg gct tca gtg aag atg tcc tgc aag gct tct ggc tac acc ttt     144
Pro Gly Ala Ser Val Lys Met Ser Cys Lys Ala Ser Gly Tyr Thr Phe
        35                  40                  45 acc agc tac tgg atg cac tgg gtg aaa cag agg cct gga cag ggt ctg     192
Thr Ser Tyr Trp Met His Trp Val Lys Gln Arg Pro Gly Gln Gly Leu
    50                  55                  60 gaa tgg att ggc gct att tat cct gga aac agt gat agc tac aac cag     240
Glu Trp Ile Gly Ala Ile Tyr Pro Gly Asn Ser Asp Ser Tyr Asn Gln
65                  70                  75                  80 aag ttc aag ggc aag gcc aaa ctg act gca gtc aca tcc acc agc act     288
Lys Phe Lys Gly Lys Ala Lys Leu Thr Ala Val Thr Ser Thr Ser Thr
                85                  90                  95 gcc tac atg gag ctc agc agc ctg aca aat gag gac tct gcg gtc tat     336
Ala Tyr Met Glu Leu Ser Ser Leu Thr Asn Glu Asp Ser Ala Val Tyr
            100                 105                 110 tac tgt aca agt gtt atg gcc tac tgg ggt caa gga acc tca gtc acc     384
Tyr Cys Thr Ser Val Met Ala Tyr Trp Gly Gln Gly Thr Ser Val Thr
        115                 120                 125 gtc tcc tca gct agc acc aag ggc cca tcg gtc ttc ccc ctg gca ccc     432
Val Ser Ser Ala Ser Thr Lys Gly Pro Ser Val Phe Pro Leu Ala Pro
    130                 135                 140 tcc tcc aag agc acc tct ggg ggc aca gcg gcc ctg ggc tgc ctg gtc     480
Ser Ser Lys Ser Thr Ser Gly Gly Thr Ala Ala Leu Gly Cys Leu Val
145                 150                 155                 160 aag gac tac ttc ccc gaa ccg gtg acg gtg tcg tgg aac tca ggc gcc     528
Lys Asp Tyr Phe Pro Glu Pro Val Thr Val Ser Trp Asn Ser Gly Ala
                165                 170                 175 ctg acc agc ggc gtg cac acc ttc ccg gct gtc cta cag tcc tca gga     576
Leu Thr Ser Gly Val His Thr Phe Pro Ala Val Leu Gln Ser Ser Gly
            180                 185                 190
```

| | | |
|---|---|---|
| ctc tac tcc ctc agc agc gtg gtg acc gtg ccc tcc agc agc ttg ggc<br>Leu Tyr Ser Leu Ser Ser Val Val Thr Val Pro Ser Ser Ser Leu Gly<br>        195                    200                  205 | | 624 |
| acc cag acc tac atc tgc aac gtg aat cac aag ccc agc aac acc aag<br>Thr Gln Thr Tyr Ile Cys Asn Val Asn His Lys Pro Ser Asn Thr Lys<br>210                    215                    220 | | 672 |
| gtg gac aag aaa gtt gag ccc aaa tct tgt gac aaa act cac aca tgc<br>Val Asp Lys Lys Val Glu Pro Lys Ser Cys Asp Lys Thr His Thr Cys<br>225                    230                235              240 | | 720 |
| cca ccg tgc cca gca cct gaa ctc ctg ggg gga ccg tca gtc ttc ctc<br>Pro Pro Cys Pro Ala Pro Glu Leu Leu Gly Gly Pro Ser Val Phe Leu<br>                  245                  250              255 | | 768 |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>        260                    265                  270 | | 816 |
| gtc aca tgc gtg gtg gtg gac gtg agc cac gaa gac cct gag gtc aag<br>Val Thr Cys Val Val Val Asp Val Ser His Glu Asp Pro Glu Val Lys<br>            275                    280                  285 | | 864 |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>        290                    295                  300 | | 912 |
| ccg cgg gag gag cag tac aac agc acg tac cgt gtg gtc agc gtc ctc<br>Pro Arg Glu Glu Gln Tyr Asn Ser Thr Tyr Arg Val Val Ser Val Leu<br>305                    310                315              320 | | 960 |
| acc gtc ctg cac cag gac tgg ctg aat ggc aag gag tac aag tgc aag<br>Thr Val Leu His Gln Asp Trp Leu Asn Gly Lys Glu Tyr Lys Cys Lys<br>                  325                  330              335 | | 1008 |
| gtc tcc aac aaa gcc ctc cca gcc ccc atc gag aaa acc atc tcc aaa<br>Val Ser Asn Lys Ala Leu Pro Ala Pro Ile Glu Lys Thr Ile Ser Lys<br>            340                    345                  350 | | 1056 |
| gcc aaa ggg cag ccc cga gaa cca cag gtg tac acc ctg ccc cca tcc<br>Ala Lys Gly Gln Pro Arg Glu Pro Gln Val Tyr Thr Leu Pro Pro Ser<br>        355                    360                  365 | | 1104 |
| cgg gat gag ctg acc aag aac cag gtc agc ctg acc tgc ctg gtc aaa<br>Arg Asp Glu Leu Thr Lys Asn Gln Val Ser Leu Thr Cys Leu Val Lys<br>370                    375                    380 | | 1152 |
| ggc ttc tat ccc agc gac atc gcc gtg gag tgg gag agc aat ggg cag<br>Gly Phe Tyr Pro Ser Asp Ile Ala Val Glu Trp Glu Ser Asn Gly Gln<br>385                    390                395              400 | | 1200 |
| ccg gag aac aac tac aag acc acg cct ccc gtg ctg gac tcc gac ggc<br>Pro Glu Asn Asn Tyr Lys Thr Thr Pro Pro Val Leu Asp Ser Asp Gly<br>                  405                    410              415 | | 1248 |
| tcc ttc ttc ctc tac agc aag ctc acc gtg gac aag agc agg tgg cag<br>Ser Phe Phe Leu Tyr Ser Lys Leu Thr Val Asp Lys Ser Arg Trp Gln<br>                    420                  425              430 | | 1296 |
| cag ggg aac gtc ttc tca tgc tcc gtg atg cat gag gct ctg cac aac<br>Gln Gly Asn Val Phe Ser Cys Ser Val Met His Glu Ala Leu His Asn<br>        435                    440                  445 | | 1344 |
| cac tac acg cag aag agc ctc tcc ctg tct ccg ggt aaa tga<br>His Tyr Thr Gln Lys Ser Leu Ser Leu Ser Pro Gly Lys<br>450                    455                    460 | | 1386 |

<210> SEQ ID NO 145
<211> LENGTH: 461
<212> TYPE: PRT
<213> ORGANISM: Artificial
<220> FEATURE:
<223> OTHER INFORMATION: Synthetic Construct

<400> SEQUENCE: 145

```
Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Ala Ile Tyr Pro Gly Asn Ser Asp Ser Tyr Asn Gln
65                  70                  75                  80

Lys Phe Lys Gly Lys Ala Lys Leu Thr Ala Val Thr Ser Thr Ser Thr
                85                  90                  95

Ala Tyr Met Glu Leu Ser Ser Leu Thr Asn Glu Asp Ser Ala Val Tyr
            100                 105                 110

Tyr Cys Thr Ser Val Met Ala Tyr Trp Gly Gln Gly Thr Ser Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415
```

```
Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

<210> SEQ ID NO 146
<211> LENGTH: 711
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(711)

<400> SEQUENCE: 146

```
atg gac atg agg gct cct gca cag att ttt ggc ttc ttg ttg ctc ttg      48
Met Asp Met Arg Ala Pro Ala Gln Ile Phe Gly Phe Leu Leu Leu Leu
1               5                   10                  15 ttt cca ggt acc aga tgt gac atc cag atg acc cag tct cca tcc tcc      96
Phe Pro Gly Thr Arg Cys Asp Ile Gln Met Thr Gln Ser Pro Ser Ser
                20                  25                  30 tta tct gcc tct ctg gga gaa aga gtc agt ctc act tgt cgg gca agt     144
Leu Ser Ala Ser Leu Gly Glu Arg Val Ser Leu Thr Cys Arg Ala Ser
            35                  40                  45 cag gac att ggt aat agc tta aac tgg ctt cag cag gaa cca gat gga     192
Gln Asp Ile Gly Asn Ser Leu Asn Trp Leu Gln Gln Glu Pro Asp Gly
        50                  55                  60 act att aaa cgc ctg atc tac gcc aca tcc aat tta gat tct ggt gtc     240
Thr Ile Lys Arg Leu Ile Tyr Ala Thr Ser Asn Leu Asp Ser Gly Val
65                  70                  75                  80 tcc aaa agg ttc agt ggc agt agg tct ggg tca gat tat tct ctc acc     288
Ser Lys Arg Phe Ser Gly Ser Arg Ser Gly Ser Asp Tyr Ser Leu Thr
                85                  90                  95 atc agc agc ctt gag tct gaa gat ttt gta gac tat tac tgt cta caa     336
Ile Ser Ser Leu Glu Ser Glu Asp Phe Val Asp Tyr Tyr Cys Leu Gln
            100                 105                 110 tat gct agt tct ccg tgg acg ttc ggt gga ggc acc aag ctg gaa atc     384
Tyr Ala Ser Ser Pro Trp Thr Phe Gly Gly Gly Thr Lys Leu Glu Ile
        115                 120                 125 aag cgt acg gtg gct gca cca tct gtc ttc atc ttc ccg cca tct gat     432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc     528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac     576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac     624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc     672
Glu Lys His Lys Val Tyr Ala Cys Glu Val Thr His Gln Gly Leu Ser
    210                 215                 220
```

```
tcg ccc gtc aca aag agc ttc aac agg gga gag tgt tga         711
Ser Pro Val Thr Lys Ser Phe Asn Arg Gly Glu Cys
225                 230                 235

<210> SEQ ID NO 147
<211> LENGTH: 236
<212> TYPE: PRT
<213> ORGANISM: Artificial
<220> FEATURE:
<223> OTHER INFORMATION: Synthetic Construct

<400> SEQUENCE: 147

Met Asp Met Arg Ala Pro Ala Gln Ile Phe Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Asn Ser Leu Asn Trp Leu Gln Gln Glu Pro Asp Gly
    50                  55                  60

Thr Ile Lys Arg Leu Ile Tyr Ala Thr Ser Asn Leu Asp Ser Gly Val
65                  70                  75                  80

Ser Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Ala Ser Ser Pro Trp Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 148
<211> LENGTH: 486
<212> TYPE: DNA
<213> ORGANISM: Mus musculus

<400> SEQUENCE: 148
atggagacgc tccctgcctc ttgggtcttg acgctgcttt gtctaggttc ccaccttcta       60
caggcagtta tcagcacaac cgtgatccca tcatgcatcc aggagaatc cgaggataac      120 tgtaccgcct tagttcagat ggaagacgat ccccgtgtgg ctcaagtgca gattacaaag     180
tgtagttctg acatggacgg ctactgcttg catggccagt gcatctacct ggtggacatg     240
agagagaaat tctgcagatg tgaagtgggc tacactggtc tgcgatgtga gcacttcttt     300
ctaactgttc accaacccct gagcaaagaa tacgttgcgt tgacagtgat tctcattttc     360
```

```
ctgtttctca tcataaccgc tggatgcata tactatttct gcagatggta caaaaatcga    420
aaaagtaaaa aatcgaggga ggaatatgag agagtgacct caggggaccc agtgctgcca    480
caggtc                                                                486
```

<210> SEQ ID NO 149
<211> LENGTH: 492
<212> TYPE: DNA
<213> ORGANISM: Macaca fascicularis

<400> SEQUENCE: 149

```
atggagatgc tctctgccgg aagggtccct gcgctgctgc tctgcctggg tttccatctt     60
ctacaggcag tcctcagtac aactgtgatt ccatcatgta tcccaggaga gtccagtgat    120
aactgcacag ctttagttca gacagaagac aatccacgtg tggctcaagt gtcaataaca    180
aagtgtaact ctgacatgaa tggctactgt ttgcatggac agtgcatcta cctggtggac    240
atgagtcaaa attactgcag gtgtgaagtg ggttatactg gtgtccgatg tgaacatttc    300
tatttaaccg tccaccaacc tttaagcaaa gaatatgtgg ctttgaccgt gattcttatt    360
attttgtttc ttatcatagt tgtcggttcc acatattatt tctgcagatg gtacaggaat    420
cgaaaaagta aagaaccaaa gaaggaatat gagagagtta cctcagggga tccagagttg    480
ccgcaagtct ga                                                        492
```

<210> SEQ ID NO 150
<211> LENGTH: 342
<212> TYPE: PRT
<213> ORGANISM: Mus musculus

<400> SEQUENCE: 150

```
Met Glu Thr Leu Pro Ala Ser Trp Val Leu Thr Leu Leu Cys Leu Gly
1               5                   10                  15

Ser His Leu Leu Gln Ala Val Ile Ser Thr Thr Val Ile Pro Ser Cys
            20                  25                  30

Ile Pro Gly Glu Ser Glu Asp Asn Cys Thr Ala Leu Val Gln Met Glu
        35                  40                  45

Asp Asp Pro Arg Val Ala Gln Val Gln Ile Thr Lys Cys Ser Ser Asp
    50                  55                  60

Met Asp Gly Tyr Cys Leu His Gly Gln Cys Ile Tyr Leu Val Asp Met
65                  70                  75                  80

Arg Glu Lys Phe Cys Arg Cys Glu Val Gly Tyr Thr Gly Leu Arg Cys
                85                  90                  95

Glu His Phe Phe Leu Thr Val His Gln Pro Leu Ser Lys Glu Tyr Val
            100                 105                 110

Gly Pro Thr Ile Lys Pro Cys Pro Pro Cys Lys Cys Pro Ala Pro Asn
        115                 120                 125

Leu Leu Gly Gly Pro Ser Val Phe Ile Phe Pro Pro Lys Ile Lys Asp
    130                 135                 140

Val Leu Met Ile Ser Leu Ser Pro Ile Val Thr Cys Val Val Val Asp
145                 150                 155                 160

Val Ser Glu Asp Asp Pro Asp Val Gln Ile Ser Trp Phe Val Asn Asn
                165                 170                 175

Val Glu Val His Thr Ala Gln Thr Gln Thr His Arg Glu Asp Tyr Asn
            180                 185                 190

Ser Thr Leu Arg Val Val Ser Ala Leu Pro Ile Gln His Gln Asp Trp
        195                 200                 205
```

```
Met Ser Gly Lys Glu Phe Lys Cys Lys Val Asn Asn Lys Asp Leu Pro
    210                 215                 220

Ala Pro Ile Glu Arg Thr Ile Ser Lys Pro Lys Gly Ser Val Arg Ala
225                 230                 235                 240

Pro Gln Val Tyr Val Leu Pro Pro Glu Glu Met Thr Lys Lys
                245                 250                 255

Gln Val Thr Leu Thr Cys Met Val Thr Asp Phe Met Pro Glu Asp Ile
                260                 265                 270

Tyr Val Glu Trp Thr Asn Asn Gly Lys Thr Glu Leu Asn Tyr Lys Asn
                275                 280                 285

Thr Glu Pro Val Leu Asp Ser Asp Gly Ser Tyr Phe Met Tyr Ser Lys
                290                 295                 300

Leu Arg Val Glu Lys Lys Asn Trp Val Glu Arg Asn Ser Tyr Ser Cys
305                 310                 315                 320

Ser Val Val His Glu Gly Leu His Asn His Thr Thr Lys Ser Phe
                325                 330                 335

Ser Arg Thr Pro Gly Lys
                340

<210> SEQ ID NO 151
<211> LENGTH: 343
<212> TYPE: PRT
<213> ORGANISM: Macaca fascicularis

<400> SEQUENCE: 151

Met Glu Met Leu Ser Ala Gly Arg Val Pro Ala Leu Leu Leu Cys Leu
1               5                   10                  15

Gly Phe His Leu Leu Gln Ala Val Leu Ser Thr Thr Val Ile Pro Ser
                20                  25                  30

Cys Ile Pro Gly Glu Ser Ser Asp Asn Cys Thr Ala Leu Val Gln Thr
            35                  40                  45

Glu Asp Asn Pro Arg Val Ala Gln Val Ser Ile Thr Lys Cys Asn Ser
50                  55                  60

Asp Met Asn Gly Tyr Cys Leu His Gly Gln Cys Ile Tyr Leu Val Asp
65                  70                  75                  80

Met Ser Gln Asn Tyr Cys Arg Cys Glu Val Gly Tyr Thr Gly Val Arg
                85                  90                  95

Cys Glu His Phe Tyr Leu Thr Val His Gln Pro Leu Ser Lys Glu Tyr
            100                 105                 110

Val Gly Pro Thr Ile Lys Pro Cys Pro Cys Lys Cys Pro Ala Pro
            115                 120                 125

Asn Leu Leu Gly Gly Pro Ser Val Phe Ile Phe Pro Pro Lys Ile Lys
130                 135                 140

Asp Val Leu Met Ile Ser Leu Ser Pro Ile Val Thr Cys Val Val Val
145                 150                 155                 160

Asp Val Ser Glu Asp Asp Pro Asp Val Gln Ile Ser Trp Phe Val Asn
                165                 170                 175

Asn Val Glu Val His Thr Ala Gln Thr Gln Thr His Arg Glu Asp Tyr
            180                 185                 190

Asn Ser Thr Leu Arg Val Val Ser Ala Leu Pro Ile Gln His Gln Asp
            195                 200                 205

Trp Met Ser Gly Lys Glu Phe Lys Cys Lys Val Asn Asn Lys Asp Leu
    210                 215                 220

Pro Ala Pro Ile Glu Arg Thr Ile Ser Lys Pro Lys Gly Ser Val Arg
225                 230                 235                 240
```

Ala Pro Gln Val Tyr Val Leu Pro Pro Glu Glu Met Thr Lys
            245                 250                 255

Lys Gln Val Thr Leu Thr Cys Met Val Thr Asp Phe Met Pro Glu Asp
                260                 265                 270

Ile Tyr Val Glu Trp Thr Asn Asn Gly Lys Thr Glu Leu Asn Tyr Lys
            275                 280                 285

Asn Thr Glu Pro Val Leu Asp Ser Asp Gly Ser Tyr Phe Met Tyr Ser
        290                 295                 300

Lys Leu Arg Val Glu Lys Asn Trp Val Glu Arg Asn Ser Tyr Ser
305                 310                 315                 320

Cys Ser Val Val His Glu Gly Leu His Asn His His Thr Thr Lys Ser
                325                 330                 335

Phe Ser Arg Thr Pro Gly Lys
            340

<210> SEQ ID NO 152
<211> LENGTH: 275
<212> TYPE: PRT
<213> ORGANISM: Artificial
<220> FEATURE:
<223> OTHER INFORMATION: An artificially synthesized peptide sequence

<400> SEQUENCE: 152

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Ala Val Leu Ser Thr Thr Val Ile Pro Ser Cys Ile Pro Gly
225                 230                 235                 240

Glu Ser Ser Asp Asn Cys Thr Ala Leu Val Gln Thr Glu Asp Asn Pro
                245                 250                 255

```
Arg Val Ala Gln Val Ser Ile Thr Lys Cys Gly Ser Thr His His His
            260                 265                 270
His His His
        275
```

DIAGNOSIS AND TREATMENT OF CANCER USING ANTI-EREG ANTIBODY

TECHNICAL FIELD

The present invention relates to methods for diagnosing and treating cancer, cell proliferation inhibitors, and anticancer agents.

BACKGROUND ART

A member of the epidermal growth factor (hereinafter referred to as EGF) family purified by Toyoda et al. was named "epiregulin (EREG)". EREG is known to function as a cancer growth inhibitor that induces morphological changes of HeLa cells (Non-Patent Document 1). The amino acid sequence of mouse-derived EREG (mature protein) purified by Toyoda et al. consists of 46 amino acid residues, and shares a sequence identity of about 24% to 50% with other members of the EGF family. Mouse EREG showed low affinity to the EGF receptor on A431 cells (a human epithelial carcinoma cell line). The cloning and expression analysis of the human EREG gene by Toyoda et al. showed that, while other members of the EGF family are expressed ubiquitously in human tissues, the EREG expression is detectable in macrophages, placenta, and various types of cancer cells (Non-Patent Document 2). In addition, the soluble form of EREG was shown to have proliferation-suppressing effect on several types of cancer cells (WO94/29340).

Takahashi et al. showed that the activation of Erk (MPK3) and p38 (MAPK14) in differentiated arterial vascular smooth muscle cells (hereinafter referred to as VSMC) from rats induces dedifferentiation of the cells. Furthermore, it was demonstrated that EREG secreted by VSMC acts as an autocrine and/or paracrine differentiation factor. Unsaturated lysophosphatidic acid and PDGFB homodimer, which may act as differentiation factors of VSMC, rapidly up-regulated the mRNA expression of EREG in an Erk– and p38 MAPK-dependent manner. Reverse transcriptase polymerase chain reaction (hereinafter referred to as RT-PCR) analysis, and immunohistochemical or immunohistochemistry (hereinafter referred to as IHC) analysis revealed localized EREG expression in atherosclerotic arteries and balloon-injured rat arteries. From these results, Takahashi and others speculated that EREG might be involved in the progression of vascular remodeling such as atherosclerosis (Non-Patent Document 3).

Minn et al. identified several gene clusters related to lung metastasis of breast cancer based on in vivo selection, transcriptome analysis, functional analysis, and clinical research, and showed that EREG is one of the genes (Non-Patent Document 4).

Furthermore, Shirasawa et al. showed that EREG is expressed not only in keratinocytes but also in tissue macrophages, and that EREG-knockout mice develop chronic dermatitis. Examinations in the analysis of these mice revealed that EREG plays an important role in immunity- and inflammatory-related responses of keratinocytes and macrophages at the boundary with the external environment (Non-Patent Document 5).

As described above, the connection between EREG and dermatitis, cancer metastasis, and atherosclerosis has been indicated. However, there are still no specific descriptions on the effect of EREG-binding antibodies that have neutralizing activity and cytotoxic activity on EREG-expressing cancer cells.

[Non-Patent Document 1] J. Biol. Chem. 270: 7495-7500, 1995
[Non-Patent Document 2] Biochem. J. 326: 69-75, 1997
[Non-Patent Document 3] Circulation 108: 2524-2529, 2003
[Non-Patent Document 4] Nature 436: 518-524, 2005
[Non-Patent Document 5] Proc. Nat. Acad. Sci. 101: 13921-13926, 2004

DISCLOSURE OF THE INVENTION

Problems to be Solved by the Invention

An objective of the present invention is to provide anti-EREG antibodies and uses thereof. More specifically, an objective of the present invention is to provide novel methods for diagnosing and treating cancer using anti-EREG antibodies, novel cell proliferation inhibitors and anticancer agents comprising anti-EREG antibodies, and novel anti-EREG antibodies.

Means for Solving the Problems

The present inventors discovered that EREG is highly expressed in cancer cells such as colon cancer cells. Furthermore, when complement-dependent cytotoxicity (CDC) activity and antibody-dependent cell-mediated cytotoxicity (ADCC) activity of anti-EREG antibodies were measured, the anti-EREG antibodies were found to have CDC activity and ADCC activity in EREG-expressing cells. The present inventors also showed that the anti-EREG antibodies have proliferation-suppressing effect on cancer cell lines via neutralization. Furthermore, from the above-mentioned findings, the present inventors discovered that the anti-EREG antibodies were effective for diagnosis, prevention, and treatment of various types of primary and metastatic cancers, and thereby completed the present invention. More specifically, the present inventors completed the present invention by discovering that EREG is useful as a tool for treating or diagnosing cancers in which the EREG expression is enhanced, including colon cancer, lung adenocarcinoma, pancreatic cancer, stomach cancer, and kidney cancer.

The present invention provides pharmaceutical compositions comprising an antibody that binds to an EREG protein as an active ingredient. The present invention also provides cell proliferation inhibitors comprising an antibody that binds to an EREG protein as an active ingredient. The present invention further provides anticancer agents comprising an antibody that binds to an EREG protein as an active ingredient. Preferably, the antibody that binds to an EREG protein has cytotoxic activity. More preferably, the antibody also has neutralizing activity. In a preferred embodiment of the present invention, the cancers that can be targeted for treatment are colon cancer, lung adenocarcinoma, pancreatic cancer, stomach cancer, and kidney cancer. Anticancer agents comprising an anti-EREG antibody of the present invention are useful for treatment of these cancers which are primary or metastatic cancers and have elevated expression of EREG. Particularly preferred targets for treatment of the present invention are primary colon cancer, metastatic colon cancer, and pancreatic cancer.

Furthermore, the present invention provides pharmaceutical compositions comprising an antibody that binds to an EREG protein and a pharmaceutically acceptable carrier. Pharmaceutical compositions of the present invention are useful for treating and/or preventing cancers that have elevated expression of EREG. That is, the present invention relates to the use of an antibody that binds to an EREG protein for the manufacturing of pharmaceutical compositions for treating and/or preventing cancer.

In another embodiment, the present invention provides methods for inducing cell injury in cells that express an EREG protein by contacting EREG-expressing cells with an antibody that binds to an EREG protein. The present invention also provides methods for suppressing proliferation of cells that express an EREG protein by contacting EREG protein-expressing cells with an antibody that binds to an EREG protein. The antibody that binds to an EREG protein preferably has cytotoxic activity. Cells that express an EREG protein are preferably cancer cells.

Furthermore, in another embodiment, the present invention provides antibodies that bind to an EREG protein and have cytotoxic activity in cells that express the EREG protein. Preferably, the cytotoxic activity is ADCC activity. Preferably, the cytotoxic activity is CDC activity. The present invention also provides antibodies to which a cytotoxic substance is binding. In the present invention, the cytotoxic substances that may be binding to the antibody include chemotherapeutic agents, radioisotopes, and toxic peptides. Preferably, in the present invention, antibody itself has cytotoxic activity.

The present invention further provides antibodies that bind to an EREG protein, and which have cytotoxic activity and neutralizing activity against EREG protein-expressing cells.

In another embodiment, the present invention provides the use of an EREG protein as a cancer diagnostic marker.

Furthermore, in another embodiment, the present invention provides methods for diagnosing cancer, which comprises detecting an EREG protein using an antibody that binds to the EREG protein. In the methods of the present invention, preferably, the extracellular region of the EREG protein is detected. Preferably, the methods of the present invention are carried out using an antibody that recognizes the EREG protein. Preferably, the EREG protein in blood, serum, or plasma, or EREG protein isolated from cells is detected in the methods of the present invention.

In another embodiment, the present invention provides methods for diagnosing cancer which comprise the following steps of:
(a) collecting a sample from a subject; and
(b) using an antibody that binds to EREG protein to detect the EREG protein contained in the collected sample.

In the present invention, any sample can be used as the above-mentioned sample as long as it can be collected from the subject. In one embodiment, blood sample collected from a subject is used. A preferred blood sample in the present invention is serum. In another embodiment, samples collected surgically or by biopsy from a subject may be used. The methods of diagnosis can be used for any cancer as long as it is a cancer in which the target cancer cells express an EREG protein. Cancers that are preferred in the present invention are colon cancer, lung adenocarcinoma, pancreatic cancer, stomach cancer, and kidney cancer. Based on the present invention, both primary and metastatic foci of these cancers can be diagnosed. Cancers that are particularly preferred are primary colon cancer, metastatic colon cancer, and pancreatic cancer.

In the present invention, the step of collecting a sample from a subject can also be expressed as the step of providing a sample collected from a subject.

Furthermore, in another embodiment, the present invention provides methods for diagnosing cancer, which comprise the steps of: (1) administering to a subject a radioisotope-labeled antibody that binds to an EREG protein; and (2) detecting accumulation of the radioisotope. In a certain embodiment, the radioisotope is a positron-emitting nuclide. A preferred positron-emitting nuclide of the present invention can be selected, for example, from the group consisting of $^{11}C$, $^{13}N$, $^{15}O$, $^{18}F$, $^{45}Ti$, $^{55}Co$, $^{64}Cu$, $^{66}Ga$, $^{68}Ga$, $^{76}Br$, $^{89}Zr$, and $^{124}I$.

Furthermore, in another embodiment, the present invention provides methods for diagnosing cancer, in which the expression of a gene encoding the EREG protein is detected.

Furthermore, in another embodiment, the present invention provides diagnostic agents and kits to be used in the methods for diagnosis of the present invention.

In addition, the present invention provides methods of screening for candidate compounds as cancer therapeutic agents. In the present invention, compounds can be selected as a candidate cancer therapeutic agent by using, for example, the EREG expression level as an index. Alternatively, compound can be selected as a candidate cancer therapeutic agent by using the neutralizing effect against cell proliferation stimulating activity of EREG as an indicator.

More specifically, the present invention provides the following:

[1] a pharmaceutical composition comprising as an active ingredient an antibody that binds to an EREG protein;

[2] a cell proliferation inhibitor comprising as an active ingredient an antibody that binds to an EREG protein;

[3] an anticancer agent comprising as an active ingredient an antibody that binds to an EREG protein;

[4] the anticancer agent of [3], wherein the antibody that binds to an EREG protein is an antibody that has cell proliferation inhibitory activity;

[5] the anticancer agent of [3] or [4], wherein the antibody that binds to an EREG protein is an antibody of any of (1) to (57) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3;

(2) an antibody comprising the H chain of (1), wherein the H chain has the amino acid sequence of positions 117 to 452 in the amino acid sequence of SEQ ID NO: 8 as CH;

(3) an antibody comprising the H chain of (1), wherein the H chain has the amino acid sequence of positions 117 to 446 in the amino acid sequence of SEQ ID NO: 10 as CH;

(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;

(5) an antibody comprising the L chain of (4), wherein the L chain has the amino acid sequence of positions 107 to 213 in the amino acid sequence of SEQ ID NO: 18 as CL;

(6) an antibody comprising the L chain of (4), wherein the L chain has the amino acid sequence of positions 107 to 213 in the amino acid sequence of SEQ ID NO: 20 as CL;

(7) an antibody comprising the H chain of (1) and the L chain of (4);

(8) an antibody comprising the H chain of (2) and the L chain of (5);

(9) an antibody comprising the H chain of (3) and the L chain of (6);

(10) an antibody comprising an H chain having the amino acid sequence of SEQ ID NO: 49 as CDR1, the amino acid sequence of SEQ ID NO: 51 as CDR2, and the amino acid sequence of SEQ ID NO: 53 as CDR3;

(11) an antibody comprising the H chain of (10), wherein the H chain has CH derived from mouse IgG 1;

(12) an antibody comprising the H chain of (10), wherein the H chain has the amino acid sequence of positions 117 to 446 in the amino acid sequence of SEQ ID NO: 10 as CH;

(13) an antibody comprising an L chain having the amino acid sequence of SEQ ID NO: 55 as CDR1, the amino acid sequence of SEQ ID NO: 57 as CDR2, and the amino acid sequence of SEQ ID NO: 59 as CDR3;
(14) an antibody comprising the L chain of (13), wherein the L chain has CL derived from the mouse κ chain;
(15) an antibody comprising the L chain of (13), wherein the L chain has the amino acid sequence of positions 107 to 213 in the amino acid sequence of SEQ ID NO: 20 as CL;
(16) an antibody comprising the H chain of (10) and the L chain of (13);
(17) an antibody comprising the H chain of (11) and the L chain of (14);
(18) an antibody comprising the H chain of (12) and the L chain of (15);
(19) an antibody comprising an H chain having the amino acid sequence of SEQ ID NO: 61 as CDR1, the amino acid sequence of SEQ ID NO: 63 as CDR2, and the amino acid sequence of SEQ ID NO: 65 as CDR3;
(20) an antibody comprising the H chain of (19), wherein the H chain has CH derived from mouse IgG1;
(21) an antibody comprising the H chain of (19), wherein the H chain has the amino acid sequence of positions 117 to 446 in the amino acid sequence of SEQ ID NO: 10 as CH;
(22) an antibody comprising an L chain having the amino acid sequence of SEQ ID NO: 67 as CDR1, the amino acid sequence of SEQ ID NO: 69 as CDR2, and the amino acid sequence of SEQ ID NO: 71 as CDR3;
(23) an antibody comprising the L chain of (22), wherein the L chain has CL derived from of the mouse κ chain;
(24) an antibody comprising the L chain of (22), wherein the L chain has the amino acid sequence of positions 107 to 213 in the amino acid sequence of SEQ ID NO: 20 as CL;
(25) an antibody comprising the H chain of (19) and the L chain of (22);
(26) an antibody comprising the H chain of (20) and the L chain of (23);
(27) an antibody comprising the H chain of (21) and the L chain of (24);
(28) an antibody comprising an H chain having the amino acid sequence of SEQ ID NO: 73 as CDR1, the amino acid sequence of SEQ ID NO: 75 as CDR2, and the amino acid sequence of SEQ ID NO: 77 as CDR3;
(29) an antibody comprising the H chain of (28), wherein the H chain has CH derived from mouse IgG1;
(30) an antibody comprising the H chain of (28), wherein the H chain has the amino acid sequence of positions 117 to 446 in the amino acid sequence of SEQ ID NO: 10 as CH;
(31) an antibody comprising an L chain having the amino acid sequence of SEQ ID NO: 79 as CDR1, the amino acid sequence of SEQ ID NO: 81 as CDR2, and the amino acid sequence of SEQ ID NO: 83 as CDR3;
(32) an antibody comprising the L chain of (31), wherein the L chain has CL derived from the mouse κ chain;
(33) an antibody comprising the L chain of (31), wherein the L chain has the amino acid sequence of positions 107 to 213 in the amino acid sequence of SEQ ID NO: 20 as CL;
(34) an antibody comprising the H chain of (28) and the L chain of (31);
(35) an antibody comprising the H chain of (29) and the L chain of (32);
(36) an antibody comprising the H chain of (30) and the L chain of (33);
(37) an antibody comprising an H chain having the amino acid sequence of SEQ ID NO: 85 as CDR1, the amino acid sequence of SEQ ID NO: 87 as CDR2, and the amino acid sequence of SEQ ID NO: 89 as CDR3;
(38) an antibody comprising the H chain of (37), wherein the H chain has CH derived from mouse IgG1;
(39) an antibody the H chain of (37), wherein the H chain has the amino acid sequence of positions 117 to 446 in the amino acid sequence of SEQ ID NO: 10 as CH;
(40) an antibody comprising an L chain having the amino acid sequence of SEQ ID NO: 91 as CDR1, the amino acid sequence of SEQ ID NO: 93 as CDR2, and the amino acid sequence of SEQ ID NO: 95 as CDR3;
(41) an antibody comprising the L chain of (40), wherein the L chain has-CL derived from the mouse κ chain;
(42) an antibody comprising the L chain of (40), wherein the L chain has the amino acid sequence of positions 107 to 213 in the amino acid sequence of SEQ ID NO: 20 as CL;
(43) an antibody comprising the H chain of (37) and the L chain of (40);
(44) an antibody comprising the H chain of (38) and the L chain of (41);
(45) an antibody comprising the H chaih of (39) and the L chain of (42);
(46) an antibody comprising an H chain having the amino acid sequence of SEQ ID NO: 97 as CDR1, the amino acid sequence of SEQ ID NO: 99 as CDR2, and the amino acid sequence of SEQ ID NO: 101 as CDR3;
(47) an antibody comprising the H chain of (46), wherein the H chain has CH derived from mouse IgG1;
(48) an antibody comprising the H chain of (46), wherein the H chain has the amino acid sequence of positions 117 to 446 in the amino acid sequence of SEQ ID NO: 10 as CH;
(49) an antibody comprising an L chain having the amino acid sequence of SEQ ID NO: 103 as CDR1, the amino acid sequence of SEQ ID NO: 105 as CDR2, and the amino acid sequence of SEQ ID NO: 107 as CDR3;
(50) an antibody comprising the L chain of (49), wherein the L chain has CL derived from the mouse κ chain;
(51) an antibody comprising the L chain of (49), wherein the L chain has the amino acid sequence of positions 107 to 213 in the amino acid sequence of SEQ ID NO: 20 as CL;
(52) an antibody comprising the H chain of (46) and the L chain of (49);
(53) an antibody comprising the H chain of (47) and the L chain of (50);
(54) an antibody comprising the H chain of (48) and the L chain of (51);
(55) an antibody comprising one or more amino acid substitutions, deletions, additions, and/or insertions in the antibody of any of (1) to (54), which has equivalent activity as the antibody of any of (1) to (54);
(56) an antibody that binds to the same EREG protein epitope as the antibody of any of (1) to (55); and
(57) a minibody of the antibody of any of (1) to (56);
[6] the anticancer agent of any one of [3] to [5], wherein the antibody that binds to EREG protein recognizes Ala at position 29 to Sec at position 69, or Val at position 63 to Leu at position 108, in the amino acid sequence of SEQ ID NO: 21;
[7] the anticancer agent of any one of [3] to [6], wherein the cancer is any cancer selected from the group consisting of colon cancer, lung adenocarcinoma, pancreatic cancer, stomach cancer, and kidney cancer;
[8] the anticancer agent of [7], wherein the cancer is primary cancer;
[9] the anticancer agent of [7], wherein the cancer is metastatic cancer;
[10] an antibody that binds to an EREG protein, and which has cell proliferation inhibitory activity against cells expressing the EREG protein;

[11] the antibody of [10], wherein the cell proliferation inhibitory activity is cytotoxic activity;
[12] the antibody of [11], wherein the cytotoxic activity is ADCC activity;
[13] the antibody of [11], wherein the cytotoxic activity is CDC activity;
[14] the antibody of any one of [10] to [13], which additionally has neutralizing activity against the EREG protein;
[15] The antibody of [10], wherein the cell proliferation inhibitory activity is neutralizing activity;
[16] a minibody produced from the antibody of [10];
[17] the antibody of any one of [10] to [16], wherein a chemotherapeutic agent or a toxic peptide is bound to the antibody;
[18] an antibody that binds to an EREG protein, wherein any one cytotoxic substance selected from the group consisting of a chemotherapeutic agent, a toxic peptide, and a radioisotope is bound to the antibody;
[19] the antibody of any one of [10] to [18], which is an antibody of any of (1) to (57) below:
(1) an antibody comprising an H chain having the amino acid sequence of SEQ ID NC): 2 CDR1, the amino acid sequence of SEQ ID NO: 4 as CDR2, and the amino acid sequence of SEQ ID NO: 6 as CDR3;
(2) an antibody comprising the H chain of (1), wherein the H chain has the amino acid sequence of positions 117 to 452 in the amino acid sequence of SEQ ID NO: 8 as CH;
(3) an antibody comprising the H chain of (1), wherein the H chain has the amino acid sequence of positions 117 to 446 in the amino acid sequence of SEQ ID NO: 10 as CH;
(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;
(5) an antibody comprising the L Chain of (4), wherein the L chain has the amino acid sequence of positions 107 to 213 in the amino acid sequence of SEQ ID NO: 18 as CL;
(6) an antibody comprising the L chain of (4), wherein the L chain has the amino acid sequence of positions 107 to 213 in the amino acid sequence of SEQ ID NO: 20 as CL;
(7) an antibody comprising the H chain of (1) and the L chain of (4);
(8) an antibody comprising the H chain of (2) and the L chain of (5);
(9) an antibody comprising the H chain of (3) and the L chain of (6);
(10) an antibody comprising H chain having the amino acid sequence of SEQ ID NO: 49 as CDR1, the amino acid sequence of SEQ ID NO: 51 as CDR2, and the amino acid sequence of SEQ ID NO: 53 as cDR3;
(11) an antibody comprising the H chain of (10), wherein the H chain has CH derived from mouse IgG1;
(12) an antibody comprising the H chain of (10), wherein the H chain has the amino acid sequence of positions 117 to 446 in the amino acid sequence of SEQ ID NO: 10 as CH;
(13) an antibody comprising an L chain having the amino acid sequence of SEQ ID NO: 55 as CDR1, the amino acid sequence of SEQ ID NO: 57 as CDR2, and the amino acid sequence of SEQ ID NO: 59 as CDR3;
(14) an antibody comprising the L chain of (13), wherein the L chain has CL derived from the mouse κ chain;
(15) an antibody comprising the L chain of (13), wherein the L chain has the amino acid sequence of positions 107 to 213 in the amino acid sequence of SEQ ID NO: 20 as CL;
(16) an antibody comprising the H chain of (10) and the L chain of (13);
(17) an antibody comprising the H chain of (11) and the L chain of (14);
(18) an antibody comprising the H chain of (12) and the L chain of (15);
(19) an antibody comprising an H chain having the amino acid sequence of SEQ ID NO: 61 as CDR1, the amino acid sequence of SEQ ID NO: 63 as CDR2, and the amino acid sequence of SEQ ID NO: 65 as CDR3;
(20) an antibody comprising the H chain of (19), wherein the H chain has CH derived from mouse IgG1;
(21) an antibody comprising the H chain of (19), wherein the H chain has the amino acid sequence of positions 117 to 446 in the amino acid sequence of SEQ ID NO: 10 as CH;
(22) an antibody comprising an L chain having the amino acid sequence of SEQ ID NO: 67 as CDR1, the amino acid sequence of SEQ ID NO: 69 as CDR2, and the amino acid sequence of SEQ ID NO: 71 as CDR3;
(23) an antibody comprising the L chain of (22), wherein the L chain has CL derived from of the mouse κ chain;
(24) an antibody comprising the L chain of (22), wherein the L chain has the amino acid sequence of positions 107 to 213 in the amino acid sequence of SEQ ID NO: 20 as CL;
(25) an antibody comprising the H chain of (19) and the L chain of (22);
(26) an antibody comprising the H chain of (20) and the L chain of (23);
(27) an antibody comprising the H chain of (21) and the L chain of (24);
(28) an antibody comprising an H chain having the amino acid sequence of SEQ ID NO: 73 as CDR1, the amino acid sequence of SEQ ID NO: 75 as CDR2, and the amino acid sequence of SEQ ID NO: 77 as CDR3;
(29) an antibody comprising the H chain of (28), wherein the chain has CH derived from mouse IgG1;
(30) an antibody comprising the H chain of (28), wherein the H chain has the amino acid sequence of positions 117 to 446 in the amino acid sequence of SEQ ID NO: 10 as CH;
(31) an antibody comprising an L chain having the amino acid sequence of SEQ ID NO: 79 as CDR1, the amino acid sequence of SEQ ID NO: 81 as CDR2, and the amino acid sequence of SEQ ID NO: 83 as CDR3;
(32) an antibody comprising the L chain of (31), wherein the L chain has CL derived from the mouse κ chain;
(33) an antibody comprising the L chain of (31), wherein the L chain has the amino acid sequence of positions 107 to 213 in the amino acid sequence of SEQ ID NO: 20 as CL;
(34) an antibody comprising the H chain of (28) and the L chain of (31);
(35) an antibody comprising the H chain of (29) and the L chain of (32);
(36) an antibody comprising the H chain of (30) and the L chain of (33);
(37) an antibody comprising an H chain having the amino acid sequence of SEQ ID NO: 85 as CDR1, the amino acid sequence of SEQ ID NO: 87 as CDR2, and the amino acid sequence of SEQ ID NO: 89 as CDR3;
(38) an antibody comprising the H chain of (37), wherein the H chain has CH derived from mouse IgG1;
(39) an antibody comprising the H chain of (37), wherein the H chain has the amino acid sequence of positions 117 to 446 in the amino acid sequence of SEQ ID NO: 10 as CH;
(40) an antibody comprising an L chain having the amino acid sequence of SEQ ID NO: 91 as CDR1, the amino acid sequence of SEQ ID No: 93 as CDR2, and the amino acid sequence of SEQ ID NO: 95 as CDR3;
(41) an antibody comprising, the L chain of (40), wherein the L chain has CL derived from the mouse κ chain;

(42) an antibody comprising the L chain of (40), wherein the L chain has the amino acid sequence of positions 107 to 213 in the amino acid sequence of SEQ ID NO: 20 as CL,
(43) an antibody comprising the H chain of (37) and the L chain of (40);
(44) an antibody comprising the H chain of (38) and the L chain of (41);
(45) an antibody comprising the H chain of (39) and the L chain of (42);
(46) an antibody comprising an H chain having the amino acid sequence of SEQ ID NO: 97 as CDR1, the amino acid sequence of SEQ ID NO: 99 as CDR2, and the amino acid sequence of SEQ ID NO: 101 as CDR3;
(47) an antibody comprising the H chain of (46), wherein the H chain has CH derived from mouse IgG1;
(48) an antibody comprising the H chain of (46), wherein the H chain has the amino acid sequence of positions 117 to 446 in the amino acid sequence of SEQ ID NO: 10 as CH;
(49) an antibody comprising an L chain having the amino acid sequence of SEQ ID NO: 103 as CDR1, the amino acid sequence of SEQ ID NO: 105 as CDR2, and the amino acid sequence of SEQ ID NO: 107 as CDR3;
(50) an antibody comprising the L chain of (49), wherein the L chain has CL derived from the mouse κ chain;
(51) an antibody comprising the L chain of (49), wherein the L chain has the amino acid sequence of positions 107 to 213 in the amino acid sequence of SEQ ID NO: 20 as CL;
(52) an antibody comprising the H chain of (46) and the L chain of (49);
(53) an antibody comprising the H chain of (47) and the L chain of (50);
(54) an antibody comprising the H chain of (48) and the L chain of (51);
(55) an antibody comprising one or more amino acid substitutions, deletions, additions, and/or insertions in the antibody of any of (1) to (54), which has equivalent activity as the antibody of any of (1) to (54);
(56) an antibody that binds to the same EREG protein epitope as the antibody of any of (1) to (55); and
(57) a minibody of the antibody of any of (1) to (56);
[20] the antibody of any one of [10] to [20], wherein the antibody recognizes Ala at position 29 to Ser at position 69, or Val at position 63 to Leu at position 108, in the amino acid sequence of SEQ 11) NO: 21;
[21] use of an EREG protein or an EREG mRNA, or both, as a cancer diagnostic marker;
[22] a method for diagnosis of cancer, comprising combining an EREG protein with an antibody that binds to the EREG protein;
[23] a method for diagnosis of cancer, comprising the steps of:
(a) collecting a sample from a subject; and
(b) detecting an EREG protein contained in the collected sample using an antibody that binds to the EREG protein;
[24] a method for diagnosis of cancer, comprising the steps of: (1) administering to a subject a radioisotope-labeled antibody that binds to an EREG protein; and (2) detecting accumulation of said radioisotope;
[25] the method of diagnosis of [22], wherein the radioisotope is a positron-emitting nuclide;
[26] the method of diagnosis of [25], wherein the positron-emitting nuclide is any one nuclide selected from the group consisting of $^{11}C$, $^{13}N$, $^{15}O$, $^{18}F$, $^{45}Ti$, $^{55}co$, $^{64}cu$, $^{66}Ga$, $^{68}Ga$, $^{76}Br$, $^{89}Zr$, and $^{124}I$;
[27] a method for diagnosis of cancer, comprising detecting the expression of a gene encoding an EREG protein;

[28] the method of diagnosis of any one of [22] to [27], wherein the cancer is any cancer selected from the group consisting of colon cancer, lung adenocarcinoma, pancreatic cancer, stomach cancer, and kidney cancer;
[29] the method of diagnosis of [28], wherein the cancer is primary cancer;
[30] the method of diagnosis of [28], wherein the cancer is metastatic cancer;
[31] a diagnostic agent for use in a method for diagnosis of cancer, which comprises an antibody that binds to an EREG protein;
[32] a kit for use in a method for diagnosis of cancer, which comprises an antibody that binds to an EREG protein, and a biological sample comprising an EREG protein;
[33] a method of screening for a candidate compound as cancer therapeutic agent, which comprises the steps of:
(1) contacting EREG-expressing cells with a test compound;
(2) measuring the EREG expression level in the EREG-expressing cells; and
(3) selecting a compound that lowers the EREG expression level compared to a control as a candidate therapeutic agent for cancer;
[34] the method of [33], wherein the EREG expression level is evaluated by the level of the EREG protein secreted into a culture supernatant;
[35] a method of screening for a candidate compound as cancer therapeutic agent, which comprises the steps of:
(1) culturing cells that proliferate in an EREG-dependent manner, in the presence of EREG and a test compound;
(2) measuring the cell proliferation level; and
(3) selecting a test compound that suppresses cell proliferation compared to a control as a candidate therapeutic agent for cancer.

Effects of the Invention

The EREG gene expression was confirmed to be significantly elevated in cancer cells based on gene expression analysis of various cancer tissues and cancer cell lines. On the other hand, the EREG expression is very low in normal cells. Therefore, EREG is useful as a specific marker for cancer detection.

The cytotoxic effect of anti-EREG antibodies against EREG-expressing cells was confirmed in the present invention. While the EREG expression is very low in normal cells, it is elevated in cancer cells. This supports the possibility that cancer cell-specific cytotoxic effect could be obtained in vivo, for example, by administering an anti-EREG antibody.

Furthermore, in the present invention, it was confirmed that EREG-dependent cell proliferation is neutralized by anti-EREG antibodies. Therefore, in a preferred embodiment, in addition to the cytotoxic effect, anti-EREG antibodies inhibit cancer cell proliferation by neutralizing the cell proliferation effect of EREG.

BRIEF DESCRIPTION OF THE DRAWINGS

FIG. 21-1 shows the results of sandwich ELISA for antigenic proteins using mouse anti-EREG antibodies and human chimeric anti-EREG antibodies.

FIG. 21-2 is the continuation of FIG. 22-1.

FIG. 21-3 is the continuation of FIG. 22-2.

MODE FOR CARRYING OUT THE INVENTION

Figure 1:
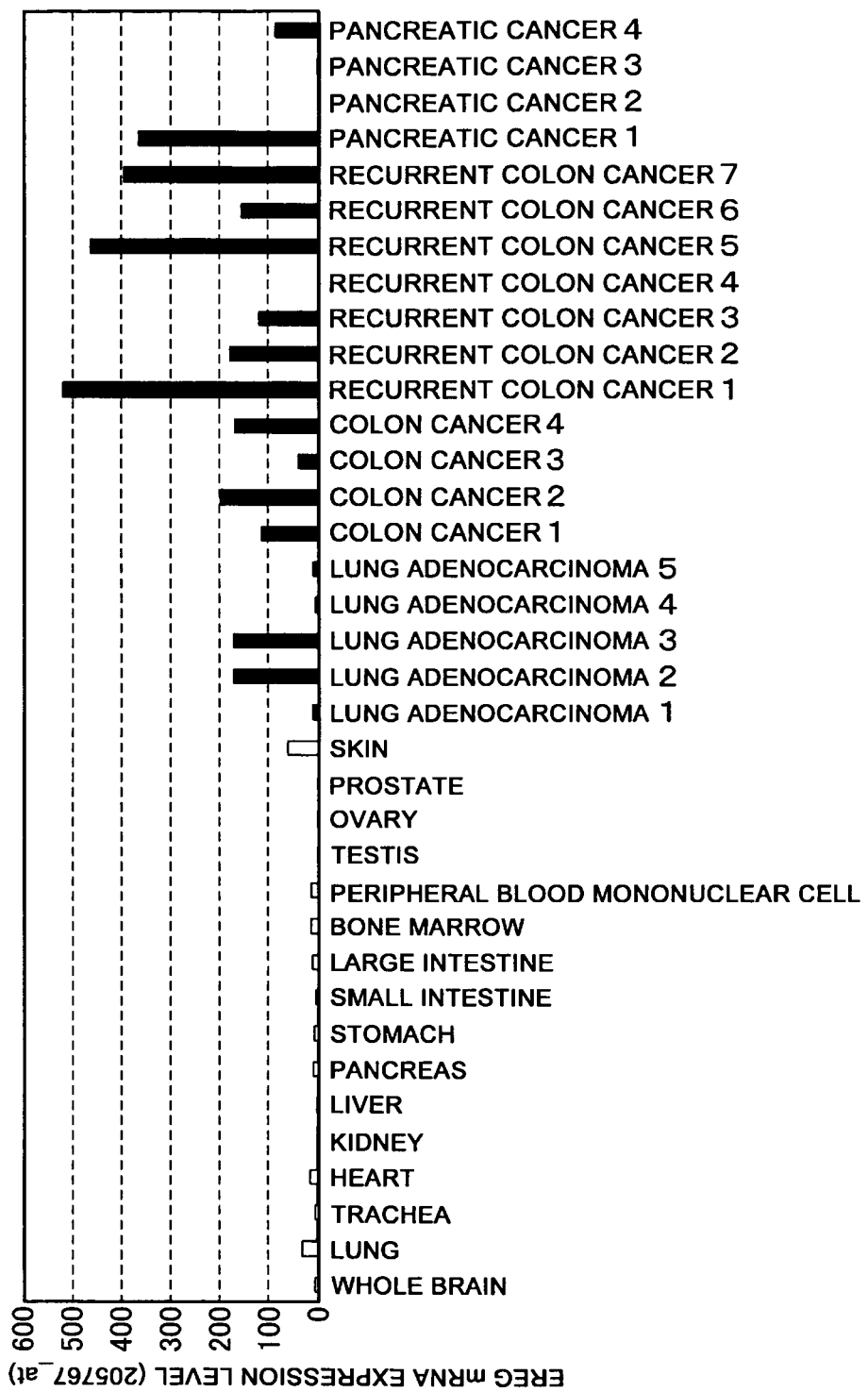
FIG. 1 shows the levels of EREG mRNA transcript in normal tissues and cancer tissues. The vertical axis indicates the signal intensity of Probe ID: 205767_at HG-U133A. The intensity is relative to the mean value of the expression scores of all the genes on GeneChip U133A, which was set to 100.

EREG is a membrane-bound epidermal growth factor protein. Its amino acid sequence and its encoding gene sequence are disclosed in GenBank Accession Number NP_001423 (SEQ ID NO: 22) and NM_001432 (SEQ ID NO: 21), respectively. In the present invention, the EREG protein refers to both the full-length protein and fragments thereof. "Fragments" refers to polypeptides comprising any region of the EREG protein, and may not have the function of the naturally-occurring EREG protein. Without being limited thereto, an example of the fragments is a fragment comprising the extracellular region of the EREG protein. Positions 29 to 122 in the amino acid sequence of SEQ ID NO: 22 correspond to the extracellular region of the EREG protein. Positions 123 to 140 in the amino acid sequence of SEQ ID NO: 22 correspond to the transmembrane region.

In the present invention, it was shown by analyses of clinical samples and cancer cell lines that the EREG gene is highly and frequently expressed in primary colon cancer, metastatic colon cancer, lung adenocarcinoma, pancreatic cancer, stomach cancer, and kidney cancer tissues. Furthermore, it was also shown that EREG protein was highly expressed in cancer cell lines. That is, the EREG protein is useful as a diagnostic marker for cancer.

Detection of EREG Gene Expression

In the present invention, methods for diagnosing cancer comprise the step of detecting the EREG gene expression. In one embodiment of the methods of the present invention, the expression of EREG protein is detected.

In the present invention, detection includes quantitative and qualitative detection. Examples of the qualitative detection include the following measurements:

measurement only for the presence or absence of the EREG protein;

measurement to see whether or not the EREG protein is present above a certain amount; and measurement that compares the amount of the EREG protein with that of other samples (for example, a control sample).

On the other hand, examples of quantitative detection include measurement of the EREG protein concentration, and measurement of the amount of the EREG protein.

Test samples of the present invention are not particularly limited as long as they are samples that may contain an EREG protein. Specifically, samples collected from the body of organisms such as mammals are preferred. Samples collected from humans are more preferred. Specific examples of the test samples include blood, interstitial fluid, plasma, extravascular fluid, cerebrospinal fluid, synovial fluid, pleural fluid, serum, lymphatic fluid, saliva, and urine. Preferred samples are blood samples. Blood samples include serum, plasma, and whole blood. Of these blood samples, serum is preferred. Test samples obtained from samples such as immobilized specimens of tissue or cells collected from the body of an organism, and cell culture solution are also included in the test samples of the present invention.

The cancers that are diagnosed by the present invention are not particularly limited and may be any cancer. Specific examples include colon cancer, metastatic colon cancer, lung adenocarcinoma, pancreatic cancer, stomach cancer, and kidney cancer. In the present invention, both primary and metastatic foci of these cancers can be diagnosed. Primary colon cancer, metastatic colon cancer, and pancreatic cancer are particularly preferable in the present invention.

In the present invention, cancer is detected when an EREG protein is detected in a test sample. More specifically, if the amount of the EREG protein detected in a test sample is larger than that in a negative control or a healthy individual, it is determined that the subject has cancer or is at high risk of being affected with cancer in the future. That is, the present invention relates to methods for detecting cancer which comprise the steps of:
(1) detecting the EREG expression in a biological sample collected from a subject; and
(2) determining that the subject has cancer if the EREG expression detected in step (1) is higher than that of a control.

In the present invention, the control includes a negative control and a biological sample from a healthy individual. A negative control can be obtained by collecting biological samples from healthy individuals, and mixing the biological samples as necessary. The EREG expression in a control can be detected together with the EREG expression in the biological sample of a subject. Alternatively, the EREG expression in biological samples of many healthy individuals can be detected in advance, and a standard expression level in healthy individuals can be determined statistically. More specifically, for example, the mean value±2× standard deviation (S.D.), or mean value±3× standard deviation (S.D.) may be used as the standard value. Statistically, 80% of the healthy individuals are within ±2× standard deviation (S.D.) from the mean value, and 90% of the healthy individuals are within ±3× standard deviation (S.D.) from the mean value.

Alternatively, the EREG expression level in a control can be determined using an ROC curve. A receiver operating characteristic (ROC) curve is a graph with detection sensitivity on the vertical axis, and false positive rate (i.e., "1-specificity") on the horizontal axis. In the present invention, an ROC curve can be obtained by plotting the changes of sensitivity to false positive rate, as a result of continuously varying the standard values for determining the EREG expression level in a biological sample.

The "standard value" used for obtaining an ROC curve is a numerical value temporarily used for statistical analysis. In general, "standard values" for obtaining an ROC curve are continuously varied within a range that covers all selectable standard values. For example, the standard values can be varied between the minimum and maximum values of EREG measured in the population analyzed.

Based on the ROC curve obtained, standard values that are expected to yield the desired detection sensitivity and accuracy can be selected. Standard values that are statistically determined by an ROC curve or such are also called "cut-off values". In step (2) of the above methods of cancer detection based on cut-off values, the EREG expression detected in step (1) is compared to the cut-off value. Detection of a higher EREG expression in step (1) than the cut-off value means detection of cancer in the subject.

In the present invention, the EREG expression level can be determined by any method. More specifically, the EREG expression level can be determined by evaluating the amount of EREG mRNA, the amount of EREG protein, and the biological activity of EREG protein. The amount of EREG mRNA and EREG protein can be determined by the methods described herein. Alternatively, one can evaluate the cell proliferation-inducing activity as a biological activity of EREG, using cells whose proliferation is induced in an EREG-dependent manner.

Subjects in the present invention may be any animal species that express an EREG protein. For example, many non-human mammals such as monkeys, cattle, sheep, mice, dogs, cats, and hamsters are known to express EREG protein. Therefore, these animals are included in the subjects of the present invention. Subjects that are particularly preferred are humans. As a matter of course, when a non-human animal is used as a subject, the EREG protein for the animal species is detected.

Preferred embodiments of the diagnostic methods of the present invention include methods of cancer diagnosis that comprise the step of detecting an EREG protein on a section of immobilized tissue or cells obtained from a patient affected with an aforementioned cancer. Furthermore, other embodiments of the present invention include diagnostic methods comprising the step of detecting cell-released EREG protein in the blood. In particular, the present invention is preferably a method of cancer diagnosis that comprises the step of detecting a fragment comprising the extracellular domain of the EREG protein present in the blood.

Methods for detecting the EREG protein contained in a test sample are not particularly limited. An immunological method that uses an anti-EREG antibody for detection is preferred. The immunological methods that may be used include:
radioimmunoassay (RIA);
enzyme immunoassay (EIA);
fluorescence immunoassay (FIA);
luminescence immunoassay (LIA);
immunoprecipitation (IP);
turbidimetric immunoassay (TIA);
Western blotting (WB);
immunohistochemical staining (IHC); and
single radial immunodiffusion (SRID).

Of the above techniques, enzyme immunoassay is a preferred immunological assay. More specifically, enzyme-linked immunosorbent assay (ELISA) is a preferred enzyme immunoassay. An embodiment of ELISA is, for example, sandwich ELISA. The above-mentioned immunological methods such as ELISA are methods known to those skilled in the art.

The following method is, for example, a common detection method that uses an anti-EREG antibody. After an anti-EREG antibody is immobilized onto a support, the support is blocked to avoid non-specific binding of proteins to the support. For example, bovine serum albumin (BSA), gelatin, or albumin is used for blocking. Various methods for binding antibodies to a support are known. For example, synthetic resins such as polystyrene resins physically adsorb antibodies. Alternatively, antibodies may be chemically bound to a support into which functional groups are introduced. Bifunctional linkers can be used to bind antibodies chemically.

Then, a test sample is added to the support for incubation. During the incubation, the anti-EREG antibodies bound to the support bind with the EREG protein in the test sample. Subsequently, EREG bound to the support via the anti-EREG antibody is detected. Prior to detection of EREG bound to the support, the support may be washed. EREG bound to the support may be detected, for example, using a second antibody that recognizes EREG. The second antibody can be labeled with a labeling substance. Alternatively, the second antibody can be labeled indirectly by using a third antibody (secondary antibody) that recognizes the second antibody. As described above, the EREG protein in a test sample can be detected by qualitatively or quantitatively detecting the EREG protein bound to the anti-EREG antibody on the support. Several specific examples are further described below.

In the present invention, the following materials may be utilized as a support to immobilize an anti-EREG antibody: insoluble polysaccharides: agarose, cellulose, and such; synthetic resins: silicon resin, polystyrene resin, polyacrylamide resin, nylon resin, polycarbonate resin, and such; and insoluble support such as glass.

Such a support is used in the form of beads or plates. In the case of beads, a column or the like filled with beads can be used. In the case of a plate, a multi-well plate (96-well multi-well plate, or such), or a biosensor chip can be used. For binding an anti-EREG antibody to a support, an anti-EREG antibody can be bound to a support by commonly used methods such as chemical bonding or physical adsorption. Commercially available supports can be suitably used.

Binding of an anti-EREG antibody to an EREG protein is generally performed in a buffer. For example, phosphate buffer, Tris buffer, citric acid buffer, borate buffer, carbonate buffer, or such is used as the buffer. Furthermore, incubation can be suitably carried out using commonly used conditions, such as incubation at a temperature between 4° C. and room temperature for one to 24 hours. So long as the binding between the EREG protein and anti-EREG antibody is not interrupted, anything can be used for washing after incubation, and for example, a buffer containing a surfactant such as Tween 20 or such can be suitably used.

In the method of detecting an EREG protein in the present invention, a control sample can be suitably prepared in addition to the test sample in which the EREG protein content will be detected. The control sample includes, for example, a negative control sample containing no EREG protein and a positive control sample containing the EREG protein. In this case, by comparing the results obtained from a negative control sample containing no EREG protein with the results obtained from a positive control sample containing the EREG protein, the presence or absence of the EREG protein in the test sample can be confirmed. Furthermore, after preparing a series of control samples with stepwise changes in concentration, and obtaining detection results for each control sample as a numerical value, a standard curve can be obtained based on the values of the EREG protein concentration and their corresponding measured values. The EREG protein contained in a test sample can be quantitatively determined according to the standard curve, and the result of measuring the EREG protein contained in the test sample.

In a preferred embodiment of detection of the EREG protein bound to a support via an anti-EREG antibody, a method that uses an anti-EREG antibody labeled with a labeling substance is used. For example, the EREG protein can be detected by contacting a test sample with the anti-EREG antibody immobilized onto a support, washing it as necessary, and then adding a labeled antibody that specifically recognizes the EREG protein.

Anti-EREG antibodies can be labeled by generally known methods. A labeling substance known to those skilled in the art such as fluorescent dyes, enzymes, coenzymes, chemiluminescent substances, and radioactive substances can be used as the labeling substance. Specifically, the following labeling substances are used for labeling antibodies: radioisotopes: $^{32}P$, $^{14}C$, $^{125}I$, $^{3}H$, $^{131}I$, and such;

fluorescent dyes: fluorescein, rhodamine, dansyl chloride, umbelliferone, and such;

enzymes: luciferase, peroxidase, alkaline phosphatase, β-galactosidase, β-glucosidase, horseradish peroxidase, glucoamylase, lysozyme, saccharide oxidase, micro peroxidase, and such; and binding affinity substances: biotin, and such.

When using biotin as a labeling substance, biotin-labeled antibodies can be detected using avidin bound to an enzyme such as alkaline phosphatase. For binding a labeling substance to an anti-EREG antibody, known methods such as the glutaraldehyde method, maleimide method, pyridyl disulfide method, or periodic acid method can be used.

Methods for detecting labeling substances are also known. For example, when detecting an anti-EREG antibody labeled with a radioactive substance, the radioactivity can be detected by a liquid scintillation counter. An anti-EREG antibody labeled with an enzyme can be detected by adding a substrate to the labeled anti-EREG antibody, and then detecting the substrate's enzymatic change. Combination of an enzyme that catalyzes color reaction or luminescence reaction with a substrate is known. Specific examples of a substrate for peroxidase detection include 2,2-azinobis(3-ethylbenzothiazoline-6-sulfonic acid) diammonium salt (ABTS), 1,2-phenylenediamine(ortho-phenylenediamine), and 3,3',5,5'-tetramethylbenzidine (TMB). When these coloring substrates are used, the reaction can be traced by an absorption photometer. When the substrate is a fluorescence emitting substance, enzymatic change of the substrate can be detected by a spectrofluorometer.

In the present invention, a particularly preferred embodiment of the methods for detecting the EREG protein is, for example, a method that uses a biotin-labeled anti-EREG antibody and avidin. Specifically, avidin or streptavidin bound to an enzyme can be used to detect the biotin-labeled anti-EREG antibody. Avidin and streptavidin bound to an enzyme such as alkaline phosphatase or peroxidase are known.

In the present invention, another embodiment of the methods for detecting the EREG protein includes a method that uses one or more types of primary antibodies that specifically recognize the EREG protein, and one or more types of secondary antibodies that specifically recognize the primary antibodies.

When using a secondary antibody, an anti-EREG antibody derived from a species different from that of the antibody bound to a support (solid-phase antibody) is used as the liquid-phase antibody. The liquid-phase antibody binds to the EREG protein trapped by the solid-phase antibody, and the secondary antibody binds to the liquid-phase antibody. The secondary antibody can bind to the liquid-phase antibody, but cannot bind to the solid-phase antibody. Therefore, the amount of the secondary antibody remaining on the support depends on the amount of the liquid-phase antibody bound to the support via the EREG protein. As a result of the above-mentioned operation, the EREG protein in a test sample can be detected by qualitatively or quantitatively detecting the secondary antibodies bound. In this case, the secondary antibody can be suitably labeled with a labeling substance.

In the present invention, another embodiment of the methods for detecting the EREG protein is, for example, a detection method that uses aggregation reaction. In this method, the EREG protein can be detected using a carrier adsorbed with an anti-EREG antibody. Any carrier may be used for adsorbing the antibody, as long as it is insoluble and stable, and does not cause non-specific reactions. For example, latex particles, bentonite, collodion, kaolin, or immobilized sheep erythrocytes can be used. Latex particles have excellent homogeneity and stability, and thus are preferred carriers. Latex particles that can be used are, for example, polystyrene latex particles, styrene-butadiene copolymer latex particles, or polyvinyl toluene latex particles. Alternatively, latex particles into which functional groups such as carboxyl groups have been introduced are also known. For example, polystyrene latex particles are preferred latex particles.

When mixed with an antibody, latex particles that have a hydrophobic surface physically adsorb the antibody. Alternatively, if the latex particles have functional groups, the antibody can be bound chemically. Antibody-bound particles are mixed with a sample, and this is stirred for a given period of time. Since the degree of particle aggregation becomes larger as the concentration of EREG protein in the sample increases, the EREG protein can be detected by assessing the degree of aggregation with the naked eye. Furthermore, the EREG protein can also be detected by measuring the increase in turbidity or scattered light caused by aggregation using a spectrophotometer or such.

In the present invention, another embodiment of the methods for detecting the EREG protein includes, for example, a method that uses a biosensor utilizing the surface plasmon resonance phenomenon. The use of a biosensor utilizing the surface plasmon resonance phenomenon enables real-time observation of protein-protein interactions as surface plasmon resonance signals without the need of protein labeling. For example, by using a biosensor such as BIAcore (Biacore), binding between the EREG protein and an anti-EREG antibody can be detected. Specifically, a test sample is contacted with a sensor chip onto which an anti-EREG antibody is immobilized, and the EREG protein that binds to the anti-EREG antibody can be detected as a change in resonance signals.

EREG is a membrane protein whose expression is elevated specifically in cancer cells. Therefore, cancer cells or cancer tissues can be detected by anti-EREG antibodies. For example, cancer cells contained in cells or tissues collected from a living body are detected by immunohistochemical analysis using anti-EREG antibodies. Alternatively, cancer tissues in a living body can be detected with anti-EREG antibodies. More specifically, the present invention relates to methods of cancer detection which comprise the steps of: (1) administering to a subject a radioisotope-labeled antibody that binds to an EREG protein; and (2) detecting accumulation of the radioisotope. In order to trace the antibody administered into a living body, the antibody may be labeled for detection. For example, the behavior of antibodies labeled with a fluorescent substance, luminescent substance, or radioisotope can be traced in vivo. Antibodies labeled with a fluorescent substance or a luminescent substance can be observed using an endoscope or a laparoscope. When using a radioisotope, the localization of an antibody can be imaged by tracing the radioactivity of the radioisotope. In the present invention, the localization of an anti-EREG antibody in vivo demonstrates the presence of cancer cells.

A positron-emitting nuclide can be used as a radioisotope for antibody labeling for the detection of cancer in a living body. For example, antibodies can be labeled with positron-emitting nuclides such as $^{18}$F, $^{55}$Co, $^{64}$Cu, $^{66}$Ga, $^{68}$Ga, $^{76}$Br, $^{89}$Zr, and $^{124}$I. Anti-EREG antibodies can be labeled with these positron-emitting nuclides by known methods (Acta Oncol. 32, 825-830, 1993).

After administering an anti-EREG antibody labeled with a positron-emitting nuclide to humans or animals, radiation emitted by the radioactive nuclide is measured from outside the body using PET (positron emission tomography scanner), and then converted into an image by computed tomography methods. PET is an instrument for non-invasively obtaining data on the in vivo behavior of drugs and such. Radiation intensity can be quantitatively converted into an image as signal intensity using PET. By using PET as described above, antigenic molecules that are highly expressed in a particular cancer can be detected without collecting samples from patients. In addition to the above-mentioned nuclides, anti-EREG antibodies can be radiolabeled with short-lived nuclides using positron-emitting nuclides such as $^{11}$C, $^{13}$N, $^{15}$O, $^{18}$F, and $^{45}$Ti.

The use of a medical cyclotron for production of short-lived nuclides using the above-mentioned nuclides, techniques for producing short-lived radiolabeled compounds, and such, are currently under research and development. Anti-EREG antibodies can be labeled with various radioisotopes using such techniques. Anti-EREG antibodies administered to patients gather at primary foci and metastatic foci according to the specificity of the anti-EREG antibodies at each site of the pathological tissue. If the anti-EREG antibodies are labeled with positron-emitting nuclides, the presence of primary foci and metastatic foci can be detected from the localization of their radioactivity by detecting radioactivity. For use in such diagnostic purpose, emission activity values of 25-4000 keV gamma particles or positrons can be suitably used. Furthermore, therapeutic effects can be expected by selecting a suitable nuclide and administering it in large quantities. To obtain anticancer effect by radiation, nuclides that provide emission values of 70-700 keV gamma particles or positrons can be used.

In another embodiment of the methods of the present invention, the expression of EREG mRNA is detected. In the present invention, detection includes quantitative and qualitative detection. Examples of qualitative detection include the following measurement techniques:
simple measurement for the presence or absence of EREG mRNA;
measurement to see whether or not the EREG mRNA is present above a certain amount; and
measurement that compares the amount of EREG mRNA to that of other samples (for example, a control sample).

On the other hand, quantitative detection includes, for example, measurement of the EREG mRNA concentration, and measurement of the amount of EREG mRNA.

Any sample that may contain EREG mRNA may be used as a test sample of the present invention. Samples collected from the body of an organism such as mammal are preferred, and samples collected from humans are more preferred. Specific examples of the test samples include blood, interstitial fluid, plasma, extravascular fluid, cerebrospinal fluid, synovial fluid, pleural fluid, serum, lymphatic fluid, saliva, and urine. Preferred samples are blood samples. Blood samples include serum, plasma, and whole blood. Test samples of the present invention also include samples obtained from test samples, such as cell culture solutions and specimens of immobilized tissues or cells collected from the body of an organism.

The cancer for diagnosis is not particularly limited. Specific examples include colon cancer, lung adenocarcinoma, pancreatic cancer, stomach cancer, and kidney cancer. In the present invention, both primary and metastatic foci of these cancers can be diagnosed. Primary colon cancer, metastatic colon cancer, and pancreatic cancer are particularly preferable.

Subjects in the present invention may be any animal species that expresses the EREG protein. For example, many non-human mammals such as monkeys, cattle, sheep, mice, dogs, cats, and hamsters are known to express EREG Particularly suitable subjects are humans. When a non-human animal species is used as a subject, the EREG mRNA of the animal species is detected.

Specific embodiments of the detection method are described below. First, a sample is prepared from a subject. Then, EREG mRNAs included in the sample are detected. In the present invention, it is also possible to detect cDNAs synthesized from mRNAs. In the present invention, detection of the EREG mRNA or EREG-encoding cDNA in a test sample means detection of cancer in the patient. For example, if a greater amount of EREG mRNA or EREG-encoding cDNA is detected in the test sample than in a negative control or a healthy individual, it can be determined that the subject has cancer or is at high risk of being affected by cancer in the future.

Methods of mRNA detection are known. Specifically, for example, the Northern blotting method, RT-PCR method, DNA array method, and such may be used in the present invention.

The detection methods of the present invention described above can be automated using various automatic testing devices. Through automation, large quantities of sample can be examined at a time.

A further objective of the present invention is to provide diagnostic agents or kits for cancer diagnosis which comprise reagents for detecting the EREG protein in a test sample. The diagnostic agents of the present invention comprise at least an anti-EREG antibody. When the diagnostic agents or kits of the present invention are based on an EIA method such as ELISA, a carrier for immobilizing the antibody may be included. Alternatively, a carrier-bound antibody may be provided. If the diagnostic agents or kits of the present invention are based on an aggregation method that uses a carrier such as latex, they may include an antibody-adsorbed carrier.

Kits for cancer diagnosis can be produced by combining the diagnostic agents for cancer of the present invention with another element used for detecting EREG. More specifically, the present invention relates to kits for cancer diagnosis which comprise an EREG-binding antibody and a control sample comprising a biological sample containing EREG. The kits of the present invention may additionally comprise a reagent for immunoassay of EREG. For example, as regents for ELISA, chromogenic substrates for detecting enzymatic labels or washing solutions for washing the solid phase can be combined. In addition, instructions that describe the measurement operation can be attached to the kits.

Furthermore, the present invention provides diagnostic agents or kits for cancer diagnosis which comprise a reagent for detecting EREG mRNA or EREG-encoding cDNA in a test sample. The diagnostic agents of the present invention contain at least an EREG-encoding DNA (SEQ ID NO: 21; a DNA consisting of the nucleotide sequence of NM_001423) or an oligonucleotide comprising at least 15 nucleotides complementary to the complementary strand of the DNA.

Herein, the term "complementary strand" refers to the other strand with respect to one of the strands of a double-stranded nucleic acid consisting of A:T (U in the case of RNA) and G:C base pairs. In addition, "complementary" refers not only to cases of completely complementary sequences within a region of at least 15 consecutive nucleotides, but also to cases of at least 70%, preferably at least 80%, more preferably 90%, and even more preferably 95% homology or higher in a nucleotide sequence. Homology may be determined using an algorithm described herein.

Such oligonucleotides can be used as probes or primers for detecting or amplifying EREG-encoding DNA, and probes or primers for detecting the expression of these DNAs. Furthermore, the probes can be used in the form of a DNA array substrate.

When such oligonucleotides are used as primers, their lengths are normally 15 bp to 100 bp. The preferred lengths of the primers are 17 bp to 30 bp. Any primer that can amplify at least a portion of the EREG-encoding DNA or a complementary strand thereof may be used as a primer. Furthermore, when they are used as primers, their 3'-end regions can be made to be complementary, and for the 5' ends, restriction enzyme recognition sequences or tags can be added.

Furthermore, any oligonucleotide that hybridizes specifically to at least a portion of the EREG-encoding DNA, or to a complementary strand thereof can be used as a probe. The nucleotide sequence of the probe for mRNA detection is selected from the nucleotide sequences complementary to the sense strand of EREG. The chain length of the probe is usually at least 15 bp or longer.

In the present invention, oligonucleotides can be made into probes by suitable labeling. Methods for labeling oligonucleotides are known. For example, oligonucleotides can be labeled by phosphorylating the 5' ends of the oligonucleotides, using T4 polynucleotide kinase with $^{32}$P-labeled ATP as a substrate. Alternatively, examples of the methods include methods that incorporate a labeled substrate nucleotide using a DNA polymerase and a random hexamer oligonucleotide or such as a primer (random priming methods, etc.). In random priming methods, Klenow enzyme or such is used as a DNA polymerase. Furthermore, nucleotides can be labeled with a radioisotope such as $^{32}$P, a fluorescent dye, biotin, digoxin, or the like.

The oligonucleotides of the present invention can be produced using, for example, a commercially available oligonucleotide synthesizer. The probes may be produced as double-stranded DNA fragments obtained by restriction enzyme treatment or the like.

In the diagnostic agents or kits mentioned above, sterilized water, physiological saline, vegetable oil, surfactants, lipids, solubilizers, buffers, protein stabilizers (BSA, gelatin, or such), preservatives, blocking solutions, reaction solution, reaction-stopping solution, reagents for treating samples, and such may be combined as necessary, in addition to the oligonucleotides and antibodies, which are the active ingredients.

Production of Anti-EREG Antibodies

The anti-EREG antibodies used in the present invention may be derived from any origin, and may be of any type and in any form, as long as they specifically bind to an EREG protein. Specifically, known antibodies such as non-human animal antibodies (for example, mouse antibodies, rat antibodies, and camel antibodies), human antibodies, chimeric antibodies, and humanized antibodies can be used. In the present invention, the antibodies used may be monoclonal antibodies or polyclonal antibodies. Monoclonal antibodies are preferred.

Anti-EREG antibodies to be used in the present invention can be obtained as polyclonal or monoclonal antibodies using known techniques. In particular, monoclonal antibodies derived from a mammal are preferable as the anti-EREG antibodies for use in the present invention. The monoclonal antibodies derived from a mammal include antibodies produced by hybridoma, and antibodies produced by a host transformed by genetic engineering techniques with an expression vector containing an antibody gene.

A monoclonal antibody-producing hybridoma can be prepared essentially by using the following known technique. First, immunization is performed using the EREG protein as a sensitizing antigen according to a general immunization method. Immunocytes that are obtained from the immunized animals are then fused to known parent cells by a general cell fusion method to obtain hybridomas. Furthermore, hybridomas that produce an anti-EREG antibody can be selected by screening for cells that produce the antibodies of interest using a general screening method.

Specifically, monoclonal antibodies are prepared as follows. First, the EREG gene can be expressed to obtain EREG protein for use as the sensitizing antigen for antibody production. The nucleotide sequence of the EREG gene is disclosed as GenBank Accession No. NM_001432 (SEQ ID NO: 21) and such. Specifically, the EREG-encoding gene sequence is inserted into a known expression vector, and it is used to transform an appropriate host cell. Then, the human EREG protein of interest can be purified by a known method from the host cell or its culture supernatant. Alternatively, a purified naturally-derived EREG protein may be similarly used. Furthermore, as used in the present invention, a fusion protein produced by fusing a desired partial peptide of an EREG protein with another polypeptide may be used as an immunogen. For example, Fc fragments of antibodies, peptide tags, or such can be used to produce a fusion protein for use as an immunogen. A vector that expresses the fusion protein can be produced by fusing the desired genes encoding two or more types of polypeptide fragments in frame, and inserting the fused genes into an expression vector as described above. Methods for producing fused proteins are described in Molecular Cloning 2nd ed. (Sambrook, J. et al., Molecular Cloning 2nd ed., 9.47-9.58, Cold Spring Harbor Lab. press, 1989).

The EREG protein purified in this manner can be used as a sensitizing antigen for immunization of mammals. A partial peptide of EREG can also be used as a sensitizing antigen. For example, the following peptides can be used as a sensitizing antigen:
peptides obtained from the amino acid sequence of human EREG by chemical synthesis;
peptides obtained by inserting a portion of the EREG gene into an expression vector and expressing it; and
peptides obtained by degrading the EREG protein with a protease.

There are no limitations on the region or size of the partial EREG peptides used. The preferred region can be selected from the amino acid sequence composing the extracellular domain of EREG (positions 29 to 122 in the amino acid sequence of SEQ ID NO: 22). The number of amino acids constituting a peptide to be used as the sensitizing antigen is preferably at least three or more, for example, five or more, or six or more. More specifically, a peptide comprising 8 to 50 residues, or preferably 10 to 30 residues can be used as a sensitizing antigen.

The mammal to be immunized with the sensitizing antigen is not particularly limited. To obtain monoclonal antibodies by the cell fusion method, the animal to be immunized is preferably selected in consideration of the compatibility with the parent cells to be used for cell fusion. Generally, rodents are preferred as the animal to be immunized. Specifically, mice, rats, hamsters, or rabbits can be used as the animal to be immunized. In addition, monkeys and such may be used as the animal to be immunized.

The above-described animals can be immunized with a sensitizing antigen according to a known method. For example, as a general method, immunization can be performed by injecting a mammal intraperitoneally or subcutaneously with a sensitizing antigen. Specifically, the sensitizing antigen is administered to mammals several times every four to 21 days. The sensitizing antigen is diluted at an appropriate dilution with PBS (Phosphate-Buffered Saline), physiological saline, or such, and then used for immunization. Furthermore, the sensitizing antigen may be administered together with an adjuvant. For example, the sensitizing antigen can be prepared by mixing with a Freund's complete adjuvant, and then emulsifying it. Furthermore, an appropriate carrier can be used for immunization using the sensitizing antigen. Particularly when a partial peptide with a small molecular weight is used as a sensitizing antigen, the sensitizing antigen peptide is desirably bound to a carrier protein such as albumin or keyhole limpet hemocyanin, and then used for immunization.

Mammals are immunized as described, and after an increase in the amount of desired antibody in the serum is confirmed, immunocytes are collected from the mammals and subjected to cell fusion. A particularly preferred immunocyte is a splenocyte.

A mammalian myeloma cell is used as a cell to be fused with the above-mentioned immunocyte. The myeloma cells preferably comprise a suitable selection marker for screening. A selection marker confers characteristics to cells for their survival (or failure to survive) under a specific culturing condition. Hypoxanthine-guanine phosphoribosyltransferase deficiency (hereinafter abbreviated as HGPRT deficiency), and thymidine kinase deficiency (hereinafter abbreviated as TK deficiency) are known as selection markers. Cells having HGPRT or TK deficiency have hypoxanthine-aminopterin-thymidine sensitivity (hereinafter abbreviated as HAT sensitivity). HAT-sensitive cells cannot carry out DNA synthesis in a HAT selection medium, and are thus killed. However, when the cells are fused with normal cells, they can continue to synthesize DNA using the salvage pathway of the normal cells, and therefore they can grow in the HAT selection medium.

HGPRT-deficient and TK-deficient cells can be selected in a medium containing 6-thioguanine or 8-azaguanine (hereinafter abbreviated as 8AG), and 5'-bromodeoxyuridine, respectively. Normal cells are killed since they incorporate these pyrimidine analogs into their DNA. However, cells that are deficient in these enzymes can survive in the selection medium, since they cannot incorporate these pyrimidine analogs. Alternatively, a selection marker referred to as G418 resistance provides resistance to 2-deoxystreptamine-type antibiotics (gentamycin analogs) from the neomycin-resistance gene. Various types of myeloma cells that are suitable for cell fusion are known. For example, myeloma cells including the following cells can be used to produce the monoclonal antibodies of the present invention:
P3 (P3x63Ag8.653) (J. Immunol. (1979) 123, 1548-1550);
P3x63Ag8U.1 (Current Topics in Microbiology and Immunology (1978) 81, 1-7);
NS-1 (Kohler. G. and Milstein, C. Eur. J. Immunol. (1976) 6, 511-519);
MPC-11 (Margulies. D. H. et al., Cell (1976) 8, 405-415);
SP2/0 (Shulman, M. et al., Nature (1978) 276, 269-270);
FO (de St. Groth, S. F. et al., J. Immunol. Methods (1980) 35, 1-21);
S194 (Trowbridge, I. S. J. Exp. Med. (1978) 148, 313-323); and
R210 (Galfre, G. et al., Nature (1979) 277, 131-133).

Cell fusion of the above-mentioned immunocytes with myeloma cells is essentially performed according to a known method, for example, the method of Kohler and Milstein et al. (Kohler. G. and Milstein, C., Methods Enzymol. (1981) 73, 3-46).

More specifically, the above-mentioned cell fusion can be performed in a standard nutritional culture medium in the presence of, for example, a cell-fusion accelerator. A cell-fusion accelerator may be, for example, polyethylene glycol (PEG), Sendai virus (HVJ), or the like. If desired, an auxiliary agent such as dimethylsulfoxide can be added to further enhance fusion efficiency.

The ratio of immunocytes to myeloma cells used can be established at one's discretion. For example, the number of immunocytes is preferably set to one to ten times of that of myeloma cells. As a medium to be used for the above-mentioned cell fusion, for example, RPMI1640 medium and MEM medium, which are appropriate for the growth of the above-mentioned myeloma cell line, or other standard media that are used for this type of cell culture can be used. Moreover, a serum supplement solution such as fetal calf serum (FCS) can be added to the media.

Cell fusion is performed by thoroughly mixing predetermined amounts of the above-mentioned immunocytes and myeloma cells in the above-mentioned medium, adding and mixing with a PEG solution pre-heated to approximately 37° C., so as to form the desired fused cells (hybridomas). In the cell fusion method, for example, PEG with an average molecular weight of approximately 1000 to 6000 can generally be added at a concentration of 30 to 60% (w/v). Subsequently, the agent for cell fusion or the like which is unfavorable for the growth of hybridomas can be removed by successively adding an appropriate medium such as those listed above, removing the supernatant after centrifugation, and repeating these steps.

Hybridomas obtained in this manner can be selected using a selection medium appropriate for the selection markers carried by myelomas used for cell fusion. For example, cells that have HGPRT and TK deficiencies can be selected by culturing them in a HAT medium (a medium containing hypoxanthine, aminopterin, and thymidine). More specifically, when HAT-sensitive myeloma cells are used for cell fusion, cells that successfully fuse with normal cells can be selectively grown in the HAT medium. Culturing using the above-mentioned HAT medium is continued for a sufficient period of time to kill the cells other than the hybridoma of interest (non-fused cells). More specifically, the hybridoma of interest can be selected, typically by culturing for several days to several weeks. Subsequently, hybridomas that produce the antibody of interest can be screened and monocloned by carrying out a standard limiting dilution method. Alternatively, an EREG-recognizing antibody can be prepared using the method described in International Patent Publication No. WO 03/104453.

An antibody of interest can be suitably screened and singly cloned by a screening method based on known antigen-antibody reaction. For example, the antigen is bound to a carrier such as polystyrene beads or the like, or a commercially available 96-well microtiter plate, followed by reaction with the culture supernatant of the hybridomas. Then, after the carrier is washed, it is reacted with an enzyme-labeled secondary antibody or the like. If the antibody of interest that reacts with the sensitizing antigen is contained in the culture supernatant, the secondary antibody will bind to the carrier via the antibody. Ultimately, the presence of the antibody of interest in the culture supernatant can be determined by detecting secondary antibodies bound to the carrier. Hybridomas producing desired antibodies that can bind to the antigen can be cloned by the limiting dilution method or the like. Antigens used for immunization as well as an operably equivalent EREG protein can be suitably used in this case. For example, the extracellular domain of EREG or an oligopeptide comprising a partial amino acid sequence composing this region may be used as the antigen.

In addition to the above-mentioned method where hybridomas are obtained by immunizing non-human animals with an antigen, an antibody of interest can be obtained by antigen sensitization of human lymphocytes. More specifically, first, human lymphocytes are sensitized with the EREG protein in vitro. Then, immunosensitized lymphocytes are fused with a suitable fusion partner. For example, human-derived myeloma cells that have infinite division potential can be used as a fusion partner (see Japanese Patent Publication Kokoku Publication No. (JP-B) H01-59878 (examined, approved Japanese patent application published for opposition)). Anti-EREG antibodies obtained by this method are human antibodies that have binding activity to an EREG protein.

Alternatively, anti-EREG human antibodies can also be obtained by administering an EREG protein that serves as an antigen to a transgenic animal having a complete human antibody gene repertoire. Antibody-producing cells of the immunized animal can be immortalized by cell fusion with a suitable fusion partner, or by treatment such as Epstein-Barr virus infection. Human antibodies against the EREG protein can be isolated from the immortalized cells obtained in this manner (see International Patent Publication Nos. WO 94/25585, WO 93/12227, WO 92/03918, and WO 94/02602). Furthermore, cells that produce an antibody having the reaction specificity of interest can be cloned by cloning the immortalized cells. When a transgenic animal is used as the animal to be immunized, the immune system of this animal recognizes human EREG as a foreign substance. Therefore, human antibodies against human EREG can be readily obtained.

The monoclonal antibody-producing hybridomas produced in this manner can be passaged and cultured in a standard medium. Alternatively, the hybridomas can be stored for a long period in liquid nitrogen.

The hybridomas can be cultured according to a standard method, and the monoclonal antibody of interest can be obtained from the culture supernatants. Alternatively, the hybridomas can be grown by administering them to a compatible mammal, and monoclonal antibodies can be obtained as its ascites. The former method is suitable for obtaining highly purified antibodies.

In the present invention, an antibody encoded by an antibody gene cloned from antibody-producing cells can be used. The cloned antibody gene can be incorporated into a suitable vector and then introduced into a host to express the antibody. Methods for isolating an antibody gene, introducing the gene into a vector, and transforming host cells have been established (see for example, Vandamme, A. M. et al., Eur. J. Biochem. (1990) 192, 767-775).

For example, a cDNA encoding the variable region (V region) of an anti-EREG antibody can be obtained from hybridoma cells producing the anti-EREG antibody. Usually, in order to accomplish this, first, total RNA is extracted from the hybridoma. For example, the following methods can be used as methods for extracting mRNA from cells:
the guanidine ultracentrifugation method (Chirgwin, J. M. et al., Biochemistry (1979) 18, 5294-5299); and
the AGPC method (Chomczynski, P. et al., Anal. Biochem. (1987) 162, 156-159).

The extracted mRNA can be purified using an mRNA purification kit (GE Healthcare Bio-Sciences) or the like. Alternatively, kits for directly extracting total mRNA from cells, such as the QuickPrep mRNA Purification Kit (GE Healthcare Bio-Sciences), are also commercially available. Total RNA can be obtained from the hybridoma by using such kits. A cDNA encoding the antibody V region can be synthesized from the obtained mRNA using reverse transcriptase. cDNA can be synthesized using the AMV Reverse Transcriptase First-strand cDNA Synthesis Kit (SEIKAGAKU CORPORATION) or the like. To synthesize and amplify cDNA, the 5'-Ampli FINDER RACE Kit (Clontech) and the 5'-RACE method using PCR (Frohman, M. A. et al., Proc. Natl. Acad. Sci. USA (1988) 85, 8998-9002; Belyavsky, A. et al., Nucleic Acids Res. (1989) 17, 2919-2932) can be used. Furthermore, in the process of such cDNA synthesis, appropriate restriction enzyme sites, which will be described later, can be introduced into both ends of the cDNA.

The cDNA fragment of interest is purified from the obtained PCR product, and then ligated to a vector DNA. The recombinant vector is prepared in this manner and introduced into *Escherichia coli* or the like, and after colonies are selected, the desired recombinant vector can be prepared from the *E. coli* that formed the colonies. Whether or not the recombinant vector has the cDNA nucleotide sequence of interest can be confirmed by a known method, such as the dideoxynucleotide chain termination method.

In order to obtain genes encoding the variable regions, the PCR method that uses primers for amplifying the variable region genes can be used. First, a cDNA library is obtained by synthesizing cDNAs using the extracted mRNAs as templates. It is convenient to use a commercially available kit for cDNA library synthesis. In practice, since the amount of mRNA obtainable from only a small number of cells is extremely minute, the yield of such mRNA from direct purification is low. Therefore, purification is usually performed after adding a carrier RNA that does not contain an antibody gene. Alternatively, when a certain amount of RNA can be extracted, efficient extraction can be accomplished by using just the RNA of antibody-producing cells. For example, addition of carrier RNA may not be required when RNA is extracted from ten or more, 30 or more, or preferably 50 or more antibody-producing cells.

The antibody genes are amplified by the PCR method using the obtained cDNA library as a template. The primers used for amplification of the antibody genes by the PCR method are known. For example, primers for human antibody gene amplification can be designed based on the disclosure of an article (J. Mol. Biol. (1991) 222, 581-597) and the like. The nucleotide sequences of these primers vary depending on the subclass of immunoglobulin. Therefore, when a cDNA library of an unknown subclass is used as the template, various possibilities need to be considered when performing the PCR method.

More specifically, when the objective is to obtain genes encoding human IgG, one may use primers capable of amplifying genes encoding γ1 to γ5 for the heavy chain, and genes encoding the κ chain and λ chain for the light chain. To amplify genes of the IgG variable region, generally, a primer that anneals to the portion corresponding to the hinge region is used as the 3'-end primer. Meanwhile, a primer corresponding to each subclass can be used as the 5'-end primer.

PCR products obtained by the primers for gene amplification of the heavy chain and light chain subclasses are made into independent libraries. Using the libraries synthesized in this manner, immunoglobulins comprising a combination of heavy and light chains can be reconstituted. The antibodies of interest can be screened by using the activity of the reconstituted immunoglobulins to bind to EREG as an index.

For example, when the objective is to obtain antibodies against EREG, it is more preferable that the binding of the antibodies to EREG is specific. For instance, it is possible to screen for antibodies that bind to EREG as described below:
(1) contacting EREG with an antibody comprising the V region encoded by a cDNA obtained from a hybridoma;
(2) detecting the binding between EREG and the antibody; and
(3) selecting an antibody that binds to EREG Methods for detecting the binding between an antibody and EREG are known. Specifically, a test antibody is reacted with EREG immobilized onto a support, and then this is reacted with a labeled antibody that recognizes the test antibody. If the labeled antibody on the support is detected after washing, this proves that the test antibody binds to EREG. For labeling, enzymatically active proteins such as peroxidase or β-galactosidase, or fluorescent substances such as FITC can be used. In order to evaluate the binding activity of the antibody, specimens of immobilized EREG-expressing cells can be used.

Alternatively, for an antibody screening method that uses the binding activity as an index, a phage vector-based panning method may be used. When the antibody genes are obtained as libraries of the heavy-chain and light-chain subclasses as described above, phage vector-based screening methods are advantageous. Genes encoding variable regions of the heavy and light chains can be made into a single-chain Fv (scFv) gene by linking the genes via suitable linker sequences. Phages expressing an scFv on their surface can be obtained by inserting a gene encoding the scFv into a phage vector. DNA encoding an scFv having the binding activity of interest can be collected by contacting the phage with an antigen of interest, and then collecting antigen-bound phage. scFv having the binding activity of interest can be concentrated by repeating this operation as necessary.

An antibody-encoding polynucleotide of the present invention may encode a full-length antibody or a portion of the antibody. "A portion of an antibody" refers to any portion of an antibody molecule. Hereinafter, the term "antibody fragment" may be used to refer to a portion of an antibody. A preferred antibody fragment of the present invention comprises the complementarity determination region (CDR) of an antibody. More preferably, an antibody fragment of the present invention comprises all of the three CDRs that constitute a variable region.

Once a cDNA encoding the V region of an anti-EREG antibody of interest is obtained, this cDNA is digested with restriction enzymes that recognize the restriction enzyme sites inserted to both ends of the cDNA. A preferred restriction enzyme recognizes and digests a nucleotide sequence that is less likely to appear in the nucleotide sequence constituting the antibody gene. Furthermore, to insert a single copy of the digested fragment into a vector in the correct direction, a restriction enzyme that provides sticky ends is preferred. A cDNA encoding the anti-EREG antibody V region, which has been digested as described above, is inserted into a suitable expression vector to obtain the antibody expression vector. In this step, a chimeric antibody can be obtained by fusing a gene encoding the antibody constant region (C region) with the above-mentioned gene encoding the V region in frame. Herein, "chimeric antibody" refers to an antibody whose constant and variable regions are derived from different origins. Therefore, in addition to interspecies chimeric antibodies such as mouse-human chimeric antibodies, human-human intraspecies chimeric antibodies are also included in the chimeric antibodies of the present invention. A chimeric antibody expression vector can also be constructed by inserting the aforementioned V-region gene into an expression vector into which a constant region gene has been introduced.

More specifically, for example, the restriction enzyme recognition sequence for a restriction enzyme that digests the aforementioned V-region gene can be placed at the 5' end of an expression vector carrying a DNA encoding a desired antibody constant region (C region). The chimeric antibody expression vector is constructed by digesting the two genes using the same combination of restriction enzymes, and fusing them in frame.

To produce an anti-EREG antibody for use in the present invention, the antibody gene can be incorporated into an expression vector so that it is expressed under the regulation of an expression control region. The expression regulatory region for antibody expression includes, for example, an enhancer or a promoter. Then, by transforming suitable host cells with this expression vector, recombinant cells that express the anti-EREG antibody-encoding DNA can be obtained.

To express an antibody gene, a DNA encoding the antibody heavy chain (H-chain) and a DNA encoding the antibody light chain (L-chain) can be incorporated separately into expression vectors. An antibody molecule comprising the H chain and L chain can be expressed by simultaneously transfecting (co-transfecting) the H-chain and L-chain-incorporated vectors into the same host cell. Alternatively, DNAs encoding the H chain and L chain can be incorporated into a single expression vector to transform a host cell with the vector (see International Patent Publication No. WO 94/11523).

Many combinations of hosts and expression vectors for isolating an antibody gene and then introducing the gene into an appropriate host to produce the antibody are known. Any of these expression systems can be applied to the present invention. When using eukaryotic cells as a host, animal cells, plant cells, and fungal cells can be used. More specifically, animal cells that may be used in the present invention are, for example, the following cells:
(1) mammalian cells such as CHO, COS, myeloma, baby hamster kidney (BHK), HeLa, and Vero cells;
(2) amphibian cells such as *Xenopus oocytes*; and
(3) insect cells such as sf9, sf21, Tn5.

In addition, as a plant cell system, an antibody gene expression system using cells derived from the *Nicotiana* genus such as *Nicotiana tabacum* is known. Callus-cultured cells can be used to transform plant cells.

Furthermore, the following cells can be used as fungal cells; yeasts: the *Saccharomyces* genus, for example, *Saccharomyces cerevisiae*, and the *Pichia* genus, for example, *Pichia pastoris*; and filamentous fungi: the *Aspergillus* genus, for example, *Aspergillus niger*.

Antibody gene expression systems that utilize prokaryotic cells are also known. For example, when using bacterial cells, *E. coli* cells, *Bacillus subtilis* cells, and such may be used in the present invention.

Expression vectors comprising the antibody genes of interest are introduced into these cells by transformation. By culturing the transformed cells in vitro, the desired antibodies can be obtained from the transformed cell culture.

In addition to the above host cells, transgenic animals can also be used to produce a recombinant antibody. That is, the antibody can be obtained from an animal into which the gene encoding the antibody of interest is introduced. For example, the antibody gene can be inserted in frame into a gene that encodes a protein produced inherently in milk to construct a fused gene. Goat β-casein or such can be used, for example, as the protein secreted in milk. A DNA fragment containing the fused gene inserted with the antibody gene is injected into a goat embryo, and then this embryo is introduced into a female goat. Desired antibodies can be obtained as a protein fused with the milk protein from milk produced by the transgenic goat born from the goat that received the embryo (or progeny thereof). To increase the volume of milk containing the desired antibody produced by the transgenic goat, hormones can be used on the transgenic goat as necessary (Ebert, K. M. et al., Bio/Technology (1994) 12, 699-702).

Animal-derived antibody C regions can be used for the C regions of a recombinant antibody of the present invention. For example, Cγ1, Cγ2a, Cγ2b, Cγ3, Cμ, Cδ, Cα1, Cα2, and Cε can be used for the mouse antibody H-chain C-region, and Cκ and Cλ can be used for the L-chain C-region. In addition to mouse antibodies, antibodies of animals such as rats, rabbits, goat, sheep, camels, and monkeys can be used as animal antibodies. Their sequences are known. Furthermore, the C region can be modified to improve the stability of the antibodies or their production.

In the present invention, when administering antibodies to humans, genetically recombinant antibodies that have been artificially modified for the purpose of reducing xenoantigenicity against humans, or the like can be used. Examples of the genetically recombinant antibodies include chimeric antibodies and humanized antibodies. These modified antibodies can be produced using known methods.

A chimeric antibody is an antibody whose variable regions and constant regions are of different origins. For example, an antibody comprising the heavy-chain and light-chain variable regions of a mouse antibody and the heavy-chain and light-chain constant regions of a human antibody is a mouse-human interspecies chimeric antibody. A recombinant vector expressing a chimeric antibody can be produced by ligating a DNA encoding a mouse antibody variable region to a DNA encoding a human antibody constant region, and then inserting it into an expression vector. The recombinant cells that have been transformed with the vector are cultured, and the incorporated DNA is expressed to obtain the chimeric antibody produced in the culture. Human C regions are used for the C regions of chimeric antibodies and humanized antibodies.

For example, Cγ1, Cγ2, Cγ3, Cγ4, Cμ, Cδ, Cα1, Cα2, and Cε can be used as an H-chain C region. Cκ and Cλ can be used as an L-chain C region. The amino acid sequences of these C regions and the nucleotide sequences encoding them are known. Furthermore, the human antibody C region can be modified to improve the stability of an antibody or its production.

Generally, a chimeric antibody consists of the V region of an antibody derived from a non-human animal, and a C region derived from a human antibody. On the other hand, a humanized antibody consists of the complementarity determining region (CDR) of an antibody derived from a non-human animal, and the framework region (FR) and C region derived from a human antibody. Since the antigenicity of a humanized antibody in human body is reduced, a humanized antibody is useful as an active ingredient for therapeutic agents of the present invention.

For example, mouse-human chimeric antibodies that can be obtained by linking the amino acid sequences constituting the human constant regions and the variable regions of an anti-EREG monoclonal antibody (B3#18) prepared based on the present invention are preferred monoclonal antibodies in the present invention. More specifically, the present invention provides mouse-human chimeric monoclonal antibodies comprising H and L chains having the following amino acid sequences.

H chain: the amino acid sequence of positions 1 to 446 in the amino acid sequence of SEQ ID NO: 10 (the signal sequence of positions −19 to −1 is removed)
L chain: the amino acid sequence of positions 1 to 213 in the amino acid sequence of SEQ ID NO: 20 (the signal sequence of positions −20 to −1 is removed)

Furthermore, other preferred examples of the chimeric antibodies of the present invention include the following antibodies.

An antibody comprising an H chain having the sequence in which the signal sequence (−19 to −1) has been removed from the amino acid sequence of SEQ ID NO: 129, and an L chain having the sequence in which the signal sequence (−19 to −1) has been removed from the amino acid sequence of SEQ ID NO: 131.

An antibody comprising an H chain having the sequence in which the signal sequence (−19 to −1) has been removed from the amino acid sequence of SEQ ID NO: 133, and an L chain having the sequence in which the signal sequence (−19 to −1) has been removed from the amino acid sequence of SEQ ID NO: 135.

An antibody comprising an H chain having the sequence in which the signal sequence (−19 to −1) has been removed from the amino acid sequence of SEQ ID NO: 137, and an L chain having the sequence in which the signal sequence (−19 to −1) has been removed from the amino acid sequence of SEQ ID NO: 139.

An antibody comprising an H chain having the sequence in which the signal sequence (−19 to −1) has been removed from the amino acid sequence of SEQ ID NO: 141, and an L chain having the sequence in which the signal sequence (−19 to −1) has been removed from the amino acid sequence of SEQ ID NO: 143.

An antibody comprising an H chain having the sequence in which the signal sequence (−19 to −1) has been removed from the amino acid sequence of SEQ ID NO: 145 and an L chain having a sequence in which the signal sequence (−19 to −1) has been removed from the amino acid sequence of SEQ ID NO: 147.

The antibody variable region generally comprises three complementarity-determining regions (CDRs) separated by four framework regions (FRs). CDR is a region that substantially determines the binding specificity of an antibody. The amino acid sequences of CDRs are highly diverse. On the other hand, the FR-constituting amino acid sequences are often highly homologous even among antibodies with different binding specificities. Therefore, generally, the binding specificity of a certain antibody can be transferred to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known.

Specifically, for example, overlap extension PCR is known as a method for grafting a mouse antibody CDR to a human FR. In overlap extension PCR, a nucleotide sequence encoding a mouse antibody CDR to be grafted is added to the primers for synthesizing a human antibody FR. Primers are prepared for each of the four FRs. It is generally considered that when grafting a mouse CDR to a human FR, selecting a human FR that is highly homologous to a mouse FR is advantageous for maintaining the CDR function. That is, it is generally preferable to use a human FR comprising an amino acid sequence highly homologous to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, overlapping CDR regions of the products synthesized using a human antibody gene as the template are annealed for complementary strand synthesis reaction. By this reaction, human FRs are ligated through the mouse CDR sequences.

The full length of the V-region gene, in which three CDRs and four FRs are ultimately ligated, is amplified using primers that anneal to its 5' and 3' ends and which have suitable restriction enzyme recognition sequences. A vector for human antibody expression can be produced by inserting the DNA obtained as described above and a DNA that encodes a human antibody C region into an expression vector so that they will ligate in frame. After inserting this integration vector into a host to establish recombinant cells, the recombinant cells are cultured, and the DNA encoding the humanized antibody is expressed to produce the humanized antibody in the cell culture (see, European Patent Publication No. EP 239,400, and International Patent Publication No. WO 96/02576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. As necessary, amino acid residues in an FR may be substituted so that the CDRs of a reshaped human antibody form an appropriate antigen-binding site. For example, amino acid sequence mutations can be introduced into FRs by applying the PCR method used for fusing a mouse CDR with a human FR. More specifically, partial nucleotide sequence mutations can be introduced into primers that anneal to the FR sequence. Nucleotide sequence mutations are introduced into the FRs synthesized using such primers. Mutant FR sequences having the desired characteristics can be selected by measuring and evaluating the activity of the amino acid-substituted mutant antibody to bind to the antigen by the above-mentioned method (Sato, K. et al., Cancer Res. 1993, 53, 851-856).

Methods for obtaining human antibodies are also known. For example, human lymphocytes are sensitized in vitro with a desired antigen or cells expressing a desired antigen. Then, by fusing the sensitized lymphocytes with human myeloma cells, desired human antibodies having the antigen-binding activity can be obtained (see JP-B H01-59878). U266 or such can be used as the fusion partner human myeloma cell.

Alternatively, a desired human antibody can be obtained by using a desired antigen to immunize a transgenic animal that comprises the entire repertoire of human antibody genes (see International Patent Publication Nos. WO 93/12227, WO 92/03918, WO 94/02602, WO 94/25585, WO 96/34096, and WO 96/33735). Furthermore, techniques to obtain human antibodies by panning a human antibody library are also known. For example, the V region of a human antibody is expressed as a single chain antibody (scFv) on the phage surface using a phage display method, and phages that bind to the antigen can be selected. By analyzing the genes of selected phages, the DNA sequences encoding the V regions of human antibodies that bind to the antigen can be determined. After determining the DNA sequences of scFvs that bind to the antigen, the V region sequence is fused in frame with the desired human antibody C region sequence, and this is inserted into a suitable expression vector to produce an expression vector. This expression vector can be introduced into suitable expression cells such as those described above, and the human antibody-encoding gene can be expressed to obtain the human antibodies. Such methods are well known (International Patent Publication Nos. WO 92/01047, WO 92/20791, WO 93/06213, WO 93/11236, WO 93/19172, WO 95/01438, and WO 95/15388).

The antibody used in the present invention is not limited to bivalent antibodies represented by IgG, but includes monovalent antibodies and multivalent antibodies represented by IgM, as long as it binds to the EREG protein. The multivalent antibody of the present invention includes a multivalent antibody that has the same antigen binding sites, and a multivalent antibody that has partially or completely different antigen binding sites. The antibody used in the present invention is not limited to the whole antibody molecule, but includes minibodies and modified products thereof, as long as they bind to the EREG protein.

A minibody contains an antibody fragment lacking a portion of a whole antibody (for example, whole IgG). As long as it has the ability to bind the EREG antigen, partial deletions of an antibody molecule are permissible. Antibody fragments of the present invention preferably contain a heavy-chain variable region (VH) and/or a light-chain variable region (VL). The amino acid sequence of VH or VL may have substitutions, deletions, additions, and/or insertions. Furthermore, as long as it has the ability to bind the EREG antigen, VH and/or VL can be partially deleted. The variable region may be chimerized or humanized. Specific examples of the antibody fragments include Fab, Fab', F(ab')2, and Fv. Specific examples of minibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the minibodies of the present invention.

Fragments of antibodies can be obtained by treating an antibody with an enzyme to produce antibody fragments. Known enzymes that produce antibody fragments are, for example, papain, pepsin, and plasmin. Alternatively, genes encoding these antibody fragments can be constructed, introduced into expression vectors, and then expressed in appropriate host cells (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Digestive enzymes cleave specific sites of an antibody fragment, and yield antibody fragments with the following specific structures. When genetic engineering techniques are used on such enzymatically obtained antibody fragments, any portion of the antibody can be deleted.
Papain digestion: F(ab)2 or Fab
Pepsin digestion: F(ab')2 or Fab'
Plasmin digestion: Facb Therefore, minibodies of the present invention may be antibody fragments lacking any region, as long as they have binding affinity to EREG. Furthermore, according to the present invention, the antibodies desirably maintain their effector activity, particularly in the treatment of cell proliferative diseases such as cancer. More specifically, preferred minibodies of the present invention have both binding affinity to EREG and effector function. The antibody effector function includes ADCC activity and CDC activity. Particularly preferably, therapeutic antibodies of the present invention have ADCC activity and/or CDC activity as effector function.

A diabody refers to a bivalent antibody fragment constructed by gene fusion (Hollinger P. et al., Proc. Natl. Acad. Sci. USA 90: 6444-6448 (1993); EP404,097; WO 93/11161; and such). A diabody is a dimer composed of two polypeptide chains. Generally, in each polypeptide chain constituting the dimer, VL and VH are linked by a linker within the same chain. The linker in a diabody is generally short enough to prevent binding between VL and VH. Specifically, the amino acid residues constituting the linker are, for example, five residues or so. Therefore, VL and VH that are encoded by the same polypeptide chain cannot form a single-chain variable region fragment, and form a dimer with another single chain variable region fragment. As a result, diabodies have two antigen binding sites.

scFv can be obtained by ligating the H-chain V region and L-chain V region of an antibody. In scFv, the H-chain V region and L-chain V region are ligated via a linker, preferably a peptide linker (Huston, J. S. et al., Proc. Natl. Acad. Sci. U.S.A., 1988, 85, 5879-5883). The H-chain V region and L-chain V region of scFv may be derived from any of the antibodies described herein. The peptide linker for ligating the V regions is not particularly limited. For example, any single-chain peptide consisting of 3 to 25 residues or so can be used as the linker. More specifically, for example, peptide linkers described below or such can be used.

PCR methods such as those described above can be used for ligating the V regions. For ligation of the V regions by PCR methods, first, a whole DNA or a DNA encoding a desired partial amino acid sequence selected from the following DNAs can be used as a template:
a DNA sequence encoding the H chain or the H-chain V region of the above-mentioned antibody; and
a DNA sequence encoding the L chain or the L-chain V region of the above-mentioned antibody.

DNAs encoding the H-chain and L-chain V regions are individually amplified by PCR methods using a pair of primers that have sequences corresponding to the sequences of both ends of the DNA to be amplified. Then, a DNA encoding the peptide linker portion is prepared. The DNA encoding the peptide linker can also be synthesized using PCR. To the 5' end of the primers used, nucleotide sequences that can be ligated to each of the individually synthesized V-region amplification products are added. Then, PCR reaction is carried out using the "H-chain V region DNA", "peptide linker DNA", and "L-chain V region DNA", and the primers for assembly PCR.

The primers for assembly PCR consist of the combination of a primer that anneals to the 5' end of the "H-chain V region DNA" and a primer that anneals to the 3' end of the "L-chain V region DNA". That is, the primers for assembly PCR are a primer set that can amplify a DNA encoding the full-length sequence of scFv to be synthesized. On the other hand, nucleotide sequences that can be ligated to each V-region DNA are added to the "peptide linker DNA". Thus, these DNAs are ligated, and the full-length scFv is ultimately produced as an amplification product using the primers for assembly PCR. Once the scFv-encoding DNA is constructed, expression vectors containing the DNA, and recombinant cells transformed by these expression vectors can be obtained according to conventional methods. Furthermore, the scFvs can be obtained by culturing the resulting recombinant cells and expressing the scFv-encoding DNA.

sc(Fv)2 is a minibody prepared by ligating two VHs and two VLs with linkers or such to form a single chain (Hudson et al., J. Immunol. Methods 1999; 231: 177-189). sc(Fv)2 can be produced, for example, by joining scFvs with a linker.

Moreover, antibodies in which two VHs and two VLs are arranged in the order of VH, VL, VH, and VL ([VH]-linker-[VL]-linker-[VH]-linker-[VL]), starting from the N-terminal side of a single chain polypeptide, are preferred.

The order of the two VHs and the two VLs is not particularly limited to the above-mentioned arrangement, and they may be placed in any order. Examples include the following arrangements:

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

Any arbitrary peptide linker can be introduced by genetic engineering, and synthetic linkers (see, for example, those disclosed in Protein Engineering, 9(3), 299-305, 1996) or such can be used as linkers for linking the antibody variable regions. In the present invention, peptide linkers are preferable. The length of the peptide linkers is not particularly limited, and can be suitably selected by those skilled in the art according to the purpose. The length of amino acid residues composing a peptide linker is generally 1 to 100 amino acids, preferably 3 to 50 amino acids, more preferably 5 to 30 amino acids, and particularly preferably 12 to 18 amino acids (for example, 15 amino acids).

Any amino acid sequences composing peptide linkers can be used, as long as they do not inhibit the binding activity of scFv. Examples of the amino acid sequences used in peptide linkers include:

```
Ser

Gly-Ser

Gly-Gly-Ser

Ser-Gly-Gly

Gly-Gly-Gly-Ser              (SEQ ID NO: 23)

Ser-Gly-Gly-Gly              (SEQ ID NO: 24)

Gly-Gly-Gly-Gly-Ser          (SEQ ID NO: 25)

Ser-Gly-Gly-Gly-Gly          (SEQ ID NO: 26)

Gly-Gly-Gly-Gly-Gly-Ser      (SEQ ID NO: 27)

Ser-Gly-Gly-Gly-Gly-Gly      (SEQ ID NO: 28)

Gly-Gly-Gly-Gly-Gly-Gly-Ser  (SEQ ID NO: 29)

Ser-Gly-Gly-Gly-Gly-Gly-Gly  (SEQ ID NO: 30)

(Gly-Gly-Gly-Gly-Ser (SEQ ID NO: 31))n (Ser-Gly-Gly-Gly-Gly (SEQ ID NO: 32))n
``` in which n is an integer of 1 or larger. The amino acid sequences of the peptide linkers can be selected appropriately by those skilled in the art according to the purpose. For example, n, which determines the length of the peptide linkers, is generally 1 to 5, preferably 1 to 3, more preferably 1 or 2.

Therefore, a particularly preferred embodiment of sc(Fv)2 in the present invention is, for example, the following sc(Fv)2:

[VH]-peptide linker (15 amino acids)-[VL]-peptide linker (15 amino acids)-[VH]-peptide linker (15 amino acids)-[VL]

Alternatively, synthetic chemical linkers (chemical crosslinking agents) can be used to link the V regions. Crosslinking agents routinely used to crosslink peptide compounds and such can be used in the present invention. For example, the following chemical crosslinking agents are known. These crosslinking agents are commercially available:

N-hydroxy succinimide (NHS);
disuccinimidyl suberate (DSS);
bis(sulfosuccinimidyl) suberate (BS3);
dithiobis(succinimidyl propionate) (DSP);
dithiobis(sulfosuccinimidyl propionate) (DTSSP);
ethylene glycol bis(succinimidyl succinate) (EGS);
ethylene glycol bis(sulfosuccinimidyl succinate) (sulfo-EGS);
disuccinimidyl tartrate (DST);
disulfosuccinimidyl tartrate (sulfo-DST);
bis[2-(succinimidoxycarbonyloxy)ethyl]sulfone (BSOCOES); and
bis[2-(sulfosuccinimidoxycarbonyloxy)ethyl]sulfone (sulfo-BSOCOES).

Usually, three linkers are required to link four antibody variable regions. The multiple linkers to be used may all be of the same type or different types. In the present invention, a preferred minibody is a diabody or an sc(Fv)2. Such minibody can be obtained by treating an antibody with an enzyme, such as papain or pepsin, to generate antibody fragments, or by constructing DNAs that encode these antibody fragments, introducing them into expression vectors, and then expressing them in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

Any EREG-recognizing antibody can be used as the antibody of the present invention. Preferred antibodies include the antibodies of (1) to (57) below. These antibodies may be, for example, full-length antibodies, minibodies, animal antibodies, chimeric antibodies, humanized antibodies, or human antibodies:

(1) an antibody comprising an H chain having the amino acid sequence of SEQ ID NO: 2 (sequence of the B3#18 antibody H-chain CDR1) as CDR1, the amino acid sequence of SEQ ID NO: 4 (sequence of the B3#18 antibody H-chain CDR2) as CDR2, and the amino acid sequence of SEQ ID NO: 6 (sequence of the B3#18 antibody H-chain CDR3) as CDR3;

(2) an antibody comprising the H chain of (1), wherein the H chain has the amino acid sequence of positions 117 to 452 in the amino acid sequence of SEQ ID NO: 8 (sequence of the B3#18 antibody CH) as CH (H-chain constant region);

(3) an antibody comprising the H chain of (1), wherein the H chain has the amino acid sequence of positions 117 to 446 in the amino acid sequence of SEQ ID NO: 10 (sequence of the CH of the mouse-human chimeric DF 151 antibody) as CH;

(4) an antibody comprising an L chain having the amino acid sequence of SEQ ID NO: 12 (sequence of the B3#18 antibody L-chain CDR1) as CDR1, the amino acid sequence of SEQ ID NO: 14 (sequence of the B3#18 antibody L-chain CDR2) as CDR2, and the amino acid sequence of SEQ ID NO: 16 (sequence of the B3#18 antibody L-chain CDR3) as CDR3;

(5) an antibody comprising the L chain of (4), wherein the L chain has the amino acid sequence of positions 107 to 213 in the amino acid sequence of SEQ ID NO: 18 (sequence of the B3#18 antibody CL) as CL (L-chain constant region);

(6) an antibody comprising the L chain of (4), wherein the L chain has the amino acid sequence of positions 107 to 213 in the amino acid sequence of SEQ ID NO: 20 (sequence of the CL of the mouse-human chimeric B3#18 antibody) as CL;

(7) an antibody comprising the H chain of (1) and the L chain of (4);

(8) an antibody comprising the H chain of (2) and the L chain of (5);

(9) an antibody comprising the H chain of (3) and the L chain of (6);

(10) an antibody comprising an H chain having the amino acid sequence of SEQ ID NO: 49 as CDR1, the amino acid sequence of SEQ ID NO: 51 as CDR2, and the amino acid sequence of SEQ ID NO: 53 as CDR3;

(11) an antibody comprising the H chain of (10), wherein the H chain has CH derived from mouse IgG1;

(12) an antibody comprising the H chain of (10), wherein the H chain has the amino acid sequence of positions 117 to 446 in the amino acid sequence of SEQ ID NO: 10 as CH;

(13) an antibody comprising an L chain having the amino acid sequence of SEQ ID NO: 55 as CDR1, the amino acid sequence of SEQ ID NO: 57 as CDR2, and the amino acid sequence of SEQ ID NO: 59 as CDR3;

(14) an antibody comprising the L chain of (13), wherein the L chain has CL derived from the mouse κ chain;

(15) an antibody comprising the L chain of (13), wherein the L chain has the amino acid sequence of positions 107 to 213 in the amino acid sequence of SEQ ID NO: 20 as CL;

(16) an antibody comprising the H chain of (10) and the L chain of (13);

(17) an antibody comprising the H chain of (11) and the L chain of (14);

(18) an antibody comprising the H chain of (12) and the L chain of (15);

(19) an antibody comprising an H chain having the amino acid sequence of SEQ ID NO: 61 as CDR1, the amino acid sequence of SEQ ID NO: 63 as CDR2, and the amino acid sequence of SEQ ID NO: 65 as CDR3;

(20) an antibody comprising the H chain of (19), wherein the H chain has CH derived from mouse IgG 1;

(21) an antibody comprising the H chain of (19), wherein the H chain has the amino acid sequence of positions 117 to 446 in the amino acid sequence of SEQ ID NO: 10 as CH;

(22) an antibody comprising an L chain having the amino acid sequence of SEQ ID NO: 67 as CDR1, the amino acid sequence of SEQ ID NO: 69 as CDR2, and the amino acid sequence of SEQ ID NO: 71 as CDR3;

(23) an antibody comprising the L chain of (22), wherein the L chain has CL derived from the mouse κ chain;

(24) an antibody comprising the L chain of (22), wherein the L chain has the amino acid sequence of positions 107 to 213 in the amino acid sequence of SEQ ID NO: 20 as CL;

(25) an antibody comprising the H chain of (19) and the L chain of (22);

(26) an antibody comprising the H chain of (20) and the L chain of (23);

(27) an antibody comprising the H chain of (21) and the L chain of (24);

(28) an antibody comprising an H chain having the amino acid sequence of SEQ ID NO: 73 as CDR1, the amino acid sequence of SEQ ID NO: 75 as CDR2, and the amino acid sequence of SEQ ID NO: 77 as CDR3;

(29) an antibody comprising the H chain of (28), wherein the H chain has CH derived from mouse IgG 1;

(30) an antibody comprising the H chain of (28), wherein the H chain has the amino acid sequence of positions 117 to 446 in the amino acid sequence of SEQ ID NO: 10 as CH;

(31) an antibody comprising an L chain having the amino acid sequence of SEQ ID NO: 79 as CDR1, the amino acid sequence of SEQ ID NO: 81 as CDR2, and the amino acid sequence of SEQ ID NO: 83 as CDR3;

(32) an antibody comprising the L chain of (31), wherein the L chain has CL derived from the mouse κ chain;

(33) an antibody comprising the L chain of (31), wherein the L chain has the amino acid sequence of positions 107 to 213 in the amino acid sequence of SEQ ID NO: 20 as CL;

(34) an antibody comprising the H chain of (28) and the L chain of (31);

(35) an antibody comprising the H chain of (29) and the L chain of (32);

(36) an antibody comprising the H chain of (30) and the L chain of (33);

(37) an antibody comprising an H chain having the amino acid sequence of SEQ ID NO: 85 as CDR1, the amino acid sequence of SEQ ID NO: 87 as CDR2, and the amino acid sequence of SEQ ID NO: 89 as CDR3;

(38) an antibody comprising the H chain of (37), wherein the H chain has CH derived from mouse IgG 1;

(39) an antibody comprising the H chain of (37), wherein the H chain has the amino acid sequence of positions 117 to 446 in the amino acid sequence of SEQ ID NO: 10 as CH;

(40) an antibody comprising an L chain having the amino acid sequence of SEQ ID NO: 91 as CDR1, the amino acid sequence of SEQ ID NO: 93 as CDR2, and the amino acid sequence of SEQ ID NO: 95 as CDR3;

(41) an antibody comprising the L chain of (40), wherein the L chain has CL derived from the mouse κ chain;

(42) an antibody comprising the L chain of (40), wherein the L chain has the amino acid sequence of positions 107 to 213 in the amino acid sequence of SEQ ID NO: 20 as CL;

(43) an antibody comprising the H chain of (37) and the L chain of (40);

(44) an antibody comprising the H chain of (38) and the L chain of (41);

(45) an antibody comprising the H chain of (39) and the L chain of (42);

(46) an antibody comprising an H chain having the amino acid sequence of SEQ ID NO: 97 as CDR1, the amino acid sequence of SEQ ID NO: 99 as CDR2, and the amino acid sequence of SEQ ID NO: 101 as CDR3;

(47) an antibody comprising the H chain of (46), wherein the H chain has CH derived from mouse IgG 1;

(48) an antibody comprising the H chain of (46), wherein the H chain has the amino acid sequence of positions 117 to 446 in the amino acid sequence of SEQ ID NO: 10 as CH;

(49) an antibody comprising an L chain having the amino acid sequence of SEQ ID NO: 103 as CDR1, the amino acid sequence of SEQ ID NO: 105 as CDR2, and the amino acid sequence of SEQ ID NO: 107 as CDR3;

(50) an antibody comprising the L chain of (49), wherein the L chain has CL derived from the mouse κ chain;

(51) an antibody comprising the L chain of (49), wherein the L chain has the amino acid sequence of positions 107 to 213 in the amino acid sequence of SEQ ID NO: 20 as CL;

(52) an antibody comprising the H chain of (46) and the L chain of (49);

(53) an antibody comprising the H chain of (47) and the L chain of (50);

(54) an antibody comprising the H chain of (48) and the L chain of (51);

(55) an antibody comprising one or more amino acid substitutions, deletions, additions, and/or insertions in the antibody of any of (1) to (54), which has equivalent activity as the antibody of any of (1) to (54);
(56) an antibody that binds to the same EREG protein epitope as the antibody of any of (1) to (55); and
(57) a minibody of the antibody of any of (1) to (56).

An example of VH in the above-mentioned H chain of (1), which has the CDRs listed below, includes a VH having the amino acid sequence of SEQ ID NO: 44 (sequence of the B3#18 antibody VH):
CDR1: the amino acid sequence of SEQ ID NO: 2 (sequence of the B3#18 (EP27) antibody H-chain CDR1);
CDR2: the amino acid sequence of SEQ ID NO: 4 (sequence of the B3#18 (EP27) antibody H-chain CDR2); and
CDR3: the amino acid sequence of SEQ ID NO: 6 (sequence of the B3#18 (EP27) antibody H-chain CDR3).

An example of VL in the above-mentioned L chain of (4), which has the CDRs listed below, includes a VL having the amino acid sequence of SEQ ID NO: 46 (sequence of the B3#18 antibody VL):
CDR1: the amino acid sequence of SEQ ID NO: 12 (sequence of the B3#18 (EP27) antibody L-chain CDR1);
CDR2: the amino acid sequence of SEQ ID NO: 14 (sequence of the B3#18 (EP27) antibody L-chain CDR2); and
CDR3: the amino acid sequence of SEQ ID NO: 16 (sequence of the B3#18 (EP27) antibody L-chain CDR3).

An example of VH in the above-mentioned H chain of (10), which has the CDRs listed below, includes a VH having the amino acid sequence of SEQ ID NO: 109 (sequence of the C7 (EP03) VH):
CDR1: the amino acid sequence of SEQ ID NO: 49 (sequence of the C7 (EP03) antibody H-chain CDR1);
CDR2: the amino acid sequence of SEQ ID NO: 51 (sequence of the C7 (EP03) antibody H-chain CDR2); and
CDR3: the amino acid sequence of SEQ ID NO: 53 (sequence of the C7 (EP03) antibody H-chain CDR3).

An example of VL in the above-mentioned L chain of (13), which has the CDRs listed below, includes a VL having the amino acid sequence of SEQ ID NO: 111 (sequence of the C7 (EP03) antibody VL):
CDR1: the amino acid sequence of SEQ ID NO: 55 (sequence of the C7 (EP03) antibody L-chain CDR1);
CDR2: the amino acid sequence of SEQ ID NO: 57 (sequence of the C7 (EP03) antibody L-chain CDR2); and
CDR3: the amino acid sequence of SEQ ID NO: 59 (sequence of the C7 (EP03) antibody L-chain CDR3).

An example of VH in the above-mentioned H chain of (19), which has the CDRs listed below, includes a VH having the amino acid sequence of SEQ ID NO: 113 (sequence of the #15 (EP08) VH):
CDR1: the amino acid sequence of SEQ ID NO: 61 (sequence of the #15 (EP08) antibody H-chain CDR1);
CDR2: the amino acid sequence of SEQ ID NO: 63 (sequence of the #15 (EP08) antibody H-chain CDR2); and
CDR3: the amino acid sequence of SEQ ID NO: 65 (sequence of the #15 (EP08) antibody H-chain CDR3).

An example of VL in the above-mentioned L chain of (22), which has the CDRs listed below, includes a VL having the amino acid sequence of SEQ ID NO: 115 (sequence of the #15 (EP08) antibody VL):
CDR1: the amino acid sequence of SEQ ID NO: 67 (sequence of the #15 (EP08) antibody L-chain CDR1);
CDR2: the amino acid sequence of SEQ ID NO: 69 (sequence of the #15 (EP08) antibody L-chain CDR2); and
CDR3: the amino acid sequence of SEQ ID NO: 71 (sequence of the #15 (EP08) antibody L-chain CDR3).

An example of VH in the above-mentioned H chain of (28), which has the CDRs listed below, includes a VH having the amino acid sequence of SEQ ID NO: 117 (sequence of the B2#30 (EP20) VH):
CDR1: the amino acid sequence of SEQ ID NO: 73 (sequence of the B2#30 (EP20) antibody H-chain CDR1);
CDR2: the amino acid sequence of SEQ ID NO: 75 (sequence of the B2#30 (EP20) antibody H-chain CDR2); and
CDR3: the amino acid sequence of SEQ ID NO: 77 (sequence of the B2#30 (EP20) antibody H-chain CDR3).

An example of VL in the above-mentioned L chain of (31), which has the CDRs listed below, includes a VL having the amino acid sequence of SEQ ID NO: 119 (sequence of the B2#30 (EP20) antibody VL):
CDR1: the amino acid sequence of SEQ ID NO: 79 (sequence of the B2#30 (EP20) antibody L-chain CDR1);
CDR2: the amino acid sequence of SEQ ID NO: 81 (sequence of the B2#30 (EP20) antibody L-chain CDR2); and
CDR3: the amino acid sequence of SEQ ID NO: 83 (sequence of the B2#30 (EP20) antibody L-chain CDR3).

An example of VH in the above-mentioned H chain of (37), which has the CDRs listed below, includes a VH having the amino acid sequence of SEQ ID NO: 121 (sequence of the B3#8 (EP24) VH):
CDR1: the amino acid sequence of SEQ ID NO: 85 (sequence of the B3#8 (EP24) antibody H-chain CDR1);
CDR2: the amino acid sequence of SEQ ID NO: 87 (sequence of the B3#8 (EP24) antibody H-chain CDR2); and
CDR3: the amino acid sequence of SEQ ID NO: 89 (sequence of the B3#8 (EP24) antibody H-chain CDR3).

An example of VL in the above-mentioned L chain of (40), which has the CDRs listed below, includes a VL having the amino acid sequence of SEQ ID NO: 123 (sequence of the B3#8 (EP24) antibody VL):
CDR1: the amino acid sequence of SEQ ID NO: 91 (sequence of the B3#8 (EP24) antibody L-chain CDR1);
CDR2: the amino acid sequence of SEQ ID NO: 93 (sequence of the B3#8 (EP24) antibody L-chain CDR2); and
CDR3: the amino acid sequence of SEQ ID NO: 95 (sequence of the B3#8 (EP24) antibody L-chain CDR3).

An example of VH in the above-mentioned H chain of (46), which has the CDRs listed below, includes a VH having the amino acid sequence of SEQ ID NO: 125 (sequence of the B3#41 (EP29) VH):
CDR1: the amino acid sequence of SEQ ID NO: 97 (sequence of the B3#41 (EP29) antibody H-chain CDR1);
CDR2: the amino acid sequence of SEQ ID NO: 99 (sequence of the B3#41 (EP29) antibody H-chain CDR2); and
CDR3: the amino acid sequence of SEQ ID NO: 101 (sequence of the B3#41 (EP29) antibody H-chain CDR3).

An example of VL in the above-mentioned L chain of (49), which has the CDRs listed below, includes a VL having the amino acid sequence of SEQ ID NO: 127 (sequence of the B3#41 (EP29) antibody VL):
CDR1: the amino acid sequence of SEQ ID NO: 103 (sequence of the B3#41 (EP29) antibody L-chain CDR1);
CDR2: the amino acid sequence of SEQ ID NO: 105 (sequence of the B3#41 (EP29) antibody L-chain CDR2); and
CDR3: the amino acid sequence of SEQ ID NO: 107 (sequence of the B3#41 (EP29) antibody L-chain CDR3).

The above-mentioned antibodies of (1) to (57) include not only monovalent antibodies but also multivalent antibodies with two or more valencies. Multivalent antibodies of the present invention include multivalent antibodies whose antigen binding sites are all the same and multivalent antibodies whose antigen binding sites are partially or completely different.

A preferred embodiment of the above-mentioned antibody of (55) is an antibody in which the CDR has not been modified. For example, among the above-mentioned antibodies of (55), a preferred embodiment of "an antibody having one or more amino acid substitutions, deletions, additions, and/or insertions in the antibody of (1) and having an activity equivalent to that of the antibody of (1)" is "an antibody having an activity equivalent to that of the antibody of (1) and having one or more amino acid substitutions, deletions, additions, and/or insertions in the antibody of (1), and also comprising an H chain having the amino acid sequence of SEQ ID NO: 2 as CDR1, the amino acid sequence of SEQ ID NO: 4 as CDR2, and the amino acid sequence of SEQ ID NO: 6 as CDR3". Preferred embodiments of other antibodies included in the above-mentioned antibody of (55) can be expressed in a similar manner.

A method of introducing mutations into polypeptides is one of the methods well known to those skilled in the art for preparing polypeptides that are functionally equivalent to a certain polypeptide. For example, those skilled in the art can prepare an antibody functionally equivalent to an antibody of the present invention by introducing appropriate mutations into the antibody using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. Amino acid mutations may also occur naturally. In this way, the antibodies of the present invention also comprise antibodies comprising amino acid sequences with one or more amino acid mutations in the amino acid sequences of the antibodies of the present invention, and which are functionally equivalent to the antibodies of the present invention.

The number of amino acids that are mutated in such mutants is generally considered to be 50 amino acids or less, preferably 30 amino acids or less, and more preferably 10 amino acids or less (for example, 5 amino acids or less).

It is desirable that the amino acid residues are mutated into amino acids in which the properties of the amino acid side chains are conserved. For example, the following categories have been established depending on the amino acid side chain properties:
hydrophobic amino acids (A, I, L, M, F, P, W, Y, and V);
hydrophilic amino acids (R, D, N, C, E, Q, G, H, K, S, and T);
amino acids having aliphatic side chains (G, A, V, L, I, and P);
amino acids having hydroxyl-containing side chains (S, T, and Y);
amino acids having sulfur-containing side chains (C and M);
amino acids having carboxylic acid- and amide-containing side chains (D, N, E, and Q);
amino acids having basic side chains (R, K, and H); and
amino acids having aromatic ring-containing side chains (H, F, Y, and W)
(amino acids are represented by one-letter codes in parentheses).

Polypeptides comprising a modified amino acid sequence, in which one or more amino acid residues in a certain amino acid sequence is deleted, added, and/or substituted with other amino acids, are known to retain their original biological activities (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413). That is, generally in an amino acid sequence constituting a certain polypeptide, the activity of the polypeptide is highly likely to be maintained when amino acids classified into the same group are mutually substituted. In the present invention, the above-mentioned substitution between amino acids within the same amino acid group is referred to as conservative substitution.

The present invention provides antibodies that bind to the same epitope as the anti-EREG antibodies disclosed in the present application. More specifically, the present invention relates to antibodies that recognize the same epitope as the antibody of any of (1) to (57) mentioned above, and uses thereof. Such antibodies can be obtained, for example, by the following method.

Whether a test antibody shares the epitope of a certain antibody can be confirmed by checking whether the two antibodies compete for the same epitope. Competition between antibodies can be detected by cross-blocking assay and such. For example, competitive ELISA vis a preferred cross-blocking assay.

Specifically, in a cross-blocking assay, the wells of a microtiter plate are coated with the EREG protein which is then pre-incubated with or without a candidate competing antibody, and an anti-EREG antibody of the present invention is then added. The amount of the anti-EREG antibody of the present invention bound to the EREG protein in the wells indirectly correlates with the binding ability of the candidate competing antibody (test antibody) that competes for binding to the same epitope. More specifically, the greater the affinity the test antibody has for the same epitope, the lower the activity of the anti-EREG antibody of the present invention to bind to the EREG protein-coated wells. In other words, the greater the affinity the test antibody has for the same epitope, the higher the activity of the test antibody to bind to the EREG protein-coated wells.

The amount of antibody bound to the wells can be easily measured by labeling the antibodies in advance. For example, a biotin-labeled antibody can be measured using an avidin-peroxidase conjugate and a suitable substrate. In particular, cross-blocking assays using enzyme labels such as peroxidase are called competitive ELISA assays. The antibodies can be labeled with other detectable or measurable labeling substances. More specifically, radiolabels and fluorescent labels are known.

Furthermore, when the test antibody comprises a constant region derived from a species different from that of the anti-EREG antibody of the present invention, measurement can be done for either one of the antibodies bound to the wells using a labeled antibody that recognizes its constant region. If the antibodies are derived from the same species but belong to different classes, the antibodies bound to the wells can be measured using antibodies that distinctively recognize individual classes.

If a candidate competing antibody can block binding of the EREG antibody by at least 20%, preferably by at least 20% to 50%, and even more preferably, by at least 50%, as compared to the binding activity obtained in a control experiment performed in the absence of the candidate competing antibody, the candidate competing antibody is either an antibody that binds substantially to the same epitope or one that competes for binding to the same epitope as an anti-EREG antibody of the present invention. Antibodies that bind to the same epitope as the anti-EREG antibodies include, for example, the above-mentioned antibody of (57), but are not limited thereto.

As described above, the above-mentioned antibodies of (1) to (57) include not only monovalent antibodies but also multivalent antibodies. Multivalent antibodies of the present invention include multivalent antibodies whose antigen binding sites are all the same and multivalent antibodies whose antigen binding sites are partially or completely different.

Antibodies bound to various types of molecules such as polyethylene glycol (PEG) can also be used as modified antibodies. Moreover, chemotherapeutic agents, toxic peptides, or radioactive chemical substances can be bound to the antibodies. Such modified antibodies (hereinafter referred to as antibody conjugates) can be obtained by subjecting the obtained antibodies to chemical modification. Methods for modifying antibodies are already established in this field. Furthermore, as described below, such antibodies can also be obtained in the molecular form of a bispecific antibody designed using genetic engineering techniques to recognize not only EREG proteins, but also chemotherapeutic agents, toxic peptides, radioactive chemical compounds, or such. These antibodies are included in the "antibodies" of the present invention.

Chemotherapeutic agents that bind to anti-EREG antibodies to drive the cytotoxic activity include the following: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, vinblastine, vinorelbine, and vincristine.

In the present invention, preferred chemotherapeutic agents are low-molecular-weight chemotherapeutic agents. Low-molecular-weight chemotherapeutic agents are unlikely to interfere with antibody function even after binding to antibodies. In the present invention, low-molecular-weight chemotherapeutic agents usually have a molecular weight of 100 to 2000, preferably 200 to 1000. Examples of the chemotherapeutic agents demonstrated herein are all low-molecular-weight chemotherapeutic agents. The chemotherapeutic agents of the present invention include prodrugs that are converted to active chemotherapeutic agents in vivo. Prodrug activation may be enzymatic conversion or non-enzymatic conversion.

Furthermore, the antibodies can be modified using toxic peptides such as ricin, abrin, ribonuclease, onconase, DNase I, *Staphylococcal* enterotoxin-A, pokeweed antiviral protein, gelonin, diphtheria toxin, *Pseudomonas* exotoxin, *Pseudomonas* endotoxin, L-asparaginase, and PEG L-Asparaginase. In another embodiment, one or two or more of the low-molecular-weight chemotherapeutic agents and toxic peptides can be combined and used for antibody modification. The bonding between an anti-EREG antibody and the above-mentioned low-molecular weight chemotherapeutic agent may be covalent bonding or non-covalent bonding. Methods for producing antibodies bound to these chemotherapeutic agents are known.

Furthermore, proteinaceous pharmaceutical agents or toxins can be bound to antibodies by gene recombination techniques. Specifically, for example, it is possible to construct a recombinant vector by fusing a DNA encoding the above-mentioned toxic peptide with a DNA encoding an anti-EREG antibody in frame, and inserting this into an expression vector. This vector is introduced into suitable host cells, the obtained transformed cells are cultured, and the incorporated DNA is expressed. Thus, an anti-EREG antibody bound to the toxic peptide can be obtained as a fusion protein. When obtaining an antibody as a fusion protein, the proteinaceous pharmaceutical agent or toxin is generally positioned at the C terminus of the antibody. A peptide linker can be positioned between the antibody and the proteinaceous pharmaceutical agent or toxin.

Furthermore, the antibody used in the present invention may be a bispecific antibody. A bispecific antibody refers to an antibody that carries variable regions that recognize different epitopes within the same antibody molecule. The bispecific antibody may have antigen-binding sites that recognize different epitopes on an EREG molecule. Two molecules of such a bispecific antibody can bind to one molecule of EREG. As a result, stronger cytotoxic action can be expected.

Alternatively, the bispecific antibody may be an antibody in which one antigen-binding site recognizes EREG, and the other antigen-binding site recognizes a cytotoxic substance. Specifically, cytotoxic substances include chemotherapeutic agents, toxic peptides, and radioactive chemical substances. Such a bispecific antibody binds to EREG-expressing cells, and at the same time, captures cytotoxic substances. This enables the cytotoxic substances to directly act on EREG-expressing cells. Therefore, bispecific antibodies that recognize cytotoxic substances specifically injure tumor cells and suppress tumor cell proliferation.

Furthermore, in the present invention, bispecific antibodies that recognize antigens other than EREG may be combined. For example, it is possible to combine bispecific antibodies that recognize non-EREG antigens that are specifically expressed on the surface of target cancer cells like EREG.

Methods for producing bispecific antibodies are known. For example, two types of antibodies recognizing different antigens may be linked to prepare a bispecific antibody. The antibodies to be linked may be half molecules each having an H chain or an L chain, or may be quarter molecules consisting of only an H chain. Alternatively, bispecific antibody-producing fused cells can be prepared by fusing hybridomas producing different monoclonal antibodies. Bispecific antibodies can also be prepared by genetic engineering techniques.

Antibody genes constructed as described above can be obtained through expression by known methods. In the case of mammalian cells, the antibody genes can be expressed by operably linking the antibody gene to be expressed with an effective commonly used promoter, and a polyA signal on the 3' downstream side of the antibody gene. An example of the promoter/enhancer is human cytomegalovirus immediate early promoter/enhancer.

Other promoters/enhancers that can be used for antibody expression include viral promoters/enhancers, or mammalian cell-derived promoters/enhancers such as human elongation factor 1α (HEF1α). Specific examples of viruses whose promoters/enhancers may be used include retrovirus, polyoma virus, adenovirus, and simian virus 40 (SV40).

When an SV40 promoter/enhancer is used, the method of Mulligan et al. (Nature (1979) 277, 108) may be utilized. An HEF1α promoter/enhancer can be readily used for expressing a gene of interest by the method of Mizushima et al (Nucleic Acids Res. (1990) 18, 5322).

In the case of *E. coli*, the antibody gene to be expressed is operably linked to an effective commonly used promoter and a signal sequence for antibody secretion to express the gene.

Examples of the promoter include the lacZ promoter and araB promoter. When the lacZ promoter is used, the method of Ward et al., (Nature (1989) 341, 544-546; FASEB J. (1992) 6, 2422-2427) may be used. Alternatively, the araB promoter can be used for expressing a gene of interest by the method of Better et al. (Science (1988) 240, 1041-1043).

With regard to the signal sequence for antibody secretion, the pelB signal sequence (Lei, S. P. et al., J. Bacteriol. (1987) 169, 4379) may be used for production in the periplasm of *E. coli*. After the antibody produced in the periplasm is isolated, the antibody structure is refolded by using a protein denaturant like guanidine hydrochloride or urea so that the antibody will have the desired binding activity.

The replication origin inserted into the expression vector includes, for example, those derived from SV40, polyoma virus, adenovirus, or bovine papilloma virus (BPV). In order to amplify the gene copy number in the host cell system, a selection marker can be inserted into the expression vector. Specifically, the following selection markers can be used:
the aminoglycoside transferase (APH) gene;
the thymidine kinase (TK) gene;
the *E. coli* xanthine guanine phosphoribosyltransferase (Ecogpt) gene;
the dihydrofolate reductase (dhfr) gene, etc.

Any expression system, for example, a eukaryotic cell system or a prokaryotic cell system can be used to produce antibodies used in the present invention. Examples of eukaryotic cells include animal cells such as established mammalian cell system, insect cell system, and filamentous fungus cells and yeast cells. Examples of prokaryotic cells include bacterial cells such as *E. coli* cells. Antibodies used in the present invention are preferably expressed in mammalian cells. For example, mammalian cells such as CHO, COS, myeloma, BHK, Vero, or HeLa cells can be used.

Then, the transformed host cell is then cultured in vitro or in vivo to induce production of an antibody of interest. The host cells are cultured according to known methods. For example, DMEM, MEM, RPMI 1640, or IMDM can be used as the culture medium. A serum supplement solution such as fetal calf serum (FCS) can also be used in combination.

Antibodies expressed and produced as described above can be purified by using a single known method or a suitable combination of known methods generally used for purifying proteins. Antibodies can be separated and purified by, for example, appropriately selecting and combining affinity columns such as protein A column, chromatography column, filtration, ultrafiltration, salt precipitation, dialysis, and such (Antibodies A Laboratory Manual. Ed Harlow, David Lane, Cold Spring Harbor Laboratory, 1988).

Known means can be used to measure the antigen-binding activity of the antibodies (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), or a fluoroimmunoassay can be used.

The antibodies used in the present invention may be antibodies with a modified sugar chain. It is known that the cytotoxic activity of an antibody can be increased by modifying its sugar chain. Known antibodies having modified sugar chains include the following:
antibodies with modified glycosylation (for example, WO 99/54342);
antibodies deficient in fucose attached to sugar chains (for example, WO 00/61739 and WO 02/31140);
antibodies having a sugar chain with bisecting GlcNAc (for example, WO 02/79255), etc.

The antibodies used in the present invention are preferably antibodies having cytotoxic activity.

In the present invention, the cytotoxic activity includes, for example, antibody-dependent cell-mediated cytotoxicity (ADCC) activity and complement-dependent cytotoxicity (CDC) activity. In the present invention, CDC activity refers to complement system-mediated cytotoxic activity. ADCC activity refers to the activity of injuring a target cell when a specific antibody attaches to its cell surface antigen. An Fcγ receptor-carrying cell (immune cell, or such) binds to the Fc portion of the antigen via the Fcγ receptor and the target cell is damaged.

An anti-EREG antibody can be tested to see whether it has ADCC activity or CDC activity using known methods (for example, Current Protocols in Immunology, Chapter 7. Immunologic studies in humans, Editor, John E. Coligan et al., John Wiley & Sons, Inc., (1993) and the like).

First, specifically, effector cells, complement solution, and target cells are prepared.

(1) Preparation of Effector Cells

Spleen is removed from a CBA/N mouse or the like, and spleen cells are isolated in RPMI1640 medium (manufactured by Invitrogen). After washing in the same medium containing 10% fetal bovine serum (FBS, manufactured by HyClone), the cell concentration is adjusted to $5 \times 10^6$/mL to prepare the effector cells.

(2) Preparation of Complement Solution

Baby Rabbit Complement (manufactured by CEDARLANE) is diluted 10-fold in a culture medium (manufactured by Invitrogen) containing 10% FBS to prepare a complement solution.

(3) Preparation of Target Cells

The target cells can be radioactively labeled by incubating cells expressing the EREG protein with 0.2 mCi of sodium chromate-$^{51}$Cr (manufactured by GE Healthcare Bio-Sciences) in a DMEM medium containing 10% FBS for one hour at 37° C. For EREG protein-expressing cells, one may use cells transformed with a gene encoding the EREG protein, primary colon cancer, metastatic colon cancer, lung adenocarcinoma, pancreatic cancer, stomach cancer, kidney cancer cells, colon cancer cells, esophageal cancer cells, stomach cancer cells, pancreatic cancer cells, or such. After radioactive labeling, cells are washed three times in RPMI164O medium containing 10% FBS, and the target cells can be prepared by adjusting the cell concentration to $2 \times 10^5$/mL.

ADCC activity or CDC activity can be measured by the method described below. In the case of ADCC activity measurement, the target cell and anti-EREG antibody (50 μL each) are added to a 96-well U-bottom plate (manufactured by Becton Dickinson), and reacted for 15 minutes on ice. Thereafter, 100 μL of effector cells are added and incubated in a carbon dioxide incubator for four hours. The final concentration of the antibody is adjusted to 0 or 10 μg/mL. After culturing, 100 μL of the supernatant is collected, and the radioactivity is measured with a gamma counter (COBRAII AUTO-GAMMA, MODEL D5005, manufactured by Packard Instrument Company). The cytotoxic activity (%) can be calculated using the obtained values according to the equation: $(A-C)/(B-C) \times 100$, wherein A represents the radioactivity (cpm) in each sample, B represents the radioactivity (cpm) in a sample where 1% NP-40 (manufactured by Nacalai Tesque) has been added, and C represents the radioactivity (cpm) of a sample containing the target cells only.

Meanwhile, in the case of CDC activity measurement, 50 μL of target cell and 50 μL of an anti-EREG antibody are added to a 96-well flat-bottomed plate (manufactured by Becton Dickinson), and reacted for 15 minutes on ice. Thereafter, 100 µL of the complement solution is added, and incubated in a carbon dioxide incubator for four hours. The final concentration of the antibody is adjusted to 0 or 3 µg/mL. After incubation, 100 µL of supernatant is collected, and the radioactivity is measured with a gamma counter. The cytotoxic activity can be calculated in the same way as in the ADCC activity determination.

On the other hand, in the case of measuring the cytotoxic activity of an antibody conjugate, 50 µL of target cell and 50 µL of an anti-EREG antibody conjugate are added to a 96-well flat-bottomed plate (manufactured by Becton Dickinson), and reacted for 15 minutes on ice. This is then incubated in a carbon dioxide incubator for one to four hours. The final concentration of the antibody is adjusted to 0 or 3 µg/mL. After culturing, 100 µL of supernatant is collected, and the radioactivity is measured with a gamma counter. The cytotoxic activity can be calculated in the same way as in the ADCC activity determination.

An antibody of the present invention having cytotoxic activity is more preferably an antibody that has neutralizing activity. Generally, "neutralizing activity" refers to the activity to inhibit the biological activity of a ligand such as viruses or toxins towards cells. More specifically, "substances having neutralizing activity" refers to substances that bind to the ligand or to a receptor binding to the ligand, and inhibit the binding between the ligand and the receptor. When the ligand binding of a receptor is blocked by neutralizing activity, the receptor-mediated biological activity cannot be exerted. Antibodies that have such neutralizing activity are generally referred to as neutralizing antibodies. The neutralizing activity can be measured by comparing the biological activities in the presence and absence of a test substance of which the neutralizing activity is to be evaluated, in the presence of the ligand of interest.

In the present invention, ligand binding of the EGF receptor, which is considered to be the main receptor of EREG, results in dimerization of the receptor, and activation of the intracellular tyrosine kinase domain of the receptor. The activated tyrosine kinase forms phosphorylated tyrosine-containing peptides by autophosphorylation, and the peptides associate with various signal transduction accessory molecules. They are mainly PLCγ (phospholipase Cγ), Shc, Grb2, and such. Of these accessory molecules, the former two are further phosphorylated by the EGF receptor tyrosine kinase. The main signal transduction pathway from the EGF receptor is the pathway in which phosphorylation is transduced in the order of Shc, Grb2, Sos, Ras, Raf/MAPK kinase/MAP kinase. Furthermore, an alternative pathway which is from PLCγ to PKC is considered to exist.

Since such intracellular signal cascades vary depending on the cell type, suitable molecules can be targeted in the target cell of interest, and the target molecules are not limited to the above-mentioned factors. Commercially available kits for measuring in vivo signal activation can be suitably used (for example, the protein kinase C activity assay system (GE Healthcare Bio-Sciences)).

Furthermore, in vivo signaling activation can be detected using as an index, the transcription-inducing effect on a target gene present downstream of the in vivo signaling cascade. Changes in the transcriptional activity can be detected based on the principle of reporter assay. More specifically, a reporter gene such as green fluorescence protein (GFP) or luciferase is positioned downstream of the transcriptional factor or promoter region of the target gene, and the reporter activity is measured. The change in transcriptional activity can be measured based on the reporter activity.

Furthermore, since the EGF receptor usually functions to promote cell proliferation, in vivo signaling activation can be evaluated by measuring the proliferation activity of target cells. In the present invention, the neutralizing activity of a neutralizing antibody of the present invention is evaluated by assessing the cell proliferation activity. However, the present invention is not limited to this method, and the neutralizing activity can be assessed by suitably applying the aforementioned methods to selected target cells.

Specifically, for example, by measuring the below-mentioned cell proliferation activity, the neutralizing activity of an anti-EREG antibody can be evaluated or measured. For example, a method that measures the incorporation of [$^{3}$H]-labeled thymidine added to the medium by living cells as an index of DNA replication ability is used.

As a more convenient method, a dye exclusion method that measures under a microscope the ability of a cell to release a dye such as trypan blue to the outside of the cell, or the MTT method is used. The latter makes use of the ability of living cells to convert 3-(4,5-dimethylthiazol-2-yl)-2,5-diphenyl tetrazolium bromide (MTT), which is a tetrazolium salt, to a blue formazan product. More specifically, a test antibody is added to the culture solution of a test cell, and after a certain period of time, the MTT solution is added to the culture solution, and this is left to stand for a certain time for MTT to be incorporated into the cell. As a result, MTT which is a yellow compound is converted to a blue compound by the action of succinate dehydrogenase in the mitochondria of the cell. After dissolving this blue product for coloration, absorbance is measured and used as an indicator for the number of viable cells.

Besides MTT, reagents such as MTS, XTT, WST-1, and WST-8 are commercially available (Nacalai Tesque, and such) and can be suitably used. Furthermore, methods that evaluate cell proliferation activity using cellular ATP or impedance of cell culture as an indicator are known. For activity measurements, a binding antibody that has the same isotype as the anti-EREG antibody but does not have the neutralizing activity can be used as a control antibody in the same manner as the anti-EREG antibody, and it can be determined that the activity is present when the anti-EREG antibody has a stronger neutralizing activity than the control antibody.

The cells whose proliferation is suppressed by the anti-EREG antibody are not particularly limited as long as they express an EREG protein. Preferred EREG-expressing cells are, for example, cancer cells. Specifically, cells derived from colon cancer, lung adenocarcinoma, pancreatic cancer, stomach cancer, or kidney cancer are suitable as the EREG-expressing cells of the present invention. According to the present invention, effective cell proliferation-suppressing effect can be obtained for both primary and metastatic foci of these cancers. The more preferable cancer cells are cells of primary colon cancer, metastatic colon cancer, lung adenocarcinoma, pancreatic cancer, stomach cancer, and kidney cancer. Therefore, the anti-EREG antibody can be used for the purpose of treating or preventing cell proliferation-induced diseases such as colon cancer, lung adenocarcinoma, pancreatic cancer, stomach cancer, and kidney cancer. These cancers may be targets for the treatment or prevention regardless of whether they are primary foci or metastatic foci. More preferably, the anti-EREG antibody can be used for the purpose of treating and/or preventing primary colon cancer, metastatic colon cancer, or pancreatic cancer. Furthermore, among these cancers, cancers that proliferate in an EREG-dependent manner are preferred targets for the treatment and/or prevention of the present invention.

The present invention also provides polynucleotides encoding the antibodies of the present invention, and polynucleotides that hybridize under stringent conditions to these polynucleotides and encode antibodies having an activity equivalent to that of the antibodies of the present invention. The present invention also provides vectors containing these polynucleotides and transformants (including transformed cells) containing such vectors.

The polynucleotides of the present invention are polymers comprising multiple nucleotides or base pairs of deoxyribonucleic acids (DNA) or ribonucleic acids (RNA), and are not particularly limited, as long as they encode the antibodies of the present invention. The polynucleotides of the present invention may also contain non-natural nucleotides.

The polynucleotides of the present invention can be used to express antibodies using genetic engineering techniques. Furthermore, they can be used as probes in the screening of antibodies that are functionally equivalent to the antibodies of the present invention. Specifically, a DNA that hybridizes under stringent conditions to the polynucleotide encoding an antibody of the present invention, and encodes an antibody having an activity equivalent to that of the antibody of the present invention, can be obtained by techniques such as hybridization and gene amplification techniques (for example, PCR), using the polynucleotide encoding an antibody of the present invention, or a portion thereof, as a probe. Such DNAs are included in the polynucleotides of the present invention. Hybridization techniques are well known to those skilled in the art (Sambrook, J. et al., Molecular Cloning 2nd ed., 9.47-9.58, Cold Spring Harbor Lab. press, 1989).

Conditions for hybridization include, for example, those with low stringency. Examples of conditions of low stringency include post-hybridization washing under conditions of 0.1×SSC and 0.1% SDS at 42° C., and preferably under conditions of 0.1×SSC and 0.1% SDS at 50° C. More preferable hybridization conditions include those of high stringency. High stringency conditions include, for example, conditions of 5×SSC and 0.1% SDS at 65° C. Under these conditions, higher temperature can be expected to efficiently yield polynucleotides with high homology. However, several factors such as temperature and salt concentration can influence hybridization stringency, and those skilled in the art can suitably select these factors to achieve similar stringencies.

A functionally equivalent antibody encoded by a polynucleotide obtained by these hybridization and gene amplification techniques in the present invention usually has a high homology to the amino acid sequences of the antibodies of the present invention. The antibodies of the present invention also include antibodies that are functionally equivalent to and have high amino acid sequence homology to the antibodies of the present invention. The term "high homology" generally refers to amino acid identity of at least 50% or higher, preferably 75% or higher, more preferably 85% or higher, still more preferably 95% or higher. Polypeptide homology can be determined by the algorithm described in literature (Wilbur, W. J. and Lipman, D. J. Proc. Natl. Acad. Sci. USA (1983) 80, 726-730).

Pharmaceutical Compositions

In another aspect, the present invention provides pharmaceutical compositions comprising an antibody that binds to an EREG protein as an active ingredient. In addition, the present invention relates to a cell proliferation inhibitor, in particular an anticancer agent, comprising an antibody that binds to an EREG protein as an active ingredient. Cell proliferation inhibitors and anticancer agents of the present invention are preferably administered to a subject affected by cancer, or to a subject who is likely to be affected by cancer.

In the present invention, a cell proliferation inhibitor comprising as an active ingredient an antibody that binds to an EREG protein can also be described as a method for suppressing cell proliferation which comprises the step of administering an antibody that binds to an EREG protein to a subject, or as use of an antibody that binds to an EREG protein in the production of a cell proliferation inhibitor.

Furthermore, in the present invention, an anticancer agent comprising as an active ingredient an antibody that binds to an EREG protein can also be described as a method for preventing or treating cancer which comprises the step of administering an antibody that binds to an EREG protein to a subject, or as use of an antibody that binds to an EREG protein in the production of an anticancer agent.

In the present invention, the phrase "comprising an antibody that binds to EREG as an active ingredient" means comprising an anti-EREG antibody as the main active substance, and does not limit the content percentage of the anti-EREG antibody.

The antibody included in the pharmaceutical composition of the present invention (for example, cell proliferation inhibitor and anticancer agent; same hereinafter) is not particularly limited as long as it binds to an EREG protein, and examples include antibodies described herein.

The pharmaceutical compositions of the present invention can be administered orally or parenterally to a patient. Preferably, the administration is parenteral administration. Specifically, the method of administration is, for example, administration by injection, transnasal administration, transpulmonary administration, or transdermal administration. Examples of administration by injection include systemic and local administrations of a pharmaceutical composition of the present invention by intravenous injection, intramuscular injection, intraperitoneal injection, subcutaneous injection, or such. A suitable administration method may be selected according to the age of the patient and symptoms. The dosage may be selected, for example, within the range of 0.0001 mg to 1000 mg per kg body weight in each administration. Alternatively, for example, the dosage for each patient may be selected within the range of 0.001 to 100,000 mg/body. However, the pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, perfumes, preservatives, stabilizers, buffers, suspending agents, isotonization agents, binders, disintegrants, lubricants, fluidity promoting agents, and flavoring agents; and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium chain fatty acid triglyceride, polyoxyethylene hardened castor oil 60, saccharose, carboxymethyl cellulose, corn starch, inorganic salt, and such.

The present invention also provides methods for inducing damages in EREG-expressing cells and methods for suppressing cell proliferation by contacting EREG-expressing cells with antibodies that bind to the EREG protein.

More specifically, the present invention includes the following embodiments.

A method for inducing cell injury in EREG-expressing cells, which comprises the step of contacting the EREG protein-expressing cells with an EREG protein-binding antibody.

A method for suppressing the proliferation of EREG-expressing cells, which comprises the step of contacting the EREG protein-expressing cells with an EREG protein-binding antibody.

The aforementioned method, wherein the EREG protein-binding antibody has cytotoxic activity.

The aforementioned method, wherein the EREG protein-binding antibody has neutralizing activity.

The aforementioned method, wherein the EREG protein-binding antibody is an antibody of any of (1) to (57) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3;
(2) an antibody comprising the H chain of (1), wherein the H chain has the amino acid sequence of positions 117 to 452 in the amino acid sequence of SEQ ID NO: 8 as CH;
(3) an antibody comprising the H chain of (1), wherein the H chain has the amino acid sequence of positions 117 to 446 in the amino acid sequence of SEQ ID NO: 10 as CH;
(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;
(5) an antibody comprising the L chain of (4), wherein the L chain has the amino acid sequence of positions 107 to 213 in the amino acid sequence of SEQ ID NO: 18 as CL;
(6) an antibody comprising the L chain of (4), wherein the L chain has the amino acid sequence of positions 107 to 213 in the amino acid sequence of SEQ ID NO: 20 as CL;
(7) an antibody comprising the H chain of (1) and the L chain of (4);
(8) an antibody comprising the H chain of (2) and the L chain of (5);
(9) an antibody comprising the H chain of (3) and the L chain of (6);
(10) an antibody comprising an H chain having the amino acid sequence of SEQ ID NO: 49 as CDR1, the amino acid sequence of SEQ ID NO: 51 as CDR2, and the amino acid sequence of SEQ ID NO: 53 as CDR3;
(11) an antibody comprising the H chain of (10), wherein the H chain has CH derived from mouse IgG 1;
(12) an antibody comprising the H chain of (10), wherein the H chain has the amino acid sequence of positions 117 to 446 in the amino acid sequence of SEQ ID NO: 10 as CH;
(13) an antibody comprising an L chain having the amino acid sequence of SEQ ID NO: 55 as CDR1, the amino acid sequence of SEQ ID NO: 57 as CDR2, and the amino acid sequence of SEQ ID NO: 59 as CDR3;
(14) an antibody comprising the L chain of (13), wherein the L chain has CL derived from the mouse ic chain;
(15) an antibody comprising the L chain of (13), wherein the L chain has the amino acid sequence of positions 107 to 213 in the amino acid sequence of SEQ ID NO: 20 as CL;
(16) an antibody comprising the H chain of (10) and the L chain of (13);
(17) an antibody comprising the H chain of (11) and the L chain of (14);
(18) an antibody comprising the H chain of (12) and the L chain of (15);
(19) an antibody comprising an H chain having the amino acid sequence of SEQ ID NO: 61 as CDR1, the amino acid sequence of SEQ ID NO: 63 as CDR2, and the amino acid sequence of SEQ ID NO: 65 as CDR3;
(20) an antibody comprising the H chain of (19), wherein the H chain has CH derived from mouse IgG1;
(21) an antibody comprising the H chain of (19), wherein the H chain has the amino acid sequence of positions 117 to 446 in the amino acid sequence of SEQ ID NO: 10 as CH;
(22) an antibody comprising an L chain having the amino acid sequence of SEQ ID NO: 67 as CDR1, the amino acid sequence of SEQ ID NO: 69 as CDR2, and the amino acid sequence of SEQ ID NO: 71 as CDR3;
(23) an antibody comprising the L chain of (22), wherein the L chain has CL derived from the mouse κ chain;
(24) an antibody comprising the L chain of (22), wherein the L chain has the amino acid sequence of positions 107 to 213 in the amino acid sequence of SEQ ID NO: 20 as CL;
(25) an antibody comprising the H chain of (19) and the L chain of (22);
(26) an antibody comprising the H chain of (20) and the L chain of (23);
(27) an antibody comprising the H chain of (21) and the L chain of (24);
(28) an antibody comprising an H chain having the amino acid sequence of SEQ ID NO: 73 as CDR1, the amino acid sequence of SEQ ID NO: 75 as CDR2, and the amino acid sequence of SEQ ID NO: 77 as CDR3;
(29) an antibody comprising the H chain of (28), wherein the H chain has CH derived from mouse IgG1;
(30) an antibody comprising the H chain of (28), wherein the H chain has the amino acid sequence of positions 117 to 446 in the amino acid sequence of SEQ ID NO: 10 as CH;
(31) an antibody comprising an L chain having the amino acid sequence of SEQ ID NO: 79 as CDR1, the amino acid sequence of SEQ ID NO: 81 as CDR2, and the amino acid sequence of SEQ ID NO: 83 as CDR3;
(32) an antibody comprising the L chain of (31), wherein the L chain has CL derived from the mouse κ chain;
(33) an antibody comprising the L chain of (31), wherein the L chain has the amino acid sequence of positions 107 to 213 in the amino acid sequence of SEQ ID NO: 20 as CL;
(34) an antibody comprising the H chain of (28) and the L chain of (31);
(35) an antibody comprising the H chain of (29) and the L chain of (32);
(36) an antibody comprising the H chain of (30) and the L chain of (33);
(37) an antibody comprising an H chain having the amino acid sequence of SEQ ID NO: 85 as CDR1, the amino acid sequence of SEQ ID NO: 87 as CDR2, and the amino acid sequence of SEQ ID NO: 89 as CDR3;
(38) an antibody comprising the H chain of (37), wherein the H chain has CH derived from mouse IgG1;
(39) an antibody comprising the H chain of (37), wherein the H chain has the amino acid sequence of positions 117 to 446 in the amino acid sequence of SEQ ID NO: 10 as CH;
(40) an antibody comprising an L chain having the amino acid sequence of SEQ ID NO: 91 as CDR1, the amino acid sequence of SEQ ID NO: 93 as CDR2, and the amino acid sequence of SEQ ID NO: 95 as CDR3;
(41) an antibody comprising the L chain of (40), wherein the L chain has CL derived from the mouse κ chain;
(42) an antibody comprising the L chain of (40), wherein the L chain has the amino acid sequence of positions 107 to 213 in the amino acid sequence of SEQ ID NO: 20 as CL;

(43) an antibody comprising the H chain of (37) and the L chain of (40);
(44) an antibody comprising the H chain of (38) and the L chain of (41);
(45) an antibody comprising the H chain of (39) and the L chain of (42);
(46) an antibody comprising an H chain having the amino acid sequence of SEQ ID NO: 97 as CDR1, the amino acid sequence of SEQ ID NO: 99 as CDR2, and the amino acid sequence of SEQ ID NO: 101 as CDR3;
(47) an antibody comprising the H chain of (46), wherein the H chain has CH derived from mouse IgG1;
(48) an antibody comprising the H chain of (46), wherein the H chain has the amino acid sequence of positions 117 to 446 in the amino acid sequence of SEQ ID NO: 10 as CH;
(49) an antibody comprising an L chain having the amino acid sequence of SEQ ID NO: 103 as CDR1, the amino acid sequence of SEQ ID NO: 105 as CDR2, and the amino acid sequence of SEQ ID NO: 107 as CDR3;
(50) an antibody comprising the L chain of (49), wherein the L chain has CL derived from the mouse κ chain;
(51) an antibody comprising the L chain of (49), wherein the L chain has the amino acid sequence of positions 107 to 213 in the amino acid sequence of SEQ ID NO: 20 as CL;
(52) an antibody comprising the H chain of (46) and the L chain of (49);
(53) an antibody comprising the H chain of (47) and the L chain of (50);
(54) an antibody comprising the H chain of (48) and the L chain of (51);
(55) an antibody comprising one or more amino acid substitutions, deletions, additions, and/or insertions in the antibody of any of (1) to (54), which has equivalent activity as the antibody of any of (1) to (54);
(56) an antibody that binds to the same EREG protein epitope as the antibody of any of (1) to (55); and
(57) a minibody of the antibody of any of (1) to (56).
The aforementioned method, wherein the EREG protein-expressing cells are cancer cells.

As described above, the above-mentioned antibodies of (1) to (57) include not only monovalent antibodies but also multivalent antibodies with two or more valencies. Multivalent antibodies of the present invention include multivalent antibodies whose antigen binding sites are all the same, and multivalent antibodies whose antigen binding sites are partially or completely different.

The EREG protein-binding antibodies are described above as EREG protein-binding antibodies included in the cell proliferation inhibitors of the present invention. Cells that are bound by the anti-EREG antibodies are not particularly limited as long as the cells are EREG-expressing cells. Preferred EREG-expressing cells of the present invention are cancer cells. More preferably, the cells are colon cancer, lung adenocarcinoma, pancreatic cancer, stomach cancer, and kidney cancer cells. Methods of the present invention can be applied to both primary and metastatic foci of these cancers. More preferred cancer cells are primary colon cancer, metastatic colon cancer, and pancreatic cancer cells.

In the present invention "contacting" is accomplished, for example, by adding an antibody to a culture solution of EREG-expressing cells cultured in a test tube. In this case, the antibody can be added in the form of, for example, a solution or a solid obtained by freeze-drying or the like. When adding the antibody as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The concentration for addition is not particularly limited, but the final concentration in the culture that may be suitably used is preferably in the range of 1 pg/mL to 1 g/mL, more preferably 1 ng/mL to 1 mg/mL, and even more preferably 1 μg/mL to 1 mg/mL.

Furthermore, in another embodiment, "contacting" in the present invention is carried out by administration to a non-human animal to which an EREG-expressing cell has been transplanted into the body, or to an animal carrying cancer cells endogenously expressing EREG The method of administration may be oral or parenteral administration. The method of administration is particularly preferably parenteral administration, and specifically, the method of administration is, for example, administration by injection, transnasal administration, transpulmonary administration, or transdermal administration. Examples of administration by injection include systemic and local administrations of pharmaceutical compositions, cell proliferation inhibitors and anticancer agents of the present invention by intravenous injection, intramuscular injection, intraperitoneal injection, subcutaneous injection, or such. A suitable administration method may be selected according to the age of the test animal and symptoms. When administering as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The dosage may be selected, for example, within the range of 0.0001 mg to 1000 mg per kg body weight in each administration. Alternatively, for example, the dosage for each patient may be selected within the range of 0.001 to 100,000 mg/body. However, the antibody dose of the present invention is not limited to these doses.

The following method is suitably used as a method for evaluating or measuring cell damage induced by contacting EREG-expressing cells with an anti-EREG antibody. Examples of a method for evaluating or measuring the cytotoxic activity in a test tube include methods for measuring the above-mentioned antibody-dependent cell-mediated cytotoxicity (ADCC) activity, complement-dependent cytotoxicity (CDC) activity, and such. Whether or not an anti-EREG antibody has ADCC activity or CDC activity can be measured by known methods (for example, Current protocols in Immunology, Chapter 7. Immunologic studies in humans, Editor, John E. Coligan et al., John Wiley & Sons, Inc., (1993) and the like). For activity measurements, a binding antibody having the same isotype as anti-EREG antibody but not having any cell-damaging activity can be used as a control antibody in the same manner as the anti-EREG antibody, and it can be determined that the activity is present when the anti-EREG antibody shows a stronger cytotoxic activity than the control antibody.

The isotype of an antibody is defined by the sequence of its H chain constant region in the antibody amino acid sequence. The isotype of an antibody is ultimately determined in vivo by class switching that arises from genetic recombinations in chromosomes which occur during maturation of antibody-producing B-cells. Difference in isotype is reflected in the difference of physiological and pathological functions of antibodies. Specifically, for example, the strength of cytotoxic activity is known to be influenced by antibody isotype in addition to the expression level of the antigen. Therefore, when measuring the above-described cell damaging activity, an antibody of the same isotype as the test antibody is preferably used as the control.

To evaluate or measure cell damaging activity in vivo, for example, EREG-expressing cancer cells are intradermally or subcutaneously transplanted to a non-human test animal, and then a test antibody is intravenously or intraperitoneally administered daily or at the interval of few days, starting from the day of transplantation or the following day. Cytotoxicity can be defined by daily measurement of tumor size. In a similar manner to the evaluation in a test tube, cytotoxicity can be determined by administering a control antibody having the same isotype, and observing that the tumor size in the anti-EREG antibody-administered group is significantly smaller than the tumor size in the control antibody-administered group. When using a mouse as the non-human test animal, it is suitable to use a nude (nu/nu) mouse whose thymus has been made genetically defective so that its T lymphocyte function is lost. The use of such a mouse can eliminate the participation of T lymphocytes in the test animals when evaluating or measuring the cytotoxicity of the administered antibody.

The same method used for measuring neutralizing activity mentioned above can be suitably applied as a method for evaluating or measuring the contact-mediated inhibitory effect of an anti-EREG antibody on the proliferation of EREG-expressing cells.

As a method for evaluating or measuring cell proliferation-inhibiting activity in vivo, the same method described above for evaluating or measuring cytotoxicity in vivo can be suitably used.

Screening Methods

The present inventors showed that EREG secreted by cells induces the proliferation of cells growing in an EREG-dependent manner. Furthermore, it was also confirmed that the EREG expression is specifically enhanced in cancer cells. Therefore, cancer treatment can be accomplished by suppressing the EREG expression in EREG-expressing cells. More specifically, in the present invention, it is shown that compounds that suppress the EREG expression in cancer cells are useful as candidate compounds as cancer therapeutic agents. Based on these findings, the present invention provides methods of screening for candidate compounds as cancer therapeutic agents, which comprise the steps of:
(1) contacting EREG-expressing cells with a test compound;
(2) measuring the EREG expression level in the EREG-expressing cells; and
(3) selecting a compound that lowers the EREG expression compared to a control as a candidate therapeutic agent for cancer.

In the present invention, for example, EREG-expressing cancer cells may be used as the EREG-expressing cells. Specifically, for example, any cancer cell line showing enhanced EREG expression in FIG. 2 can be used for the screening methods of the present invention. More specifically, cells that may be used for the screening methods of the present invention include the following cancer cell lines. All the examples of cell lines listed below can be obtained from a cell bank. Culturing conditions for these cell lines are already established. More specifically, the cells can be cultured, for example, under the conditions shown in Table 2.

Esophageal cancer cell line: TE2
Stomach cancer cell lines: GT3
  MKN45
  2M
  2MD3
Colon cancer cell lines: CACO2
  DLD1
  hCT116
  LOVO
Liver cancer cell line: Alexander
Pancreatic cancer cell lines: Capan1
  Paca2
  PK-1
Kidney cancer cell lines: Caki1
  Caki2
Lung cancer cell lines: A549
  H157
  H1648
  H2009
  H23
  H2347
  H522

These cell lines are cultured in the presence of a test compound, and the EREG expression level in the cell lines is measured. The EREG expression level can be evaluated by measuring the amount of intracellular mRNA, or the amount of EREG protein secreted inside the cell, on the cell surface, or to the outside of the cell. Any method described herein may be used as a method for measuring EREG mRNA or EREG protein. The present inventors confirmed the cell proliferation-inducing effect of secreted EREG in cells that proliferate in an EREG-dependent manner. Therefore, a preferred embodiment of the present invention is a method of screening for candidate compounds as anti-cancer agents, which uses the amount of extracellularly secreted EREG as an index.

In the present invention, a test compound that lowers the EREG expression compared to a control is selected as the candidate compound of interest. As the control in the present invention, for example, the same cell line cultured in the absence of the test compound may be used. Alternatively, for a control, one may use a cell line cultured in the presence of a compound whose effect on the EREG expression is already known. By using such a control, a compound having a greater effect than a certain compound can be selected.

In the present invention, one can screen for cancer therapeutic agents using the neutralizing effect of a test compound against EREG as an index. More specifically, the present invention relates to methods of screening for candidate compounds as cancer therapeutic agents, which comprise the steps of:
(1) culturing cells that proliferate in an EREG-dependent manner, in the presence of EREG and a test compound;
(2) measuring the cell proliferation level; and
(3) selecting a test compound that suppresses cell proliferation compared to a control as a candidate therapeutic agent for cancer.

In the present invention, "cells that proliferate in an EREG-dependent manner" refers to cells showing dose-dependent cell proliferation mediated by EREG. For example, in the Examples described below, the AsPC1 pancreatic cancer cell line shows dose-dependent cell proliferation mediated by EREG. Furthermore, according to findings by the present inventors, the EREG dependency can be conferred by expressing an EGF receptor/G-CSF receptor chimeric receptor. More specifically, mouse cells transformed with DNA encoding a chimeric receptor comprising the extracellular domain of EGF receptor and the intracellular domain of G-CSF receptor exhibit dose-dependent cell proliferation to human EREG. Therefore, cells in which the EGFR dependency has been artificially induced in this way can also be used for the screening methods of the present invention.

The proliferation level of cells proliferating in an EREG-dependent manner cultured in the presence of EREG and a test compound is then measured. Cell proliferation can be measured by any method. For example, the number of viable cells can be compared using a commercially available reagent for counting viable cells, as described in the Examples. Alternatively, systems for efficient, larger-scale screening are also commercially available. For example, a system that can evaluate the number of viable cells in each well using a multi-well plate is in practical use. Based on the result of comparing the viable cell number, test compounds that suppress the increase in cell number compared to a control can be selected as candidate compounds for cancer therapeutic agents.

In the screening methods of the present invention, for example, the same cell line cultured in the absence of a test compound can be used as a control. Alternatively, one can use a cell line cultured in the presence of a compound that has clear effect on the cell proliferation-inducing action depending on the EREG secretion as a control. By using such a control, one can select a compound that has greater effect than a certain compound.

Candidate compounds selected by screening methods of the present invention are useful as candidate compounds of anticancer therapeutic agent that work to suppress the EREG function. In the present invention, the cancer therapeutic effect of anti-EREG antibodies was confirmed. Therefore, compounds selected by the screening methods of the present invention can be expected to have similar effects as the antibodies. If necessary, candidate compounds selected by the screening methods of the present invention are further evaluated for their effect on other cancer cell lines or primary culture cells, and also for their effect such as toxicity against normal cells. Compounds that are useful as cancer therapeutic agents can be selected through such evaluation. A series of evaluation methods for cancer therapeutic agents are already established.

In the screening methods of the present invention, various naturally-occurring and artificially-synthesized compounds can be used as test compounds. For example, protein libraries and antibody libraries are preferred as the test compound libraries of the present invention. Alternatively, phage libraries presenting proteins or antibodies may be used as the test compounds. Furthermore, libraries of artificially-synthesized compounds such as combinatorial libraries may be used as the test compounds.

All prior art references cited herein are incorporated by reference into this description.

EXAMPLES

Herein below, the present invention will be specifically described with reference to the Examples, but it is not to be construed as being limited thereto.

Example 1

Analysis of the Human EREG Gene Expression in Various Types of Cancers 1-1. GeneChip Analysis of the Human EREG Gene Expression To search for a gene of which expression is enhanced specifically in cancer tissues such as colon cancer and pancreatic cancer tissues, comprehensive gene expression analysis was carried out for normal tissues, cancer tissues, and cancer cell lines using GeneChip U-133A (manufactured by Affymetrix).

Total RNAs were prepared from normal tissues, cancer tissues, and cancer cell lines shown in Tables 1 and 2 by conventional methods using ISOGEN (manufactured by Nippon Gene). Gene expression analysis was carried out using 10 µg each of these total RNAs, and subjecting them to transcript analysis on GeneChip U-133A (manufactured by Affymetrix). This method was carried out according to the Expression Analysis Technical Manual (manufactured by Affymetrix). For searching genes of which expression is enhanced in cancer tissues or cancer cells, the mean value of the expression scores of all the genes was normalized to 100.

Figure 2:
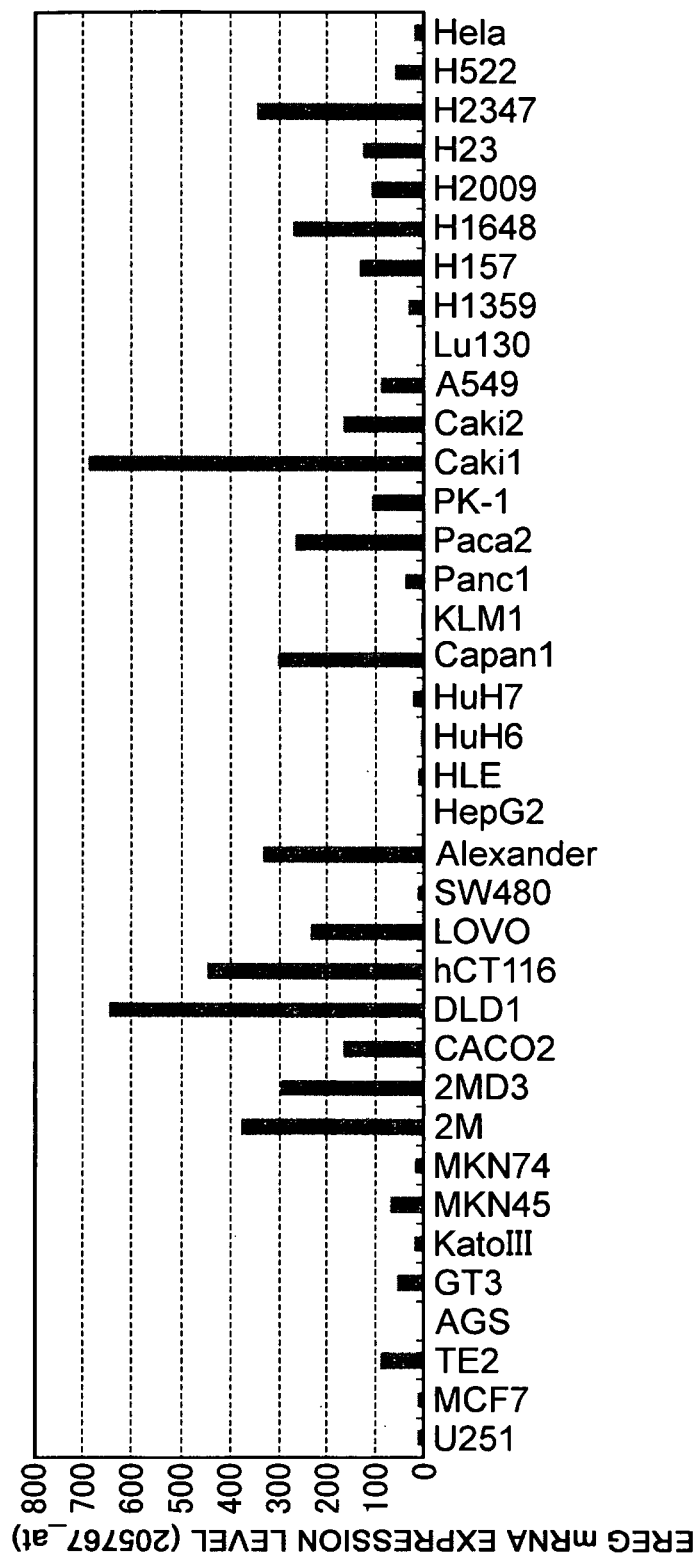
FIG. 2 shows the levels of EREG mRNA transcript in cancer cell lines. The vertical axis indicates the signal intensity of Probe ID: 205767_at HG-U133A. The intensity is relative to the mean value of the expression scores of all the genes on GeneChip U133A, which was set to 100.

We found that the expression of human EREG mRNA (probe ID: 205767_at HG-U133A) was enhanced in primary colon cancer, metastatic colon cancer, lung adenocarcinoma, and pancreatic cancer tissues, and colon cancer cell lines (CACO2, DLD 1, HCT116, and LOVO), stomach cancer cell lines (2M and 2MD3), liver cancer cell line (Alexander), pancreatic cancer cell lines (Capan1 and Paca2), kidney cancer cell lines (Caki1 and Caki2), and primary colon cancer, metastatic colon cancer, lung adenocarcinoma, pancreatic cancer, stomach cancer, and kidney cancer cell lines (H157, H1648, H2009, H23, and H2347), while no remarkable expression of human EREG mRNA could be observed in the normal tissues examined (FIGS. 1 and 2).

From the above finding, it became apparent that, while expression of the human EREG gene (probe ID: 205767_at HG-U133A) is very low in normal tissues, expression of the human EREG gene is enhanced in a wide variety of cancers including primary colon cancer, metastatic colon cancer, lung adenocarcinoma, pancreatic cancer, stomach cancer, kidney cancer, colon cancer, pancreatic cancer, stomach cancer and kidney cancer.

TABLE 1

Tissues used for EREG gene expression analysis

| Tissue | Source |
|---|---|
| Whole brain | Clontech 64020-1 |
| Lung | Clinical sample, 1 case |
| Trachea | Clontech 64091-1 |
| Heart | Ambion 7966 |
| Kidney | Ambion 7976 |
| Liver | Clinical sample (Surgery) |
| Pancreas | Ambion 7954 |
| Stomach | Clinical sample (Surgery) |
| Small intestine | Ambion 7984 |
| Large intestine | Ambion 7986 |
| Bone marrow | Clontech 64106-1 |
| Peripheral blood mononuclear cell | Clinical sample, 1 case |
| Testis | Clontech 64027-1 |
| Prostate | Ambion 7988 |
| Ovary | Ambion 7974 |
| Skin | Stratagene 735031 |
| Lung adenocarcinoma 1 | Clinical sample, 1 case |
| Lung adenocarcinoma 2 | Clinical sample, 1 case |
| Lung adenocarcinoma 3 | Clinical sample, 1 case |
| Lung adenocarcinoma 4 | Clinical sample, 1 case |
| Lung adenocarcinoma 5 | Clinical sample, 1 case |
| Primary colon cancer 1 | Clinical sample, 1 case |
| Primary colon cancer 2 | Clinical sample, 1 case |
| Primary colon cancer 3 | Clinical sample, 1 case |
| Primary colon cancer 4 | Clinical sample, 1 case |
| Metastatic colon cancer 1 | Clinical sample, 1 case |
| Metastatic colon cancer 2 | Clinical sample, 1 case |
| Metastatic colon cancer 3 | Clinical sample, 1 case |
| Metastatic colon cancer 4 | Clinical sample, 1 case |
| Metastatic colon cancer 5 | Clinical sample, 1 case |
| Metastatic colon cancer 6 | Clinical sample, 1 case |

TABLE 1-continued

Tissues used for EREG gene expression analysis

| Tissue | Source |
| --- | --- |
| Metastatic colon cancer 7 | Clinical sample, 1 case |
| Pancreatic cancer 1 | Clinical sample, 1 case |
| Pancreatic cancer 2 | Clinical sample, 1 case |
| Pancreatic cancer 3 | Clinical sample, 1 case |
| Pancreatic cancer 4 | Clinical sample, 1 case |

TABLE 2

Cell lines and culture conditions used for the EREG gene expression analysis

| Type of cancer | Cell line | Medium | Serum (%) |
| --- | --- | --- | --- |
| Brain tumor | U251 | DMEM | 10 |
| Breast cancer | MCF7 | RPMI1640 | 10 |
| Esophageal cancer | TE2 | RPMI1640 | 10 |
| Stomach cancer | AGS | RPMI1640 | 10 |
| | GT3 | DMEM | 10 |
| | KatoIII | RPMI1640:DMEM = 1:1 | 10 |
| | MKN45 | RPMI1640 | 10 |
| | MKN74 | RPMI1640 | 10 |
| | 2M | DMEM | 10 |
| | 2MD3 | DMEM | 10 |
| Colon cancer | CACO2 | DMEM | 20 |
| | DLD1 | RPMI1640 | 10 |
| | hCT116 | McCoy5A | 10 |
| | LOVO | HamF12:DMEM = 1:1 | 10 |
| | SW480 | RPMI1640 | 10 |
| Liver cancer | Alexander | DMEM | 10 |
| | HepG2 | DMEM | 10 |
| | HLE | DMEM | 10 |
| | HuH6 | DMEM | 10 |
| | HuH7 | DMEM | 10 |
| Pancreatic cancer | Capan1 | DMEM | 20 |
| | KLM1 | RPMI1640 | 10 |
| | Panc1 | RPMI1640 | 10 |
| | Paca2 | RPMI1640 | 10 |
| | PK-1 | RPMI1640 | 10 |
| Kidney cancer | Caki1 | RPMI1640 | 10 |
| | Caki2 | RPMI1640 | 10 |
| Lung cancer | A549 | DMEM | 10 |
| | Lu130 | RPMI1640 | 10 |
| | H1359 | RPMI1640 | 10 |
| | H157 | RPMI1640 | 10 |
| | H1648 | HamF12:DMEM = 1:1 | 10 |
| | H2009 | HamF12:DMEM = 1:1 | 10 |
| | H23 | RPMI1640 | 10 |
| | H2347 | RPMI1640 | 10 |
| | H522 | RPMI1640 | 10 |
| Cervical cancer | Hela | DMEM | 10 |

Example 2

Preparation of Anti-EREG Monoclonal Antibody 2-1. Establishment of Cells Expressing the Full-Length Human EREG The full-length human EREG cDNA (NM_001432) comprising the sequence shown in SEQ ID NO: 21 was isolated by conventional methods. The gene fragment was cloned into an expression vector (pMCN) for mammalian cells, and the resulting vector was named hEREG/pMCN. pMCN enables induced expression of a foreign gene under the control of a mouse CMV promoter (ACCESSION No. U68299), and is a vector into which a neomycin resistance gene has been incorporated. A CHO cell line that stably expresses full-length human EREG was established by introducing hEREG/pMCN into the CHO DG44 cell line (Invitrogen) by electroporation, and selecting the cells in the presence of 500 μg/mL of Geneticin. The cell line established was named EREG_DG 2-2. Preparation of Soluble Human EREG/Mouse IgG2a Fc-Fusion Protein (sEREG_mFc)

Soluble human EREG/mouse IgG2a Fc-fusion protein (hereinafter, sEREG_mFc) was prepared as an immunizing antigen for anti-EREG antibody production.

sEREG_mFc was constructed by fusion of the extracellular domain of human EREG (amino acids 7 to 122) to the mouse IgG2a constant region via the CpoI recognition sequence in the hinge region, and cloning into the pMCDN vector, which was prepared by inserting the DHFR gene into the pMCN expression vector. The vector constructed was named sEREG-mFc/pMCDN. The sequence represented by SEQ ID NO: 33 shows the nucleotide sequence of the sEREG-mFc gene, and the sequence represented by SEQ ID NO: 34 shows the amino acid sequence of sEREG-mFc. An sEREG-mFc-expressing CHO cell line was established by introducing sEREG-mFc/pMCDN into the CHO DG44 cell line (Invitrogen) by electroporation, and selecting the cells in the presence of 500 μg/mL of Geneticin.

Then, sEREG-mFc was purified from the culture supernatant. The culture supernatant was applied onto a HiTrap Protein G HP (Amersham, CAT#17-0404-01) column, unbound materials were washed out with a binding buffer (20 mM sodium phosphate (pH 7.0)), and sEREG-mFc of interest was eluted with an elution buffer (0.1 M glycine-HCl (pH 2.7)). The eluate was immediately neutralized by collection into a tube containing a neutralization buffer (1 M Tris-HCl (pH 9.0)). Then, the eluted sEREG-mFc was separated by gel filtration using Superdex 200 HR 10/30 (Amersham) so that the solvent of this solution was replaced with PBS. The purified protein was quantified using DC protein assay (BIO-RAD), in which the protein concentration was converted using the included bovine IgG as a standard.

2-3. Preparation of Anti-EREG Monoclonal Antibody

Balb/c mice and MRL/MpJ-Tnfrsf6<1pr>/Crlj mice (Charles River Japan) were used as the animals for immunization. Immunization was initiated at the $5^{th}$ to $8^{th}$ week. For the first immunization, sEREG-mFc was emulsified using Freund's complete adjuvant (FCA, Beckton Dickinson), and administered subcutaneously (100 μg/head). Two weeks later, sEREG-mFc was emulsified using Freund's incomplete adjuvant (FIA, Beckton Dickinson), and administered subcutaneously (50 μg/head). Subsequently, boosting immunization was performed at one-week intervals for two to three times, and for the final immunization, sEREG-mFc was diluted with PBS, and then administered to the tail vein (50 μg/head).

At four days after the final immunization, spleen cells were extirpated and mixed with mouse myeloma cells P3-X63Ag8U1 (P3U1, purchased from ATCC) at 2:1 ratio, and cell fusion was carried out by gradual addition of PEG 1500 (Roche Diagnostics). RPMI1640 medium (GIBCO BRL) was added carefully to dilute PEG 1500, and then PEG 1500 was removed by centrifugation. Then, the cells were resuspended in RPMI1640 containing 10% FBS, 1× HAT media supplement (SIGMA), and 0.5× BM-Condimed H1 Hybridoma cloning supplement (Roche Diagnostics) (hereinafter referred to as HAT medium), and seeded into a 96-well culture plate at 200 μL/well. The screening was performed by evaluating the binding activity to human EREG_DG using a flow cytometer. Clones showing a positive binding activity obtained by this analysis were monocloned by the limiting dilution method.

Furthermore, monoclonal antibodies were obtained by immunizing the mice by the DNA inoculation method using the Helios gene gun system (Bio-Rad). The cartridge tubing was coated with gold-DNA (full-length human EREG expression vector) particles according to the Helios gene gun operation manual. 50 mg of 1.0-μm gold particles were weighed out, suspended and mixed in 0.1 mL of 0.05 M spermidine solution. 0.1 mL of 1 mg/mL plasmid solution was added to this and then vortexed. Subsequently, 0.1 mL of 1 M $CaCl_2$ was added, and this was left to stand for ten minutes. After brief centrifugation, the supernatant was removed. The pellet was suspended in ethanol, and then centrifuged. After repeating the ethanol dehydration step three times, the pellet was ultimately suspended in 6 mL of 0.05 mg/mL polyvinylpyrollidone-ethanol solution. The solution was drawn into the tubing for coating, and the tubing was coated, dried, and cut into 0.5-inch-long segments using a tube cutter.

DNA immunization was performed on four- to five-week-old MRL/MpJ-Tnfrsf6<1pr>/Crlj mice (approximately 200 psi helium pressure) at an interval of one to three times a week, and the anti-EREG antibody titer in the serum was monitored intermittently during this period. A cell line forcedly expressing EREG ($5 \times 10^6$ cells/head) was administered intraperitoneally or to the tail vein of individuals that were confirmed to have an increased serum antibody titer. After rearing for two to three days, the spleen was extirpated, and mononuclear cells containing antibody-producing cells were isolated. Cell fusion and cloning was performed by the same method as in the case of immunization with sEREG-mFc.

The antibodies were purified from the culture supernatant of hybridomas cultured in a HAT medium supplemented with serum. The serum added to the medium was FBS (Ultra low IgG) (GIBCO BRL). The antibodies were purified from the culture supernatant using HiTrap Protein G HP by the same method as the sEREG_mFc purification method described in Example 2-2. The HiTrap Protein G HP eluate fractions were subjected to solvent substitution with PBS using a PD__10 column (Amersham), and then stored at 4° C. The purified antibodies were quantified using DC protein assay (BIO-RAD), in which the protein concentration was calculated using the included bovine IgG as a standard.

As a result, clones B2#30 (IgG1, Kappa), B3#18 (IgG2b, Kappa), B3#41 (IgG1, Kappa), and such, which are shown in Table 3, were successfully isolated.

TABLE 3

The antibody subtypes and cross-species reactivity of the isolated anti-EREG mouse monoclonal antibodies, and the epitope sites recognized by them.

| Antibody ID | Antibody name | Antibody subtype | Epitope | Mouse cross-reactivity | Simian cross-reactivity |
| --- | --- | --- | --- | --- | --- |
| EP02 | C1 | IgG2a/κ | ereg | +++ | NA |
| EP03 | C7 | IgG1/κ | ereg | +++ | +++ |
| EP04 | #6 | IgG2b/κ | ereg | + | NA |
| EP05 | #9 | IgG1/κ | ereg | ++ | NA |
| EP06 | #11 | IgG1/κ | ereg | + | NA |
| EP07 | #13 | IgG1/κ | ereg | − | NA |
| EP08 | #15 | IgG1/κ | ereg | − | +++ |
| EP09 | #19 | IgG1/κ | ereg | + | NA |
| EP10 | #20 | IgG2b/κ | ereg | ++ | NA |
| EP11 | #24 | IgG1/κ | ereg | + | NA |
| EP12 | #26 | IgG1/κ | ereg | − | NA |
| EP14 | #31 | IgG1/κ | ereg | ++ | NA |
| EP15 | #32 | IgG2b/κ | (ereg) | − | NA |
| EP16 | #33 | IgG1/κ | ereg | ++ | NA |
| EP17 | #34 | IgG1/κ | ereg | − | NA |
| EP18 | #35 | IgG2b/κ | ereg | − | NA |
| EP19 | B2#15 | IgG1/κ | ereg | ++ | NA |
| EP20 | B2#30 | IgG1/κ | ereg | +++ | +++ |
| EP22 | B3#2 | IgG1/κ | ereg | − | NA |
| EP23 | B3#7 | IgG1/κ | ereg | − | NA |
| EP24 | B3#8 | IgG1/κ | ereg | +++ | +++ |
| EP25 | B3#10 | IgG1/κ | Nterm | +++ | NA |
| EP26 | B3#13 | IgG1/κ | ereg | − | NA |
| EP27 | B3#18 | IgG2b/κ | ereg | ++ | +++ |
| EP29 | B3#41 | IgG1/κ | (ereg) | +++ | +++ |
| EP30 | B3#44 | IgG1/κ, λ | ereg | − | NA |
| EP31 | B3#52 | IgG1/κ | ereg | +++ | NA |
| EP32 | B3#61 | IgG1/κ | Nterm | +++ | NA |
| EP33 | B3#62 | IgG1/κ | ereg | +++ | NA |

*Note (ereg): Binds, but with low reactivity
NA: Not analyzed 2-4. Evaluation of Binding Activity by Flow Cytometry Flow cytometry was used to evaluate the binding of the antibodies obtained by the above-mentioned methods to EREG_DG Anti-EREG antibodies diluted to a suitable concentration were added to EREG_DG suspended in an FACS Buffer (1% FBS/PBS) at a density of $1 \times 10^5$ cells/mL, and this was then allowed to react on ice for 60 minutes. After washing the cells once with the FACS Buffer, an FITC-labeled anti-mouse IgG antibody was added, and this was allowed to react on ice for 30 minutes. After the reaction was completed, the supernatant was removed by centrifugation. The cells were then resuspended in 150 μL of FACS Buffer, and then subjected to flow cytometric analysis.

FACS Calibur (Becton Dickinson) was used as the flow cytometer. The living cell population was selected by gating a histogram of forward scatter and side scatter. In addition to the binding activity to EREG_DG, the binding activity to the DLD1 human colon cancer cell line was also evaluated. As confirmed by the result shown in FIG. 2, the human EREG gene expression was similarly enhanced in the DLD 1 human colon cancer cell line as in EREG_DG cells.

Figure 3:
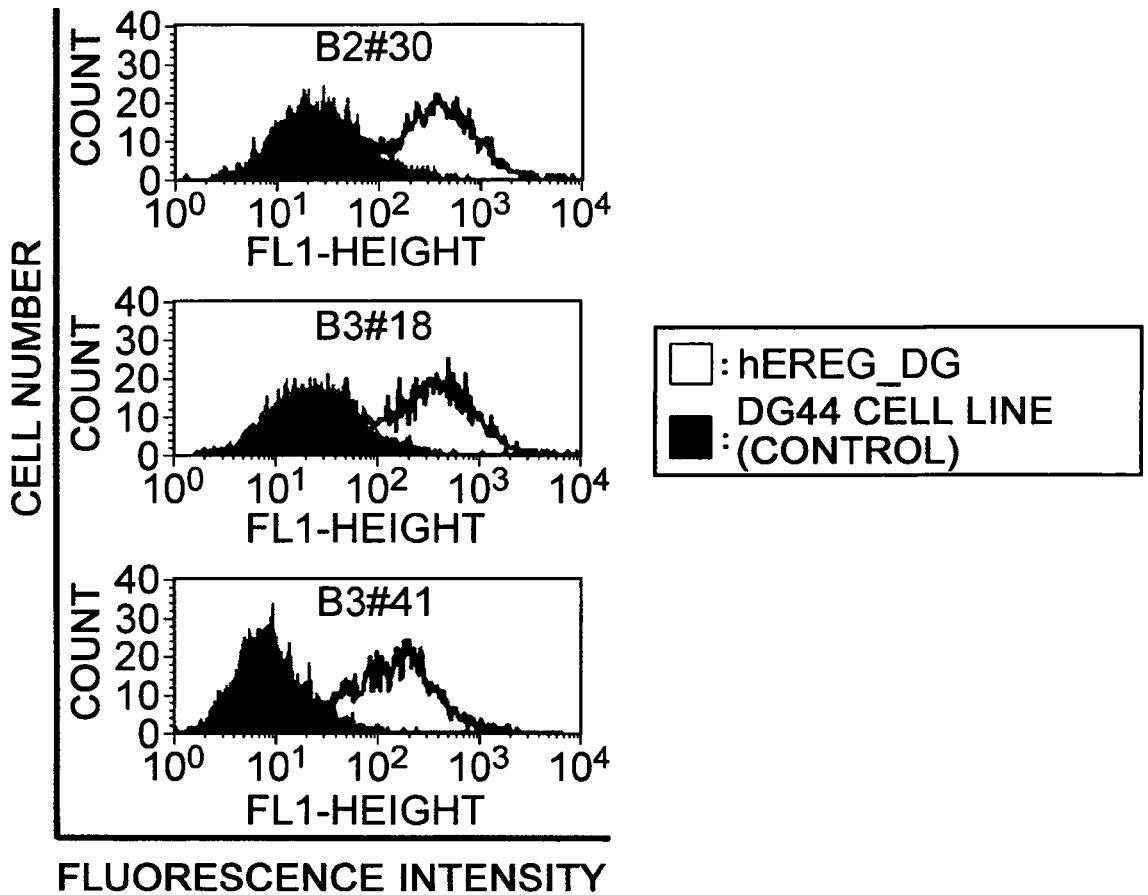
FIG. 3 shows the binding of anti-EREG monoclonal antibodies to EREG-DG cells by flow cytometry. The vertical axis indicates the cell number (fluorescent count), and the horizontal axis indicates the fluorescence intensity value.

As shown in FIG. 3, anti-EREG monoclonal antibodies (B2#30, B3#18, and B3#41) produced by hybridomas bound strongly to EREG_DG, but not to the parental DG44 cells. These results revealed that these monoclonal antibodies specifically bind to EREG present on the cell membrane.

Figure 4:
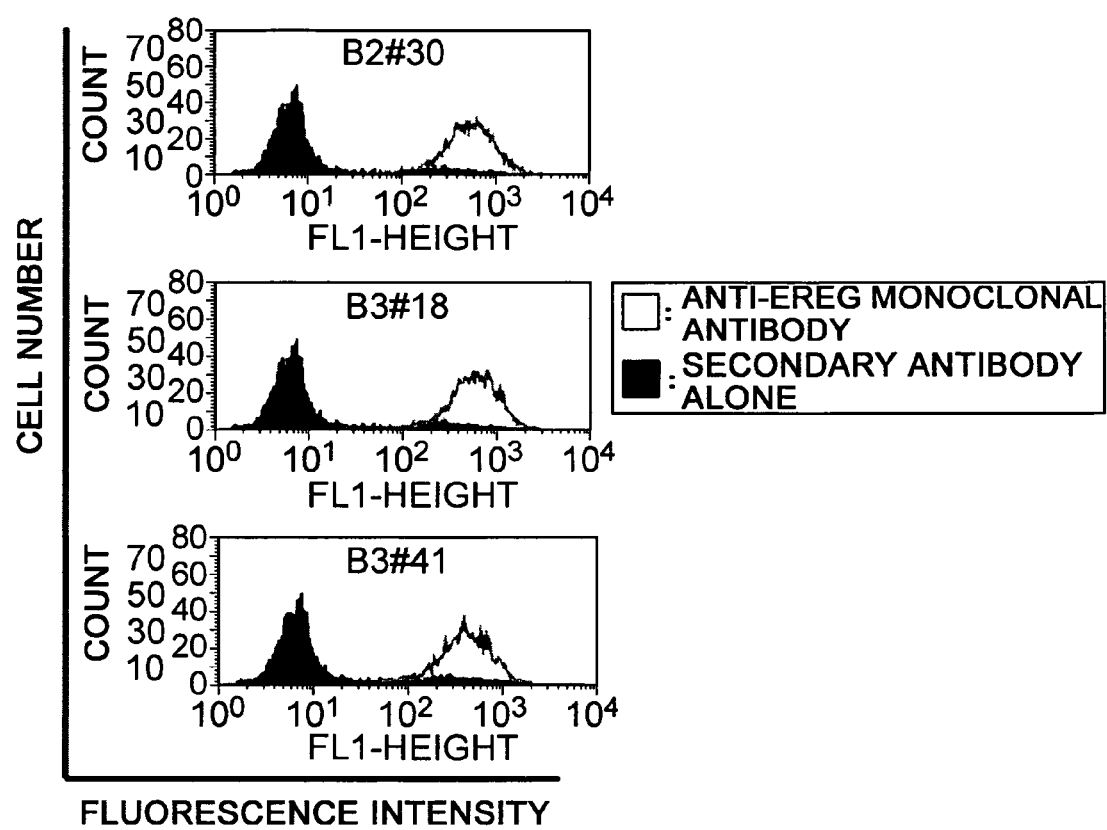
FIG. 4 shows the binding of anti-EREG monoclonal antibodies to the DLD 1 colon cancer cell line by flow cytometry. The vertical axis indicates the cell number (fluorescent count), and the horizontal axis indicates the fluorescence intensity value.

Furthermore, the above-described anti-EREG monoclonal antibodies of the present invention were confirmed to bind specifically to DLD 1 which has enhanced human EREG gene expression (FIG. 4), as well as to EREG_DG.

Enhanced human EREG gene expression in bladder cancer (Thogersen, V. et al., Cancer Res. 61:6227-6233, 2001), pancreatic cancer (Zhu. Z., et al., Biochem. Biophys. Res. Commun. 273: 1019-1024, 2000), prostate cancer (Torring, N., et al., Anticancer Res. 20: 91-95, 2000), colon cancer (Baba, I., et al., Cancer Res. 60: 6886-6889, 2000), and such, has been reported. However, the present inventors showed for the first time that the enhanced human EREG gene expression correlates with the enhanced human EREG protein expression.

Example 3

Measurement of Complement-Dependent Cytotoxicity (CDC) Activity and Antibody-Dependent Cellular Cytotoxicity (ADCC) Activity Induced by the Anti-EREG Monoclonal Antibodies 3-1. Measurement for CDC activity by the anti-EREG monoclonal antibodies The DLD1 human colon cancer cell line was used as the target cell. RPMI1640 medium (GIBCO BRL) containing 10% FBS was used to maintain DLD1 cells. $5 \times 10^5$ DLD1 cells were collected by centrifugation (1000 rpm, five minutes, 4° C.). The cell pellet was suspended in approximately 200 µL of medium containing 3.7 MBq of Chromium-51 (Code No. CJS4, Amersham Pharmacia Biotech), and then cultured in a 5% carbon dioxide incubator for one hour at 37° C. These cells were washed three times with the medium, then adjusted to a cell density of $1 \times 10^4$ cells/mL in the medium, and then dispensed into a 96-well flat-bottomed plate at 100 µL/well.

Then, an anti-EREG monoclonal antibody (B3#18_IgG2b) and a control mouse IgG2a antibody (Cat. No. 553453, BD Biosciences Pharmingen) diluted into the medium were added at 50 µL per well. The final concentration of the antibody was adjusted to 10 µg/mL. Then, baby rabbit complement (Cat. No. CL3441, Cederlane) diluted 5-fold in the medium was added at 50 µL/well, and then the plate was left to stand in a 5% carbon dioxide incubator for 1.5 hours at 37° C. Thereafter, this plate was centrifuged (1000 rpm for five minutes at 4° C.), 100 µL of the supernatant was collected from each well of the plate, and the radioactivity of the collected supernatant was measured using a gamma counter (1480 WIZARD 3", Wallac). The specific chromium release rate was determined based on the following equation:

Specific chromium release rate (%)=$(A-C) \times 100/(B-C)$ where
A represents the radioactivity (cpm) in each well;
B represents the mean value of radioactivity (cpm) in wells where 100 µL of 2% NP_40 solution (Nonidet P_40, Code No. 252-23, Nacalai Tesque) was added to 100 µL of the cells; and
C represents the mean value of radioactivity (cpm) in wells where 100 µL of the medium has been added to 100 µL of the cells. The measurements were conducted in duplicate, and the mean value and standard deviation were calculated for the specific chromium release rate of the supernatant derived from each well.

Figure 5:
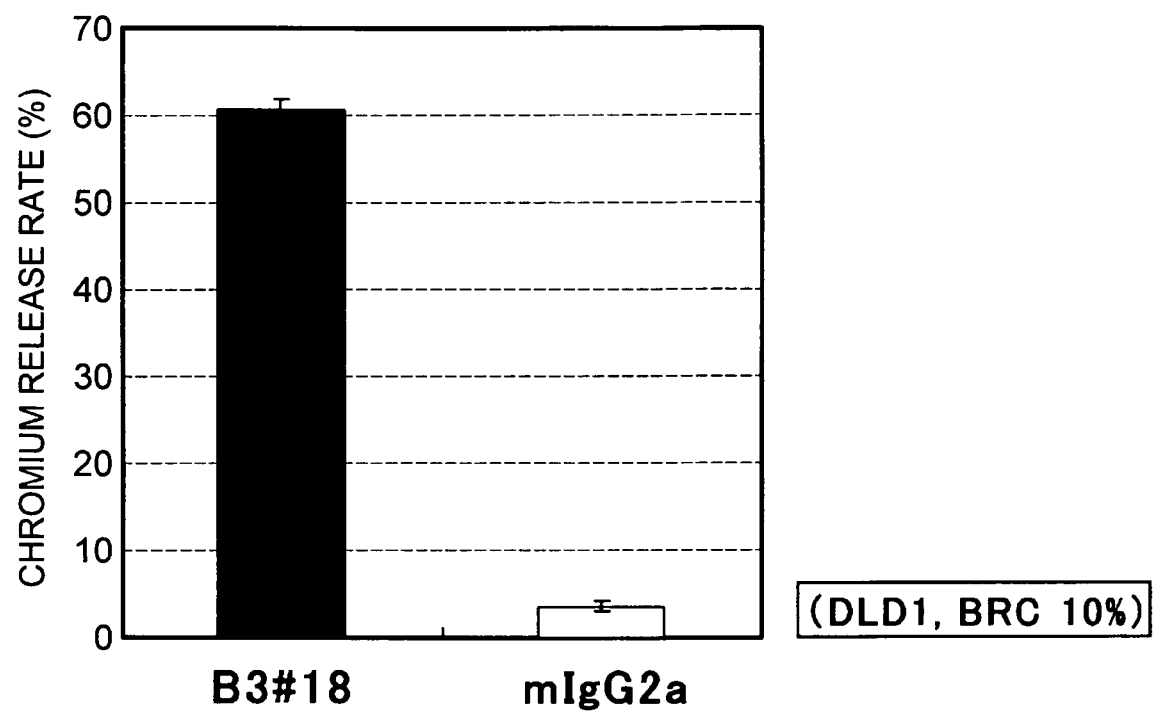
FIG. 5 shows the CDC activity of anti-EREG monoclonal antibodies against the DLD 1 colon cancer cell line. The vertical axis indicates the chromium release rate (%), and the horizontal axis indicates the name of antibody.

The anti-EREG monoclonal antibodies used in the experiment were confirmed to have CDC activity, as shown in FIG. 5. On the other hand, the control mouse IgG2a antibody did not show CDC activity at the same concentration.

3-2. Measurement for ADCC Activity by the Anti-EREG Monoclonal Antibodies

As in the case of CDC activity measurement, the DLD1 human colon cancer cell line was used for ADCC activity measurement. Specifically, the cells were cultured in a 96-well flat-bottomed plate, and then incubated with Chromium-51. Each well was washed with RPMI1640 medium (Invitrogen) containing 10% FBS, and then 100 µL of the medium was added. Then, 50 µL each of an anti-EREG monoclonal antibody (B2#30, B3#18, and B3#41) diluted into the medium was added to the wells of the plate. The antibody was added at a final concentration of 1 µg/mL. Then, 50 µL of an effector cell solution ($1 \times 10^7$ cells/mL) was added to each well, then the plate was left to stand in a 5% carbon dioxide incubator for four hours at 37° C., and then the specific chromium release rate was determined. Effector cells were obtained by culturing the spleen cells of a Balb/c mouse (Charles River Japan) in a medium containing 50 ng/mL of recombinant human interleukin-2 (Cat. No. 200-02, Peprotech) for five days, or by culturing the bone marrow cells from the same mouse in a medium containing 50 ng/mL of recombinant human interleukin-2 and 10 ng/mL of recombinant mouse GM-CSF (Cat. No. 315-03, Peprotech) for six days.

Figure 6:
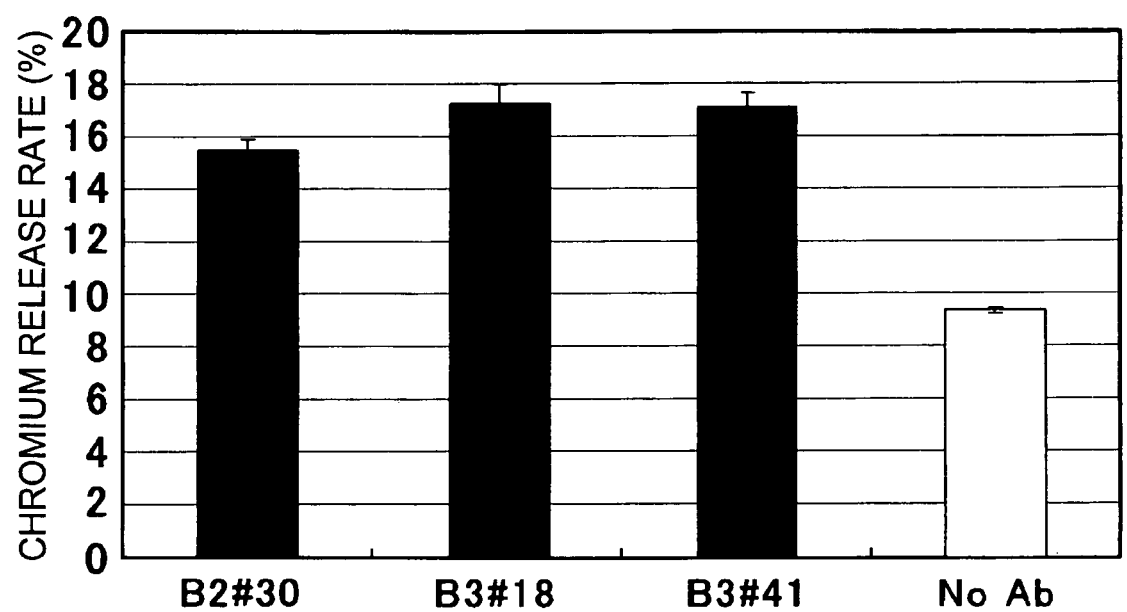
FIG. 6 shows the ADCC activity of anti-EREG monoclonal antibodies against the DLD 1 colon cancer cell line. The vertical axis indicates the chromium release rate (%), and the horizontal axis indicates the name of antibody.

The results showed that all of the anti-EREG monoclonal antibodies used in the experiment induced ADCC activity against DLD1 (FIG. 6).

Example 4

Measurement for Neutralizing Activity of the Anti-EREG Monoclonal Antibodies on Cell Proliferation Enhanced by Human EREG 4-1. Establishment of a Ba/F3 cell line that expresses EGFR-mG-CSF chimeric receptor (EGFR_BAF)

Using standard methods, the human EGF receptor comprising the sequence shown in SEQ ID NO: 35 (GenBank Acc. No. NM_005228) (hereinafter referred to as "EGFR") was isolated, and then a vector that can express a chimeric receptor of human EGF receptor fused with mG-CSFR was prepared. In brief, the vector (pCV_hEGFR/mG-CSFR) expresses a chimeric receptor (hEGFR/mG-CSFR) comprising the extracellular domain (Met7-Ser645) of human EGFR and the intracellular domain of mouse G-CSF (NM_007782). The nucleotide sequence and amino acid sequence of the hEGFR/mG-CSFR chimeric receptor are shown in SEQ ID NOs: 39 and 40, respectively.

Fifteen µg of the linearized chimeric receptor (hEGFR/mG-CSFR) expression vector (pCV_hEGFR/mG-CSFR) obtained by digestion with PvuI was transfected into Ba/F3 cells by electroporation (Gene Pulser; BioRad) at a setting of 0.33 kV and 950 µFD. Transfected cells were selected in RPMI1640 medium containing 10% FBS (GIBCO), 200 µg/mL Geneticin, and recombinant human EREG (R&D Systems, Cat: 1195-EP/CF, 200 ng/mL) and EGFR_BAF cell line was isolated.

4-2. Evaluation of EREG-Dependency of EGFR BAF

An experiment was carried out to measure the human EREG concentration-dependent cell proliferation of EGFR_BAF isolated by the method described in 4-1. To remove human EREG from the culture, the cells were centrifuged and resuspended in RPMI1640+10% FBS medium, and then the cells were seeded into each well of a 96-well plate at a density of $2 \times 10^4$ cells/100 µL. Human EREG (R&D Systems) diluted into the medium was added to the cells at various concentrations (7.8 to 250 ng/mL), and then the cells were incubated under 5% $CO_2$ at 37° C. After incubation for three days, the Cell Count Reagent SF reagent (Nacalai Tesque) was added and coloring was developed for two hours according to the instructions, and the absorbance (450/655 nm) of the reaction solution was measured using Benchmark Plus (Bio-Rad).

Similarly, the human EREG-dependent proliferation of the AsPC1 human pancreatic cancer cell line and DLD1 human colon cancer cell line was examined in the same manner as described above. CHO-S-SFMII (GIBCO) was used as the medium.

Figure 7:
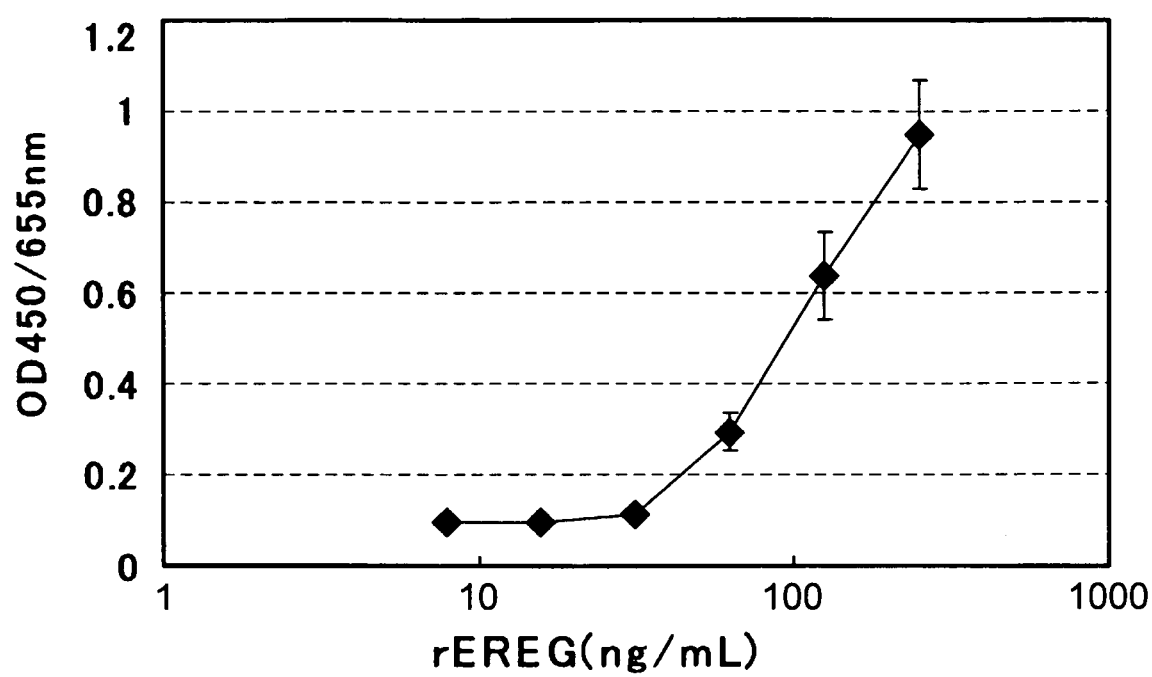
FIG. 7 shows the dependence of proliferation of EGFR-BAF cells on human EREG. The vertical axis indicates the absorbance at 450 nm (reference wavelength of 655 nm), and the horizontal axis indicates the EREG concentration (ng/mL).
Figure 8:
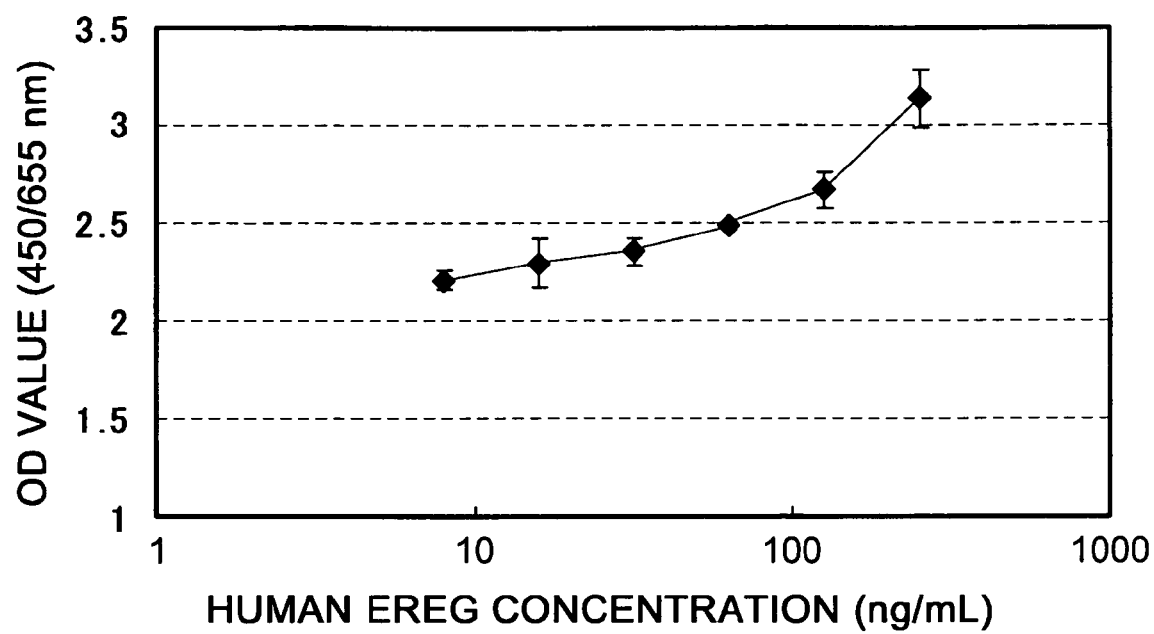
FIG. 8 shows the dependence of proliferation of the AsPC 1 pancreatic cancer cell line on human EREG. The vertical axis indicates the absorbance at 450 nm (reference wavelength of 655 nm), and the horizontal axis indicates the EREG concentration (ng/mL).
Figure 9:
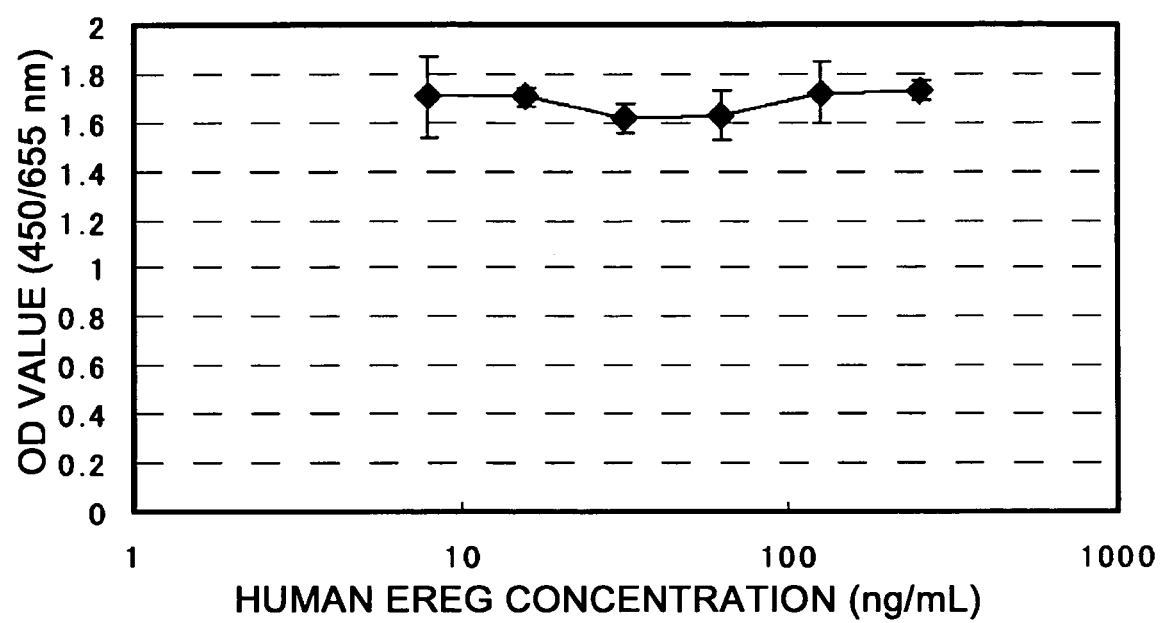
FIG. 9 shows the dependence of proliferation of the DLD1 colon cancer cell line on human EREG. The vertical axis indicates the absorbance at 450 nm (reference wavelength of 655 nm), and the horizontal axis indicates the EREG concentration (ng/mL).

The result showed that EGFR_BAF (FIG. 7) and AsPC1 (FIG. 8) proliferated in a human EREG concentration-dependent manner. However, DLD1 was found not to have human EREG dependency (FIG. 9).

4-3. Measurement for Neutralizing Activity of the Anti-EREG Monoclonal Antibodies on Human EREG-Dependent Cell Proliferation On the EGFR BAF proliferation dependent on human EREG, neutralizing activity of the anti-EREG monoclonal antibodies was examined. EGFR_BAF was suspended in RPMI1640+10% FBS medium containing human EREG (final concentration of 125 ng/mL), and the cells were seeded into a 96-well plate at a density of $2 \times 10^4$ cells per well. An anti-EREG monoclonal antibody diluted into the medium was added to the cells at various concentrations (0.008 to 25 µg/mL), and then the cells were cultured in a 5% $CO_2$ incubator for three days at 37° C. After culturing, the Cell Count Reagent SF reagent (Nacalai Tesque) was added and coloring was developed for two hours. Then, the absorbance of the reaction solution at 450 nm was measured using Benchmark Plus (Bio-Rad) by setting the reference wavelength at 655 nm.

The cell proliferation rate was calculated by using the measured value at 0 µg/mL antibody concentration as the reference (OD value at each antibody concentration/OD value of the reference×100(%)). Anti-human EREG goat polyclonal antibody known to have inhibitory activity (R&D Systems, Cat: AF1195) was used as a positive control. The attached document of this antibody product indicates its neutralizing activity against the human EREG-dependent proliferation of the Balb/3T3 fibroblast cell line. However, the attached document does not describe any information regarding the proliferation-suppressing effect in cancer cell lines.

Furthermore, neutralizing activity of the anti-EREG monoclonal antibodies in AsPC1 as the target cell was measured by the same method as described above, and the measurement was carried out under the following three antibody concentration conditions: 25, 2.5, and 0.25 µg/mL.

Figure 10:
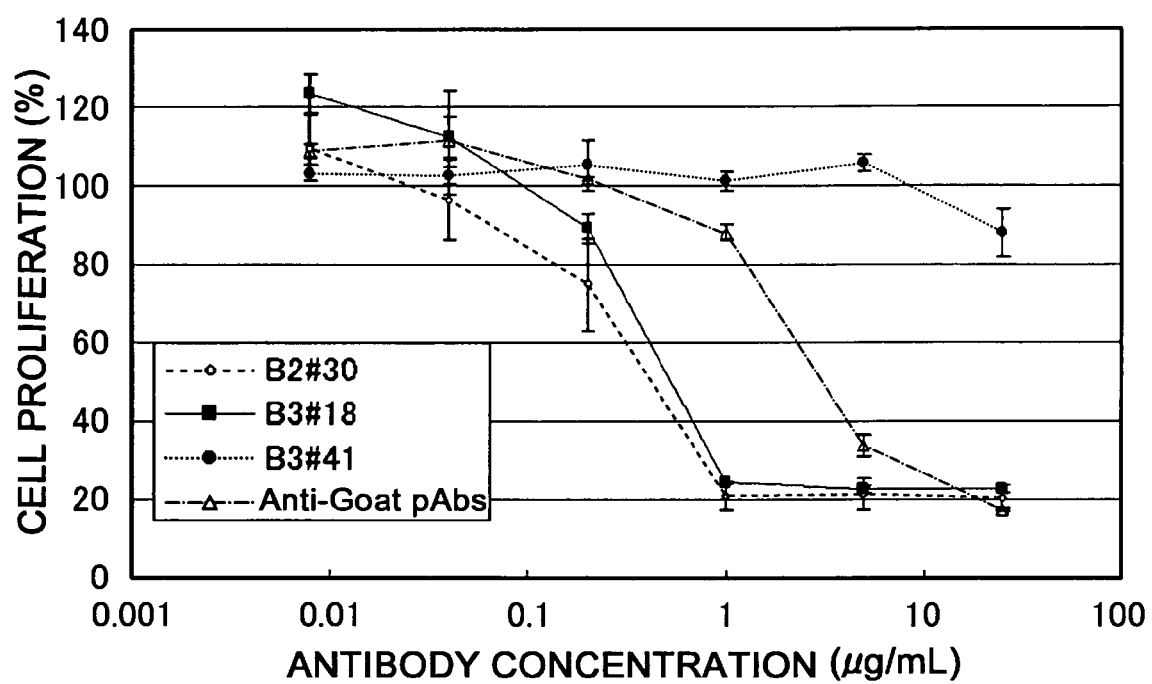
FIG. 10 shows the neutralizing activity of anti-human EREG monoclonal antibodies in EGFR-BAF cells. The vertical axis indicates the cell proliferation rate (absorbance at each antibody concentration/absorbance of the control×100%), and the horizontal axis indicates the antibody concentration (µg/mL).
Figure 11:
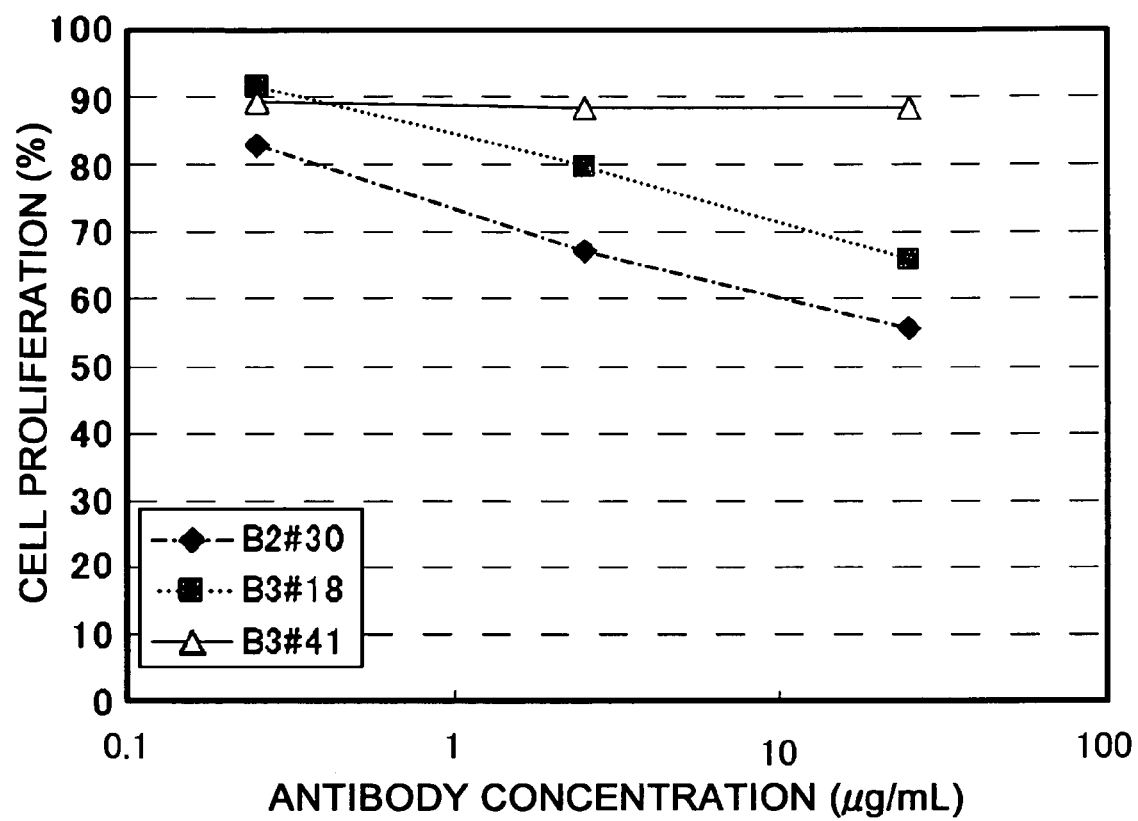
FIG. 11 shows the neutralizing activity of anti-human EREG monoclonal antibodies in the AsPC1 pancreatic cancer cell line. The vertical axis indicates the cell proliferation rate (absorbance at each antibody concentration/absorbance of the control×100%), and the horizontal axis indicates the antibody concentration (µg/mL).

The results are shown in FIGS. 10 and 11 respectively.

In both of the EGFR_BAF and AsPC1, B2#30 and B3#18 showed neutralizing activity, and B3#41 showed a very weak neutralizing activity. Furthermore, the neutralizing activity of the known anti-hEREG goat polyclonal antibody was found to be very weak, as compared to B2#30 and B3#18.

Accordingly, B2#30 and B3#18 were found to have neutralizing activity for EREG, and to suppress proliferation of the AsPC 1 pancreatic cancer cell line.

The present study demonstrates that the anti-EREG monoclonal antibodies (B2#30 and B3#18) isolated in this study have cell-killing effect mediated by ADCC activity and CDC activity, as well as suppressing effect on human EREG-dependent cell proliferation (neutralizing activity), and that the antibodies can be used as antibody pharmaceuticals with a novel mechanism against cancer cells that have enhanced expression of the human EREG gene.

Example 5

Nucleotide Sequence Determination for the Anti-EREG Monoclonal Antibody Variable Regions Nucleotide sequences of the antibody variable regions were determined for hybridoma antibody B3#18 (EP27) which showed neutralizing activity for EREG, as well as ADCC activity and CDC activity against the DLD1 cell line. The antibody variable-region sequences were amplified by the RT-PCR from total RNA of the B3#18 anti-EREG antibody-producing hybridomas. Total RNA was extracted from $1 \times 10^7$ hybridoma cells by the RNeasy Plant Mini Kit (QIAGEN).

A RACE library was constructed from 1 µg of total RNA using the SMART RACE cDNA Amplification Kit (CLONTECH). The reverse transcription reaction was performed for one hour and thirty minutes at 42° C. The 5'-end cDNA sequence was amplified with synthetic oligonucleotide MHC-IgG2b (SEQ ID NO: 41) which is complementary to the mouse IgG2b constant region sequence, or synthetic oligonucleotide kappa (SEQ ID NO: 42) which is complementary to the mouse κ chain constant region nucleotide sequence. The components of the PCR solution (in 50 µL) are as follows:

5 µL of 10× Advantage 2 PCR Buffer;

5 µL of 10× Universal Primer A Mix;

0.2 mM dNTPs (dATP, dGTP, dCTP, and dTTP);

1 µL of Advantage 2 Polymerase Mix (the above were manufactured by CLONTECH);

2.5 µL of reverse transcription reaction product; and 10 pmole of synthetic oligonucleotide MHC-IgG2b or kappa.

The PCR conditions are as follow.

An initial temperature of 94° C. for 30 seconds, followed by five cycles of 94° C. for five seconds and 72° C. for three minutes;

Five cycles of 94° C. for five seconds, 70° C. for ten seconds, and 72° C. for three minutes; and 25 cycles of 94° C. for five seconds, 68° C. for ten seconds, and 72° C. for three minutes.

Finally, the reaction product was elongated at 72° C. for seven minutes. Each PCR product separated by an agarose gel was purified using the QIAquick Gel Extraction Kit (manufactured by QIAGEN), and then cloned into the pGEM-T Easy vector (manufactured by Promega). The nucleotide sequence of the clone was determined. For B3#18, the nucleotide sequence and amino acid sequence of the H-chain variable region are shown in SEQ ID NO: 43 and SEQ ID NO: 44, respectively, and the nucleotide sequence and amino acid sequence of the L-chain variable region are shown in SEQ ID NO: 45 and SEQ ID NO: 46, respectively.

The variable region sequences of C7 (EP03), #15 (EP08), B2#30 (EP20), B3#8 and B3#41 (EP29) were determined by same methods. Synthetic oligonucleotide MHC-IgG1 (SEQ ID NO: 47, 5'-ccatggagttagtttgggcagcagatcc-3') which is complementary to the mouse IgG1 constant region sequence was used to amplify the heavy-chain variable regions. The determined variable-region nucleotide sequences are shown in SEQ ID NOs: 108 (EP03, heavy chain), 110 (EP03, light chain), 112 (EP08, heavy chain), 114 (EP08, light chain), 116 (EP20, heavy chain), 118 (EP20, light chain), 120 (EP24, heavy chain), 122 (EP24, light chain), 124 (EP29, heavy chain), and 126 (EP29, light chain). The translated sequences of the variable regions are shown in SEQ ID NOs: 109 (EP03, heavy chain), 111 (EP03, light chain), 113 (EP08, heavy chain), 115 (EP08, light chain), 117 (EP20, heavy chain), 119 (EP20, light chain), 121 (EP24, heavy chain), 123 (EP24, light chain), 125 (EP29, heavy chain), and 127 (EP29, light chain). The ID numbers for the variable-region sequences, and the CDR1, CDR2, and CDR3 amino acid sequences of each antibody are summarized in Table 4.

TABLE 4

The anti-EREG monoclonal antibody CDR sequences ad their sequence ID numbers

|  | | CDR1 | CDR2 | CDR3 | Variable region nucleotide sequence ID number | Variable region translated sequence ID number |
|---|---|---|---|---|---|---|
| EP03 | Heavy chain | NYWMN (SEQ ID NO: 49) | RIHPSDSETHYNQKFKN (SEQ ID NO: 51) | LYYYTMDY (SEQ ID NO: 53) | (SEQ ID NO: 108) | (SEQ ID NO: 109) |
|  | Light chain | KASQDINKNIA (SEQ ID NO: 55) | YTSTLQP (SEQ ID NO: 57) | LQYDNLPYT (SEQ ID NO: 59) | (SEQ ID NO: 110) | (SEQ IDNO: 111) |
| EP08 | Heavy chain | SYWNMH (SEQ ID NO: 61) | EINPYNGGTNYNEKFKS (SEQ ID NO: 63) | WKLGTY (SEQ ID NO: 65) | (SEQ ID NO: 112) | (SEQ ID NO: 113) |
|  | Light chain | RASQEISGYLS (SEQ ID NO: 67) | AASTLDS (SEQ ID NO: 69) | LQYASYPRT (SEQ ID NO: 71) | (SEQ ID NO: 114) | (SEQ ID NO: 115) |
| EP20 | Heavy chain | VYSLH (SEQ ID NO: 73) | VISTYYGDAIYNQKEKG (SEQ ID NO: 75) | EGNGNPLDY (SEQ ID NO: 77) | (SEQ ID NO: 116) | (SEQ ID NO: 117) |
|  | Light chain | TASSSVSSSYLH (SEQ ID NO: 79) | STSNLAS (SEQ ID NO: 81) | HQYHRSPLT (SEQ ID NO: 83) | (SEQ ID NO: 118) | (SEQ ID NO: 119) |
| EP24 | Heavy chain | SYGVH (SEQ ID NO: 85) | VIWRDGSTTYNSALKS (SEQ ID NO: 87) | NWNGLMDY (SEQ ID NO: 89) | (SEQ ID NO: 120) | (SEQ ID NO: 121) |
|  | Light chain | RASQDISYYLN (SEQ ID NO: 91) | YTSRLHS (SEQ ID NO: 93) | QQGHTVPWT (SEQ ID NO: 95) | (SEQ ID NO: 122) | (SEQ ID NO: 123) |
| EP27 | Heavy chain | DTYIQ (SEQ ID NO: 2) | RIDPLNGNTKYVPKFQG (SEQ ID NO: 4) | SGTLFDF (SEQ ID NO: 6) | (SEQ ID NO: 43) | (SEQ ID NO: 44) |
|  | Light chain | KASQDIHKYIA (SEQ ID NO: 12) | YTSTLQP (SEQ ID NO: 14) | LQYDNLRT (SEQ ID NO: 16) | (SEQ ID NO: 45) | (SEQ ID NO: 46) |
| EP29 | Heavy | SYWMH (SEQ ID NO: 97) | AIYPGNSDSYNQKFKG (SEQ ID NO: 99) | VMAY (SEQ ID NO: 101) | (SEQ ID NO: 124) | (SEQ ID NO: 125) |
|  | Light | RASQDIGNSLN (SEQ ID NO: 103) | ATSNLDS (SEQ ID NO: 105) | LQYASSPWT (SEQ ID NO: 107) | (SEQ ID NO: 126) | (SEQ ID NO: 127) |

Example 6

Confirmation of the EREG-Binding Activity of the Recombinant Chimeric Antibodies It was confirmed that the recombinant chimeric antibodies comprising the isolated antibody variable region and the human IgG1/IgK constant region sequences binds to EREG as follows. The sequence of each heavy-chain variable region was amplified by PCR, and then inserted into the heavy-chain cloning site in a human chimeric antibody expression vector. Then, a light-chain variable region sequence was amplified by PCR, and then inserted into the light-chain cloning site in the above-mentioned human chimeric antibody expression vector into which the heavy chain sequence has been introduced. In the mammalian cell expression vectors constructed, both the antibody heavy chain and light chain genes are designed to be transcribed under the control of mouse CMV promoters. The sequence ID numbers of the nucleotide sequences and translated sequences for each human chimeric antibody are summarized in Table 5.

TABLE 5

Sequence ID numbers of the human chimeric antibodies

|  |  | Nucleotide sequence ID number | Amino acid sequence ID number |
|---|---|---|---|
| Chimeric EP03 | Heavy chain | SEQ ID NO: 128 | SEQ ID NO: 129 |
|  | Light chain | SEQ ID NO: 130 | SEQ ID NO: 131 |
| Chimeric EP08 | Heavy chain | SEQ ID NO: 132 | SEQ ID NO: 133 |
|  | Light chain | SEQ ID NO: 134 | SEQ ID NO: 135 |
| Chimeric EP20 | Heavy chain | SEQ ID NO: 136 | SEQ ID NO: 137 |
|  | Light chain | SEQ ID NO: 138 | SEQ ID NO: 139 |
| Chimeric EP24 | Heavy chain | SEQ ID NO: 140 | SEQ ID NO: 141 |
|  | Light chain | SEQ ID NO: 142 | SEQ ID NO: 143 |
| Chimeric EP27 | Heavy chain | SEQ ID NO: 9 | SEQ ID NO: 10 |
|  | Light chain | SEQ ID NO: 19 | SEQ ID NO: 20 |
| Chimeric EP29 | Heavy chain | SEQ ID NO: 144 | SEQ ID NO: 145 |
|  | Light chain | SEQ ID NO: 146 | SEQ ID NO: 147 |

DG44 cells were transformed by the electroporation method with a human chimeric antibody expression vector. Recombinant cell clones were selected on geneticin resistance, which is conferred by a selection marker in the human chimeric antibody expression vector. The antibody in the culture supernatant of the recombinant clones was quantified by sandwich ELISA using anti-human antibodies, and recombinant antibody-expressing cells were selected. Human chimeric antibodies were purified from the culture supernatant of the selected recombinant cells using a HiTrap Protein A column (Amersham Bioscience) according to the attached manual.

Figure 12:
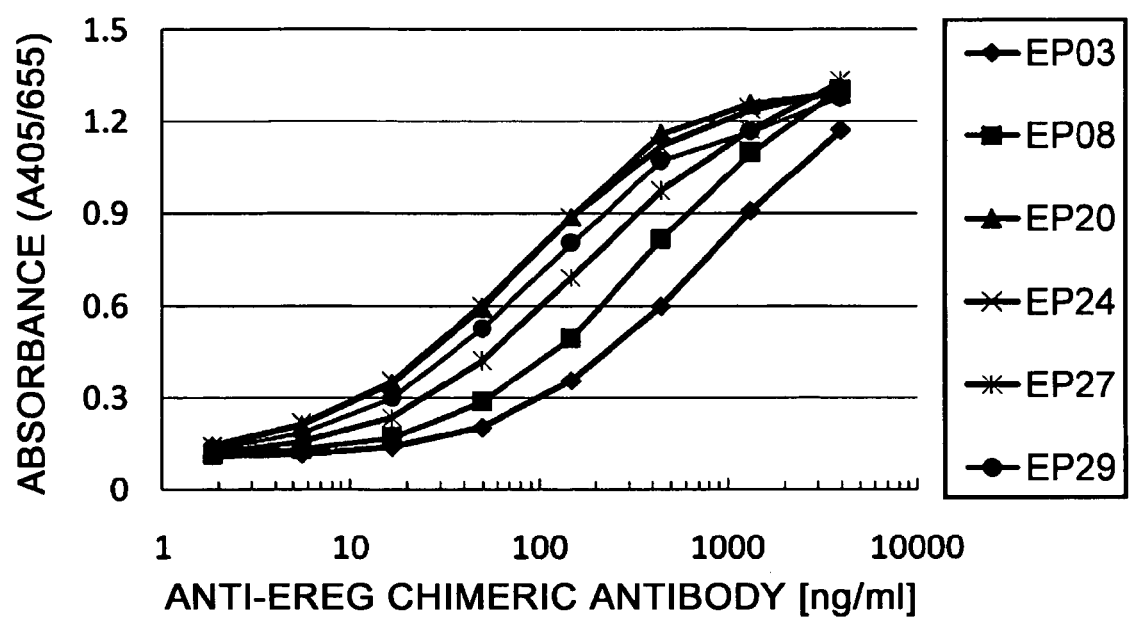
FIG. 12 shows the binding of chimeric antibodies, which were reconstituted by identifying the sequence of variable region, to EREG.

Nunc-Immuno plates, which was coated with sEREG-mFc and then blocked with a solution containing BSA, was used to analyze the binding of the purified chimeric antibodies to EREG. After the chimeric antibodies were added to bind, the plates were incubated for one hour, and then washed. Subsequently, an alkaline phosphatase-labeled anti-human IgG antibody (BIOSOURCE, AHI0305) was added and allowed to react. After washing, the bound chimeric antibody was quantified by adding a chromogenic reagent, Sigma 104. As shown in FIG. 12, the chimeric antibodies bound to EREG in a dose-dependent manner. From the above-mentioned results, the isolated antibody variable region sequences were confirmed to be truly those of the anti-EREG antibodies.

Example 7

In vitro ADCC Activity by Chimeric Anti-EREG Antibodies

Figure 13:
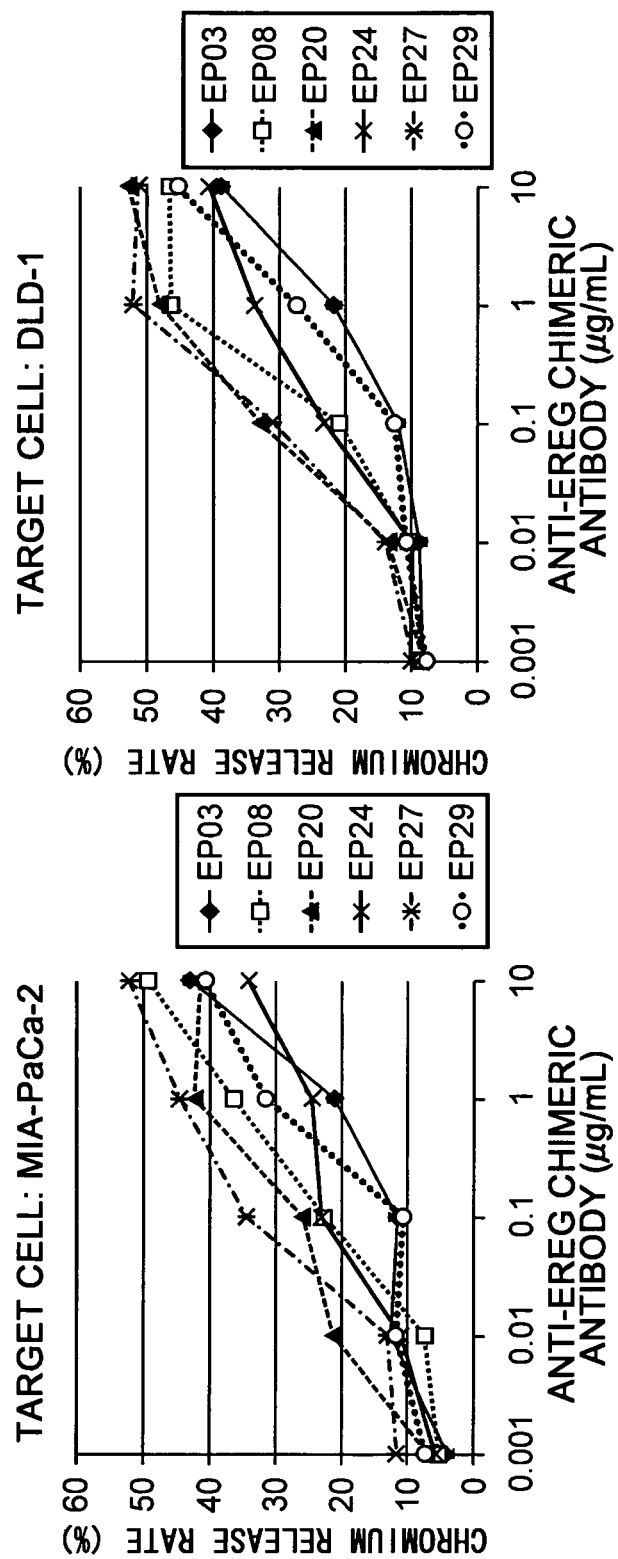
FIG. 13 shows the ADCC-inducing activity of chimeric antibodies against cancer cell lines.

FIG. 13 shows in vitro ADCC activity by anti-EREG chimeric antibodies and human PBMC. Using a syringe injected with 200 μL of 1000 units/mL heparin solution (Novo Heparin for injection, 5000 units, Novo Nordisk), 50 mL of peripheral blood was collected from each healthy individual. This peripheral blood was diluted two-fold with PBS(−) and divided into four aliquots. For lymphocyte separation, they were added to Leucosep tubes (Cat. No. 227290, Greiner Bio-One) into which 15 mL of Ficoll-Paque PLUS (GE Healthcare) had been added in advance, and subjected to centrifugation. After centrifugation at 2150 rpm, room temperature for ten minutes, the monocyte fraction was collected. The cells were washed once with Dulbecco's Modified Eagle's Medium (manufactured by SIGMA) containing 10% FBS (hereinafter referred to as 10% FBS/D-MEM), and then the cell density was adjusted to $5 \times 10^6$/mL in 10% FBS/D-MEM to prepare a human PBMC solution.

DLD-1 and MIA-PaCa2 cells were Chromium-51-labeled by a method similar to that of Example 3. An antibody solution adjusted to each concentration was added to the target cells, and allowed to bind at room temperature for 15 minutes. Then, the human PBMC solution ($5 \times 10^5$ cells/well) was added, and the cells were incubated in a 5% carbon dioxide incubator for approximately four hours. The radioactivity in the supernatant after incubation was measured using a gamma counter, and the chromium release rate was calculated by the method described in Example 3. ADCC activity was induced by all of the chimeric antibodies, and the EP20, EP27, and EP08 chimeric antibodies had particularly strong activity. The strengthness of ADCC induction by each of the antibodies showed a similar tendency in the MIA-PaCa2 pancreatic cancer cell line and the DLD-1 colon cancer cell line.

Example 8

Binding to EREG Orthologues and Epitope Analysis of Anti-EREG Antibodies

Figure 14:
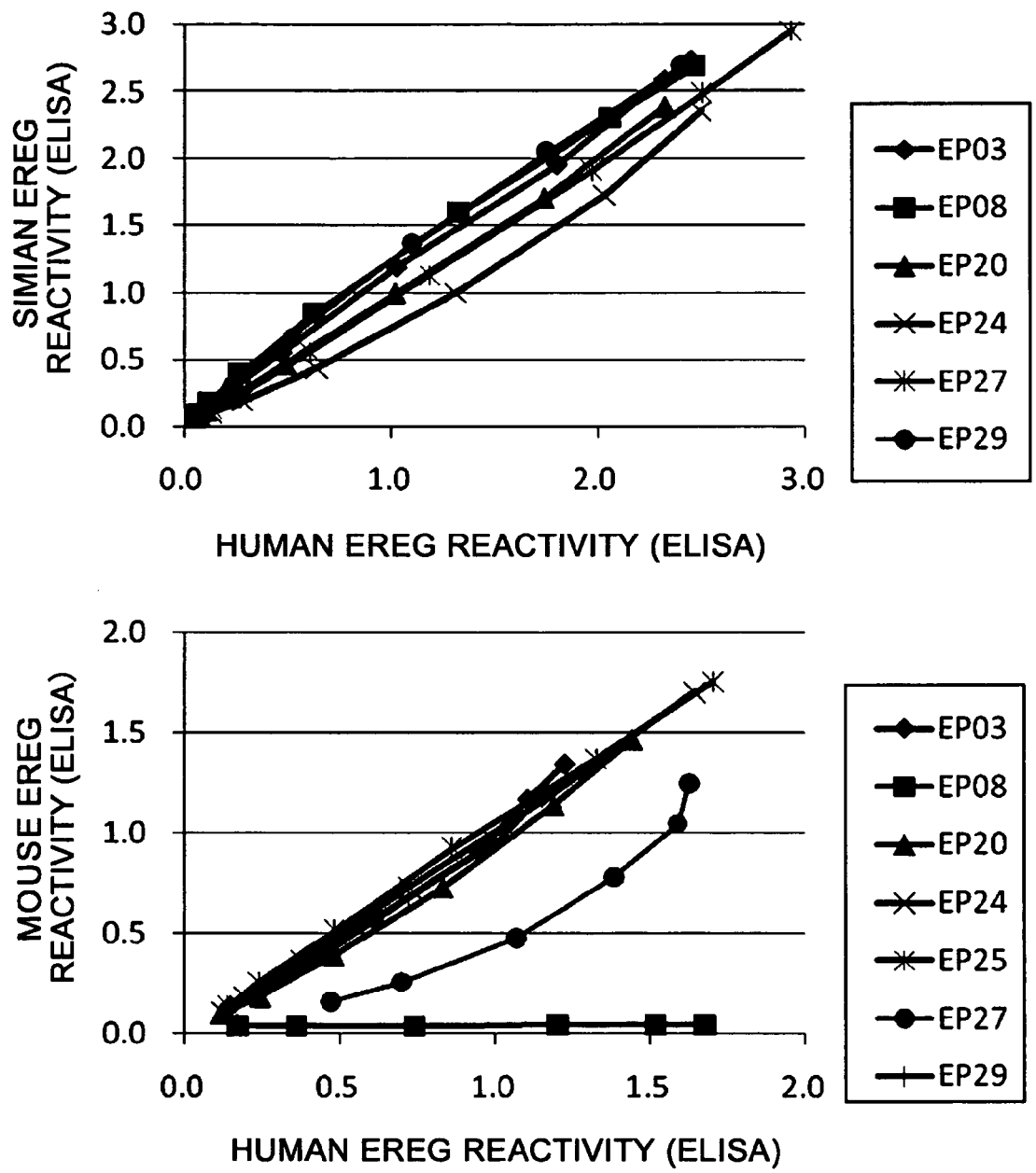
FIG. 14 shows the binding of the chimeric antibodies to EREG orthologues.

The binding of isolated antibodies to mouse EREG and simian EREG was analyzed. Full-length mouse EREG cDNA (NM_007950) and simian EREG cDNA (XM_001102069) were amplified by PCR from cDNA libraries, and cloned. The isolated sequences are shown in SEQ ID NOs: 148 and 149, respectively. Soluble mouse EREG/mouse IgG2a Fc fusion protein (hereinafter, mouse EREG-mFc) and soluble simian EREG/mouse IgG2a Fc fusion protein (hereinafter, simian EREG-mFc) were prepared by the method described in Example 2. The mouse EREG-mFc and simian EREG-mFc sequences are shown in SEQ ID NOs: 150 and 151, respectively. Nunc-Immuno plates were coated with human EREG-mFc, mouse EREG-mFc, and simian EREG-mFc respectively, and then blocked with a solution containing BSA. Subsequently, the binding of the purified chimeric antibodies was analyzed. After addition of the chimeric antibodies, the plates were incubated for one hour and then washed. Subsequently, an alkaline phosphatase-labeled anti-human IgG antibody (BIOSOURCE, AHI0305) was added and allowed to react. After washing, the bound chimeric antibody was quantified by adding a chromogenic reagent, Sigma 104 (FIG. 14). Differences at the degree of saturation in antibody binding to EREG at the same antibody concentration were demonstrated by plotting the reactivity towards various types of EREG at the same antibody concentration as "human EREG-mFc" on the horizontal axis against "mouse EREG-mFc" on the vertical axis, or "human EREG-mFc" on the horizontal axis against "simian EREG-mFc" on the vertical axis. The plot along the horizontal axis indicates the binding selectivity towards human EREG, and this shows that EP08 binds to human EREG, but it does not bind to mouse EREG. The parabolic plot for EP27 indicates that EP27 binds to the mouse molecule, but a higher concentration of the antibody is required for the binding saturation. In other words, EP27 has a lower binding affinity for mouse EREG than for human EREG. An antibody that produces a diagonal plot means that the antibody has an equivalent affinity for EREG of non-human species as for human EREG. The result obtained by above analysis for hybridoma-producing mouse antibodies is summarized in Table 3. The result is represented by four levels of reactivity relative to the human molecule: no reactivity (−); very low reactivity (+); slightly lower reactivity (++); and equivalent reactivity (+++).

The binding towards partial fragments of the extracellular domain of human EREG was analyzed to determine antibody epitope. The N-terminal partial sequence fragment of $^{29}$Ala to $^{69}$Ser of human EREG of SEQ ID NO: 21 was expressed as a GST fusion protein and purified to homogeneity. The sequence of the obtained recombinant protein is shown in SEQ ID NO: 152. A soluble human EREG fragment (EGF domain; corresponding to $^{63}$Val to $^{108}$Leu of SEQ ID NO: 21) comprising a mature structure was purchased from R&D Systems (cat. no. 1195-EP/CF). Fragments of the EREG protein were immobilized onto an immuno plate, and the binding of the antibodies was examined by ELISA. The result is summarized in Table 3. Most of the antibodies bound to the soluble EREG fragment that comprises the EGF domain (indicated as "ereg" in Table 3). EP25 and EP32 bound to the N-terminal fragment ("Nterm"). All of the isolated antibodies bound to either one of the peptide fragments, and none of the antibodies recognized the sequence beyond residue 109.

Example 9

Activation of the EGF Receptor Signaling by EREG-Expressing Cells

Soluble EREG has been reported as a low-affinity ligand for EGF receptors (reference documents: Shelly et al. (1998)

Figure 15:
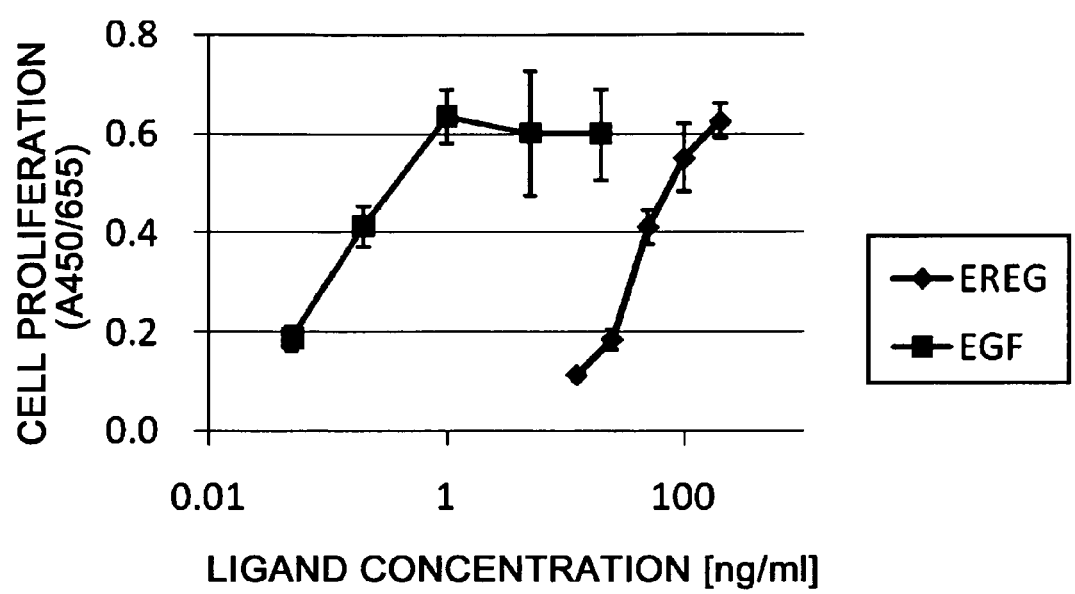
FIG. 15 shows the result of comparing the activation of the EGFR receptor by recombinant soluble EREG and EGF.
Figure 16:
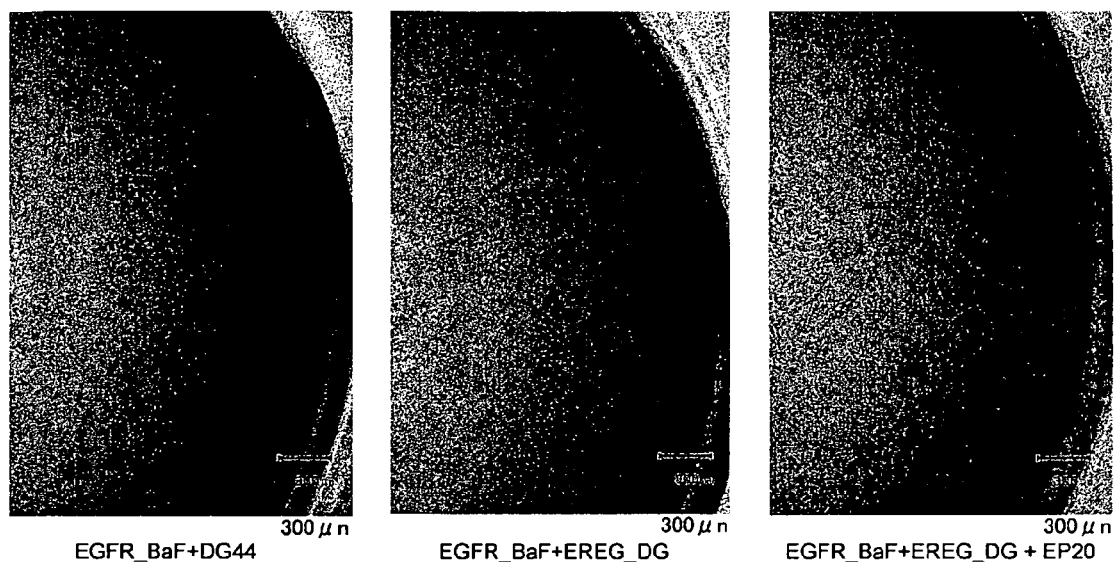
FIG. 16 shows the activation of the EGF receptor by coculturing cells forcedly expressing EREG. This activation is suppressed by anti-EREG antibodies.
Figure 17:
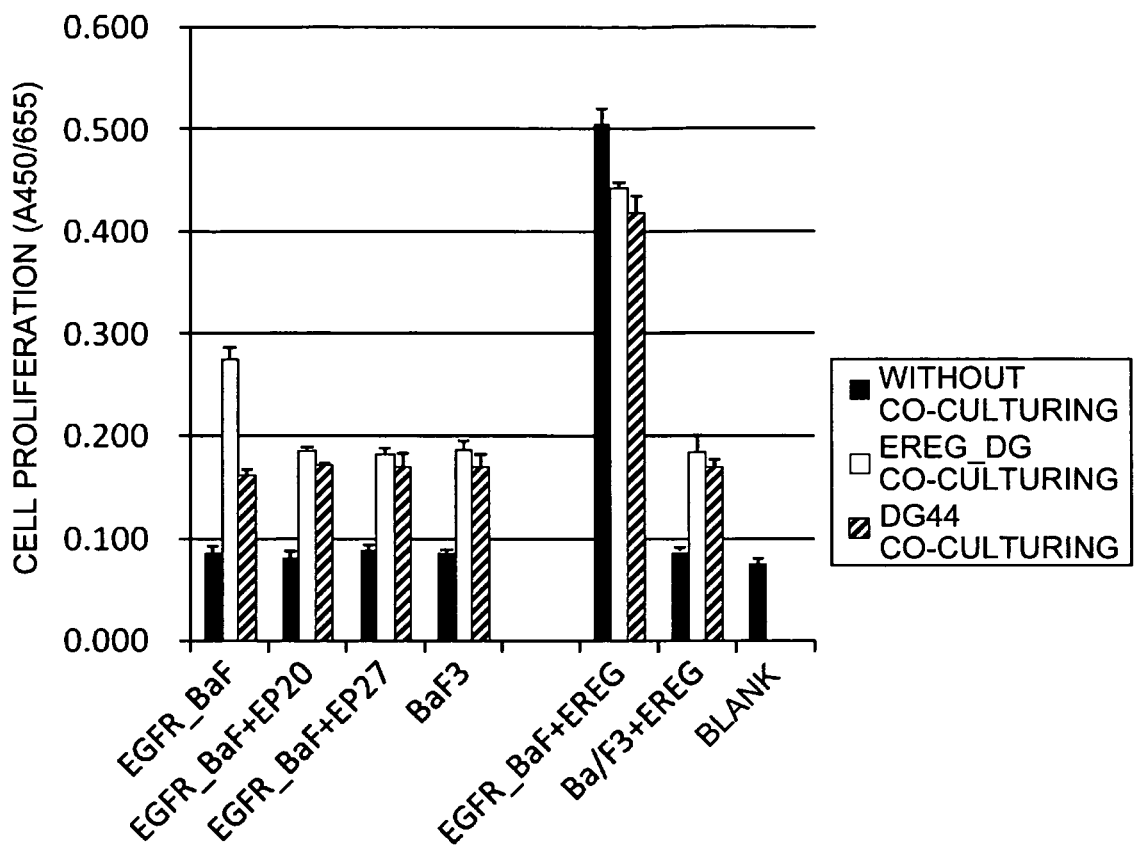
FIG. 17 shows the EGF receptor activation by coculturing cells forcedly expressing EREG, and suppression of this activation by anti-EREG antibodies.

J. Biol. Chem. 273, 10496-505; Jones et al (1999) FEBS Lett 447, 227-31). By comparison of the effects on EGFR_BaF, it was confirmed that EREG has a low activity (affinity) towards the EGF receptor, which is one-hundredth of the affinity or less of EGF (FIG. 15). EREG is not an abundant protein in the blood under physiological conditions. While increased EREG gene expression has been reported during malignant transformation, no reports show that the EREG protein was detected at a high concentration in the blood of cancer patients. The present inventors hypothesized that membrane-type EREG expressed on the cell membrane, rather than soluble EREG, stimulates a neighboring EGF receptor, and examined the hypothesis that a local activation mechanism may be present as follows. They examined whether proliferation of EGFR_BaF is not only stimulated by soluble EREG but by co-culturing EGFR_BaF with cells forcedly expressing EREG. EREG-expressing EREG_DG cells and DG44 cells (negative control) were seeded into a 96-well plate at $5 \times 10^3$ cells/well, and incubated for overnight with a medium containing FCS. On the following day, $1 \times 10^4$ EGFR_BaF cells or Ba/F3 cells (negative control) were added, and then the cells were incubated for three days. As shown in FIG. 16, the proliferation of EGFR_BaF was remarkably enhanced by co-culturing with EREG_DG cells which have forced expression of EREG. However proliferation of EGFR_BaF was not stimulated at all by co-culturing with DG44 cells which do not express EREG. The stimulated proliferation by EREG_DG was cancelled by addition of the EP20 anti-EREG antibody (10 μg/mL). The EGFR_BaF cell proliferation was quantified by adding the WST-8 reagent (FIG. 17). It was shown that proliferation of Ba/F3 cells was not stimulated by co-culturing with EREG_DG cells, and that the cell proliferation promoted by co-culturing of EGFR_BaF with EREG_DG could be suppressed completely by addition of the anti-EREG antibody.

Figure 18:
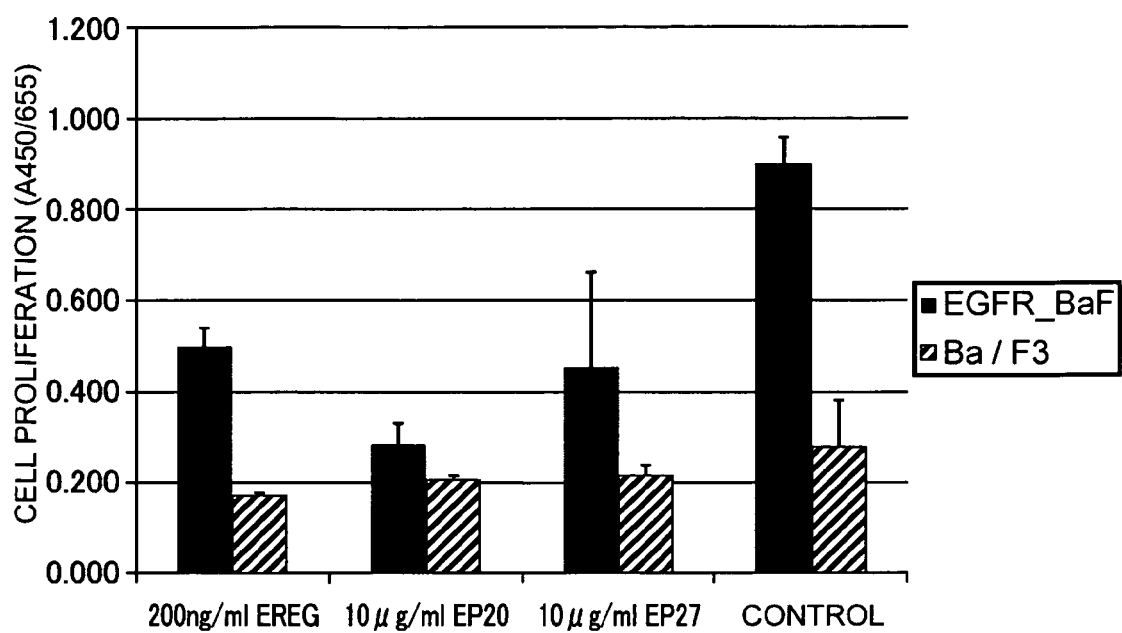
FIG. 18 shows the activation of the EGFR receptor by coculturing DLD-1 cells, and suppression of this activation by addition of anti-EREG antibodies.

GeneChip analysis showed that in addition to EREG, amphiregulin (a member of the EGF ligand family) mRNA expression was also enhanced in the DLD-1 colon cancer cells. In EGF receptor signaling, there is a redundancy among the ligand family molecules that activate the receptor, and thus theoretically, inhibition of one of the ligands is not equivalent to the receptor signaling inhibition. It was shown that by coculturing with DLD-1, proliferation of EGFR_BaF was remarkably enhanced as compared to that of Ba/F3, and that this enhanced proliferation was cancelled by addition of the EP20 or EP27 anti-EREG neutralizing antibody (FIG. 18).

Figure 19:
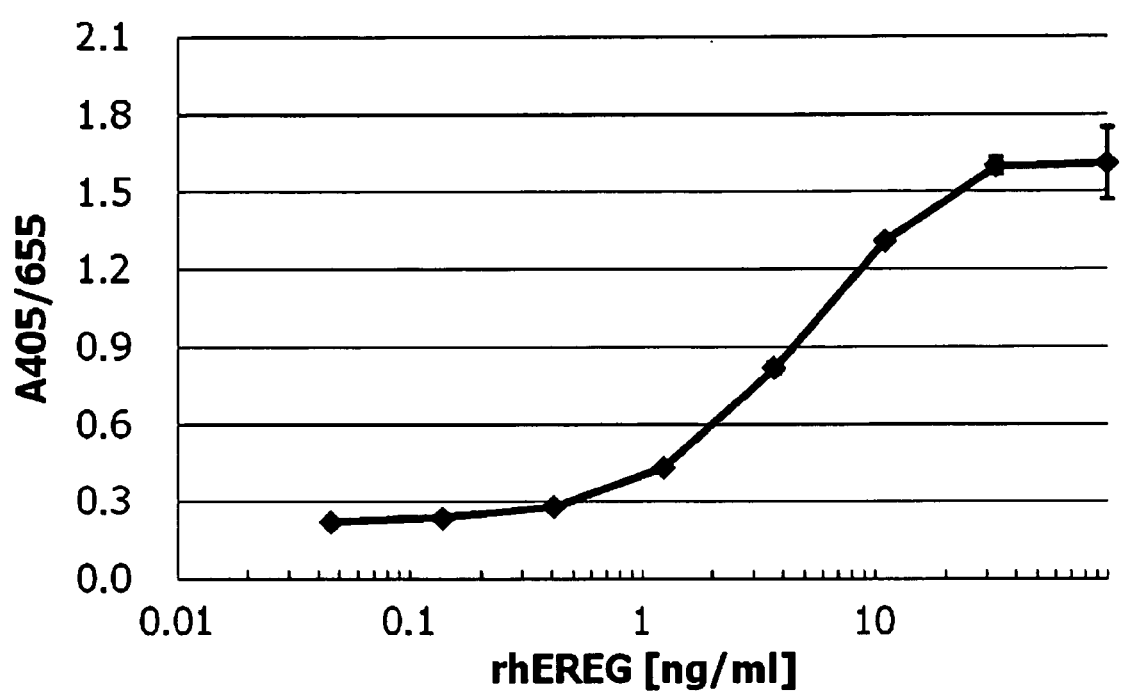
FIG. 19 shows the detection of the soluble EREG protein by sandwich ELISA using anti-EREG antibodies.

The soluble EREG protein in the culture supernatants of EREG_DG and DLD-1 cells was quantified by sandwich ELISA. An immuno plate was coated with mouse EP30 and subjected to blocking. Then, soluble recombinant human EREG (R&D Systems) used as a standard to calculate concentration and cell culture supernatant after three days of culturing was added for examination. After incubation, EREG protein was detected by addition of the chimerized EP20 antibody and an alkaline phosphatase-labeled anti-human IgG antibody in order. The detection of soluble EREG proteins using a standard is shown in FIG. 19. The concentration of EREG in the culture supernatant was lower than the detection limit (1 ng/mL). The A405/655 detection values are 0.157 for EREG_DG and 0.184 for DLD-1. The above-mentioned result shows that the EREG-mediated activation of EGF receptor signaling occurs between neighboring cells, and that membrane-type EREG is highly likely to be involved in the activation.

The result that the EREG-mediated EGF receptor activation occurs efficiently through intercellular interaction was discovered for the first time by the present invention. The finding that this activation can be suppressed by an anti-EREG antibody was also discovered for the first time.

Example 10

Detection of EREG Protein in Colon Tumors by Immunohistological Staining

Figure 20:
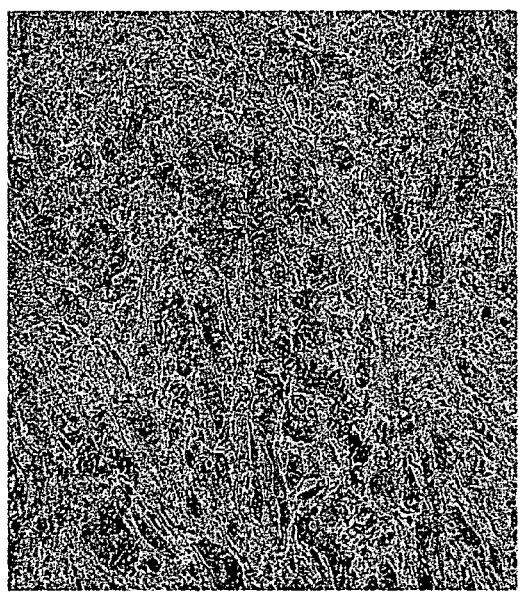
FIG. 20 shows the result of immunostaining with an anti-EREG mouse monoclonal antibody (EP27).
Figure 20:
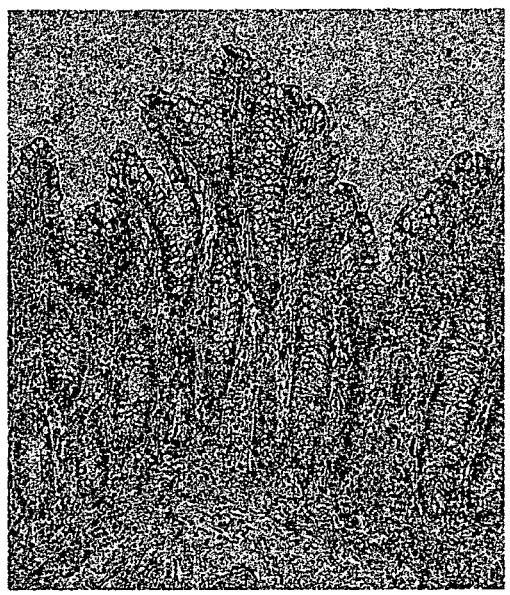

Expression of the EREG protein in tumors and localization of the protein on the cancer cell membrane were evidenced by immunohistological staining. Immunohistological staining was performed using a tissue array prepared from clinical cancer tissues, and tissue specimens were prepared as follows. Tissues removed by surgery were fixed overnight in 4% paraformaldehyde, then washed for two hours with 0.01 M phosphate buffer solution, and then embedded in paraffin by the AMeX method (reference document: Sato et al. (1986) Am. J. Pathol. 125, 431-5). A 1.5-mm-diameter cancer tissue was excised from this block, transferred to a new block of approximately 2.5×3.0 cm, and different tissues were placed in an array to prepare a tissue array. The tissue array was sliced and deparaffinized, and the sections were stained immunohistochemically using the Ventana HX Discovery System (Ventana Medical Systems, Inc.). Fifty μg/mL of an anti-EREG mouse monoclonal antibody (EP27) was added to the sliced tissues and then allowed to react. A peroxidase-labeled anti-mouse IgG antibody was used as the secondary antibody, and then color development reaction was performed using DAB. Expression of the EREG protein and its localization to the cell membrane were detected in the primary colon cancer (FIG. 20). Meanwhile, the EREG protein was not detected at all in non-cancerous tissues under the same staining conditions. Detection of the EREG protein and localization of the protein on the membrane in cancer tissues were shown for the first time in the present invention.

Example 11

Figure 22:
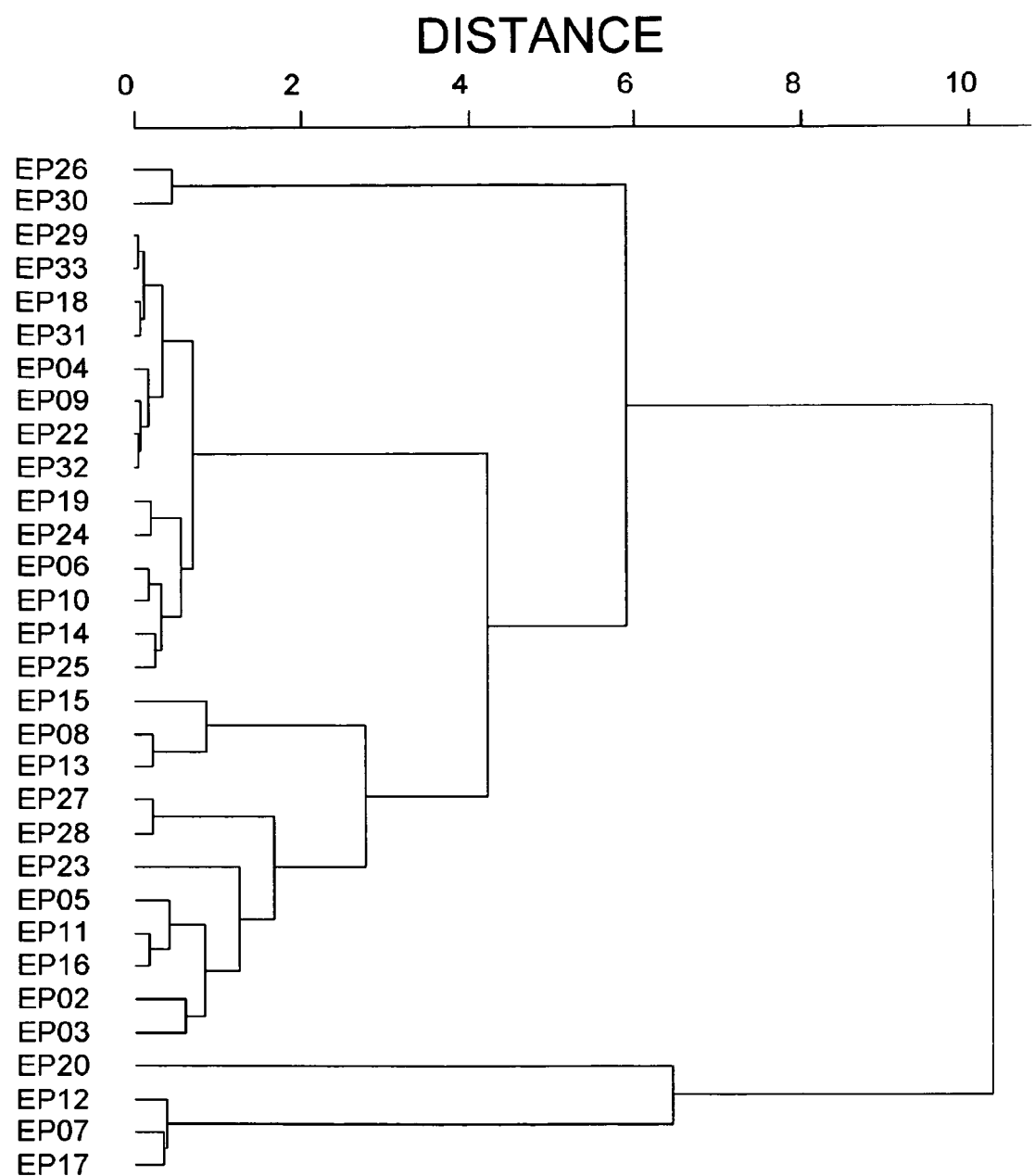
FIG. 22 shows the result which was derived from the sandwich ELISA data, by clustering analysis of the antibody binding fingerprints.

Classification of Anti-EREG Monoclonal Antibodies According to Epitope Recognition in Sandwich ELISA In Example 8, it was found that antibody recognition epitopes were mainly located in the mature EGF domain of EREG. More specifically, antibody epitopes were classified by identifying combinations of antibodies which could non-competitively bind to the same antigen molecule in a sandwich ELISA. A mouse anti-EREG antibody was diluted to 1 μg/mL, and was immobilized onto Nunc-Immuno plates. After blocking, 50 μg/mL of a soluble human EREG fragment comprising a mature EGF domain ($^{63}$Val to $^{108}$Leu of SEQ ID NO: 21) or 100 μg/mL of human EREG-mFc (SEQ ID NO: 34) was added at 100 μL/well, and therefore the antigen molecule was captured by the mouse antibody. After washing, an anti-EREG chimeric antibody was added (antibody concentration: 1, 0.33, 0.11, or 0.037 μg/mL), and the binding of the chimeric antibody to the captured antigen was quantified by addition of an alkaline phosphatase-labeled anti-human IgG antibody and a Sigma 104 chromogenic reagent. The obtained data (FIG. 21-1 to FIG. 21-3) were subjected to clustering analysis using the R statistical analysis software (URL http://www.R-project.org.), and the dendrogram is shown in FIG. 22. In FIG. 22, the farther the distance to the branching point on the horizontal axis is, the more different the reaction patterns in the sandwich ELISA system are, and the more different the modes of antigen recognition are. EP20 can bind to EREG simultaneously with many antibodies including EP27, and it turns out that the EP20 epitope is characteristic. Antibodies belonging to the cluster from EP29 to EP25 in FIG. 22 hardly allow simultaneous EREG-binding with other antibodies, and thus the antigen molecule is speculated to be deeply captured by these antibodies.

INDUSTRIAL APPLICABILITY

The EREG protein-specific antibodies of the present invention can be used as diagnostic agents for colon cancer, lung adenocarcinoma, pancreatic cancer, stomach cancer, kidney cancer, or such. The diagnostic agents of the present invention are useful for diagnosing primary or metastatic cancers. More specifically, cancers can be detected by detecting the EREG protein or EREG-encoding mRNA contained in a biological sample collected from a patient. Alternatively, the presence of primary colon cancer, metastatic colon cancer, lung adenocarcinoma, pancreatic cancer, stomach cancer, or kidney cancer can be detected in vivo by detecting the localization of EREG-expressing cells in vivo.

Furthermore, anti-EREG antibodies having cytotoxic activity in the present invention are useful for treating or preventing cancers that express an EREG protein. More specifically, cytotoxic agents or cell proliferation inhibitors for various types of cancer cells such as cells of colon cancer, lung adenocarcinoma, pancreatic cancer, stomach cancer, or kidney cancer, are provided by the present invention. Cytotoxic agents or cell proliferation inhibitors for cancer cells in the present invention may be applied to both primary and metastatic cancers.

Furthermore, according to the present invention, anti-EREG antibodies having cytotoxic activity can be used as therapeutic agents against various types of cancers such as colon cancer, lung adenocarcinoma, pancreatic cancer, stomach cancer, or kidney cancer. In the present invention, the anti-EREG antibodies are useful as therapeutic agents for both primary and metastatic cancers.

Additionally, genes encoding the antibodies of the present invention and recombinant cells transformed with these genes can be used to prepare recombinant antibodies that exhibit the above-mentioned effects or more preferable effects.

Furthermore, based on the findings of the present invention, candidate compounds can be screened to find useful cancer therapeutic agents. The present invention showed EREG-dependent proliferation of cancer. Therefore, one may consider compounds selected by the screening methods of the present invention as compounds that suppress EREG-dependent proliferation of cancer. Compounds selected by the present invention are useful as candidate compounds for evaluating the utility of anticancer agents by assessment of safety and cancer specificity.

The invention claimed is:

1. An anticancer agent comprising as an active ingredient a monoclonal antibody that binds to an EREG protein, wherein said antibody has cytotoxicity, neutralizing activity, or both, for the treatment of a cancer selected from the group consisting of colon cancer, lung cancer, and pancreatic cancer, and wherein said antibody is an antibody of any of (1) to (43) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3, and an L chain having the amino acid sequence of SEQ ID NO:12 as CDR1, the amino acid sequence of SEQ ID NO:14 as CDR2, and the amino acid sequence of SEQ ID NO:16 as CDR3;

(2) an antibody comprising the H chain and the L chain of (1), wherein the H chain has the amino acid sequence of positions 117 to 452 in the amino acid sequence of SEQ ID NO: 8 as CH;

(3) an antibody comprising the H chain and the L chain of (1), wherein the H chain has the amino acid sequence of positions 117 to 446 in the amino acid sequence of SEQ ID NO: 10 as CH;

(4) an antibody comprising the H chain and the L chain of (1), wherein the L chain has the amino acid sequence of positions 107 to 213 in the amino acid sequence of SEQ ID NO: 18 as CL;

(5) an antibody comprising the H chain and the L chain of (1), wherein the L chain has the amino acid sequence of positions 107 to 213 in the amino acid sequence of SEQ ID NO: 20 as CL;

(6) an antibody comprising the H chain of (2) and the L chain of (4);

(7) an antibody comprising the H chain of (3) and the L chain of (5);

(8) an antibody comprising an H chain having the amino acid sequence of SEQ ID NO: 49 as CDR1, the amino acid sequence of SEQ ID NO: 51 as CDR2, and the amino acid sequence of SEQ ID NO: 53 as CDR3, and an L chain having the amino acid sequence of SEQ ID NO:55 as CDR1, the amino acid sequence of SEQ ID NO:57 as CDR2, and the amino acid sequence of SEQ ID NO:59 as CDR3;

(9) an antibody comprising the H chain and the L chain of (8), wherein the H chain has CH as derived from mouse IgG1;

(10) an antibody comprising the H chain and the L chain of (8), wherein the H chain has the amino acid sequence of positions 117 to 446 in the amino acid sequence of SEQ ID NO: 10 as CH;

(11) an antibody comprising the H chain and the L chain of (8), wherein the L chain has CL derived from the mouse κ chain;

(12) an antibody comprising the H chain and the L chain of (8), wherein the L chain has the amino acid sequence of positions 107 to 213 in the amino acid sequence of SEQ ID NO: 20 as CL;

(13) an antibody comprising the H chain of (9) and the L chain of (11);

(14) an antibody comprising the H chain of (10) and the L chain of (12);

(15) an antibody comprising an H chain having the amino acid sequence of SEQ ID NO: 61 as CDR1, the amino acid sequence of SEQ ID NO: 63 as CDR2, and the amino acid sequence of SEQ ID NO: 65 as CDR3, and an L chain having the amino acid sequence of SEQ ID NO:67 as CDR1, the amino acid sequence of SEQ ID NO:69 as CDR2, and the amino acid sequence of SEQ ID NO:71 as CDR3;

(16) an antibody comprising the H chain and the L chain of (15), wherein the H chain has CH derived from mouse IgG1;

(17) an antibody comprising the H chain and the L chain of (15), wherein the H chain has the amino acid sequence of positions 117 to 446 in the amino acid sequence of SEQ ID NO: 10 as CH;

(18) an antibody comprising the H chain and the L chain of (15), wherein the L chain has CL derived from the mouse κ chain;

(19) an antibody comprising the H chain and the L chain of (15), wherein the L chain has the amino acid sequence of positions 107 to 213 in the amino acid sequence of SEQ ID NO: 20 as CL;

(20) an antibody comprising the H chain of (16) and the L chain of (18);

(21) an antibody comprising the H chain of (17) and the L chain of (19);

(22) an antibody comprising an H chain having the amino acid sequence of SEQ ID NO: 73 as CDR1, the amino acid sequence of SEQ ID NO: 75 as CDR2, and the amino acid sequence of SEQ ID NO: 77 as CDR3, and an L chain having the amino acid sequence of SEQ ID NO:79 as CDR1, the amino acid sequence of SEQ ID NO:81 as CDR2, and the amino acid sequence of SEQ ID NO:83 as CDR3;

(23) an antibody comprising the H chain and the L chain of (22), wherein the H chain has CH derived from the mouse IgG1;

(24) an antibody comprising the H chain and the L chain of (22), wherein the H chain has the amino acid sequence of positions 117 to 446 in the amino acid sequence of SEQ ID NO: 10 as CH;

(25) an antibody comprising the H chain and the L chain of (22), wherein the L chain has CL derived from the mouse κ chain;

(26) an antibody comprising the H chain and the L chain of (22), wherein the L chain has the amino acid sequence of positions 107 to 213 in the amino acid sequence of SEQ ID NO: 20 as CL;

(27) an antibody comprising the H chain of (23) and the L chain of (25);

(28) an antibody comprising the H chain of (24) and the L chain of (26);

(29) an antibody comprising an H chain having the amino acid sequence of SEQ ID NO: 85 as CDR1, the amino acid sequence of SEQ ID NO: 87 as CDR2, and the amino acid sequence of SEQ ID NO: 89 as CDR3, and an L chain having the amino acid sequence of SEQ ID NO:91 as CDR1, the amino acid sequence of SEQ ID NO:93 as CDR2, and the amino acid sequence of SEQ ID NO:95 as CDR3;

(30) an antibody comprising the H chain and the L chain of (29), wherein the H chain has CH derived from the mouse IgG1;

(31) an antibody comprising the H chain and the L chain of (29), wherein the H chain has the amino acid sequence of positions 117 to 446 in the amino acid sequence of SEQ ID NO: 10 as CH;

(32) an antibody comprising the H chain and the L chain of (29), wherein the L chain has CL derived from the mouse κ chain;

(33) an antibody comprising the H chain and the L chain of (29), wherein the L chain has the amino acid sequence of positions 107 to 213 in the amino acid sequence of SEQ ID NO: 20 as CL;

(34) an antibody comprising the H chain of (30) and the L chain of (32);

(35) an antibody comprising the H chain of (31) and the L chain of (33);

(36) an antibody comprising an H chain having the amino acid sequence of SEQ ID NO: 97 as CDR1, the amino acid sequence of SEQ ID NO: 99 as CDR2, and the amino acid sequence of SEQ ID NO: 101 as CDR3, and an L chain having the amino acid sequence of SEQ ID NO:103 as CDR1, the amino acid sequence of SEQ ID NO:105 as CDR2, and the amino acid sequence of SEQ ID NO:107 as CDR3;

(37) an antibody comprising the H chain and the L chain of (36), wherein the H chain has CH derived from mouse IgG1;

(38) an antibody comprising the H chain and the L chain of (36), wherein the H chain has the amino acid sequence of positions 117 to 446 in the amino acid sequence of SEQ ID NO: 10 as CH;

(39) an antibody comprising the H chain and the L chain of (36), wherein the L chain has CL derived from the mouse κ chain;

(40) an antibody comprising the H chain and the L chain of (36), wherein the L chain has the amino acid sequence of positions 107 to 213 in the amino acid sequence of SEQ ID NO: 20 as CL;

(41) an antibody comprising the H chain of (37) and the L chain of (39);

(42) an antibody comprising the H chain of (38) and the L chain of (40); and

(43) an antibody that binds to the same EREG protein epitope as the antibody of any of (1) to (42).

2. The anticancer agent of claim 1, wherein the cancer is a primary cancer.

3. The anticancer agent of claim 1, wherein the cancer is a metastatic cancer.

4. The anticancer agent of claim 1, wherein the cancer is colon cancer or lung cancer.

* * * * *

UNITED STATES PATENT AND TRADEMARK OFFICE
CERTIFICATE OF CORRECTION

PATENT NO. : 9,017,684 B2
APPLICATION NO. : 12/444916
DATED : April 28, 2015
INVENTOR(S) : Aburatani et al.

Page 1 of 1

It is certified that error appears in the above-identified patent and that said Letters Patent is hereby corrected as shown below:

Specification

Column 6, line 11 please replace "has-CL" with --has CL--.

Column 9, line 42 please replace "[10] to [20]" with --[10] to [19]--.

Column 35, line 43 please replace "mouse IgG 1" with --mouse IgG1--.

Column 35, line 67 please replace "mouse IgG 1" with --mouse IgG1--.

Column 36, line 25 please replace "mouse IgG 1" with --mouse IgG1--.

Column 36, line 49 please replace "mouse IgG 1" with --mouse IgG1--.

Column 49, line 49 please replace "mouse IgG 1" with --mouse IgG1--.

Signed and Sealed this
Eighth Day of March, 2016

Michelle K. Lee
*Director of the United States Patent and Trademark Office*